US012186363B2

(12) United States Patent
Stinchcomb et al.

(10) Patent No.: US 12,186,363 B2
(45) Date of Patent: *Jan. 7, 2025

(54) COMPOSITIONS AND METHODS FOR DENGUE VIRUS CHIMERIC CONSTRUCTIONS IN VACCINES

(71) Applicants: TAKEDA VACCINES, INC., Cambridge, MA (US); THE GOVERNMENT OF THE UNITED STATES OF AMERICA AS REPRESENTED BY THE SECRETARY OF THE DEPARTMENT, Atlanta, GA (US)

(72) Inventors: Dan T. Stinchcomb, Enumclaw, WA (US); Claire Kinney, Fort Collins, CO (US); Richard M. Kinney, Fort Collins, CO (US); Jill A. Livengood, Fort Collins, CO (US)

(73) Assignees: Takeda Vaccines, Inc., Cambridge, MA (US); The Government of the United States of America as Represented by the Secretary of the Department of Health and Human Services, Atlanta, GA (US)

( * ) Notice: Subject to any disclaimer, the term of this patent is extended or adjusted under 35 U.S.C. 154(b) by 261 days.

This patent is subject to a terminal disclaimer.

(21) Appl. No.: 17/478,537

(22) Filed: Sep. 17, 2021

(65) Prior Publication Data

US 2022/0062375 A1 Mar. 3, 2022

Related U.S. Application Data

(60) Continuation of application No. 16/561,755, filed on Sep. 5, 2019, now abandoned, which is a continuation of application No. 15/492,981, filed on Apr. 20, 2017, now Pat. No. 10,449,231, which is a division of application No. 14/209,808, filed on Mar. 13, 2014, now Pat. No. 9,783,579.

(60) Provisional application No. 61/800,204, filed on Mar. 15, 2013.

(51) Int. Cl.

| | |
|---|---|
| ***A61K 39/12*** | (2006.01) |
| ***A61K 31/7048*** | (2006.01) |
| ***A61K 31/713*** | (2006.01) |
| ***A61K 38/16*** | (2006.01) |
| ***C07K 14/005*** | (2006.01) |
| ***C07K 14/18*** | (2006.01) |
| ***C07K 19/00*** | (2006.01) |
| ***C12N 15/09*** | (2006.01) |
| ***C12N 15/861*** | (2006.01) |
| *A61K 39/00* | (2006.01) |
| *A61P 31/14* | (2006.01) |

(52) U.S. Cl.

CPC ........ *A61K 38/162* (2013.01); *A61K 31/7048* (2013.01); *A61K 31/713* (2013.01); *A61K 39/12* (2013.01); *C07K 14/005* (2013.01); *C07K 14/1825* (2013.01); *C07K 19/00* (2013.01); *C12N 15/09* (2013.01); *C12N 15/8613* (2013.01); *A61K 2039/5254* (2013.01); *A61K 2039/70* (2013.01); *A61P 31/14* (2018.01); *C07K 2319/00* (2013.01); *C12N 2770/24122* (2013.01); *C12N 2770/24134* (2013.01); *C12N 2770/24141* (2013.01); *C12N 2770/24143* (2013.01); *C12N 2770/24162* (2013.01); *Y02A 50/30* (2018.01)

(58) Field of Classification Search

None

See application file for complete search history.

(56) References Cited

U.S. PATENT DOCUMENTS

| | | | |
|---|---|---|---|
| 4,810,092 | A | 3/1989 | Auth |
| 5,021,347 | A | 6/1991 | Yasui et al. |
| 5,229,293 | A | 7/1993 | Matsuura et al. |
| 5,494,671 | A | 2/1996 | Lai et al. |
| 5,514,375 | A | 5/1996 | Paoletti et al. |
| 6,165,477 | A | 12/2000 | Ivy et al. |
| 6,184,024 | B1 | 2/2001 | Lai et al. |

(Continued)

FOREIGN PATENT DOCUMENTS

| | | | |
|---|---|---|---|
| CN | 10123809 | A | 8/2008 |
| CN | 101238144 | A | 8/2008 |

(Continued)

OTHER PUBLICATIONS

Pletnev, A. et al., "Chimeric Tick-Borne Encephalitis and Dengue Type 4 Viruses: Effects of Mutations on Neurovirulence in Mice." J. Virol., Aug. 1993, vol. 67, No. 8, pp. 4956-4963.

(Continued)

*Primary Examiner* — Stacy B Chen

(74) *Attorney, Agent, or Firm* — Honigman LLP

(57) ABSTRACT

Embodiments herein report compositions, uses and manufacturing of dengue virus constructs and live attenuated dengue viruses. Some embodiments concern a composition that includes, but is not limited to, a tetravalent dengue virus composition. In certain embodiments, compositions can include constructs of one or more serotypes of dengue virus, such as dengue-1 (DEN-1) virus, dengue-2 (DEN-2) virus, dengue-3 (DEN-3) or dengue-4 (DEN-4) virus constructs. In other embodiments, constructs disclosed herein can be combined in a composition to generate a vaccine against more one or more dengue virus constructs that may or may not be subsequently passaged in mammalian cells.

30 Claims, 12 Drawing Sheets

Specification includes a Sequence Listing.

(56) References Cited

U.S. PATENT DOCUMENTS

| | | | |
|---|---|---|---|
| 6,660,273 | B2 | 12/2003 | Pletnev et al. |
| 7,094,411 | B2 | 8/2006 | Kinney et al. |
| 8,673,316 | B2 | 3/2014 | Kinney et al. |
| 9,783,579 | B2 * | 10/2017 | Stinchcomb ....... A61K 31/7048 |
| 11,007,261 | B2 * | 5/2021 | Wallace ................ A61K 39/12 |
| 2006/0062803 | A1 | 3/2006 | Kinney et al. |
| 2007/0026016 | A1 | 2/2007 | Kinney et al. |
| 2010/0215692 | A1 | 8/2010 | Quentin-Millet |
| 2010/0303860 | A1 | 12/2010 | Stinchcomb et al. |
| 2011/0150771 | A1 | 6/2011 | Kinney et al. |
| 2011/0311579 | A1 | 12/2011 | Mason et al. |
| 2014/0302088 | A1 | 10/2014 | Stinchcomb et al. |
| 2015/0150961 | A1 | 6/2015 | Stinchcomb et al. |
| 2015/0265695 | A1 | 9/2015 | Yao et al. |
| 2017/0049874 | A1 | 2/2017 | Livengood et al. |
| 2017/0304426 | A1 | 10/2017 | Tornieporth et al. |
| 2019/0381163 | A1 | 12/2019 | Wallace et al. |
| 2020/0061151 | A1 | 2/2020 | Stinchcomb et al. |
| 2020/0069751 | A1 | 3/2020 | Wallace |

FOREIGN PATENT DOCUMENTS

| | | | |
|---|---|---|---|
| CN | 101238209 | A | 8/2008 |
| CN | 1012385144 | A | 8/2008 |
| DE | 29810020 | U1 | 9/1998 |
| EP | 1159968 | A1 | 12/2001 |
| EP | 2353609 | A1 | 8/2011 |
| EP | 3620174 | A1 | 3/2020 |
| EP | 3892737 | A1 | 10/2021 |
| JP | H05276941 | A | 10/1993 |
| JP | 2003-523189 | A | 8/2003 |
| JP | 2016-513970 | A | 5/2016 |
| KR | 10-2008-0018271 | A | 2/2008 |
| TW | 200740458 | A | 11/2007 |
| TW | 1726312 | B | 3/2014 |
| WO | 1990001946 | A1 | 3/1990 |
| WO | 1992003545 | A1 | 3/1992 |
| WO | 1993006214 | A1 | 4/1993 |
| WO | 1996040933 | A1 | 12/1996 |
| WO | 1998037911 | A1 | 9/1998 |
| WO | 1999063095 | A1 | 12/1999 |
| WO | 0139802 | A1 | 6/2001 |
| WO | 2001060847 | A2 | 8/2001 |
| WO | 2001060847 | A3 | 4/2002 |
| WO | 2002072036 | A1 | 9/2002 |
| WO | 2002072036 | A2 | 9/2002 |
| WO | 2002072036 | A3 | 5/2003 |
| WO | 2006134443 | A1 | 12/2006 |
| WO | 2009048658 | A9 | 6/2009 |
| WO | 2009139725 | A1 | 11/2009 |
| WO | 2010141386 | A1 | 12/2010 |
| WO | 2011038473 | A1 | 4/2011 |
| WO | 2013188315 | A1 | 12/2013 |
| WO | 2014016360 | A1 | 1/2014 |
| WO | 2014016362 | A1 | 1/2014 |
| WO | 2014074912 | A1 | 5/2014 |
| WO | 2014093182 | A1 | 6/2014 |
| WO | 2014150939 | A2 | 9/2014 |
| WO | 2016034629 | A1 | 3/2016 |
| WO | 2017005652 | A1 | 1/2017 |
| WO | 2017005654 | A1 | 1/2017 |
| WO | 2017041156 | A1 | 3/2017 |
| WO | 2017179017 | A1 | 10/2017 |
| WO | 2018052375 | A1 | 3/2018 |
| WO | 2019077622 | A1 | 4/2019 |

OTHER PUBLICATIONS

Pletnev, A. et al., "Construction and characterization of chimeric tick-borne encephalitis/ dengue type 4 viruses." Proc. Nat. Acad. Sci. USA, Medical Sciences, Nov. 1992, vol. 89: pp. 10532-10536.

Puri, B. et al., "Molecular analysis of dengue virus attenuation after serial passage in primary in dog kidney cells." J. Gen Virol., 1997, vol. 78, pp. 2287-2291.

Rice, C. et al., "Nucleotide Sequence of Yellow Fever Virus: Implications for Flavivirus Gene Expression and Evolution," Science, 1985, vol. 229, pp. 726-733.

Rice, C. et al., "Transcription of Infectious Yellow Fever RNA From Full-Length eDNA Templates Produced by In Vitro Ligation," The New Biologist, Dec. 1989, vol. 1, No. 3, pp. 285-296.

Roehrig, J. et al., "Identification of Epitopes on the E Glycoprotein of Saint Louis Encephalitis Virus Using Monoclonal Antibodies." Virology, 1983, vol. 128, pp. 118-126.

Roehrig, J. et al., "Synthetic Peptides Derived from the Deduced Amino Acid Sequence of the E-Glycoprotein of Murray Valley Encephalitis Virus Elicit Antiviral Antibody," Virology, 1989, vol. 171, pp. 49-60.

Sabchareon, A. et al., "Safety and Immunogenicity of Tetravalent Live-Attenuated Dengue Vaccines in Thai Adult Volunteers: Role of Serotype Concentration, Ratio, and Multiple Doses," Am. J. Trop. Med. Hyg., 2002, vol. 66, No. 3, pp. 264-272.

Sato, Y. et al., "Immunostimulatory DNA Sequences Necessary for Effective Intradermal Gene Immunization," Science, Jul. 19, 1996, vol. 273, No. 5273, pp. 352-354.

Seeger, C. et al., "The cloned genome of ground squirrel hepatitis virus is infectious in the animal," Proc. Nat. Acad. Sci. USA, Medical Sciences, Sep. 1984, vol. 81, pp. 5849-5852.

Sela, Michael, "The Choice of Carrier." In Synthetic Vaccines vol. I, R. Amon, (ed) CRC Press Inc., Boca Raton, FL. Chapter 6, 1987, pp. 83-92.

Smithburn, K. et al., "A Neurotropic Virus Isolated From The Blood Of a Native Of Uganda," Am. J. Trop. Med. Hyg., 1940, vol. 20, pp. 471-492.

Stocks et al: "Signal Peptidase Cleavage at the Flavivirus C-prM Junction: Dependence on the Viral NS2B-3 Protease for Efficient Processing Requires Determinants in C, the Signal Peptide, and prM," Journal Of Virology, LNKDPUBMED: 9499070, Mar. 1998, Mar. 1998 (Mar. 1998), vol. 72, No. 3, pp. 2141-2149.

Sumiyoshi, H. et al., "Complete Nucleotide Sequence of Japanese Encephalitis Virus Genome RNA," Virology, 1987, vol. 161, pp. 497-510.

Tardei, G. et al., "Evaluation of Immunoglobulin M (IgM) and IgG Enzyme Immunoassays in Serologic Diagnosis of West Nile Virus Infection," J. Clin. Microbiol. Jun. 2000, vol. 38, No. 6, pp. 2232-2239.

Trent Dennis W. et al., "Partial Nucleotide Sequence of St. Louis Encephalitis Virus RNA: Structural Proteins, NS1, ns2a, and ns2b," Virology, 1987, vol. 156, pp. 293-304.

Trent Dennis W. et al., "Recombinant dengue virus vaccines." In: Dengue and Dengue Hemorrhagic Fever. D.J. Gubler and G. Kuno (eds.). CAB International, New York, NY Chapter 18, 1997, pp. 379-403.

Troyer, J. et al., "A Live Attenuated Recombinant Dengue-4 Virus Vaccine Candidate With Restricted Capacity For Dissemination In Mosquitoes And Lack Of Transmission From Vaccinees To Mosquitoes," Am. J. Trop. Med. Hyg., 2001, vol. 65, No. 5, pp. 414-419.

Tsai et al "Japanese Encephalitis Vaccines," In Vaccines, (3rd edition) Plotkin and Orenstein (eds), W.B. Saunders Company, Philadelphia, PA. Chapter 27, 1999, pp. 672-710.

Tsai, T. et al., "Japanese Encephalitis Vaccines," In Vaccines, (2nd edition), Plotkin and Mortimer (eds.), W.B. Saunders Co., Philadelphia, PA. Chapter 24, 1994, pp. 671-713.

Update: "Surveillance for Weste Nile Virus in Overwintering Mosquitoes—New York, 2000," Morb. Mortal. Wkly. Rep., Mar. 10, 2000, vol. 49, No. 09, pp. 178-179.

Update: "West Nile Virus Activity—Northeastern United States, 2000," Morb. Mortal. Wkly. Rep., Sep. 15, 2000, vol. 49, No. 36, pp. 820-822.

Van Der Most, R. et al., "Chimeric yellow fever/dengue virus as a candidate dengue vaccine: quantification of the dengue virus-specific CD8 T-cell response," Journal of Virology, Sep. 1, 2000 2(Sep. 1, 2000), vol. 74. No. 17, pp. 8094-8101.

Vaughn, D. et al., "Testing of dengue 2 live-attenuated vaccine (strain 16681 PDK 53) in ten American volunteers," Vaccine 1996, vol. 14 No. 4, pp. 329-336.

(56) References Cited

OTHER PUBLICATIONS

Venugopal, K. et al., "Immunity to St. Louis encephalitis virus by sequential immunization with recombinant vaccinia and baculovirus derived PrM/E proteins," Vaccine, 1995, vol. 13, No. 11, pp. 1000-1005.
Wang et al., "Immune Response to Neonatal Genetic Immunization," Virology, 1997, vol. 228, pp. 278-284.
Wolff, J. et al., "Long-term persistence of plasmid DNA and foreign gene expression in mouse muscle," Hum. Mol. Genet., 1992, vol. 1, No. 6, pp. 363-369.
World Health Organization, "Dengue vaccine research: Immunization, Vaccines and Biologicals" www.who.int/immunization/research/development/dengue_vaccines/en/, Sep. 12, 2018, 3 pages.
World Health Organization, Dengue Vaccine Research, website page at www.who.int/immunuzation/research/development/dengue_vaccines/en, last updated Dec. 5, 2017, 3 pages.
World Health Organization, Updated Questions and Answers related to the dengue vaccine Dengvaxia and its use, website page at www.who.int/immunization/diseases/dengue/q_and_a_dengue_vaccine_dengvaxia_use/en/ published Dec. 22, 2017, 7 pages.
Xie, X. et al., "Membrane Topology and Function of Dengue Virus NS2A Protein," Journal of Virology, Apr. 2013, vol. 87, No. 8, pp. 4609-4622.
Yamshchikov, V. et al., "Processing of the Intracellular Form of the West Nile Virus Capsid Protein by the Viral NS2B-NS3 Protease: an In Vitro Study," Journal of Virology, LNKDPUBMED:8057458, Sep. 1994, vol. 68, No. 9, pp. 5765-5771.
Yang, X. et al., "A p300/CBP-associated factor that competes with the adenoviral oncoprotein E1A," Nature, Jul. 25, 1996, vol. 382.
Yoksan, S. et al., "Dengue Virus Vaccine Development: Study on Biological Markers of Uncloned Dengue 1-4 Viruses Serially Passaged in Primary Kidney Cells," Arbovirus Research in Australia—Proceedings 4th Symposium, T. D. St. George, B.H. Kay, and J. Blok (eds.), CSIRO/QIMR, Brisbane 1986, pp. 35-38.
Zhang et al., "Passive Protection of Mice, Goats, and Monkeys Against Japanese Encephalitis With Monoclonal Antibodies," 1989, J. Med. Virol., vol. 29, pp. 133-138.
Zhang, Y. et al., "Immunization of Mice with Dengue Structural Proteins and Nonstructural Protein NS1 Expressed by Baculovirus Recombinant Induces Resistance to Dengue Virus Encephalitis," J. Viro., Aug. 1988, vol. 62, No. 8, pp. 3027-3031.
Zhao, B. et al., "Cloning Full-Length Dengue Type 4 Viral DNA Sequences: Analysis of Genes Coding for Structural Proteins," Virology, 1986, vol. 155, pp. 77-88.
Zhao, B. et al., "Expression of Dengue Virus Structural Proteins and Nonstructural Protein NS1 by a Recombinant Vaccinia Virus," Journal of Virology, Dec. 1987, vol. 61, No. 12, pp. 4019-4022.
Anonymous, "Guidelines for plaque reduction neutralization testing of human antibodies to dengue viruses," Sep. 21, 2007 (Sep. 21, 2007), p. 1-36,; Retrieved from the Internet:; URL:http://apps.who.int/iris/bitstream/handle/10665/69687/who_ivb_07.07_eng.pdf;jsessionid=E54172674C933124415AFC5BB972E6B9?sequence=1; XP055519586.
Beatty et al., "Dengue virus NS1 triggers endothelial permeability and vascular leak that is prevented by NS1 vaccination," Sci. Transl. Med. Sep. 9, 2015, vol. 7, No. 304, pp. 1-13.
Benjamin, Sarah, "Optimization and analysis of live attenuated denvax-4 constructs," Masters Thesis: Colorado State University, Summer 2013, 97 pages.
Bhatt et al., "The global distribution and burden of dengue," Nature, Apr. 25, 2013, vol. 496 (7446), pp. 504-507.
Biswal et al., "Efficacy of a Tetravalent Dengue Vaccine in Healthy Children Aged 4-16 years: a randomised, placebo-controlled, phase 3 trial," Lancet, Mar. 17, 2020, vol. 395, pp. 1423-1433.
Biswal et al., "Efficacy of a Tetravalent Dengue Vaccine in Healthy Children and Adolescents," New England Journal of Medicine, Nov. 21, 2019, vol. 381, No. 21, pp. 2009-2019.
Biswal Presentation "Takeda Tetravalent Dengue Vaccine (TDV) Candidate: An Update (DEN-204), " Asia Dengue Summit, Jan. 13, 2016, 17 pages.
Brewoo et al., "Immunogenicity and efficacy of chimeric dengue vaccine (DENVax) formulations in interferon-deficient AG129 mice," Vaccine, Feb. 1, 2012, vol. 30, No. 8, pp. 1513-1520.
Butrapet, S. et al., "Attenuation markers of a candidate dengue type 2 vaccine virus, strain 16681 (PDK-53), are defined by mutations in the 5' noncoding region and nonstructural proteins 1 and 3," J. Virol., Apr. 2000, vol. 74, No. 7, pp. 3111-3119.
Capeding et al., "Clinical efficacy and safety of a novel tetravalent dengue vaccine in healthy children in Asia: a phase 3, randomised, observer-masked, placebo-controlled trial," Lancet, 2014, vol. 384, pp. 1358-1365.
Chambers, T. et al., "Flavivirus Genome Organization, Expression, and Replication," Annu. Rev. Microbiol. 1990, vol. 44, pp. 649-688.
Chen, W. et al., "Construction of Intertypic Chimeric Dengue Viruses Exhibiting Type 3 Antigenicity and Neurovirulence for Mice," Journal of Virology, Aug. 1995, vol. 69, No. 8, pp. 5186-5190.
Aberle, J. et al., "A DNA Immunization Model Study with Constructs Expressing the Tick-Borne Encephalitis Virus Envelope Protein E in Different Physical Forms," Journal of Immunology, 1999, vol. 163, pp. 6756-6761.
*AK Steel Corporation* v. *Sollac and Ugine*; United States Court of Appeals for the Federal Circuit; http://laws.lp.findlaw.com/fed/031074.html (Sep. 24, 2003), 8 pages.
Allison, S. et al., "Synthesis and Secretion of Recombinant Tick-Borne Encephalitis Virus Protein E in Soluble and Particulate Form," Journal of Virology, Sep. 1995, vol. 69, No. 9, pp. 5816-5820.
Alvarez, R. et al., "A Phase I Study of Recombinant Adenovirus Vector-Mediated Delivery of an Anti-erbB-2 Single-Chain (sFv) Antibody Gene for Previously Treated Ovarian and Extraovarian Cancer Patients," Mary Ann Liebert, Inc., Human Gene Therapy, Jan. 20, 1997, vol. 8, pp. 229-242.
Anderson, J. et al., "Isolation of West Nile Virus from Mosquitoes, Crows, and a Cooper's Hawk in Connecticut", Ovid: Anderson: Science, vol. Dec. 17, 1999, vol. 286(5448), pp. 2331-2333.
Arnon Ruth "Synthetic Vaccines vol. I" CRC Press, Inc. Boca Raton, Florida pp. 83-92.
Arroyo, J. et al., Molecular Basis for Attenuation of Neurovirulence of a Yellow Fever Virus/Japanese Encephalitis Virus Chimera Vaccine (ChimeriVax-JE), Journal of Virology, Jan. 2001, vol. 75, No. 2, pp. 934-942.
Asnis, D. et al., "The West Nile Virus Outbreak of 1999 in New York: The Flushing Hospital Experience," Clinical Infectious Diseases, 2000, vol. 30, pp. 413-418.
Azevedo, V. et al., "Main features of DNA-based immunization vectors," Brazilian Journal of Medical and Biological Research 1999, vol. 32, No. 2, pp. 147-153.
Bhamarapravati, N. et al., "Immunization with a live attenuated dengue-2-virus candidate vaccine (?16681-PDK 53 : clinical, immunological and biological responses in adult volunteers," Bulletin of the World Health Organization, 1987, vol. 65, No. 2, pp. 189-195.
Bhamarapravati, N. et al., "Live attenuated tetravalent dengue vaccine," Cab International, Wallingford, OX, UK, 1997, Dengue and Dengue Hamorrhagic Fever, D.J. Gubler and G. Kuno (ed), Chapter 17, pp. 367-377.
Bhatt, T. et al., "Growth characteristics of the chimeric Japanese encephalitis virus vaccine candidate, chimeriVax-je (YF/JE SA14-14-2), in culex tritaeniorhynchus, aedes albopictus, and aedes aegypti mosquitoes," Am. J. Trop. Med. Hyg., 2000, vol. 62, No. 4, pp. 480-484.
Blok, J. et al., "Comparison of a Dengue-2 Virus and Its Candidate Vaccine Derivative: Sequence Relationships with the Flaviviruses and Other Viruses," Virology, 1992, vol. 187, pp. 573-590.
Bray, M. et al., "Construction of intertypic chimeric dengue viruses by substitution of structural protein genes," Proc. Nat. Acad. Sci. USA, Medical Sciences, Nov. 1991, vol. 88, pp. 10342-10346.
Bray, M. et al., "Mice Immunized with Recombinant Vaccinia Virus Expressing Dengue 4 Virus Structural Proteins with or without Nonstructural Protein NS1 are Protected against Fatal Dengue Virus Encephalitis," Journal of Virology, Jun. 1989, vol. 63, No. 6, pp. 2853-2856.

(56) References Cited

OTHER PUBLICATIONS

Bray, M. et al., "Monkeys Immunized with Intertypic Chimeric Dengue Viruses Are Protected against Wild-Type Virus Challenge," Journal of Virology, Jun. 1996, vol. 70, No. 6, pp. 4162-4166.
Butrapet, S. et al., "Chimeric Dengue Type 2/Type 1 Viruses Induce Immune Responses in Cynomolgus Monkeys," Southeast Asian J. Trap. Med. Public Health, Sep. 2002, vol. 33, No. 3, pp. 589-599.
Butrapet, S. et al., "Determining genetic stabilities of chimeric dengue vaccine candidates based on dengue 2 PDK-53 virus by sequencing and quantitative TaqMAMA," Journal of Virological Methods, 2005, vol. 131, No. 1, pp. 1-9.
Cahour, A. et al., "Growth-Restricted Dengue Virus Mutants Containing Deletions in the 5' Noncoding Region of the RNA Genome," Virology, 1995, vol. 207, pp. 68-76.
Calvert, A. et al., "Non-structural proteins of dengue 2 virus offer limited protection to interferon-deficient mice after dengue 2 virus challenge,", Journal of General Virology, vol. 87, 2006, pp. 339-346.
Caufour, A. et al., "Construction, characterization and immunogenicity of recombinant yellow fever 17D-dengue type 2 viruses," Virus Research, 2001, vol. 79, pp. 1-14.
Chambers, T. et al., "Yellow Fever Virus/Dengue-2 Virus and Yellow Fever Virus/Dengue-4 Virus Chimeras: Biological Characterization, Immunogenicity, and Protection against Dengue Encephalitis in the Mouse Model," Journal of Virology, Mar. 2003. vol. 77, No. 6, pp. 3655-3668.
Chambers, T. et al., "Yellow Fever/Japanese Encephalitis Chimeric Viruses: Construction and Biological Properties," Journal of Virology, Apr. 1999, vol. 73, No. 4, pp. 3095-3101.
Chang, G. et al., "A Single Intramuscular Injection of Recombinant Plasmid DNA Induces Protective Immunity and Prevents Japanese Encephalitis in Mice," Journal of Virology, May 2000, vol. 74, No. 9, pp. 4244-4252.
Clarke, D. et al., "Techniques for Hemagglutination and Hemagglutination-Inhibition with Arthropod-Borne Viruses," The Rockefeller Foundation Virus Laboratories, New York, N.Y., Am. J. Trop. Med. Hyg., 1958, p. 561-573.
Cooper, J. et al., "Update: Surveillance for West Nile Virus in Overwintering Mosquitoes—New York, 2000," 3 pages.
Database UniProt Accession No. Q9WLZ7, XP-002731515, http://ibis/exam/dbfetch.jsp?id=UNIPROT%3AQ9WLZ7, 2 pages.
Database UniProt Accession No. D2KQW7 Database UniProt SubName: Full=Polyprotein (ECO:0000313 EMBL: ADA00411.1); XP002731516, retrieved from EBI accession No. UNIPROT:D2KQW7, http://ibis/exam/dbfetch.jsp?id=UNIPROT:D2KQW7 Feb. 9, 2010, 2 pages.
Database UniProt Accession No. P29991 "RecName: Full=Genome polyprotein; Contains: RecName: Full=Capsid protein C; AltName: Full=Core protein; Contains: RecName: Full=prM; Contains," XP002731514, retrieved from EBI accession No. UNIPROT: P29991; Apr. 1, 1993 http://ibis/exam/dbfetch.jsp?id=UNIPROT%3AP29991 .6 pages.
Davis, B. et al., "West Nile Virus Recombinant DNA Vaccine Protects Mouse and Horse from Virus Challenge and Expresses In Vitro a Noninfectious Recombinant Antigen That Can Be Used in Enzyme-Linked Immunosorbent Assays," Journal of Virology, May 2001, vol. 75, No. 9, pp. 4040-4047.
Deubel, V. et al., "Nucleotide Sequence and Deduced Amino Acid Sequence of the Nonstructural Proteins of Dengue Type 2 Virus, Jamaica Genotype: Comparative Analysis of the Full-Length Genome" Virology, 1988, vol. 165, pp. 234-244.
Deubel, V. et al., "Nucleotide Sequence and Deduced Amino Acid Sequence of the Structural Proteins of Dengue Type 2 Virus, Jamaica Genotype," Virology, 1986, vol. 155, pp. 365-377.
Dharakul, T. et al., "Dengue Virus-Specific Memory T Cell Responses in Human Volunteers Receiving a Live Attenuated Dengue Virus Type 2 Candidate Vaccine," JID Jul. 1994, vol. 170, pp. 27-33.
Dmitriev, I. et al., "Immunization with recombinant vaccinia viruses expressing structural and part of the nonstructural region of tick-borne encephalitis virus eDNA protect mice against lethal encephalitis," Journal of Biotechnology, 1996, vol. 44, pp. 97-103.
Duarte Dos Santos, C et al., "Complete nucleotide sequence of yellow fever virus vaccine strains 17DD and 17D-213," Virus Research 1995, vol. 35, pp. 35-41.
Durbin, A. et al., "Attenuation and Immunogenicity in Humans of a Live Dengue Virus Type-4 Vaccine Candidate with a 30 Nucleotide Deletion in its 3'-Untranslated Region," Am. J. Trop. Med. Hyg. 2001, vol. 65(5), pp. 405-413.
Falgout, B. et al., "Immunization of Mice with Recombinant Vaccinia Virus Expressing Authentic Dengue Virus Nonstructural Protein NS1 Protects against Lethal Dengue Virus Encephalitis," Journal of Virology, Sep. 1990, vol. 64, No. 9, pp. 4356-4363.
Falgout, B. et al., "Proper Processing of Dengue Virus Nonstructural Glycoprotein NS1 Requires the N-Terminal Hydrophobic Signal Sequence and the Downstream Nonstructural Protein NS2a," Journal of Virology, May 1989, vol. 63, No. 5, pp. 1852-1860.
Garmendia, A. et al., "Recovery and Identification of West Nile Virus from a Hawk in Winter," Journal of Clinical Microbiology, Aug. 2000, vol. 38, No. 8, pp. 3110-3111.
George et al., "Safety and immunogenicity of a Live Attenuated Tetravalent Dengue Vaccine Candidate in Flavivirus-Naïve Adults: A Randomized, Double-Blinded Phase 1 Clinical Trial," Journal of Infectious Diseases, Mar. 19, 2015, vol. 212, No. 7, pp. 1032-1041.
Guirakhoo, F. et al., "Construction, Safety, and Immunogenicity in Nonhuman Primates of a Chimeric Yellow Fever-Dengue Virus Tetravalent Vaccine" Journal of Virology, Aug. 2001, vol. 75, No. 16, pp. 7290-7304.
Guirakhoo, F. et al., "Immunogenicity, Genetic Stability, and Protective Efficacy of a Recombinant, Chimeric Yellow Fever-Japanese Encephalitis Virus (ChimeriVax-JE) as a Live, Attenuated Vaccine Candidate against Japanese Encephalitis," Virology, 1999, vol. 257, pp. 363-372.
Guirakhoo, F. et al., "Recombinant Chimeric Yellow Fever-Dengue Type 2 Virus Is Immunogenic and Protective in Nonhuman Primates" Journal of Virology, The American Society for Microbiology, Jun. 1, 2000, vol. 74, No. 12, pp. 5477-5485.
Guirakhoo, F. et al., "Viremia and Immunogenicity in Nonhuman Primates of a Tetravalent Yellow Fever-Dengue Chimeric Vaccine: Genetic Reconstructions, Dose Adjustment, and Antibody Responses against Wild-type Dengue Virus Isolates" Virology, 2002, vol. 298, pp. 146-159.
Hahn, Y. et al., "Nucleotide Sequence of Dengue 2 RNA and Comparison of the Encoded Proteins with Those of Other Flaviviruses," Virology, 1988, vol. 162, pp. 167-180.
Halstead, S. et al., Observations related to the pathogenesis of dengue hemorrhagic fever. II. Antigenic and Biologic Properties of Dengue Viruses and their Association with disease in the host; Yale Journal of Biology and Medicine, Apr. 1970, vol. 42, pp. 276-292.
Hashimoto, H. et al., "Molecular Cloning and Complete Nucleotide Sequence of the Genome of Japanese Encephalitis Virus Beijing-1 Strain," Virus Genes, 1988, vol. 1, No. 3, pp. 305-317.
Heinz, F. et al., "Flaviviruses" Immunochemistry of viruses II, The basis for serodiagnosis and vaccines, (edited by von Regenmortel and Neurath), Elsevier Science Publishers B.V., Chapter 14, 1990 pp. 289-305.
Hennessy, S. et al., "Effectiveness of live-attenuated Japanese encephalitis vaccine (SA14-14-2): a case-control study" The Lancet, vol. 347, Jun. 8, 1996, pp. 1583-1586.
Ho, T. et al., "DNA vaccination induces a long-term antibody response and protective immunity against pseudorabies virus in mice" Archives of Virology, 1998, vol. 143, pp. 115-125.
Chokephaibulkit K., "Combination Vaccines," Chot Mai Het Thang Phaet, Journal Of The Medical Association of Thai, Medical Association of Thailand, Aug. 1, 2002, vol. 85, No. Suppl. 2, pp. S694-S699.
Chu et al., "CD8+ T-cell Responses in Flavivirus-Naïve Individuals Following Immunization with a Live-Attenuated Tetrava-lent Dengue Vaccine Candidate" Major Article, JID, Nov. 15, 2015, vol. 212, pp. 1618-1628.
Crevat et al., "First Experience of Concomitant Vaccination Against Dengue and MMR in Toddlers," Pediatric Infectious Disease Journal, Aug. 1, 2015, vol. 34, No. 8, pp. 884-892.

(56) References Cited

OTHER PUBLICATIONS

DeLaBarrera et al., "Comparative Evaluation of Three Assays for Measurement of Dengue Virus Neutralizing Antibodies," Dengue Virus NS1 Disrupts the Endothelial Glycocalyx, Leading to Hyperpermeability, Jul. 1, 2008, vol. 79, No. 1, pp. 115-122.
Dubey et al., "Immunogenicity and safety of a tetravalent dengue vaccine in healthy adults in India: A randomized, observer-blind, placebo-controlled phase II trial," Human Vaccines and Immunotherapeutics, Aug. 20, 2015, vol. 12, No. 2, pp. 512-518.
Endy, "Dengue Human Infection Model Performance Parameters," Journal Infectious Diseases, 2014, vol. 209 (Suppl. 2), pp. S56-S60.
European Search Report dated Feb. 12, 2019 for corresponding EP application 18192701.3, 22 pages.
European Search Report dated May 3, 2019 for corresponding EP application 19161184.7, 16 pages.
European Search Report dated Nov. 13, 2018 for corresponding EP application 18192701.3, 20 pages.
European Search Report dated Nov. 13, 2018 for corresponding EP application 18192711.2, 16 pages.
European Search Report dated Nov. 13, 2018 for corresponding EP application 18192717.9, 16 pages.
European Search Report dated Nov. 13, 2018 for corresponding EP application 18192787.2, 18 pages.
European Search Report dated Nov. 13, 2018 for corresponding EP application 18192793.0, 16 pages.
European Search Report dated Nov. 13, 2018 for corresponding EP application 18192800.3, 18 pages.
European Search Report dated Nov. 13, 2018 for corresponding EP application 18192814.4, 16 pages.
European Search Report dated Nov. 29, 2018 for corresponding EP application 18192776.5, 17 pages.
Gentry et al., "Identification of distinct antigenic determinants on dengue-2 virus using monoclonal antibodies," May 1982, Am. J. Trop. Med. Hyg., vol. 31, No. 3, Pt. 1, pp. 548-555.
Glasner et al., "Dengue virus NS1 cytokine-independent vascular leak is dependent on endothelial glycocalyx components," PloS Pathog., Nov. 9, 2017, vol. 13, No. 11, pp. 1-22.
Gruenberg, A. et al., "Partial Nucleotide Sequence and Deduced Amino Acid Sequence of the Structural Proteins of Dengue Virus Type 2, New Guinea C and PUO-218 Strains" J. gen. Virol., 1988, vol. 69, pp. 1391-1398.
Hadinegoro et al., "Efficacy and Long-Term Safety of a Dengue Vaccine in Regions of Endemic Disease," New England Journal of Medicine, Sep. 24, 2015, vol. 373, No. 13, p. 1195-1206.
Henchal E. et al., "Dengue Virus-Specific and Flavivirus Group Determinants Identified with Monoclonal Antibodies by Indirect Immunofluorescence," Flavivirus-Specific and Group Determinants, Am. J. Trop Med. Hyg., 1982, vol. 31, No. 4, pp. 830-836.
Henchal et al., "Epitopic Analysis of Antigenic Determinants on the Surface of Dengue-2 Virions Using Monoclonal Antibod-ies," Am. J. Trop. Med. Hyg., 1985, vol. 34, No. 1, pp. 162-169.
Huang, C. et al., "Chimeric Dengue 2 PDK-53/West Nile NY99 Viruses Retain the Phenotypic Attenuation Markers of the Candidate PDK-53 Vaccine Virus and Protect Mice against Lethal Challenge with West Nile Virus" Journal of Virology, vol. 79, No. 12, Jun. 2005, pp. 7300-7310.
Huang, C. et al., "Concomitant administration of live attenuated Japanese encephalitis chimeric virus vaccine (JE-CV) and measles, mumps, rubella (MMR) vaccine: Randomized study in toddlers in Taiwan," Vaccine, Sep. 1, 2014, vol. 32, No. 41, pp. 5363-5369.
Jackson et al., "A phase 1 study of safety and immunogenicity following intradermal administration of a tetravalent dengue vaccine candidate," Vaccine, May 19, 2018, vol. 36, pp. 3976-3983.
JP 19920043682 Feb. 28, 1992 "Non-infective structure particle prepn., useful as vaccine—by infecting preliminarily flavivirus infected cell with cDNA integrated recombinant vaccinia virus, and then sepg. non-infective structure particles contg. E-protein of flavivirus" XP-00211903; Abtract Only.; (Cited as JP H05276941A).
King et al., "Simultaneous administration of childhood vaccines: An important public health policy that is safe and effica-cious," Pediatric Infectious Disease Jour, Lippincott Williams & Wilkins, US, Jan. 1, 1994, vol. 13, No. 5, pp. 394-407.
Konishi, E. et al., "Avipox virus-vectored Japanese encephalitis virus vaccines: use as vaccine candidates in combination with purified subunit immunogens," Vaccine, 1994, vol. 12, No. 7, pp. 633-638.
López et al., "Immunogenicity and Safety of Yellow Fever Vaccine (Stamaril) When Administered Concomitantly With a Tet-ravalent Dengue Vaccine Candidate in Healthy Toddlers at 12-13 Months of Age in Colombia and Peru :A Randomized Trial," Pediatric Infectious Disease Journal, Oct. 1, 2016, vol. 35, No. 10, pp. 1140-1147.
López-Medina et al., ""Efficacy of a Dengue Vaccine Candidate (TAK-003) in Healthy Children and Adolescents 2 Years after Vaccination,"" The Journal of Infectious Diseases, 2021, pp. 1-12.
Lorenzato Presentation "Update of Takeda's dengue candidate vaccine development programme (DEN-204)," Brazilian Tropical Medicine Congress (Medtrop) Sep. 5, 2018, 29 pages.
Mcintosh Presentation "Takeda vacuna contra el dengue," ALAPE Sep. 5-8, 2018, Luque Asunción, Paraguay, 27 pages.
Melo et al., "Immunogenicity and Safety of a Booster Injection of DTap-IPV//Hib (Pentaxim) Administered Concomitantly With Tetravalent Dengue Vaccine in Healthy Toddlers 15-18 Months of Age in Mexico : A Randomized Trial," Pediatric Infectious Disease Journal, Jun. 1, 2017, vol. 36, No. 6, pp. 602-608.
Midgley, C.M., et al., Men, R. et al., "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys," Journal of Virology, Jun. 1996, vol. 70, No. 6, pp. 3930-3937. Structural analysis of a dengue cross-reactive antibody complexed with envelope domain III reveals the molecular basis of cross-reactivity. J Immunol. May 15, 2012; 188(10): 4971-4979.
Mullard, "Sanofi's dengue vaccine rounds final corner," Nature Reviews Drug Discovery, Nov. 2014, vol. 13, pp. 801-802.
NCT02425098 "Safety and Immunogenicity With Two Different Serotype 2 Potencies of Takeda's Tetravalent Dengue Vac-cine Candidate (TDV) in Adults in Singapore," Clinical Trials.gov, Jul. 16, 2019—DEN 205, Retrieved from internet Jul. 4, 2019, 12 pages.
NCT02993757 "Immunogenicity and Safety of a Tetravalent Dengue Vaccine Administered Concomitantly or Sequentially With Gardasil," ClinicalTrials.gov, Apr. 5, 2018, Retrieved from the Internet Oct. 25, 2018, 10 pages.
NCT03525119 "Immunogenicity and Safety of Tetravalent Dengue Vaccine (TDV) Co-administered With an Hepatitis A Virus Vaccine," ClinicalTrials.gov, May 15, 2018, Retrieved from the Internet Oct. 26, 2018, 12 pages.
O'Leary S. et al., "ACIP Update: Update From the Advisory Committee on Immunization Practices," 2017, Journal of the Pediatric Infectious Diseases Society, vol. 6, No. 4, pp. 311-316.
Osorio et al., "A recombinant, chimeric tetravalent dengue vaccine candidate based on a dengue virus serotype 2 back-bone," Expert Review Of Vaccines, Apr. 2, 2016, vol. 15, No. 4, pp. 497-508.
Pinheiro-Michelsen et al., "Anti-dengue Vaccines: From Development to Clinical Trials," Frontiers in Immunology, Jun. 18, 2020, vol. 11, Art. 1252, pp. 1-18.
Press Release: "Potential Impact of Takeda's Dengue Vaccine Candidate Reinforced by Long-Term Safety and Efficacy Results," May 22, 2021, 5 pages.
Press Release: "Takeda Begins Regulatory Submissions for Dengue Vaccine Candidate in EU and Dengue-Endemic Countries," Mar. 25, 2021, 4 pages.
Press Release: "Takeda Completes Enrollment of More Than 20,000 Children and Adolescents in Global Phase 3 Trial of Dengue Vaccine Candidate" Apr. 5, 2017—DEN-301, 4 pages.
Press Release: "Takeda's Pipeline Has Potential to Contribute Signi?cantly to Revenue Growth Over Next Decade," Dec. 9, 2020, 4 pages.
Press Release: "Takeda's Dengue Vaccine Candidate Meets Primary Endpoint in Pivotal Phase 3 Efficacy Trial," Jan. 29, 2019, 4 pages.
Puerta-Guardo et al., "Dengue Virus NS1 Disrupts the Endothelial Glycocalyx, Leading to Hyperpermeability," PloS Pathog, Jul. 14, 2016, vol. 12, No. 7, pp. 1-29.

(56) References Cited

OTHER PUBLICATIONS

Putnak, et al., "Comparative Evaluation of Three Assays for Measurement of Dengue Virus Neutralizing Antibodies," The American Journal of Tropical Medicine and Hygiene, 2008, vol. 79, No. 1, pp. 115-122.
Rinderknecht et al., "Immunogenicity and Safety of an Inactivated Hepatitis A Vaccine When Coadministered With Mea-sles-mumps-rubella and Varicella Vaccines in Children Less Than 2 Years of Age," Pediatric Infectious Disease Journal, Oct. 1, 2011, vol. 30, No. 10, pp. e179-e185.
Roehrig et al., "Guidelines for Plaque-Reduction Neutralization Testing of Human Antibodies to Dengue Viruses," Viral Immunology, Jun. 1, 2008, vol. 21, No. 2, pp. 123-132.
Rupp et al., "Safety and immunogenicity of different doses and schedules of a live attenuated tetravalent dengue vaccine (TDV) in healthy adults: A Phase 1b randomized study," Vaccine, Nov. 1, 2015, vol. 33, No. 46, pp. 6351-6359.
Sabchareon, et al., "Protective efficacy of the recombinant, live-attenuated, CYD tetravalent dengue vaccine in Thai schoolchildren: a randomised, controlled phase 2b trial," The Lancet, Nov. 3, 2012, vol. 380, pp. 1559-1567.
Saez-Llorens et al., "Immunogenicity and safety of one versus two doses of tetravalent dengue vaccine in healthy chil-dren aged 2-17 years in Asia and Latin America: 18-month interim data from a phase 2, randomised, placebo-controlled study," Lancet Infect Dis, Nov. 6, 2017, vol. 18, pp. 162-170.
Saez-Llorens et al., "Safety and immunogenicity of one versus two doses of Takeda's tetravalent dengue vaccine in chil-dren in Asia and Latin America: interim results from a phase 2, randomized, placebo-controlled study," Lancet Infectious Disease, Elsevier Ltd, US, Mar. 30, 2017, vol. 17, No. 6, pp. 615-625.
Schilling et al., "Coadministration of a 9-Valent Human Papillomavirus Vaccine With Meningococcal and Tdap Vaccines," Pediatrics, Sep. 1, 2015, vol. 136, No. 3, pp. e563-e572.
Sirivichayakul et al., "Safety and immunogenicity of a Tetravalent Dengue Vaccine Candidate in Healthy Children and Adults in Dengue-Endemic Regions: A Randomized, Placebo-Controlled Phase 2 Study," Journal of Infectious Diseases, Dec. 23, 2015, vol. 213, No. 10, pp. 1562-1572.
Sridhar et al., "Effect of Dengue Serostatus on Dengue Vaccine Safety and Efficacy," New England Journal of Medicine, Jul. 26, 2018, vol. 379, No. 4, pp. 327-340.
Stanaway et al., "The global burden of dengue: an analysis from the Global Burden of Disease Study 2013," Lancet Infect Dis., Jun. 16, 2016, vol. 16, No. 6, pp. 712-723.
Takeda Vaccines, Anonymous, "Immunogenicity and Safety of Tetravalent Dengue Vaccine (TDV) Co-administered With an Hepatitis A Virus Vaccine", May 15, 2018, pp. 1-12.
Thisyakorn et al., "Dengue vaccine: a key for prevention," Expert Review of Vaccines, 2020, vol. 19, No. 6, pp. 499-506.
Timiryasova et al., "Optimization and Validation of a Plaque Reduction Neutralization Test for the Detection of Neutraliz-ing Antibodies to Four Serotypes of Dengue Virus Used in Support of Dengue Vaccine Development," American Journal Of Tropical Medicine & Hygiene, May 1, 2013, vol. 88, No. 5, pp. 962-970.
Vesikari et al., "Safety and Immunogenicity of a Booster Dose of the 1O-Valent Pneumococcal Nontypeable Haemophilus influenza Protein D Conjugate Vaccine Coadministered With Measles-Mumps-Rubella-Varicella Vaccine in Children Aged 12to 16 Months," Pediatric Infectious Disease Journal, Jun. 1, 2010, vol. 29, No. 6, pp. e47-e56.
Villar et al., "Safety and immunogenicity of a recombinant tetravalent dengue vaccine in 9-16 year olds: a randomized, controlled, phase II trial in Latin America," Pediatr Infect Dis J, Oct. 2013, vol. 32, No. 10, pp. 1102-1109.
Villar, L. et al., "Efficacy of a Tetravalent Dengue Vaccine in Children in Latin America," New England Journal of Medicine, Jan. 8, 2015, vol. 372, No. 2, pp. 113-123.
Wallace, D. et al., Presentation: "Takeda's dengue vaccine candidate in children: one or two doses?", Abstract 5th Pan American Dengue Research Network Meeting, age Apr. 20-23, 2016, DEN-204, p. 86.
Wallace, D., Presentation: "Persistence of neutralizing antibodies one year after two doses of a candidate recombinant tetra-valent dengue vaccine in subjects aged from 1.5 to 45 years," ASTMH 64th Annual Meeting, Oct. 27, 2015, DEN-203, 2 pages.
Wichmann et al., "Live-attenuated tetravalent dengue vaccines: The needs and challenges of post-licensure evaluation of vaccine safety and effectiveness," Vaccine, Oct. 1, 2017, vol. 35, No. 42, pp. 5535-5542.
Wilder-Smith et al., "Age specific differences in efficacy and safety for the CYD-tetravalent dengue vaccine," Expert Re-view of Vaccines, Apr. 2, 2016, vol. 15, No. 4, pp. 437-441.
World Health Organization, "Guidelines for plaque reduction neutralization testing of human antibodies to dengue viruses," Immunization, Vaccines and Biologicals, Sep. 21, 2007 pp. 1-36, Retrieved from the internet [retrieved on Oct. 29, 2018].
World Health Organization, "Table 3: Recommendations for Interrupted or Delayed Routine Immunization—Sum-mary of WHO position papers," Aug. 2018, 10 pages.
World Health Organization, Recommendations for all immunization programmes, Aug. 1, 2018, Retrieved from the Internet, 10 pages.
World Health Organization, Wkly Epidemiol Rec, "Dengue vaccine: WHO position paper—Sep. 2018," Sep. 7, 2018, vol. 93, pp. 457-476.
Brito, Luis A., et al., "Vaccine adjuvant formulations: A pharmaceutical perspective," Seminars in Immunology, vol. 25, No. 2, pp. 130-145, Jan. 2, 2013.
Ginley, D.M., "The development of a performance test procedure and measurement technique in a batch system NBS IR 85-3030." National Institute of Standards and Technology (NIST), Jul. 1985, pp. 1-152, retrieved from the Internet Dec. 31, 1985.
Hsiang-Chi, L. et al., "Dengue Type 4 Live-Attenuated Vaccine Viruses Passaged in Vero Cells Affect Genetic Stability and Dengue-Induced Hemorrhaging in Mice," PLOS ONE, Oct. 28, 2011 (Oct. 28, 2011), vol. 6, No. 10, p. e25800.
Huang, C. et al., "Chimeric Dengue Type 2 (Vaccine Strain PDK-53)/Dengue Type 1 Virus as a Potential Candidate Dengue Type 1 Virus Vaccine" Journal Of Virology, Apr. 2000, vol. 74, No. 7, pp. 3020-3028.
Huang, C. et al., "Dengue 2 PDK-53 virus as a chimeric carrier for tetravalent dengue vaccine development," J. Virology, Nov. 2003, vol. 77, No. 21, pp. 11436-11447.
Huang, C. et al., "Genetic and Phenotypic Characterization of Manufacturing Seeds for a Tetravalent Dengue Vaccine (DENVax)," PLOS Neglected Dis, May 2013, vol. 7, No. 5, e2243, 11 pages.
Hubálek, Z. et al., "West Nile Fever—a Reemerging Mosquito-Borne Viral Disease in Europe" Emerging Infectious Diseases, Sep.-Oct. 1999, vol. 5, No. 5, pp. 643-650.
Hunt, A. et al., "Relationships of Bunyamwera Group Viruses by Neutralization" Am. J. Trop. Med. Hyg. 1979, vol. 28, No. 4, pp. 740-749.
Jia, X. et al., "Genetic analysis of West Nile New York 1999 encephalitis virus" The Lancet, Dec. 4, 1999, vol. 354, pp. 1971-1972.
Jirakanjanakit, N. et al., "Dynamics of Susceptibility and Transmissibility of The Live Attenuated, Candidate Vaccines Dengue-1 PDK-13, Dengue-3 PGMK30F3, and Dengue-4 PDK-48 after Oral Infection in Aedes Aegypti," Am. J. Trop. Med. Hyg. 1999, vol. 61, No. 4, pp. 672-676.
Johnson, A. et al., "Detection of Anti-Arboviral Immunoglobulin G by Using a Monoclonal Antibody-Based Capture Enzyme-Linked Immunosorbent Assay," Journal of Clinical Microbiology, May 2000, vol. 38, No. 5, pp. 1827-1831.
Johnson, B. et al., "Growth Characteristics of ChimeriVax-DEN2 Vaccine Virus in Aedes Aegypti and Aedes Albopictus Mosquitoes," Am. J. Trop Med. Hyg., 2002, vol. 67, No. 3, pp. 260-265.
Kanesa-Thasan, N. et al., "Safety and immunogenicity of attenuated dengue virus vaccines (Aventis Pasteur) in human volunteers," Vaccine, 2001 vol. 19 pp. 3179-3188.

(56) References Cited

OTHER PUBLICATIONS

Kawano, H. et al., "Genetic Determinants of Dengue Type 4 Virus Neurovirulence for Mice," Journal of Virology, Nov. 1993, vol. 67, No. 11, pp. 6567-6575.
Kelly, E. et al., "Evolution of attenuating mutations in dengue-2 strain S16803 PDK50 vaccine and comparison of growth kinetics with parent virus," Virus Genes, 2011, vol. 43, pp. 18-26.
Khin, M. et al., "Infection, Dissemination, Transmission, and Biological Attributes of Dengue-2 PDK53 Candidate Vaccine Virus after Oral Infection in Aedes Aegypti," Am. J. Trop. Med. Hyg., 1994, vol. 51, No. 6, pp. 864-869.
Kimura-Kuroda, J. et al., "Topographical Analysis of Antigenic Determinants on Envelope Glycoprotein V3 (E) of Japanese Encephalitis Virus, Using Monoclonal Antibodies" Journal of Virology, Jan. 1983, vol. 45, No. 1, pp. 124-132.
Kimura-Kuroda, J. et al., "Antigenic Comparison of Envelope Protein E between Japanese Encephalitis Virus and Some Other Flaviviruses Using Monoclonal Antibodies," J. Gen. Virol., 1986, vol. 67, pp. 2663-1672.
Kinney, R. et al. "Construction of Infectious cDNA Clones for Dengue 2 Virus: Strain 16681 and Its Attenuated Vaccine Derivative, Strain PDK-531" Virology, 1997, vol. 230, No. 2, pp. 300-308.
Kinney, R. et al., "Development of New Vaccines against Dengue Fever and Japanese Encephalitis," Intervirology, 2001, vol. 44, pp. 176-197.
Klinman, D. et al., "CpG motifs as immune adjuvants," Vaccine, 1999, vol. 17, pp. 19-25.
Kochel, T. et al., "Inoculation of plasmids expressing the dengue-2 envelope gene elicit neutralizing antibodies in mice," Vaccine. 1997, vol. 15, No. 5, pp. 547-552.
Köhler, G. et al., "Continuous cultures of fused cells secreting antibody of predefined specificity," Nature, Aug. 7, 1975, vol. 256, pp. 495-497.
Konishi, E. et al., "Comparison of Protective Immunity Elicited by Recombinant Vaccinia Viruses That Synthesize E or NS1 of Japanese Encephalitis Virus," Virology, 1991, vol. 185, pp. 401-410.
Konishi, E. et al., "Generation and Characterization of a Mammalian Cell Line Continuously Expressing Japanese Encephalitis Virus Subviral Particles," Journal of Virology, Mar. 2001, vol. 75, No. 5, pp. 2204-2212.
Konishi, E. et al., "Induction of Protective Immunity against Japanese Encephalitis in Mice by Immunization with a Plasmid Encoding Japanese Encephalitis Virus Premembrane and Envelope Genes," Journal of Virology, Jun. 1998, vol. 72, No. 6, pp. 4925-4930.
Konishi, E. et al., "Mice Immunized with a Subviral Particle Containing the Japanese Encephalitis Virus prM/M and E Proteins Are Protected from Lethal JEV Infection," Virology, 1992, vol. 188, pp. 714-720.
Kozak, M. "Circumstances and Mechanisms of Inhibition of Translation by Secondary Structure in Eucaryotic mRNAs," Molecular and Cellular Biology, Nov. 1989, vol. 9, No. 11, pp. 5134-5142.
Kuno, G. et al., "Phylogeny of the Genus Flavivirus," Journal of Virology, Jan. 1998, vol. 72, No. 1, pp. 73-83.
Laemmli, U., "Cleavage of Structural Proteins during the Assembly of the Head of Bacteriophage T4," Nature, Aug. 15, 1970, vol. 227, pp. 680-685.
Lai, C. et al., "Evaluation of molecular strategies to develop a live dengue vaccine," Clinical and Diagnostic Virology, 1998, vol. 10, pp. 173-179.
Lai, C. et al., "Immunization of Monkeys with Baculovirus Recombinant-expressed Dengue Envelope and NS1 Glycoproteins Induces Partial Resistance to Challenge with Homotypic Dengue Virus," Vaccines 90: Modern approaches to New Vaccines including Prevention of AIDS, Cold Spring Harbor, NY, 1990, pp. 119-124.
Lanciotti R. et al., "Origin of the West Nile Virus Responsible for an Outbreak of Encephalitis in the Northeastern United States," Science, Dec. 17, 1999, vol. 286, pp. 2333-2337.
Liljeström, P. et al., "In Vitro Mutagenesis of a Full-Length eDNA Clone of Semliki Forest Virus: the Small 6,000-Molecular-Weight Membrane Protein Modulates Virus Release," Journal of Virology, Aug. 1991, vol. 65, No. 8, pp. 4107-4113.
Lin, Y. et al., "DNA Immunization with Japanese Encephalitis Virus Nonstructural Protein NS1 Elicits Protective Immunity in Mice," Journal of Virology, Jan. 1998, vol. 72, No. 1, pp. 191-200.
Mackow, E. et al., "The Nucleotide Sequence of Dengue Type 4 Virus: Analysis of Genes Coding for Nonstructural Proteins," Virology, 1987, vol. 159, pp. 217-228.
Mandl, C. et al., "Complete Genomic Sequence of Powassan Virus: Evaluation of Genetic Elements in Tick-Borne versus Mosquito-Borne Flaviviruses," Virology, 1993, vol. 194, pp. 173-184.
Martin, D. et al., "Standardization of Immunoglobulin M Capture Enzyme-Linked Immunosorbent Assays for Routine Diagnosis of Arboviral Infections," Journal of Clinical Microbiology, May 2000, vol. 38, No. 5, pp. 1823-1826.
Mason, P. et al., "Japanese Encephalitis Virus-Vaccinia Recombinants Produce Particulate Forms of the Structural Membrane Proteins and Induce High Levels of Protection against Lethal JEV infection," Virology, 1991, vol. 180, pp. 294-305.
Mason, P. et al., "Sequence of the Dengue-1 Virus Genome in the Region Encoding the Three Structural Proteins and the Major Nonstructural Protein NS1," Virology, 1987, vol. 161, pp. 262-267.
Men, R. et al., "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys," Journal of Virology, Jun. 1996, vol. 70, No. 6, pp. 3930-3937.
Mir, L. et al., "High-efficiency gene transfer into skeletal muscle mediated by electric pulses," Applied Biological Sciences, Proc. Natl. Acad. Sci. USA, Apr. 1999, vol. 96, pp. 4262-4267.
Monath, T. et al., "Recombinant, chimeric live, attenuated vaccine (ChimeriVax) incorporating the envelope genes of Japanese encephalitis (SA14-14-2) virus and the capsid and nonstructural genes of yellow fever (17D) virus is safe, immunogenic and protective in non-human primates," Vaccine, 1999, vol. 17 pp. 1869-1882.
Nitayaphan, S. et al., "Nucleotide Sequence of the Virulent SA-14 Strain of Japanese Encephalitis Virus and Its Attenuated Vaccine Derivative, SA-14-14-2," Virology, 1990, vol. 177, pp. 541-552.
Novello et al., "Update: West Nile Virus Activity—Northeastern United States, 2000," http://www.cdc.gov/mmwr/preview/mmwrhtml/mm4936a4.htm MMWR Weekly Sep. 15, 2000 / vol. 49, No. 36, pp. 820-822.
Nowak, T. et al., "Analysis of the Terminal 4 Sequences of West Nile Virus Structural Proteins and of the in Vitro Translation of these Proteins Allow the Proposal of a Complete Scheme of the Proteolytic Cleavages Involved in Their Synthesis," Virology, Academic Press. Orlando, Apr. 1, 1989, vol. 169, No. 2, pp. 365-376.
Osatomi et al., "Nucleotide Sequence of Dengue Type 3 Virus Genomic RNA Encoding Viral Structural Proteins," Virus Genes, Oct. 1988, vol. 2, No. 1, pp. 99-108. Abstract Only.
Osatomi, K. et al., "Complete Nucleotide Sequence of Dengue Type 3 Virus Genome RNA," Virology, 1990, vol. 176, pp. 643-647.
Osorio et al., "Safety and immunogenicity of a recombinant live attenuated tetravalent dengue vaccine (DENVax) in fla-vivirus-naive healthy adults in Colombia: a randomised, placebo-controlled, phase 1 study," Lancet Infectious Diseases, Sep. 1, 2014, vol. 14, No. 9, pp. 830-838.
Osorio, J. et al "Efficacy of a Tetravalent Chimeric Dengue Vaccine (DENVax) in Cynomolgus Macaques," Am. J. Trop. Med. Hyg., 2011, vol. 84, No. 6, pp. 978-987.
Osorio, J. et al., "Development of DENVax: A chimeric dengue-2 PDK-53-based tetravalent vaccine for protection against dengue fever," Vaccine, Jul. 11, 2011, vol. 29, No. 42, pp. 7251-7260.
Phillpotts, R. et al., "Immunisation with DNA polynucleotides protects mice against lethal challenge with St. Louis encephalitis virus." Arch Virol., 1996, vol. 141, pp. 743-749.
CN Office Action + English translation for CN application 202110718703.8 dated Sep. 2023.
CN Office Action + English translation for CN application 2023072602931350 dated Jul. 26, 2023.
Qian J et al. "Development of a high performance size exclusion chromatography method to determine the stability of Human Serum

(56) References Cited

OTHER PUBLICATIONS

Albumin in a lyophilized formulation of Interferon alfa-2b" Journal of Chromatography A, Elsevier, Amsterdam, NL, vol. 1194, No. 1 (2008).
Stefan Finke et al "Assesment of inactivated human rabies vaccines: Biochemical characterization and genetic identification of virus strains" Vaccine, Elsevier, Amsterdam, NL, vol. 30, No. 24 (2012).
Chaity Chaudhury et al "Albumin Binding to FcRn: Distinct from the FcRn—IgG Interaction" Biochemistry, vol. 45, No. 15 (2006).
Sviridov Denis et al "Coelution of Other Proteins with Albumin during Size-Exclusion HPLC: Implications of Analysis of Urinary Albumin", Clinical Chemistry, vol. 52, No. 3 (2006).
ATCC "Application of a Vero gDNA control in the detection of a residual host cell DNA in biopharmaceuticals", XP093167849, (2023).
Natalie N. Kinloch "SARS-CoV-2 RNA Quantification Using Droplet Digital RT-PCR" The Journal of Molecular Diagnostics, vol. 23, No. 8 (2021).
Changwoo Park "Comparison of Digital PCR and Quantitive PCR with Various SARS-CoV-2 Primer-Probe Sets" Journal of Microbiology and Biotechnology, vol. 31, No. 3, (2021).
Azizi Ali et al "Determination of HSV-1 UL5 and UL29 gene copy numbers in an HSV complementing Vero cell line" Journal of Biotechnology, Elsevier, Amsterdam, NL, vol. 168, No. 4 (2013).
Vernay Olivier et al "Comparative analysis of the performance of residual host cell DANN assays for viral vaccines produced in Vero cells" Journal of Virological mehtods, vol. 268, pp. 9-16 (2019).
Andre Murielle et al "Universal real-time PCR assay for quantitation and size evaluation of residual cell DANN in human viral vaccines" Biologicals, Academis Press Ltd., London, GB, vol. 44, No. 3 (2016).
Xin-Qi Zheng "Development and Evaluation of a Novel One-Step RT—qPCR Targeting the Vero Gene for the Identification of False-Positive Results Caused by Inactivated Virus Vaccine Contamination" Vaccines, vol. 11, No. 2, (2023).

* cited by examiner

Genetic variations among D2/4 chimeras (compared to wt D2 16681 and D4-1036)

| Genome | D2 | | | junction | D4 | | | | junction |
|---|---|---|---|---|---|---|---|---|---|
| Genes | NCR | C | | prM | E | | | | |
| Mutation types* | ***PDK-53*** | seed | Eng | MluI | seed | Marker | Eng | Eng | NgoMIV |
| Genome NT position | C57T | A225T | A396C | A453G | C647G/C | A1401G | C2027T | A2275 | TG2380/1CC |
| Protein-AA position | NCR | C-silent | C-R100S | prM-silent | prM-T79R/T | E-silent | E-A364V | E-M447L | E-V482A |
| D2-16681 | C | A | A(R) | A | | | | | TG(V) |
| D2-PDK-53 | ***T*** | - | - | | | | | | |
| D4-1036 | | | | | G(T) | A | C(A) | A(M) | |
| Cloned D2/4-V1 (pD2/4-VP1) | ***T*** | - | C(S) | g | - | g | T(V) | C(L) | CC(A) |
| DENVax-4 (MVS) | ***T*** | t | C(S) | g | - | g | T(V) | C(L) | CC(A) |

"-": same as wt D2 16681 or D4 1036; small nt letter: silent mutation in open reading region

*: PDK-53: D2-PDK-53 specific genotype (VS 16681), *Italics: major attenuation PDK-53 loci*; Seed: mutations found only in specified virus seed and not in the original clone; Eng: Engineered mutations for the D2/4 clones; Mlu and NgoMV: D2/4 junction engineered RE sites;

**: C8571T (PDK-53 silent mutation) was not included in most D2/4 chimeric clones

FIG. 1

| D2 | | | | | | | | | | | | |
|---|---|---|---|---|---|---|---|---|---|---|---|---|
| NS1 | NS2A | | | NS3 | | | NS4A | | NS4B | NS5 | |
| ***PDK-53*** | seed | seed | PDK-53 | ***PDK-53*** | seed | PDK-53 | seed | PDK-53 | seed | PDK53 | seed |
| G2579A<br><br>NS1-<br>G53D | A3674G<br><br>NS2A-<br>D66G | A3773A/G<br><br>NS2A-<br>K99K/R | C4018T<br><br>NS2A-<br>L181F | A5270T<br><br>NS3-<br>E250V | C5391T<br><br>NS3-<br>silent | T5547C<br><br>NS3-<br>silent | C6437T<br><br>NS4A-<br>A21V | G6599C<br><br>NS4A-<br>G75A | T7026C/T<br><br>NS4B-<br>silent | C8571T**<br><br>NS5-silent | A9750C<br><br>NS5-<br>silent |
| G(G0<br>***A(D)*** | A(D)<br>- | A(K)<br>- | C(L)<br>T(F) | A(E)<br>***T(V)*** | C<br>- | T<br>c | C(A)<br>- | G(G)<br>C(A) | T<br>- | C<br>t | A<br>- |
| ***A(D)***<br><br>***A(D)*** | -<br><br>G(G) | -<br><br>A/G(K/R) | T(F)<br><br>T(F) | ***T(V)***<br><br>***T(V)*** | -<br><br>t | c<br><br>c | -<br><br>T(V) | C(A)<br><br>C(A) | -<br><br>c/t | -<br><br>- | -<br><br>c |

*FIG. 1*
*(continued)*

| Serotype | Strain | virus origin | C57T 5´NCR | A524T prM-D29V | T900C[a] M (silent) |
|---|---|---|---|---|---|
| DENV-2 | 16681 | isolate from human | C | A | T |
| | PDK-53 | PDK cell pass of 16681 | *T* | *T* | - |
| | PDK-53-V(VV45R) | Recombinant PDK-53-V | *T* | *T* | **c** |
| | PDK-53-E(VE48R) | Recombinant PDK-53-E | *T* | *T* | **c** |

Underlined Mutations: the 3 most important attenuation loci of PDK-53

*Italics font: PDK-53 specific sequence (change from 16681)*

Bold font: Different nt sequence between PDK-53 and clone-derived V or E virus

[a]Engineered silent clone marker to differenciate original PDK-53 and recombinant (clone-derived) viruses

*FIG. 10*

| C2055T<br>E (silent) | <u>G2579A</u><br><u>NS1-G53D</u> | C4018T<br>NS2A-L181 | <u>A5270T</u><br><u>NS3-E250V</u> | T5547C<br>NS3 (silent) | G6599C<br>NS4A-G75A | C8571T<br>NS5 (silent) |
|---|---|---|---|---|---|---|
| C | G | C | A | T | G | C |
| *t* | *A* | *T* | *T/A mix* | *c* | *C* | *t* |
| *t* | *A* | *T* | **T** | *c* | *C* | **C** |
| *t* | *A* | *T* | **A** | *c* | *C* | **C** |

*FIG. 10*
*(continued)*

COMPOSITIONS AND METHODS FOR DENGUE VIRUS CHIMERIC CONSTRUCTIONS IN VACCINES

CROSS REFERENCE TO PRIOR APPLICATIONS

This patent application is a continuation of U.S. patent application Ser. No. 16/561,755, filed Sep. 5, 2019, which is a U.S. continuation of U.S. patent application Ser. No. 15/492,981, filed on Apr. 20, 2017, which is a U.S. divisional application that claims priority to U.S. patent application Ser. No. 14/209,808, filed Mar. 13, 2014, which claims the benefit of U.S. Provisional Patent Application No. 61/800,204, filed Mar. 15, 2013, the disclosures of which are all incorporated herein by reference in their entireties.

STATEMENT REGARDING FEDERALLY SPONSORED RESEARCH OR DEVELOPMENT

This invention was made with government support under Grant No. R43 A1084291-01 awarded by the National Institutes of Health. The Government has certain rights in the invention.

SEQUENCE LISTING

The instant application contains a Sequence Listing which is submitted herewith in electronically readable ASCII format via EFS-Web, and is hereby incorporated by reference in its entirety. The electronic Sequence Listing file was created on Aug. 27, 2021, is named "T08239USD1C1C1_SequenceListing" and is 346 KB in size.

FIELD

Embodiments herein report compositions, methods, uses and manufacturing procedures for dengue virus constructs and vaccine compositions thereof. Some embodiments concern a composition that includes, but is not limited to, chimeric flavivirus virus constructs that alone or in combination with other constructs can be used in a vaccine composition. In certain embodiments, compositions can include constructs of more than one serotypes of dengue virus, such as dengue-1 (DEN-1) virus, dengue-2 (DEN-2) virus, dengue-3 (DEN-3) virus and/or dengue-4 (DEN-4) virus. In other embodiments, manufacturing strategy that can improve the safety and genetic stability of recombinant live-attenuated chimeric dengue vaccine (DENVax) viruses. Certain embodiments include at least one live, attenuated dengue virus in combination with dengue virus chimeric constructs identified to be both safe and effective in vaccine compositions where the constructs have undergone additional passages in cell cultures.

BACKGROUND

Infection with dengue virus can lead to a painful fever of varying severity. To date, four serotypes of dengue virus have been identified: dengue-1 (DEN-1), dengue-2 (DEN-2), or dengue-3 (DEN-3) in combination with dengue-4 (DEN-4). Dengue fever is caused by infection of a dengue virus. Other subtypes may be discovered in the future (e.g. DEN-5). Dengue virus serotypes 1-4 can also cause dengue hemorrhagic fever (DHF), and dengue shock syndrome (DSS). The most severe consequences of infection, DHF and DSS, can be life threatening. Dengue viruses cause 50-100 million cases of debilitating dengue fever, 500,000 cases of DHF/DSS, and more than 20,000 deaths each year. To date, there is no effective vaccine to protect against dengue fever and no drug treatment for the disease. Mosquito control efforts have been ineffective in preventing dengue outbreaks in endemic areas or in preventing further geographic spread of the disease. It is estimated that 3.5 billion people are threatened by infection with dengue virus. In addition, dengue virus is a leading cause of fever in travelers to endemic areas, such as Asia. Central and South America, and the Caribbean.

All four dengue virus serotypes are endemic throughout the tropical regions of the world and constitute the most significant mosquito-borne viral threat to humans in tropical regions, worldwide. Dengue viruses are transmitted to humans primarily by *Aedes aegypti* mosquitoes. Infection with one dengue virus serotype results in life-long protection from re-infection by that serotype, but does not prevent secondary infection by one of the other three dengue virus serotypes. In fact, previous infection with one dengue virus serotype leads to an increased risk of severe disease (DHF/DSS) upon secondary infection with a different serotype. The development of an effective vaccine represents an important approach to the prevention and control of this global emerging disease. Multiple immunizations make complete vaccine coverage difficult both for public health efforts in dengue virus endemic countries as well as travelers.

SUMMARY

Embodiments herein concern compositions, methods and uses of chimeric dengue virus constructs. In some embodiments, a composition can include chimeric dengue virus constructs having an attenuated dengue virus backbone with structural genes from at least one other dengue virus serotype. Other embodiments concern at least one live, attenuated virus in combination with one or more chimeric dengue viruses. Other embodiments can include a composition of chimeric dengue viruses having a modified DEN-2 backbone (e.g. PDK-53 as a starting backbone in P1 (passage-1) and passage variability (after passage and growth in vitro on a permissive cell line) as indicated for P2, P3, . . . P8 . . . P10 etc.) and one or more structural components of DEN-1, DEN-2, DEN-3 or DEN-4. In other embodiments, an immunogenic composition is generated where when introduced to a subject, the composition produces an immune response to one or more dengue viruses in the subject. Therefore, constructs contemplated herein can be generated and passaged in vitro, and each of the passages provides an attenuated dengue virus contemplated of use in a pharmaceutically acceptable vaccine composition. In certain embodiments a live, attenuated virus can be a live, attenuated dengue-2 virus alone or in combination with one or more chimeric dengue viruses.

In certain examples, chimeric dengue virus constructs of dengue virus serotypes can include passage 7 (P7) live, attenuated viruses or chimeric viruses having nucleic acid sequences identified by SEQ ID NOS: 1, 4, 7 and 10 or polypeptide sequences indicated by SEQ ID NOS: 2, 3, 5, 6, 8, 9, 11 and 12. It is contemplated herein that any of the passages for any of the live, attenuated viruses described herein can be used in an immunogenic composition to induce immune responses to the represented dengue viruses (e.g. serotypes 1-4). In accordance with these embodiments, an immunogenic composition that includes a P-8 isolated live, attenuated virus can be administered to a subject to induce an immunogenic response against one or more dengue virus serotypes depending on the construct selected. In addition, a live, attenuated virus can be combined with one or more of these chimeric viruses. This is contemplated for each of the live, attenuated viruses isolated/produced in each subsequent cell passages (e.g. African Green Monkey Vero cell production, hereinafter: Vero cells). It is contemplated herein that any cell line (e.g. GMP-produced cell bank. FDA or EMA-approved) capable of producing dengue viruses is of use to passage any of the viral constructs at a manufacturing scale or as appropriate contemplated herein for subsequent use in a vaccine or immunogenic composition against Dengue virus.

In other embodiments, compositions contemplated herein can be combined with other immunogenic compositions against other Flaviviruses such as West Nile virus, Japanese encephalitis or any other flavivirus chimeric construct and/or live, attenuated virus. In certain embodiments, a single composition can be used against multiple flaviviruses.

In certain embodiments, an immunogenic composition of the present invention can include chimeric dengue viruses against one or more of DEN-1, DEN-2, DEN-3 and/or DEN-4, alone or in combination with a live, attenuated dengue virus composition.

In other embodiments, a construct can include a construct having adaptive mutations in the structural or non-structural regions of the virus that increase growth or production without affecting attenuation or safety of the virus when introduced to a subject. In certain embodiments, any of the contemplated chimeric dengue virus constructs can include a live, attenuated DEN-2 virus having specific mutations used as a backbone where the live attenuated DEN-2 PDK virus further includes structural proteins of one or more of prM (premembrane) and E (envelope) structural proteins of the other dengue virus serotypes. In addition, a DEN-2 backbone can include additional mutations in order to increase production of or enhance the immune response to a predetermine composition in a subject upon administration (e.g. chimeric Dengue virus 2/1, 2/3 or 2/4).

In some embodiments, structural protein genes can include prM and E genes of DEN-1, DEN-2, DEN-3 or DEN-4 on a DEN-2 backbone having one or two mutations that are part of a live, attenuated dengue virus. For example, a dengue construct, in certain embodiments can include those constructs termed DENVax-1-A, DENVax-2-F, DENVax-3-F, and DENVax-4-F (see Example section) where the DEN-2 backbone has one or more mutations (e.g. not found in the P1 or other previous passaged virus or PDK-53) from the DEN-2 live, attenuated virus previously demonstrated to be safe and effective to induce an immune response. The DEN-2 live, attenuated virus of the instant application is an improved version of the originally used DEN-2 live, attenuated virus. A chimeric construct of the instant invention can include a modified attenuated DEN-2 PDK-53 backbone, having one or more structural proteins of the second dengue virus serotype wherein the structural proteins can include additional mutations to increase an immunogenic response to the chimeric construct. In some embodiments, certain mutations acquired by attenuated DEN-2 PDK-53 can produce a conservative amino acid change or not in a constructs different from the P1 construct which can result in desirable traits for production etc.

In other embodiments, a live, attenuated DEN-2 genome can be used to generate constructs of dengue virus serotype 1 (DEN-1) and dengue virus serotype 3 (DEN-3), dengue virus serotype 4 (DEN-4) where one or more structural protein genes of the DEN-2 viral genome can be replaced by one or more structural protein genes of DEN-1, DEN-3 or DEN-4, respectively. In some embodiments, a structural protein can be the C, prM or E protein of a second dengue virus. In certain embodiments, structural protein genes include the prM and E genes of DEN-1, DEN-3 or DEN-4. These hybrid viruses express the surface antigens of DEN-1. DEN-3 or DEN-4 while retaining the attenuation phenotypes of the parent attenuated DEN-2.

Constructs disclosed herein can include chimeric constructs of DEN-4, DEN-2, DEN-1, and DEN-3 expressing surface antigens of DEN-1, DEN-3 and DEN-4 using attenuated DEN-2 virus as a backbone.

In certain embodiments, compositions of the instant invention can include a composition that comprises a single chimeric dengue virus construct disclosed herein and a pharmaceutically acceptable carrier or excipient. Alternatively, compositions of the instant invention can include a composition that comprises two or more, or three or more chimeric dengue virus constructs disclosed herein, and a pharmaceutically acceptable carrier or excipient. In accordance with these embodiments, a one or more dengue virus chimeric constructs contemplated herein can be combined with one or more, live attenuated dengue viruses. In certain embodiments, a live, attenuated virus can be a live, attenuated DEN-2 virus wherein additional mutations in the NCR, NS1 regions or other regions increase the immune response, increase viral growth or other improvement for an improved live, attenuated dengue virus.

In certain embodiments, the attenuation loci, nucleotide 5'NCR-57-T, NS1-53-Asp. and NS3-250-Val, of the DENV-2 vaccine have been previously determined, and all of these changes are shared by the common PDK-53 virus-specific genetic background of the four DENVax viruses. The genetic sequence of the three attenuation loci as well as the previously established in vitro and in vivo attenuation phenotypes of these vaccine candidates were carefully monitored for the cGMP-manufactured DENVax seeds. This report describes strategies used to generate master virus seeds (MVS) as well as their genetic and phenotypic characterization of use in the manufacture of dengue virus vaccine compositions. These MVS can be used for manufacture of clinical materials and ultimately commercial vaccine supplies.

BRIEF DESCRIPTION OF THE DRAWINGS

The following drawings form part of the present specification and are included to further demonstrate certain embodiments. Some embodiments may be better understood by reference to one or more of these drawings alone or in combination with the detailed description of specific embodiments presented.

FIG. 1 represents an exemplary chart reflecting an exemplary chimeric construct of the instant invention, DEN-2/DEN-4 compared to previously generated constructs and wild type dengue viruses.

FIG. 5A shows pooled results of several experiments summarizing the neurovirulence of wt DENV-2 16681 virus in CDC-ICR (n=72) and Taconic-ICR (n=32) newborn mice challenged ic with $10^4$ pfu of the virus. FIG. 5B shows neurovirulence of DENVax MVS tested in Taconic-ICR mice with a dose of $10^4$ pfu. FIG. 5C shows neurovirulence of DENVax MVS tested in Taconic-ICR mice with a dose of $10^3$ pfu. The numbers of animals tested per group in one experiment (n=16) or two pooled experiments (n=31 or 32) are indicated.

FIG. 9A shows IC inoculations of the virus at dose of $10^4$ PFU. FIG. 9B shows IC inoculation of the virus at dose of $10^3$ PFU.

FIG. 10 represents an exemplary chart comparing new live, attenuated viruses to previously generated live, attenuated dengue viruses.

DEFINITIONS

Figure 2:
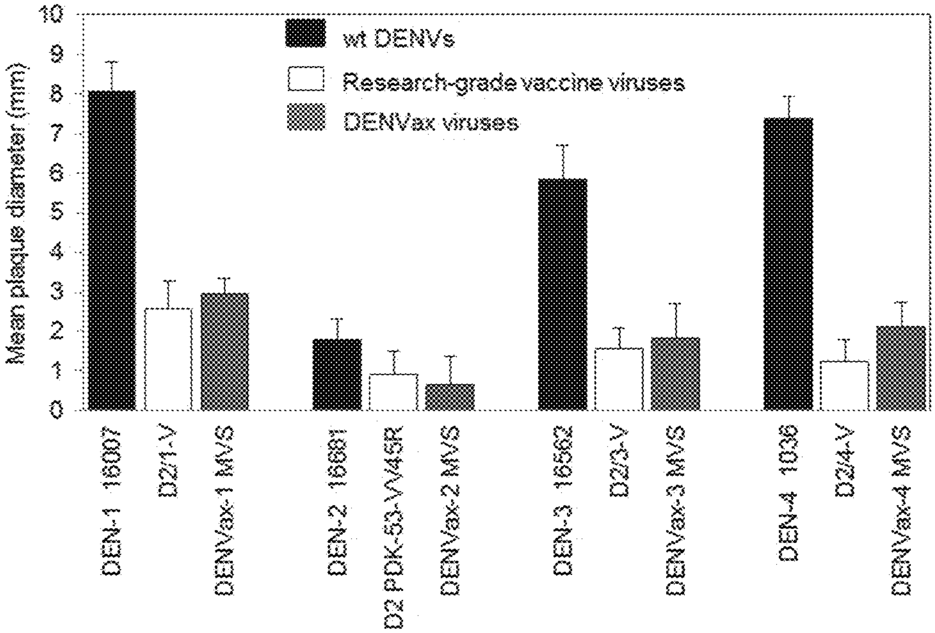
FIG. 2 represents an exemplary histogram plot comparing various responses using a live, attenuated DEN-2 backbone (with additional mutations) and a second dengue virus serotype as structural components substituted for the dengue-2 structural components (e.g. DENVax-1 MVS). This plot illustrates plaque sizes of the DENVax MVS. Wild-type Dengue viruses and previously published research-grade vaccine candidate viruses were included for control and comparison. This plot illustrates improved production of the dengue virus constructs compared to control dengue virus chimeric constructs.

As used herein, "a" or "an" may mean one or more than one of an item.

As used herein the specification, "subject" or "subjects" may include, but are not limited to, mammals such as humans or mammals, domesticated or wild, for example dogs, cats, other household pets (e. g. hamster, guinea pig, mouse, rat), ferrets, rabbits, pigs, horses, cattle, prairie dogs, wild rodents, or zoo animals.

As used herein, the terms "virus chimera," "chimeric virus," "flavivirus chimera" and "chimeric flavivirus" can mean a construct comprising a portion of the nucleotide sequence of a dengue-2 virus and further nucleotide sequence that is not from dengue-2 virus or is from a different flavivirus. A "dengue chimera" comprises at least two different dengue virus serotypes but not a different flavivirus. Thus, examples of other dengue viruses or flaviviruses include, but are not limited to, sequences from dengue-1 virus, dengue-3 virus, dengue-4 virus, West Nile virus, Japanese encephalitis virus, St. Louis encephalitis virus, tick-borne encephalitis virus, yellow fever virus and any combination thereof.

As used herein. "nucleic acid chimera" can mean a construct of the invention comprising nucleic acid comprising a portion of the nucleotide sequence of a dengue-2 virus and further nucleotide sequence that is not of the same origin as the nucleotide sequence of the dengue-2 virus. Correspondingly, any chimeric flavivirus or flavivirus chimera disclosed herein can be recognized as an example of a nucleic acid chimera.

As used herein, "a live, attenuated virus" can mean a wild-type virus, mutated or selected for traits of use in vaccine or other immunogenic compositions wherein some traits can include reduced virulence, safety, efficacy or improved growth etc.

DESCRIPTION

In the following sections, various exemplary compositions and methods are described in order to detail various embodiments. It will be obvious to one skilled in the art that practicing the various embodiments does not require the employment of all or even some of the specific details outlined herein, but rather that concentrations, times and other specific details may be modified through routine experimentation. In some cases, well-known methods or components have not been included in the description.

In accordance with embodiments of the present invention, there may be employed conventional molecular biology, protein chemistry, microbiology, and recombinant DNA techniques within the skill of the art. Such techniques are explained fully in the literature. See, e.g., Sambrook, Fritsch & Maniatis, Molecular Cloning: A Laboratory Manual, Second Edition 1989, Cold Spring Harbor Laboratory Press, Cold Spring Harbor, N.Y.; Animal Cell Culture, R. I. Freshney, ed., 1986).

Embodiments herein concern compositions, methods and uses for inducing immune responses against one or more dengue virus serotypes in a subject, individually or simultaneously. In accordance with these embodiments, attenuated dengue viruses and nucleic acid chimeras are generated and used in vaccine compositions disclosed herein. Some embodiments concern modified or mutated dengue constructs or chimeras. Other embodiments concern introducing mutations to modify the amino acid sequences of structural proteins of dengue viruses wherein the mutation increase immunogenicity to the virus.

Live, attenuated dengue viruses of all four serotypes have been developed by passaging wild-type viruses in cell culture. These are some of the most promising live, attenuated vaccine candidates for immunization against flavivirus and in particular dengue virus infection and/or disease. These vaccine candidates have been designated by a combination of their dengue serotype, the cell line through which they were passaged and the number of times they were passaged. Thus, a dengue serotype 1 wild-type virus passaged in PDK cells 13 times is designated as DEN-1 PDK-13 virus. Other vaccine candidates are DEN-2 PDK-53, DEN-3 PGMK-30/FRhL-3 (e.g. thirty passages in primary green monkey kidney cells, followed by three passages in fetal rhesus lung cells and DEN-4 PDK-48). These four candidate vaccine viruses were derived by tissue culture passage of wild-type parental DEN-1 16007, DEN-2 16681, DEN-3 16562 and DEN-4 1036 viruses, respectively.

In certain embodiments, live, attenuated dengue-2 PDK-53 vaccine virus contained a mixture of viruses, with the population containing varying nucleotide differences. After genetic characterization of the attenuating mutations, certain attenuating characteristics were outlined and engineered into a cDNA infectious clone. RNA was transcribed from this infectious clone and introduced into Vero cells as a passage 1 of the newly characterized and derived PDK-53-Vero-DEN-2-P1 virus (see for example, Table 1). This attenuated virus was created for each DEN serotype, but for DEN-1, DEN-3 and DEN-4, the prM and E genes were engineered into 3 separate cDNA infectious clones, thus generating four separate PDK-53-Vero viruses (termed herein as: PDK-53-Vero-DEN-2-P1, PDK-53-Vero-DEN-1-P1, PDK-53-Vero-DEN-3-P1, and PDK-53-Vero-DEN-4-P 1). These attenuated vaccine virus strains were passaged in Vero cells 10 times (Table 1), and each separate lineage acquired mutations upon their adaptation to grow in Vero cells (Table 3). Certain embodiments here are directed to derivation and uses for these live, attenuated dengue viruses.

Previous human clinical trials with these attenuated viruses have indicated that DEN-2 PDK-53 has the lowest infectious dose (50% minimal infectious dose of 5 plaque forming units or PFU) in humans, is strongly immunogenic, and produces no apparent safety concerns. The DEN-1 PDK-13, DEN-3 PGMK-30/FRhL-3 and DEN-4 PDK-48 vaccine virus candidates have higher 50% minimal infectious doses of 10,000, 3500, and 150 PFU, respectively, in humans. Although only one immunization with monovalent DEN-2 PDK-53 virus or DEN-4 PDK-48 virus was required to achieve 100% seroconversion in human subjects, a booster was needed to achieve the same seroconversion rate for DEN-1 PDK-13 and DEN-3 PGMK-30/FRhL-3 viruses, which have the two highest infectious doses for humans.

DEN-2 PDK-53 virus vaccine candidate, also abbreviated PDK-53, has several measurable biological markers associated with attenuation, including temperature sensitivity, small plaque size, decreased replication in mosquito C6136 cell culture, decreased replication in intact mosquitoes, loss of neurovirulence for suckling mice and decreased incidence of viremia in monkeys. Clinical trials of the candidate PDK-53 vaccine have demonstrated its safety and immunogenicity in humans. Furthermore, the PDK-53 vaccine induces dengue virus-specific T-cell memory responses in human vaccine recipients. Some embodiments herein describe an improvement on the DEN-2 PDK-53 used in chimeric constructs disclosed herein.

Immunogenic flavivirus chimeras having a dengue-2 virus backbone and at least one structural protein of another dengue virus serotype can be used for preparing the dengue virus chimeras and methods for producing the dengue virus chimeras are described. The immunogenic dengue virus chimeras are provided, alone or in combination, in a pharmaceutically acceptable carrier as immunogenic compositions to minimize, inhibit, or immunize individuals against infection by one or more serotypes, such as dengue virus serotypes DEN-1, DEN-2, DEN-3 and DEN-4, alone or in combination. When combined, the immunogenic dengue virus chimeras may be used as multivalent vaccines (e.g. bi-, tri- and tetravalent) to confer simultaneous protection against infection by more than one species or strain of flavivirus. In certain embodiments, the dengue virus chimeras are combined in an immunogenic composition useful as a bivalent, trivalent or tetravalent vaccine against the known dengue virus serotypes or confer immunity to other pathogenic flaviviruses by including nucleic acids encoding one or more proteins from a different flavivirus.

In some embodiments, avirulent, immunogenic dengue virus chimeras provided herein contain the nonstructural protein genes of the attenuated dengue-2 virus (e.g. PDK-53), or the equivalent thereof, and one or more of the structural protein genes or immunogenic portions thereof of the flavivirus against which immunogenicity is to be induced in a subject. For example, some embodiments concern a chimera having attenuated dengue-2 virus PDK-53 genome as the viral backbone, and one or more structural protein genes encoding capsid, premembrane/membrane, or envelope of the PDK-53 genome, or combinations thereof, replaced with one or more corresponding structural protein genes from DEN-1. DEN-3 or DEN-4 or other flavivirus to be protected against, such as a different flavivirus or a different dengue virus serotype. In accordance with these embodiments, a nucleic acid chimera disclosed herein can have functional properties of the attenuated dengue-2 virus and is avirulent, but expresses antigenic epitopes of the structural gene products of DEN-1. DEN-3 or DEN-4 in addition to other flaviviruses and is immunogenic (e.g. induces an immune response to the gene products in a subject). Then, these DNA constructs are used to transcribe RNA from an infectious clone, this RNA is introduced into Vero cells again producing a new progeny virus at P1. These new progeny viruses are distinguishable from PDK-53. (See e.g. P1-P10).

In another embodiment, a nucleic acid chimera can be a nucleic acid chimera having, but not limited to, a first nucleotide sequence encoding nonstructural proteins from an attenuated dengue-2 virus, and a second nucleotide sequence encoding a structural protein from dengue-4 virus alone or in combination with another flavivirus. In other embodiments, the attenuated dengue-2 virus can be vaccine strain PDK-53 having one or more mutated amino acids (see Examples). These additional mutations confer desirable traits of use as live, attenuated dengue-2 or as chimeric constructs described herein. Some embodiments include structural proteins of one or more of C, prM or E protein of a second dengue virus.

Other aspects include that chimeric viruses can include nucleotide and amino acid substitutions, deletions or insertions for example, in the control PDK-53 dengue-2 genome to reduce interference with immunogenicity responses to a targeted dengue virus serotype. These modifications can be made in structural and nonstructural proteins alone or in combination with the example modifications disclosed herein and can be generated by passaging the attenuated virus and obtaining an improved composition for inducing an immune response against one or more dengue virus serotypes.

Certain embodiments disclosed herein provide for method for making the chimeric viruses of this invention using recombinant techniques, by inserting the required substitutions into the appropriate backbone genome. Other embodiments herein concern passaging a confirmed (e.g. safe and effective) live, attenuated chimeric virus for additional improvements. In certain embodiments, a dengue-2 backbone used herein can include one or more mutations presented in Table 3. In other embodiments, a dengue-dengue chimera of the instant application can include one or more mutations as presented in Table 3. In yet other embodiments, a dengue-dengue chimera can include all of the mutations for each chimera as represented in Table 3 for Den-2/Den-1, Den-2/Den-3 or Den-2/Den-4. Pharmaceutical compositions that include a live, attenuated virus represented by the constructs of Table 3 are contemplated. For example, mono-, di-, tri- or tetravalent compositions are contemplated of use herein using chimeras and live, attenuated dengue-2 viruses as presented in Table 3.

In certain embodiments, a live, attenuated DEN-2 variant contemplated herein can be formulated into a pharmaceutical composition wherein the pharmaceutical composition can be administered alone or in combination with dengue-dengue chimeras or dengue-flavivirus chimeras. In certain embodiments, a bi-, tri or tetravaient compositions can be administered in a single application or in multiple applications to a subject. Flavivirus Chimeras Dengue virus types 1-4 (DEN-1 to DEN-4) are mosquito-borne flavivirus pathogens. The flavivirus genome contains a 5'-noncoding region (5'-NC), followed by a capsid protein (C) encoding region, followed by a premembrane/membrane protein (prM) encoding region, followed by an envelope protein (E) encoding region, followed by the region encoding the nonstructural proteins (NS1-NS2A-NS2B-NS3-NS4A-NS4B-NS5) and finally a 3' noncoding region (3'NC). The viral structural proteins are C, prM and E, and the nonstructural proteins are NS1-NS5. The structural and nonstructural proteins are translated as a single polyprotein and processed by cellular and viral proteases.

Flavivirus chimeras can be constructs formed by fusing non-structural protein genes from one type, or serotype, of dengue virus or virus species of the flaviviridae, with protein genes, for example, structural protein genes, from a different type, or serotype, of dengue virus or virus species of the flaviviridae. Alternatively, a flavivirus chimera of the invention is a construct formed by fusing non-structural protein genes from one type, or serotype, of dengue virus or virus species of the flaviviridae, with further nucleotide sequences that direct the synthesis of polypeptides or proteins selected from other dengue virus serotypes or other viruses of the flaviviridae.

In other embodiments, avirulent, immunogenic flavivirus chimeras provided herein contain the nonstructural protein genes of the attenuated dengue-2 virus, or the equivalent thereof, and one or more of the structural protein genes, or antigenic portions thereof, of the flavivirus against which immunogenicity is to be conferred. Suitable flaviviruses include, but are not limited to those listed in Table 1.

Other suitable dengue viruses for use in constructing the chimeras can be wild-type, virulent DEN-1 16007. DEN-2 16681. DEN-3 16562 and DEN-4 1036 and attenuated, vaccine-strain DEN-1 PDK-13, DEN-2 PDK-53, DEN-3 PMK-30/FRhL-3 and DEN-4 PDK-48. Genetic differences between the DEN-1, DEN-2, DEN-3 and DEN-4 wild type/attenuated virus pairs are contemplated along with changes in the amino acid sequences encoded by the viral genomes.

Sequence listings for DEN-2 PDK-53 correspond to the DEN-2 PDK-53-V variant, wherein genome nucleotide position 5270 is mutated from an A to a T and amino acid position 1725 of the polyprotein or amino acid position 250 of the NS3 protein contains a valine residue. The DEN-2 PDK-53 variant without this nucleotide mutation, DEN-2 PDK-53-E, differs from PDK-53-V only in this one position. DEN-2 PDK-53-E has an A at nucleotide position 5270 and a glutamate at polyprotein amino acid position 1725, NS3 protein amino acid position 250. It is understood that embodiments herein include modified PDK 53 that include one or more passages in a separate host cell (e.g. Vero cells, see Table 1) where desirable traits of use in vaccine compositions contemplated herein are generated.

In certain embodiments, designations of the chimeras can be based on the DEN-2 virus-specific infectious clone modified backbones and structural genes (prM-E or C-prM-E) insert of other dengue viruses or other flaviviruses. DEN-2 for the dengue-2 backbone, followed by the strain from which the structural genes are inserted. One DEN-2 backbone variant is reflected in the next letter after the number designation. One particular DEN-2 backbone variant from which the chimera was constructed is indicated by the following letter placed after a hyphen, parent 16681 (P). PDK-53-E (E), or PDK-53-V (V); the last letter indicates the C-prM-E structural genes from the parental (P) strain or its vaccine derivative (V) or the prM-E structural genes from the parental (P) or its vaccine derivative (V 1). For example; DEN-2/1-VP denotes the chimera comprising the attenuated DEN-2 PDK-53V backbone comprising a valine at NS3-250 and the C-prM-E genes from wild-type DEN-1 16007; DEN-2/1-VV denotes the DEN-2 PDK-53V backbone with the vaccine strain of dengue-1, DEN-1 PDK-13; DEN-2/1-VP1 denotes the DEN-2 PDK-53V backbone and the prM-E genes from wild-type DEN-1 16007; DEN-2/3-VP1 denotes the DEN-2 PDK-53V backbone and the prM-E genes from wild-type DEN-3 0.16562; DEN-2/4VP1 denotes the DEN-2 PDK-53V backbone and the prM-E genes from wild-type DEN-4 1036. Other chimeras disclosed herein are indicated by the same manner.

In one embodiment, chimeras disclosed herein contain attenuated dengue-2 virus PDK-53 genome as the viral backbone, in which the structural protein genes encoding C, prM and E proteins of the PDK-53 genome, or combinations thereof, can be replaced with the corresponding structural protein genes from dengue-1, dengue-3 or dengue-4 virus and optionally, another flavivirus to be protected against, such as a different flavivirus or a different dengue virus strain.

In the nonstructural protein regions, a Gly-to-Asp (wild type-to-PDK-53) mutation was discovered at nonstructural protein NS1-53 (genome nucleotide position 2579); a Leu-to-Phe (wild type-to-PDK-53) mutation was discovered at nonstructural protein NS2A-181 (genome nucleotide position 4018); a Glu-to-Val (wild type-to-PDK-53) mutation was discovered at nonstructural protein NS3-250 (genome nucleotide position 5270); and a Gly-to-Ala mutation (wild type-to-PDK-53) was discovered at nonstructural protein NS4A-75 (genome nucleotide position 6599). The live, attenuated DEN-2 virus of the instant invention further includes mutations as presented in any chimera or live, attenuated dengue-2 virus of Table 3.

PDK-53 virus strain has a mixed genotype at genome nucleotide 5270. A significant portion (approximately 29%) of the virus population encodes the non-mutated NS3-250-Glu that is present in the wild type DEN-2 16681 virus rather than the NS3-250-Val mutation. As both genetic variants are avirulent, this mutation may not be necessary in an avirulent chimera.

Previously, it was discovered that avirulence of the attenuated PDK-53 virus strain can be attributed to mutations in the nucleotide sequence encoding nonstructural proteins and in the 5' noncoding region. For example, a single mutation at NS1-53, a double mutation at NS1-53 and at 5'NC-57, a double mutation at NS1-53 and at NS3-250 and a triple mutation at NS1-53, at 5'NC-57 and at NS3-250, result in attenuation of the DEN-2 virus. Therefore, the genome of any dengue-2 virus containing such non-conservative amino acid substitutions or nucleotide substitutions at these loci can be used as a base sequence for deriving the modified PDK-53 viruses disclosed herein. Another mutation in the stem of the stem/loop structure in the 5 noncoding region will provide additional avirulent phenotype stability, if desired. Mutations to this region disrupt potential secondary structures important for viral replication. A single mutation in this short (only 6 nucleotide residues in length) stem structure in both DEN and Venezuelan equine encephalitis viruses disrupts the formation of the hairpin structure. Further mutations in this stem structure decrease the possibility of reversion at this locus, while maintaining virus viability.

Mutations disclosed herein can be achieved by any method known in the art including, but not limited to, naturally-occurring or selected clones having additional features once passaged in a cell line of interest (e.g. Vero cells). It is understood by those skilled in the art that the virulence screening assays, as described herein and as are well known in the art, can be used to distinguish between virulent and avirulent backbone structures.

Construction of Flavivirus Chimeras

Flavivirus chimeras described herein can be produced by splicing one or more of the structural protein genes of the flavivirus against which immunity is desired into a PDK-53 dengue virus genome backbone, or other methods known in the art, using recombinant engineering to remove the corresponding PDK-53 gene and replace it with a dengue-1, dengue-3 or dengue-4 virus gene or other gene known in the art.

Alternatively, using the sequences provided in the sequence listing, the nucleic acid molecules encoding the flavivirus proteins may be synthesized using known nucleic acid synthesis techniques and inserted into an appropriate vector. Avirulent, immunogenic virus is therefore produced using recombinant engineering techniques known to those skilled in the art.

A target gene can be inserted into the backbone that encodes a flavivirus structural protein of interest for DEN-1, DEN-3, DEN-4 or other flavivirus. A flavivirus gene to be inserted can be a gene encoding a C protein, a PrM protein and/or an E protein. The sequence inserted into the dengue-2 backbone can encode both PrM and E structural proteins. The sequence inserted into the dengue-2 backbone can encode all or one of C, prM and E structural proteins.

Suitable chimeric viruses or nucleic acid chimeras containing nucleotide sequences encoding structural proteins of other flaviviruses or dengue virus serotypes can be evaluated for usefulness as vaccines by screening them for the foregoing phenotypic markers of attenuation that indicate avirulence and by screening them for immunogenicity. Antigenicity and immunogenicity can be evaluated using in vitro or in vivo reactivity with flavivirus antibodies or immunoreactive serum using routine screening procedures known to those skilled in the art.

Dengue Virus Vaccines

In certain embodiments, chimeric viruses and nucleic acid chimeras can provide live, attenuated viruses useful as immunogens or vaccines. Some embodiments include chimeras that exhibit high immunogenicity to dengue-4 virus while producing no dangerous pathogenic or lethal effects.

To reduce occurrence of DHF/DSS in subjects, a tetravalent vaccine is needed to provide simultaneous immunity for all four serotypes of the virus. A tetravalent vaccine is produced by combining a live, attenuated dengue-2 virus of the instant application with dengue-2/1, dengue-2/3, and dengue-2/4 chimeras described above in a suitable pharmaceutical carrier for administration as a multivalent vaccine.

The chimeric viruses or nucleic acid chimeras of this invention can include structural genes of either wild-type or live, attenuated virus in a virulent or an attenuated DEN-2 virus backbone. For example, the chimera may express the structural protein genes of wild-type DEN-4 1036 virus, its candidate vaccine derivative in either DEN-2 backgrounds.

Viruses used in the chimeras described herein can be grown using techniques known in the art. Virus plaque titrations are then performed and plaques counted in order to assess the viability and phenotypic characteristics of the growing cultures. Wild type viruses can be passaged through cultured cell lines to derive attenuated candidate starting materials.

Chimeric infectious clones can be constructed from the various dengue serotype clones available. The cloning of virus-specific cDNA fragments can also be accomplished, if desired. The cDNA fragments containing the structural protein or nonstructural protein genes are amplified by reverse transcriptase-polymerase chain reaction (RT-PCR) from dengue virus RNA with various primers. Amplified fragments are cloned into the cleavage sites of other intermediate clones. Intermediate, chimeric dengue virus clones are then sequenced to verify the accuracy of the inserted dengue virus-specific cDNA.

Full genome-length chimeric plasmids constructed by inserting the structural protein and/or nonstructural protein gene region of dengue serotype viruses into vectors are obtainable using recombinant techniques well known to those skilled in the art.

Nucleotide and Amino Acid Analysis

The NS1-53 mutation in the DEN-2 PDK-53 vaccine virus is significant for the attenuated phenotype of this virus, because the NS1-53-Gly of the DEN-2 16681 virus is conserved in nearly all flaviviruses, including the tick-borne viruses, sequenced to date. DEN-4 vaccine virus can also contain an amino acid mutation in the NS1 protein at position 253. This locus, which is a Gln-to-His mutation in DEN-4 PDK-48 vaccine virus, is Gin in all four wild serotypes of dengue virus. This Gin residue is unique to the dengue viruses within the flavivirus genus. The NS1 protein is a glycoprotein that is secreted from flavivirus-infected cells. It is present on the surface of the infected cell and NS1-specific antibodies are present in the serum of virus-infected individuals. Protection of animals immunized with NS1 protein or passively with NS1-specific antibody has been reported. The NS1 protein appears to participate in early viral RNA replication.

The mutations that occurred in the NS2A, NS2B, NS4A, and NS4B proteins of the DEN-1, -2, -3 and -4 attenuated strains are conservative in nature. The NS4A-75 and NS4A-95 mutations of DEN-2 and DEN-4 vaccine viruses, respectively, occurred at sites of amino acid conservation among dengue viruses, but not among flaviviruses in general.

The flaviviral NS3 protein possesses at least two recognized functions: the viral proteinase and RNA helicase/NTPase. The 698-aa long (DEN-2 virus) NS3 protein contains an amino-terminal serine protease domain (NS3-51-His, -75-Asp, -135-Ser catalytic triad) that is followed by sequence motifs for RNA helicase/NTPase functions (NS3-196-GAGKT (SEQ ID NO:147), -284-DEAH, -459-GRIGR). None of the mutations in the NS3 proteins of DEN-1, DEN-2, or DEN-3 virus occurred within a recognized motif. The NS3-510 Tyr-to-Phe mutation in DEN-1 PDK-13 virus was conservative. Since the wild-type DEN-2, -3 and -4 viruses contain Phe at this position, it is unlikely that the Tyr-to-Phe mutation plays a role in the attenuation of DEN-1 virus. The NS3-182 Glu-to-Lys mutation in DEN-1 PDK-13 virus occurred at a position that is conserved as Asp or Glu in most mosquito-borne flaviviruses and it may play some role in attenuation. This mutation was located 15 amino acid residues upstream of the GAGKT helicase motif. As noted in previous reports, the NS3-250-Glu in DEN-2 16681 virus is conserved in all mosquito-borne flaviviruses except for yellow fever virus.

Nucleic acid probes selectively hybridize with nucleic acid molecules encoding the DEN-1, DEN-3 and DEN-4 viruses or complementary sequences thereof. By “selective” or “selectively” is meant a sequence which does not hybridize with other nucleic acids to prevent adequate detection of the dengue virus. Therefore, in the design of hybridizing nucleic acids, selectivity will depend upon the other components present in a sample. The hybridizing nucleic acid should have at least 70% complementarity with the segment of the nucleic acid to which it hybridizes. As used herein to describe nucleic acids, the term “selectively hybridizes” excludes the occasional randomly hybridizing nucleic acids, and thus, has the same meaning as “specifically hybridizing.” The selectively hybridizing nucleic acid of this invention can have at least 70%, 80%, 85%, 90%, 95%, 97%, 98%, and 99% complementarity with the segment of the sequence to which it hybridizes, preferably 85% or more.

Sequences, probes and primers which selectively hybridize to the encoding nucleic acid or the complementary, or opposite, strand of the nucleic acid are contemplated. Specific hybridization with nucleic acid can occur with minor modifications or substitutions in the nucleic acid, so long as functional species-specific hybridization capability is maintained. By “probe” is meant nucleic acid sequences that can be used as probes or primers for selective hybridization with complementary nucleic acid sequences for their detection or amplification, which probes can vary in length from about 5 to 100 nucleotides, or preferably from about 10 to 50 nucleotides, or most preferably about 18-24 nucleotides.

If used as primers, the composition preferably includes at least two nucleic acid molecules which hybridize to different regions of the target molecule so as to amplify a desired region. Depending on the length of the probe or primer, the target region can range between 70% complementary bases and full complementarity and still hybridize under stringent conditions. For example, for the purpose of detecting the presence of the dengue virus, the degree of complementarity between the hybridizing nucleic acid (probe or primer) and the sequence to which it hybridizes is at least enough to distinguish hybridization with a nucleic acid from other organisms.

Nucleic acid sequences encoding the DEN-4, DEN-3 or DEN-1 virus (e.g. structural elements) can be inserted into a vector, such as a plasmid, and recombinantly expressed in a living organism (e.g. into a dengue-2 backbone) to produce recombinant dengue virus peptides and/or polypeptides and/or viruses.

Nucleic Acid Detection Methods

A rapid genetic test that is diagnostic for each of the vaccine viruses described herein is provided by the current invention. This embodiment of the invention enhances analyses of viruses isolated from the serum of vaccinated humans who developed a viremia, as well as enhancing characterization of viremia in nonhuman primates immunized with the candidate vaccine viruses.

These sequences include a diagnostic TaqMan probe that serves to report the detection of the cDNA amplicon amplified from the viral genomic RNA template by using a reverse-transciptase/polymerase chain reaction (RT/PCR), as well as the forward and reverse amplimers that are designed to amplify the cDNA amplicon, as described below. In certain instances, one of the amplimers has been designed to contain a vaccine virus-specific mutation at the 3'-terminal end of the amplimer, which effectively makes the test even more specific for the vaccine strain because extension of the primer at the target site, and consequently amplification, will occur only if the viral RNA template contains that specific mutation.

Automated PCR-based nucleic acid sequence detection system can be used, or other known technology for nucleic acid detection. The TaqMan assay is a highly specific and sensitive assay that permits automated, real time visualization and quantitation of PCR-generated amplicons from a sample nucleic acid template. TaqMan can determine the presence or absence of a specific sequence. In this assay, a forward and a reverse primer are designed to anneal upstream and downstream of the target mutation site, respectively. A specific detector probe, which is designed to have a melting temperature of about 10 degree. C, higher than either of the amplimers and containing the vaccine virus-specific nucleotide mutation or its complement (depending on the strand of RT/PCR amplicon that is being detected), constitutes the third primer component of this assay.

A probe designed to specifically detect a mutated locus in one of the vaccine viral genomes will contain the vaccine-specific nucleotide in the middle of the probe. This probe will result in detectable fluorescence in the TaqMan assay if the viral RNA template is vaccine virus-specific. However, genomic RNA templates from wild-type DEN viruses will have decreased efficiency of probe hybridization because of the single nucleotide mismatch (in the case of the parental viruses DEN viruses) or possibly more than one mismatch (as may occur in other wild-type DEN viruses) and will not result in significant fluorescence. The DNA polymerase is more likely to displace a mismatched probe from the RT/PCR amplicon template than to cleave the mismatched probe to release the reporter dye (TaqMan Allelic Discrimination assay, Applied Biosystems).

One strategy for diagnostic genetic testing makes use of molecular beacons. The molecular beacon strategy also utilizes primers for RT/PCR amplification of amplicons, and detection of a specific sequence within the amplicon by a probe containing reporter and quencher dyes at the probe termini. In this assay, the probe forms a stem-loop structure. The molecular beacons assay employs quencher and reporter dyes that differ from those used in the TaqMan assay.

Pharmaceutical Compositions

Embodiments herein provide for administration of compositions to subjects in a biologically compatible form suitable for pharmaceutical administration in vivo. By “biologically compatible form suitable for administration in vivo” is meant a form of the active agent (e.g. pharmaceutical chemical, protein, gene, of the embodiments) to be administered in which any toxic effects are outweighed by the therapeutic effects of the active agent. Administration of a therapeutically active amount of the therapeutic compositions is defined as an amount effective, at dosages and for periods of time necessary to achieve the desired result. For example, a therapeutically active amount of a compound may vary according to factors such as the disease state, age, sex, and weight of the individual, and the ability of antibody to elicit a desired response in the individual. Dosage regima may be adjusted to provide the optimum therapeutic response.

In one embodiment, the compound (e.g. pharmaceutical chemical, protein, peptide etc. of the embodiments) may be administered in a convenient manner, for example, subcutaneous, intravenous, by oral administration, inhalation, intradermal, transdermal application, intravaginal application, topical application, intranasal or rectal administration.

Depending on the route of administration, the active compound may be contained in a protective buffer (e.g. FTA, F127/trehalose/albumin). In one embodiment, a composition may be orally administered. In another embodiment, the composition may be administered intravenously. In one embodiment, the composition may be administered intranasally, such as inhalation. In yet another embodiment, the composition may be administered intradermally using a needle-free system (e.g. Pharmajet®) or other intradermal administration system.

A composition may be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. It may be necessary to coat the compound with, or co-administer the compound with, a material to prevent its inactivation. The active agent may also be administered parenterally, or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms or other stabilizing formulation (e.g. FTA).

Pharmaceutical compositions suitable for injectable use may be administered by means known in the art. For example, sterile aqueous solutions (where water soluble) or dispersions and sterile powders for the extemporaneous preparation of sterile injectable solutions or dispersion may be used. In all cases, the composition can be sterile and can be fluid to the extent that easy syringability exists. It might be stable under the conditions of manufacture and storage and may be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of microorganisms can be achieved by heating, exposing the agent to detergent, irradiation or adding various antibacterial or antifungal agents.

Sterile injectable solutions can be prepared by incorporating active compound (e.g. a compound that induces an immune response to one or more dengue virus serotypes) in the required amount in an appropriate solvent with one or a combination of ingredients enumerated above, as required, followed by filtered sterilization.

Upon formulation, solutions will be administered in a manner compatible with the dosage formulation and in such amount as is therapeutically effective. The formulations are easily administered in a variety of dosage forms, such as the type of injectable solutions described above. It is contemplated that compositions are especially suitable for intramuscular, subcutaneous, intradermal, intranasal and intraperitoneal administration. A particular ratio may be sought such as a 1:1, 1:2 or other ratio (e.g. PFUs of a given dengue virus serotype)

The active therapeutic agents may be formulated within a mixture predetermined ratios. Single dose or multiple doses can also be administered on an appropriate schedule for a given situation (e.g. prior to travel, outbreak of dengue fever).

In another embodiment, nasal solutions or sprays, aerosols or inhalants may be used to deliver the compound of interest. Additional formulations that are suitable for other modes of administration include suppositories and pessaries.

Certain formulations can include excipients, for example, pharmaceutical grades of mannitol, lactose, starch, magnesium stearate, sodium saccharine, cellulose, magnesium carbonate and the like.

A pharmaceutical composition may be prepared with carriers that protect active ingredients against rapid elimination from the body, such as time-release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and others are known.

Pharmaceutical compositions are administered in an amount, and with a frequency, that is effective to inhibit or alleviate side effects of a transplant and/or to reduce or prevent rejection. The precise dosage and duration of treatment may be determined empirically using known testing protocols or by testing the compositions in model systems known in the art and extrapolating therefrom. Dosages may also vary with the severity of the condition. A pharmaceutical composition is generally formulated and administered to exert a therapeutically useful effect while minimizing undesirable side effects. In general, dose ranges from about $10^2$ to $10^6$ PFU can be administered initially and optionally, followed by a second administration within 30 days or up to 180 days later, as needed. In certain embodiments, a subject can receive dual administration of a mono, bi-, tri or tetravalent composition disclosed herein wherein the composition is a single composition mixture or has predetermined compositions of different dengue virus serotypes. In some embodiments, a DEN2/4 chimera can be present in higher concentrations than other dengue virus serotypes such as a live, attenuated dengue-1.

It will be apparent that, for any particular subject, specific dosage regimens may be adjusted over time according to the individual need.

In one embodiment, a composition disclosed herein can be administered to a subject subcutaneously or intradermally.

The pharmaceutical compositions containing live, attenuated dengue viruses may be administered to individuals, particularly humans, for example by subcutaneously, intramuscularly, intranasally, orally, topically, transdermally, parenterally, gastrointestinally, transbronchially and transalveolarly. Topical administration is accomplished via a topically applied cream, gel, rinse, etc. containing therapeutically effective amounts of inhibitors of serine proteases. Transdermal administration is accomplished by application of a cream, rinse, gel, etc. capable of allowing the inhibitors of serine proteases to penetrate the skin and enter the blood stream. In addition, osmotic pumps may be used for administration. The necessary dosage will vary with the particular condition being treated, method of administration and rate of clearance of the molecule from the body.

In certain embodiments of the methods of the present invention, the subject may be a mammal such as a human or a veterinary and/or a domesticated animal or livestock or wild animal.

Therapeutic Methods

In one embodiment of the present invention, methods provide for inducing an immune response to dengue virus serotype(s) using a mono, bi-, tri or tetravalent formulation of live, attenuated and/or chimeric viral constructs contemplated herein.

Embodiments of the present invention is further illustrated by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention or the scope of the appended claims.

EXAMPLES

The following examples are included to demonstrate certain embodiments presented herein. It should be appreciated by those of skill in the art that the techniques disclosed in the Examples which follow represent techniques discovered to function well in the practices disclosed herein, and thus can be considered to constitute preferred modes for its practice. However, those of skill in the art should, in light of the present disclosure, appreciate that many changes can be made in particular embodiments which are disclosed and still obtain a like or similar result without departing from the spirit and scope herein.

Example 1

1000%1 In some exemplary methods, compositions used to generate as referred to herein as "master virus seeds (MVS)" are disclosed. These compositions may be derived from one or more live, attenuated dengue viruses, such as DEN-1, DEN-2, DEN-3, and DEN-4. In certain methods, compositions may be derived from one or more live attenuated Dengue viruses that include but are not limited to, specific constructs disclosed herein referred to as DENVax-1, DENVax-2, DENVax-3, and DENVax-4. In other exemplary methods, strategies used to generate and characterize these compositions are provided. In yet other embodiments, tetravalent dengue virus formulations and genetic and phenotypic characterization of these formulations are provided.

Production and Analysis of Pre-Raster DENVax Viruses

Certain procedures were performed to generate pre-master dengue virus seeds, such as serial amplification and purification of dengue viruses (e.g. DENVax). First, DENVax viruses were re-derived by transfection of viral RNA transcribed from the full-length recombinant DENVax cDNA into production-certified cells (e.g. Vero cells), resulting in P1 (passage 1) virus seed. The four P1 viruses from each of dengue-1 to dengue-4 were then amplified and plaque purified to obtain the candidate pre-master vaccine P7 seeds (see Table 1). Certain tests were performed to analyze passages of dengue viruses. For example, full-length genome sequencing demonstrated that all four of the P2 (passage 2) seed viruses were genetically identical to their homologous progenitor, research-derived, research-grade candidate vaccine virus. The original plaque phenotypes were also retained in the P2 viruses. Six plaque purified viruses (P3 A-F) were isolated for each serotype of dengue virus (e.g. DENVax1-4) from the P2 seeds, and each isolated plaque was directly plaque purified two more times. The third plaque purification (P5) of each virus was amplified twice (P6 A-F and P7 A-F) in Vero cells to produce the potential pre-master P7 DENVax seeds (Table 1).

TABLE 1

Example of a cGMP Rederivation of DENVax Viruses in WCB-Vero Cells

| Passage | Seed Production/Purification | Characterizations |
|---|---|---|
| P1 | Transfect WCB-Vero with transcribed viral RNAs | Plaque titrate |
| P2 | Amplify P1 virus | Full genome sequence |
| P3 | Pick 6 plaques (A-F)/serotype from P2 plaque assay | Plaque purification |
| P4 | Pick plaques A-F from P3 plaque assay | Plaque purification |
| P5 | Pick plaques A-F from P4 plaque assay | Plaque purification |
| P6 | Amplify P5 A-F plaques | Plaque titrate |
| P7 | Pre-master seeds: Amplify P6 A-F | Full genome sequence, TaqMAMA, Plaque phenotypes |
| P8* | MVS: Amplify selected P7 virus seed | Full genetic and phenotypic characterization |
| P9 | WVS: Amplify P8 Master Seed viruses | Full genome sequence, TaqMAMA |
| P10 | BVS: Amplify P9 Working Seed viruses | Full genome sequence, TaqMAMA |

*One optimal P7 seed (A, B, C, D, E, or F) was selected based on the genetic and plaque analysis to make P8 MVS Some tests were further performed to characterize P7 DENVax seeds, such as analysis of genome sequences and plaque phenotypes of the P7 seeds, and comparison with P2 seeds (Table 2). Plaque phenotypes of the P7 viruses were generally similar to those of the P2 seeds. In some exemplary experiments, virus titers were monitored. Virus titers reached over 6.0 log pfu/ml for most of the P7 seeds, except for 5 viruses. Genome sequencing of more than 60 candidate vaccine virus seeds after 10 or more serial passages in Vero cells identified no reversion event at NS1-53 and NS3-250 of the three major attenuation determinants of the DENV-2 PDK-53 genetic vector, suggesting that these 2 loci are quite stable in candidate vaccine virus seeds. All sequence chromatograms of the 24 candidate strains generated from both forward and reverse sequencing for these two sites were homogenous without any minor nucleotide populations evident at the NS1-53 and NS3-250 genetic loci. In contrast to the NS1 and NS3 sites, different levels of reversions at the 5'NCR-57 attenuation locus were identified from multiple serially passaged research grade vaccine viruses, suggesting this locus might not be as stable as NS1 and NS3 after multiple passages in cell culture. Therefore, a sensitive mismatch amplification assay (TaqMAMA) was developed to accurately measure the reversion rate at the 5'NCR-57 locus by real-time RT-PCR. In some studies, the 5'NCR-57 reversion rates of all 24 of the P7 seeds were measured by the TaqMAMA. Depending on the concentration of the input viral RNA for each virus in the assay, the sensitivity limit of the TaqMAMA ranged between 0.01% and 0.07% reversion, which is much more sensitive than the 10-30% reversion sensitivity limit detectable by consensus genome sequence analysis. The resulting data illustrates that 15 of the 24 P7 viruses had minimal or undetectable reversion (<0.07%), one virus (DENVax-3-D) had almost 100% reversion, and 8 viruses (1 DENVax-1, 1 DENVax-2, 2 DENVax-3, and 4 DENVax-4) had partial reversion ranging from 0.08% to 12.85% (Table 2). Full-length genome sequencing was conducted for 16 of the 24 P7 viruses with low levels of 5'NCR57 reversion as measured by TaqMAMA. All the sequenced viruses maintained the other two DENVax attenuation determinants (NS1-53. NS3-250), and all had acquired additional mutations that were not present in the original, engineered recombinant cDNA clones (Table 2). In one exemplary target vaccine composition, DENVax-1-A, DENVax-2-F, DENVax-3-F, and DENVax-4-F were selected as target pre-master seed for each serotype because their genotypes and plaque phenotypes most closely resembled those of the originally designed vaccine recombinants. The DENVax-1-A, DENVax-2-F, and DENVax-4-F had two non-synonymous mutations, and the DENVax-3-F had one. The evidence suggests these additional mutations observed in these 4 pre-master seeds do not cause safety concerns or immunogenicity alterations for the viruses. These pre-master seeds were further amplified to generate the MVS (master seed, designated as P7, Table 1).

Exemplary methods provided herein used purified in-vitro transcribed viral RNA from cloned cDNA plasmid as the pure source to transfect vaccine-certified Vero cells to generate vaccine virus. Serial plaque purifications and full-genome sequence analyses were incorporated into the manufacturing procedures to ensure manufactured vaccine seeds with optimal purity and genetic stability. Six cloned viruses were prepared as potential pre-master seeds for each serotype of DENVax. Through genomic analysis, including TaqMAMA and complete genomic sequencing, as well as characterization of viral plaque phenotypes, pre-master seeds were chosen to advance to master virus seeds production for each serotype (serotypes 1-4). The selected pre-master seeds had undetectable reversions (<0.01% or <0.07%) at the 5'NCR-57 locus, with 1 or 2 amino acid substitutions in their genomes, and retained the small plaque phenotypes previously observed.

TABLE 2

Characterizations of pre-master (P7) seeds

| Virus | Clone[a] | TaqMAMA[b] | $Log_{10}$ pfu/ml | Plaque[c] | Mutations identified in genome[d] |
|---|---|---|---|---|---|
| DENVax-1 | A | ** | 6.85 | P2 | NS2A-116 I-L, NS2B-92 E-D, one silent |
| | B | * | 6.93 | P2 | nd[e] |
| | C | * | 6.93 | D | nd |
| | D | ** | 7.02 | D | C-67 K-A; one silent |
| | E | 0.57% | 7.28 | P2 | nd |
| | F | ** | 7.18 | P2 | E473 T-M; one silent |
| DENVax-2 | A | 0.03% | 6.33 | P2 | NS1-341 K-N |
| | B | * | 6.33 | P2 | E-305 K-T, two silent |
| | C | * | 5.84 | L | NS4A-18 T-A, four silent |
| | D | 0.08% | 6.20 | P2 | NS2B-99 I-L, one 3'NCR |
| | E | 0.03% | 6.31 | P2 | prM-52 K-E, NS5-412 I-V, two silent |
| | F | ** | 6.15 | P2 | prM-52 K-E, NS5-412 I-V |
| DENVax-3 | A | * | 6.00 | P2 | NS5-200 K-N, one silent, one 3'NCR |
| | B | 0.05% | 6.27 | P2 | NS2A-33 I-T, NS2A-59 M-T |
| | C | 0.30% | 6.25 | P2 | nd |
| | D | 100.00% | 6.27 | P2 | nd |
| | E | 0.31% | 6.00 | P2 | nd |
| | F | ** | 6.30 | P2 | E-223 T-S, one silent |
| DENVax-4 | A | 0.47% | 5.60 | P2 | E323 K-R/K, NS2B-21 L-F/L, NS2B-39 T-S, one silent |
| | B | * | 5.65 | D | NS2A-126 A-V; NS4A-5 N-D;NS5-383 K-R, one silent |
| | C | 4.50% | 5.90 | P2 | nd |
| | D | 12.85% | 5.97 | D | nd |
| | | 0.52% | 6.85 | S | prM-85 E-D, NS2B-45 T-A, NS5-320 M-T, NS5-551 E-G, two silent |
| | F | 0.02% | 6.93 | S | NS2A-66 D-G, NS4A-21 A-V, four silent |

[a]Cloned viruses (by serial plaque purifications) selected for further development of MVS are designated bold.

[b]*: Reversion rate < 0.07% (detection limit).

**: Reversion rate < 0.01% (detection limit)

[c]Plaque phenotypes: P2: similar to P2 virus; L = larger than P2 virus, D = similar size, but appear somewhat different in clearness of the plaques; S = smaller than P2.

[d]Substitutions differing from the engineered DENVax cDNA clones. Amino acid mutations are listed with residue position of the virus protein and the changes (wt-mutation). Total number of silent mutations in structural and non-structural genes of each seed is listed. Mutations at non-coding region (NCR) are also noted.

[e]nd = Not done. These clones had higher 5'NCR-57 reversion rates (by TaqMAMA) than other clones, so were excluded from further sequence analysis.

Example 2

In some exemplary methods, compositions of master virus seeds, working virus seeds and bulk virus seeds as well as their genetic and phenotypic characterization are described. These compositions are provided for manufacture of clinical materials and ultimately commercial vaccine supplies. Serial plaque purifications and full-genome sequence analyses were incorporated into the manufacturing process to ensure compositions of vaccine seeds with optimal safety and genetic stability for manufacture of clinical trial materials.

Production and Manufacturing Quality Controls for MVS, WVS, and BVS

In some studies, MVS of the 4 DENVax were produced by amplifying the pre-master P7 seed in certified Vero cells. In other studies. MVS were used to make large amount of WVS in cell factories. Further, the BVS stocks of DENVax were amplified from the WVS and were formulated into tetravalent drug product mixtures to be used used for human clinic trials. Quality controls for product release were performed in some exemplary methods, including, but not limited to, testing all of the MVS, WVS, and BVS for identity, infectious titer, sterility, *mycoplasma*, and in vitro and in vivo adventitious agents. All seeds passed the virus identity test using serotype-specific RT-PCR assays, which showed positive amplification corresponding to its serotype and negative for heterologous serotypes (data not shown). No detectable *mycoplasma* or adventitious agents were detected in the MVS, WVS, or BVS stocks.

Genetic Analysis of the MVS, WVS, and BYS

In certain exemplary methods, after generation of MVS from the selected pre-MVS (P7) strains selected above were produced and the respective viral RNA was sequenced again. Full-length genome sequencing revealed that the MVS for DENVax-1 was identical to its pre-master seed, while the WVS and subsequent BVS acquired 2 additional substitutions at E-483 and NS4B-108 (see Tables 2 and 3). The Ala substitution at E-483 represented part of the genotype in the MVS, but became the dominant genotype in BVS. DENVax-2 and DENVax-3 were identical to their respective pre-master seeds (Table 2 and 3). The DENVax-2 MVS was identical to its pre-master seed, and the WVS and BVS had 2 additional mutations at NS4A-36 and NS4B-111. Both mutations were partial in WVS and were the major genotype in the BVS. The MVS of DENVax-3 was again identical to the pre-master seed, but the WVS and BVS contained an additional aa substitution at NS4A-23. The DENVax-4 MVS acquired an additional amino acid mutation, at locus NS2A-99 (from Lys to Lys/Arg mixed genotype) during production of the MVS (Table 3). Its WVS and BVS retained the NS2A-99 Lys/Arg mixed genotype, and the BVS had an extra NS4B-2384 Ser/Phe mixed genotype. Consensus sequence results also confirmed that MVS, WVS as well as BV retained the three genetic determinants of attenuation at the 5'NCR-57, NS1-53, and NS3-250 loci. Analysis of the least stable attenuating locus by TaqMAMA demonstrated that the 5'NCR-57 reversion rate between <0.7% to and 0.13% among MVS, 50.07% among WVS, and between <0.07 and 0.21% among BVS. A 3% reversion at the 5'NCR-57 locus was considered the maximum permissible rate for acceptance of a vaccine lot (Table 3).

TABLE 3

Nucleotide and amino acid substitutions in DENVax seeds

| DENVax | Nucleotides | Amino Acids | Pre-master | MVS[a] | WVS[a] | BVS[a] |
|---|---|---|---|---|---|---|
| DENVax-1 | 2384 G-C | E-483 Gly-Ala | - | - | **Gly/Ala** | **Ala** |
| | 3823 A-C | NS2A-116 Ile-Leu | Leu | Leu | Leu | Leu |
| | 4407 A-T | NS2B-92 Glu-Asp | Asp | Asp | Asp | Asp |
| | 7148 C-T | NS4B-108 Thr-Ile | - | - | Ile | Ile |
| | 7311 A-G | silent | G | G | G | G |
| | TaqMAMA 5'NCR-57 reversion %[b] | | -- | - | - | - |
| DENVax-2 | 592 A-G | prM-52 Lys-Glu | Glu | Glu | Glu | Glu |
| | 6481 G-C | NS4A-36 Ala-Pro | - | - | **Ala/Pro** | **Pro** |
| | 7156 C-T | NS4B-111 Leu-Phe | - | - | **Leu/Phe** | **Phe** |
| | 8803 A-G | NS5-412 Ile-Val | Val | Val | Val | Val |
| | TaqMAMA 5'NCR-57 reversion % | | -- | - | 0.07% | 0.21% |
| DENVax-3 | 1603 A-T | E-223 Thr-Ser | Ser | Ser | Ser | Ser |
| | 6436 G-A | NS4A-23 Asp-Asn | - | - | **Asn** | **Asn** |
| | 7620 A-G | silent | G | G | G | G |
| | TagMAMA 5'NCR-57 reversion %[b] | | -- | - | - | - |
| DENVax-4 | 225 A-T | silent | T | T | T | T |
| | 3674 A-G | NS2A-66 Asp-Gly | Gly | Gly | Gly | Gly |
| | 3773 A-A/G | NS2A-99 Lys-Lys/Arg | - | **Lys/Arg** | **Lys/Arg** | **Lys/Arg** |
| | 5391 C-T | silent | T | T | T | T |
| | 6437 C-T | NS4A-21 Ala-Val | Val | Val | Val | Val |
| | 7026 T-C | silent | T/C | T/C | T/C | T/C |
| | 7538 C-C/T | NS4B-238 Ser-Ser/Phe | - | - | **Ser/Phe** | **Ser/Phe** |
| | 9750 A-C | silent | C | C | C | C |
| | TaqMAMA 5'NCR-57 reversion %[b] | | - | 0.13% | - | - |

[a]Bold: Changes started at MVS stocks.

[b]"--" indicates reversion rate < 0.01% (detection limit),

"-" indicates reversion rate < 0.07% (detection limit)

Full-genome sequence analysis revealed that an additional amino acid mutation developed in the DENVax-4 MVS, while the other three DENVax MVS lots retained the consensus genome sequence of their pre-master seeds. Overall, from deriving of the P1 seeds to the pre-master (P7) weeds, only 1 or 2 non-synonymous mutations occurred in a given seed. From P1 to MVS (P8) seeds, 2 to 7 nucleotide substitutions were identified in any given DENVax seed and only 2 to 3 of these substitutions resulted in amino acid changes. Thus, minor changes occurred. RNA viruses are error-prone in their genome replication, so genetic substitutions in flavivirus genome during cell passages are not unexpected. None of the silent mutations in the MVS were within the 5' or 3'NCR that may affect virus replication. Only the change in prM-52 Lys-Glu of the DENVax-2, and the substitution in NS2A-66 Asp-Gly of DENVax-4 are not conservative changes. The NS2A-66 mutation of the DENVax-4 is in the nonstructural backbone part of the DENV-2 PDK-53. Although NS2A-66 locus is usually Asp among various strains of DENV-2, it is usually Gly for DENV-4. It is possible that the Asp to Gly change in the DENVax-4 is relevant for fitness of the DENVax-4 in Vero cells. The DENVax-2 prM-52 mutation resides in the C-terminal portion of the prM that is cleaved out from the mature virus particles. In some exemplary methods, phenotypic characterization was performed to confirm that none of the mutations in the MVS seeds significantly altered the attenuation phenotypes of the vaccine.

The DENVax viruses demonstrated high genetic stability during the manufacturing process. The three defined DENV-2 PDK-53 attenuation loci located in 5'NCR, NS1-53, and NS3-250 remained stable in the consensus genome sequence upon serial passage of the DENVax from pre-Master strains to bulk vaccine preparations. The highly sensitive TaqMAMA of the 5'NCR-57 locus demonstrated minimal or undetectable reversion in the MVS, WVS (P9/Working), and BVS (Bulk Virus Seed for vaccines) of dengue virus serotypes. The 5'NCR-57 reversion rates of the DENVax BVS preparations (P10-equivalent) were significantly lower than the 5'NCR-57 reversion rates that evolved in research-grade vaccine candidates after 10-serial passages in Vero cells (4-74% reversion). The strategy for large-scale manufacturing of the DENVax seeds provided herein resulted in a genetically stable vaccine seed which retained the attenuation markers in the candidate vaccine viruses.

Plaque Phenotype of DENVax MVS

In one exemplary method, plaque phenotypes of the DENVax MVS were compared with wild type Dengue viruses and their homologous research-grade chimeric viruses in Vero cells (FIG. 2). All of the MVS of DENVax-1, -2, and -3 produced plaques that were significantly smaller than their wild type homologs and very similar (within 0.4-mm differences) to their homologous research-grade viruses in Vero cells. DENVax-4 MVS was also significantly smaller than the wild type DENV-4, but was slightly larger (0.9 mm difference) than the original lab derived D2/4-V chimera.

FIG. 2 represents an exemplary histogram illustrating plaque sizes of the DENVax MVS in contrast with control wild type viruses and research-grade vaccine candidate viruses. Mean plaque diameters (mm)±SD (error bars) of the virus plaques in Vero cells under agarose overlay measured on day 9 pi. The wild type DEN viruses, represented by black bars, and previously published research-grade vaccine candidate viruses, represented by white bars, were included for control and comparison to the DENVax master vaccine seeds represented by grey bars.

Temperature Sensitivity of DENVax MVS

In another exemplary method, temperature sensitivity was tested in Vero cells for the DENVax MVS and compared with their homologous wild type and the original research-grade chimeric vaccine virus. The wild type (wt) DENV-3 16562 was not temperature sensitive. The wt dengue virus serotype 1 and dengue virus serotype-4 were moderately temperature sensitive at 39° C. (titers were approximately 1.0 $\log_{10}$ pfu/ml lower at 39° C. than at 37° C., FIG. 3). Wt Dengue virus serotype-2 16681 was the most temperature sensitive of the wt Dengue viruses tested, and resulted in a 100-fold titer drop at 39° C. DENVax-1, -2, and -3 were as temperature sensitive as their original homologous research-grade chimeric vaccine viruses (FIG. 2). Titers at 39° C. dropped between 2.0 and 3.0 $\log_{10}$ pfu/ml for these DENVax strains. DENVax-4 also was temperature sensitive, demonstrating a 5-fold reduction in titer. However, the original research-grade D2/4-V demonstrated about a 10-fold reduction in titer. The final stabilized DENVax-4 MVS contained F127 (and other agents known to stabilize these formulations (FTA)), which was shown to enhance thermal stability of the Dengue viruses. The presence of the F127 in DENVax-4 MVS likely contributed to the less pronounced temperature sensitivity of the virus in the Vero culture assay. In a separate experiment, temperature sensitivity of an MSV-derived DENVax-4 strain in the absence of F127 was further evaluated. To remove the F127 from the strain, viral RNA was isolated from a DENVax-4 bulk virus preparation and was transfected into Vero cells. This DENVax-4 virus appeared to be as temperature sensitive as the D2/4 V research strain (titer reduced 1.5 $\log_{10}$ pfu/ml) on day 3 pi in the absence of F127 (FIG. 3).

Figure 3:
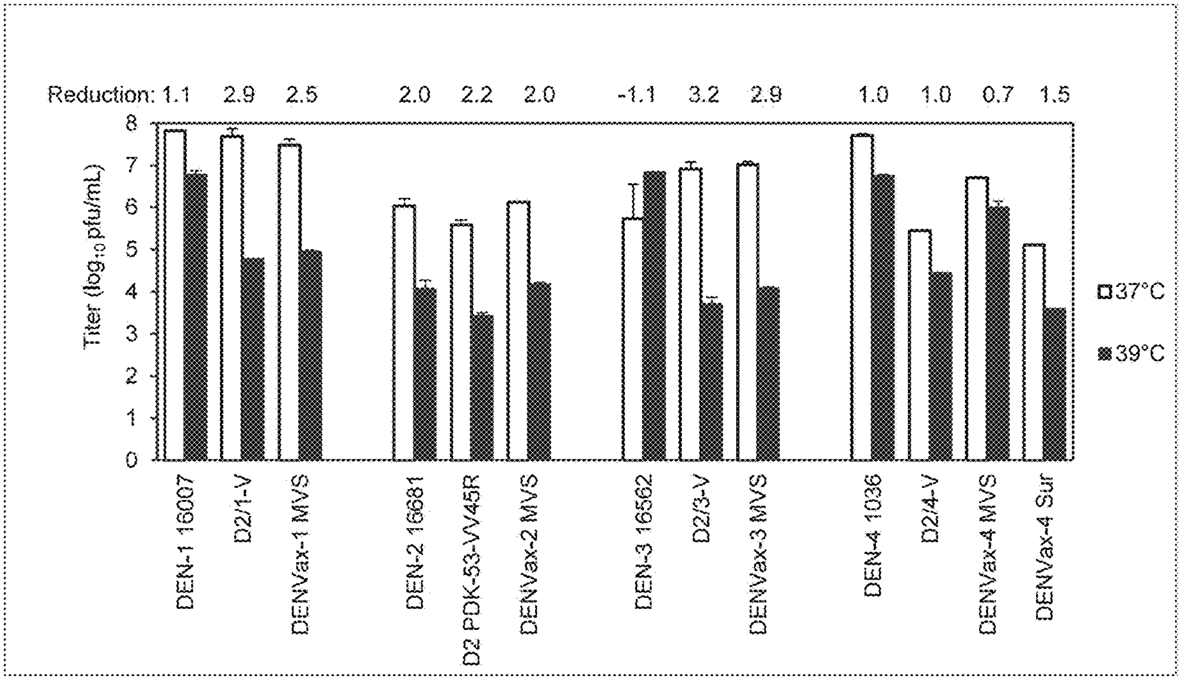
FIG. 3 represents an exemplary histogram plot that represents temperature sensitivities of DENVax MVS (Master Virus Seed). Wild type dengue viruses and previously published research-grade vaccine candidate viruses were included for comparison with the MVS grade.

FIG. 3 illustrates an exemplary histogram illustrating temperature sensitivities of DENVax MVS. The wild type Dengue viruses and previously published research-grade vaccine candidate viruses were included for comparison. The DENVax-4 MVS contains additional F-127 that can mask the temperature sensitivity results of the virus in this assay. A separate experiment analyzing a surrogate DENVax-4 in the absence of F127 was also included. Mean titers±SD (error bars) of the viruses replicated in Vero cells at 37° C. or 39° C.

DENVax MVS Replication in Mosquito C636 Cells

Figure 4:
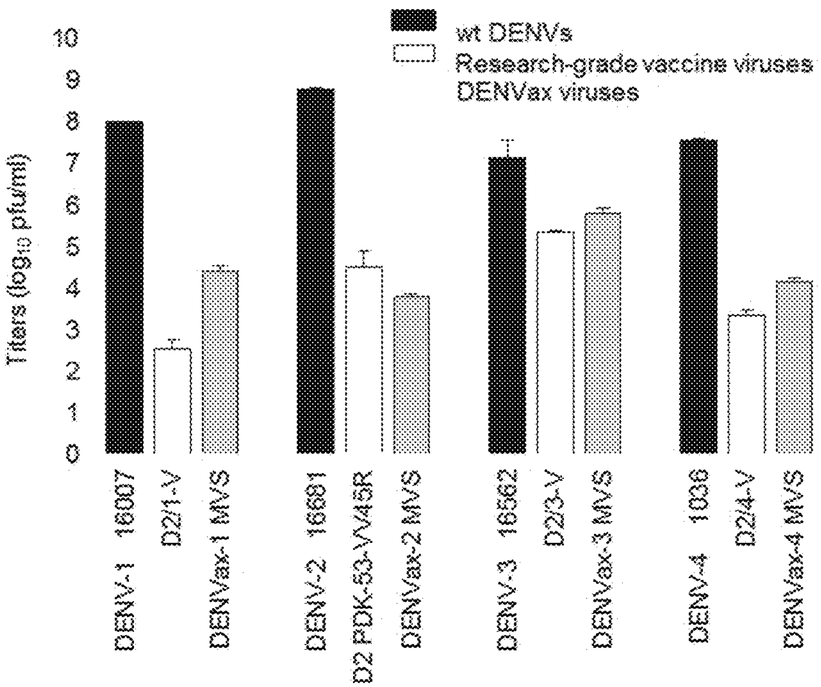
FIG. 4 represents an exemplary histogram plot that represents viral growth of DENVax MVS in C6/36 cells compared to controls. Wild-type dengue viruses and research-grade vaccine candidate viruses were included for comparison with the DENVax MVS.

In some exemplary methods, the DENVax MVS were grown in C6/36 cells to verify their retention of the in vitro attenuation phenotype, with the knowledge that the research-grade chimeric vaccine viruses retained the attenuation phenotype of the backbone DENV-2 PDK53 virus in these mosquito cells. Compared to the wt Dengue viruses, DENVax-1. DENVax-2 and DENVax-4 MVS showed significant growth reduction (at least 3 $\log_{10}$ pfu/ml reduction) in C6/36 cells on day 6 pi (FIG. 4). The DENVax-3 MSV also exhibited reduced growth compared to the wt DENV-3 16562, but the reduction was not as marked (1-2 $\log_{10}$ pfu/ml reduction). However, the C6/36 titers of the DENVax-3 seed lots were similar (within 1 $\log_{10}$ pfu/ml difference) to the C6/36 titer of the original research-grade chimeric D2/3-V vaccine virus.

FIG. 4 illustrates an exemplary histogram plotting restricted growth of DENVax MVS (grey bars) in C6/36 cells in comparison with wt Dengue viruses (black bars) and research-grade vaccine viruses (white bars). Mean titers±SD (error bars) of the viruses replicated in C6/36 cells 6 days pi.

Virus Infection, Dissemination, and Transmission Rates in Whole Mosquitoes

In some exemplary methods, the infection and dissemination rates of the DENVax were compared with their parental wt Dengue viruses. In certain exemplary experiments, oral infection experiments were conducted in *Ae. aegypti* mosquitoes. Infectious blood meals were back-titrated to measure the virus titers and only the experiments with similar virus titers in the blood meal (less than 1 $\log_{10}$ pfu/mi differences) between parental Dengue viruses and DENVax for each serotype were included for comparisons in Table 4. DENVax-1, DENVax-2, and research-grade D2 PDK-53-VV45R did not infect mosquitoes through oral feeding, which is significantly different ($p<0.0001$) from their parental viruses, DENV-1 16007 (44% infection) and DENV-2 16681 (43.3% infection). Because no mosquito was infected by DENVax-1 and -2, there was little to no dissemination concern for these two vaccine viruses. While DENVax-4 did infect some mosquitoes through oral feeding (2 out of 55), the infection rate was significantly lower ($p<0.05$) than its parental wt virus, DENV-4 1036 (8 out of 50). DENVax-3 did not infect any mosquitoes in two experiments with blood meal viral titers of 5.2±0.02 $\log_{10}$ pfu/ml (Table 4), and in a separate experiment with blood meal viral titer of 6.0 $\log_{10}$ pfu/ml, only 1 out of 30 mosquitoes became infected (data not shown). However, wt Dengue virus-3 16562 also had a very low infection rate (8%) at 5.2 logo pfu/ml, and the rate did not increase in a separate experiment with a higher blood meal viral titer at 6.2 $\log_{10}$ pfu/ml (3%, 1 positive out of 30 mosquitoes, data not shown). Although the wild type (wt) Dengue virus-3 and Dengue virus-4 had significantly lower infection rates than the wt Dengue virus-1 and Dengue virus-2, the mean virus titers in the infected mosquitoes were similar (3.1 to 3.9 $\log_{10}$ pfu/mosquito). In contrast, the DENVax-4 titers from the two infected mosquitoes were both minimal (0.7 $\log_{10}$ pfu/mosquito), which was 1,000-fold lower than the titer from the mosquitoes infected by wt Dengue virus serotype-4 1036 (3.9 f 1.5 pfu/mosquito).

For those mosquitoes that were infected, dissemination out of the midgut could be assessed by determining whether virus was present in the legs. The four parental DENVs resulted in dissemination rates ranging between 36.3% and 62.5%, and their mean virus titers (in $\log_{10}$ pfu) from the legs were between 0.9±0.3 and 2.2±0.7 (excluding negative samples). Neither of the two DENVax-4 infected mosquitoes resulted in virus dissemination to the legs (Table 4). While disseminated virus was detectable in the legs, none of the four wt Dengue viruses was detectable in saliva of orally infected mosquitoes, suggesting that oral feeding conditions may not be sufficiently sensitive to measure the transmission rate of these DENVs. Therefore, in other exemplary methods, highly stringent artificial mosquito infections by direct IT inoculation were subsequently performed (Table 4). Except for DENVax-4, all viruses (wt and DENVax) achieved 100% infection of the IT inoculated *Ae. aegypti*. The DENVax-4 inoculum had a slightly lower viral titer than the other three viral inocula, but it still successfully infected 70% of the inoculated mosquitoes. Despite the high body infection rates achieved by IT inoculation, all four DENVax viruses exhibited significantly lower ($p<0.005$) or non-detectable transmission rates (0-10%) compared to the wt Dengue viruses (43-87%, Table 4). The DENVax viruses demonstrated little to no infection and dissemination after oral feeding, and the highly stringent IT results affirmed the minimal transmission capacity of these DENVax viruses in *Ae. aegypti*.

TABLE 4

Virus infection, dissemination, and transmission rates in whole mosquitoes

| | Oral Feed | | | | | IT inoculation | | | | |
|---|---|---|---|---|---|---|---|---|---|---|
| Virus | Blood Meal[a] Mean ± SD | Infection[b] % (P/N) | Body Titer[c] Mean ± SD | p[d] | Dissemination[e] % (P/N)[f] | Inoculum pfu/dose | Infection[b] % (P/N) | Body Titer[c] Mean ± SD | Saliva[f] % (P/N) | p[d] |
| DENV-1 16007 | 6.6 | 44.0% (11/25) | 3.6 ± 1.5 | | 36.3% (4/11) | 53.9 | 100% (30/30) | 4.7 ± 0.48 | 43% (13/30) | |
| DENVax-1 | 6.9 | 0% (0/30) | NA | <0.0001 | NA | 67.8 | 100% (30/30) | 3.4 ± 0.39 | 10% (3/30) | <0.005 |
| DENV-2 16681 | 6.6 | 43.3% (13/30) | 3.1 ± 1.5 | | 38.5% (5/13) | 67.8 | 100% (30/30) | 5.2 ± 0.34 | 87% (26/30) | |
| D2 PDK53-VV45R | 6.4 | 0% (0/30) | NA | <0.0001 | NA | 56.4 | 100% (30/30) | 4.0 ± 0.20 | 0% (0/30) | <0.0001 |
| DENVax-2 | 6.4 | 0% (0/30) | NA | <0.0001 | NA | 52.7 | 100% (30/30) | 3.5 ± 0.27 | 7% (2/30) | <0.0001 |
| DENV-3 16562 | 5.2 | 8% (2/25) | 3.8 ± 0.2 | | 50% (1/23) | 34.0 | 100% (30/30) | 4.2 ± 0.50 | 67% (20/30) | |
| DENVax-3 | 5.2 ± 0.02 | 0% (0/50) | NA | 0.108 | NA | 37.3 | 100% (30/30) | 3.3 ± 0.36 | 3% (1/30) | <0.0001 |
| DENV-4 1036 | 5.8 ± 0.5 | 16% (8/50) | 3.9 ± 1.5 | | 62.5% (5/8) | 69.4 | 100% (30/30) | 5.2 ± 0.45 | 70% (21/30) | |
| DENVax-4 | 5.4 ± 0.4 | 3.6% (2/55) | 0.7 ± 0.0 | 0.033 | 0% (0/2) | 11.8 | 70% (21/30) | 1.1 ± 0.46 | 0% (0/21) | <0.0001 |

[a]Virus titers or Mean ± standard deviation if from more than 1 experiment in blood meal ($\log_{10}$ pfu/ml) by back titration

[b]Rate of virus detected in mosquito bodies. P/N = positive/total mosquitoes

[c]Mean virus titers ± standard deviation ($\log_{10}$ pfu/mosquito) in mosquito body, only positive sample are included for calculation

[d]Statistic analysis of the differences between wt DENV and DENVax by Fisher Exact probability

[e]Rate of virus detected in legs of the positively infected mosquitoes

[f]Rate of virus detected in saliva of the positively infected mosquitoes. Used to measure transmission efficiency Vector competence is an important safety component for live-attenuated flavivirus vaccine viruses. Previously, the research-grade DENV-2 PDK-53-VV45R virus and wt derivatives were tested in *Ae. aegypti*, and found that the NS1-53-Asp attenuating mutation was the dominant determinant for impaired mosquito replication. The other two major attenuation loci of the DENV-2 PDK-53 vaccine, nucleotide 5'NCR-57-T and NS3-250-Val, also exhibited some inhibiting effect on replication in mosquitoes-, thus providing additional, redundant restrictions for mosquito vector competence. Some exemplary methods described herein were used to test the mosquito oral and IT infection and replication for all four DENVax strains. DENVax-1, -2, and -3 did not infect any *Ae. aegypti* mosquitoes through oral infection (Table 4). The DENVax-4 infected only 3.6% of orally exposed mosquitoes, a level significantly lower than that of the wt DENV-4 with a replicative mean titer in the mosquito bodies lower than that of wt DENV-4 infected mosquitoes. Surprisingly, DENVax-4 was detected in the legs of the infected mosquitoes, suggesting that DENVax-4 was not able to disseminate from the mosquito midgut following oral infection. The infection rates for the DENVax-1, -2, and -4 were all significantly less than their wt counterparts, but the difference was not significant between DENVax-3 and wt DENV-3 16562 due to the very low infection rates for both viruses. Compared to other wt strains of DENV assessed in *Ae. aegypti* collected from the same Mae Sot Province, Thailand, the parental wt Dengue virus strains used for engineering DENVax appeared to have lower infectious and dissemination rates by oral infection. The wt DENV-1 PUO0359, DENV-2 PUO218, DENV-3

PaH88/88, and DENV-4 1288 used for engineering the Yellow Fever (YF) 17D vaccine-based ChimeriVax-DEN vaccines had infection rates ranging 47-77%. In contrast, the YF 17D vaccine cannot infect *Ae. aegypti*. Although the ChimeriVax strains contained the prM-E from these highly infectious wt DENV, the ChimeriVax retain the mosquito attenuation phenotype of their YF 17D replicative backbone. Results provided herein also indicated that the mosquito attenuation of DENV-2 PDK-53 backbone was maintained in the DENVax strains. In addition, using the wt Dengue virus strains with lower mosquito-infectivity in constructs included in compositions described herein provides an additional safety feature.

The oral infection results illustrate that the DENVax had minimum mosquito infectivity and dissemination capacity. In addition, the more sensitive and stringent IT infection experiments were performed to further analyze the potential of DENVax to be transmitted by *Ae. aegypti*. The IT results demonstrated that all four DENVax viruses had non-detectable or minimal mosquito transmission potential compared to their wt counterparts. DENVax transmission could only theoretically occur if (1) vector feeds on a vaccinee with a sufficient viremia titer to infect mosquito midgut, (2) the virus is capable of replicating in the midgut epithelium and able to subsequently disseminate out of the midgut, and (3) the disseminated virus can replicate in salivary gland and expectorate sufficient virus in saliva for transmission. The threshold of human viremia required to infect mosquitoes has not been established adequately, but human viremia can be $10^6$-$10^8$ mosquito infectious dose$_{50}$ ($MID_{50}$)/ml after natural wt DENV infection. This $MID_{50}$ was based on direct IT inoculation of mosquitoes with diluted human plasma. Analysis of DENVax in nonhuman primates indicated that viremia titers following DENVax immunization were very low (less than 2.4 $\log_{10}$ pfu/ml) and lasted for 2-7 days. Given the low viremia levels and the low mosquito infection, dissemination, and transmission capacity of DENVax, it is unlikely that these vaccine viruses could be transmitted by mosquitoes in nature or cause viremia.

Therefore, it is proposed that any of the passages of any of the serotypes (P1-P10) could be used in a composition to generate a safe and effective vaccine against one, two, three or all four dengue virus serotypes.

Neurovirulence in Suckling Mice

Figure 5A:
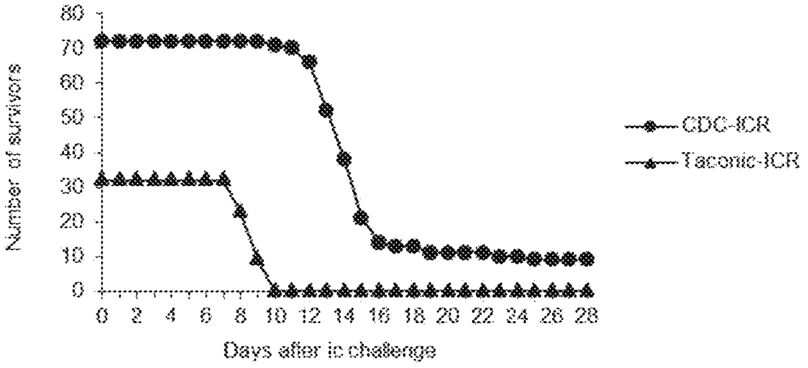
FIGS. 5A-5C represent exemplary plots of neurovirulence in newborn mice.

The original research-grade vaccine viruses were highly attenuated for neurovirulence in newborn ICR mice maintained in-house at DVBD/CDC. All of these mice survived ic (intracerebral) challenge with $10^4$ pfu of each vaccine virus. The wt Dengue virus serotype-2 16681 virus, on the other hand, resulted in 62.5%-100% mortality in these CDC-LCR mice in various experiments. In some experiments, commercial ICR mice obtained from Taconic Labs (Taconic-ICR) were used to study neurovirulence in newborn mice. It was observed that newborn Taconic-ICR mice were significantly more susceptible to Dengue virus serotype-2 infection than the previous CDC-LCR mice. FIG. 5A summarizes the neurovirulence of wt Dengue virus serotype-2 16681 in CDC-ICR colony and Taconic-ICR, newborn mice challenged ic with $10^4$ pfu of the virus. The Taconic-ICR mice (100% mortality in 32 mice, average survival time of 8.3±0.5 days) were more susceptible to ic Dengue virus serotype-2 16681 challenge than the previous CDC-ICR mice (91% fatalities in 72 mice, average survival time of 14.6±2.3 days).

Figure 5B:
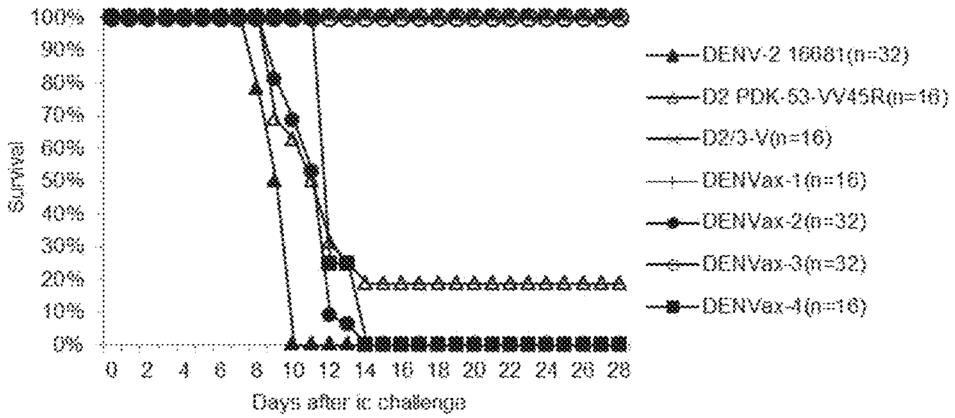

In other exemplary methods, in order to evaluate neurovirulence of the DENVax MVS, the Taconic-ICR mice initially were challenged ie (intracerebrally) with a dose of approximately $10^4$ pfu of wt Dengue virus serotype-2 16681, D2 PDK-53 VV45R, D2/3-V, or DENVax 1-4 virus in one (n=16) or two (n=31-32) experiments (FIG. 5B). At this dose, D2/3-V research grade virus, as well as DENVax-1, and DENVax-3 MVS exhibited fully attenuated neurovirulence phenotypes (no illness or mortality). As expected, wt Dengue virus serotype-2 was found to be "fatal", with average mouse survival time (AST) of 8.3±0.8 days. In these Dengue virus serotype-2-sensitive Taconic-ICR mice, the D2 PDK-53-VV45R research grade virus resulted in 81.3% mortality. The DENVax-2 MVS and DENVax-4 MVS were uniformly fatal in the Taconic-ICR, showing AST values of 9.8±1.7, 10.2±1.4, and 11.3±0.4 days, respectively.

Figure 5C:
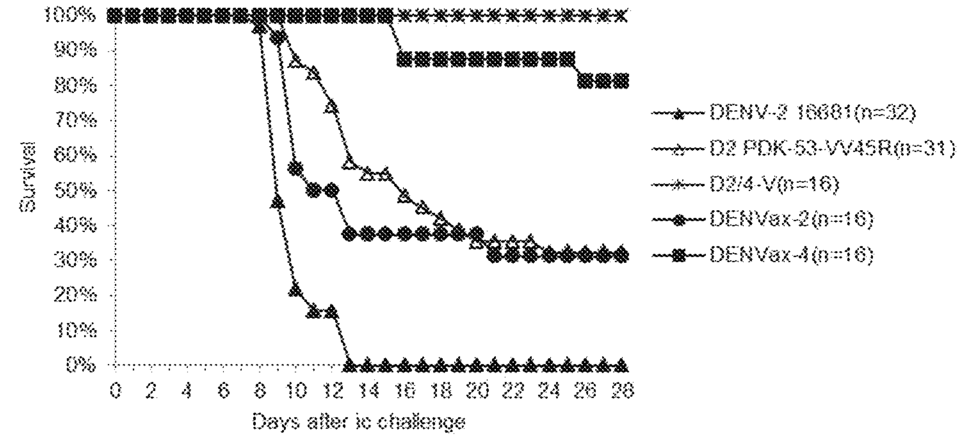

In some exemplary methods, the neurovirulence of wt Dengue virus serotype-2 16681 virus was compared with that of D2 PDK-53 VV45R, DENVax-2 MVS and DENVax-4 MVS, as well as D2/4-V research grade virus, at a 10-fold lower dose (10-pfu, FIG. 5C). The wt Dengue virus serotype-2 retained a uniformly fatal neurovirulent phenotype, with AST of 9.0±1.4 days, at this lower challenge dose. The other 4 viruses exhibited intermediate neurovirulence phenotypes, and the degree of neurovirulence was serotype-specific. The D2 PDK-53-VV45R virus and its DENVax-2 MVS cognate showed significant attenuation (32.3% survival with AST of 13.1±3.8 days and 31.2% survival with AST of 10.5±3.4 days, respectively). Both the DENVax-4 MVS and the research grade D2/4-V virus were highly attenuated for neurovirulence (81.3% survival with AST of 18.8±5.8 days and 100% survival, respectively). The results suggested that MVS of DENVax-1 and -3 exhibited complete attenuation of neurovirulence, while DENVax-2 and -4 MVS lots retained attenuation phenotypes that closely resembled their homologous research-grade virus vaccine candidates.

FIGS. 5A-5C represent exemplary graphs illustrating neurovirulence in newborn mice tested with various compositions including wt Dengue virus serotype-2 and different attenuated Dengue viruses. Pooled results of numerous experiments summarizing the neurovirulence of wt Dengue virus serotype-2 16681 virus in CDC-ICR (n=72) and Taconic-ICR (n=32) newborn mice challenged ic with $10^4$ pfu of the virus (A). Neurovirulence of DENVax MVS tested in Taconic-ICR mice with a dose of $10^4$ pfu (B) or $10^3$ pfu (C). The numbers of animals tested per group in one experiment (n=16) or two pooled experiments (n=31 or 32) are indicated.

Plaque Phenotype of WVS, and BVS

Figure 6:
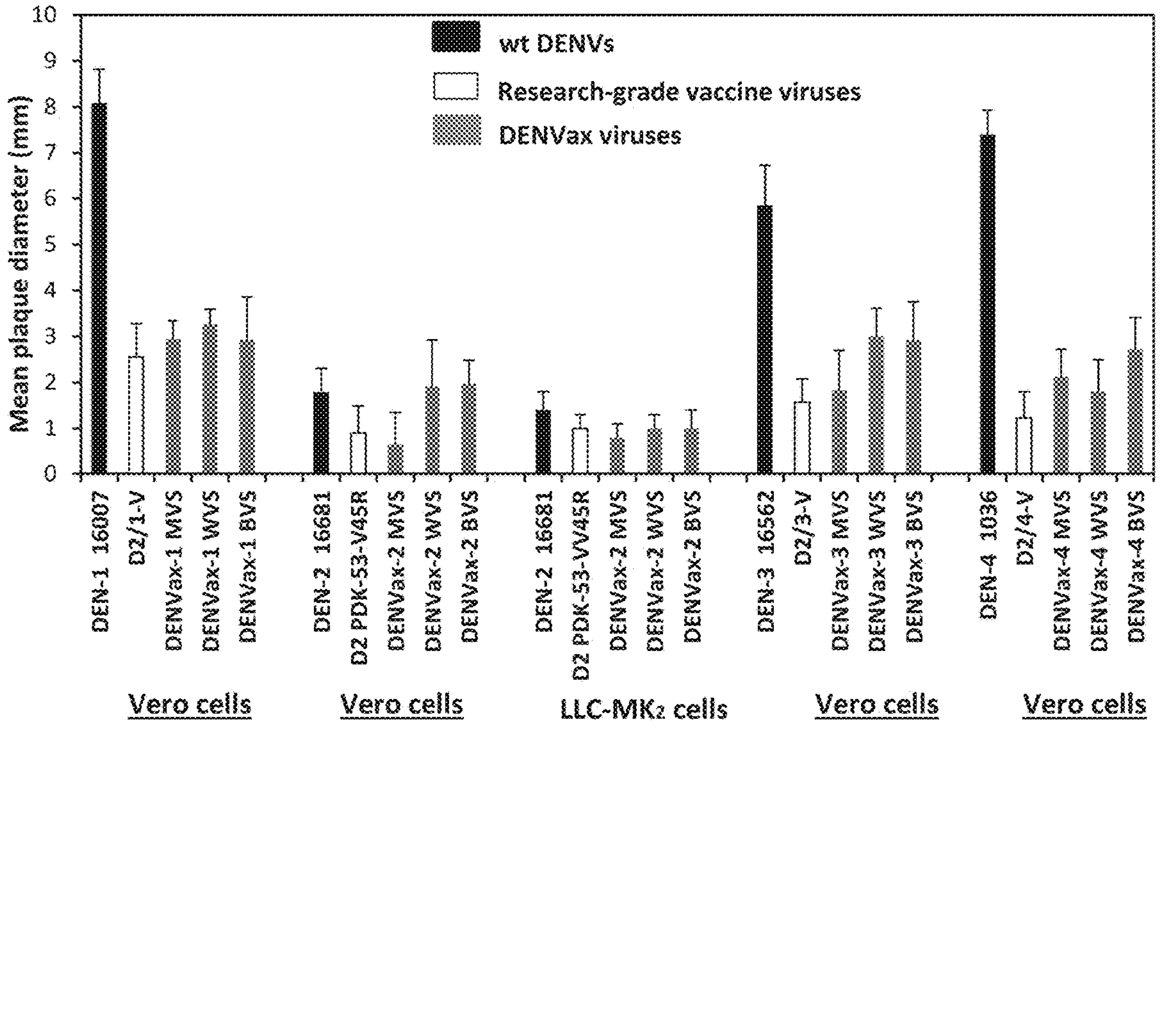
FIG. 6 represents an exemplary histogram illustrating plaque size of the DENVax MVS, WVS, and BVS. Mean plaque diameters±SD (error bars) of the virus plaques in Vero or LLC-$MK_2$ cells under agarose overlay measured on day 9 pi. Wild type DENVs and previously published research-grade vaccine candidate viruses were included for control and comparison.

Certain studies were performed to compare plaque phenotypes of WVS and BVS with MVS, wt Dengue viruses and their homologous lab derived, research-grade chimeras in Vero cells (FIG. 6). Mean plaque sizes were calculated from 10 plaques for each vaccine virus, but from reduced numbers of wt DENV-1, -3, and -4. All of the MVS viruses of DENVax-1, -2, and -3 produced plaques that were significantly smaller than their wt homologs and very similar (within 0.4-mm differences) to their homologous research-grade viruses in Vero cells. DENVax-4 MVS was also significantly smaller than the wt DENV-4, but was slightly (0.9 mm) larger than the original lab derived D2/4-V chimera. With the exception of the DENVax-2, all of the WVS and BVS of the DENVax-1, -3, -4 retained significantly smaller plaque sizes than those produced from their wt homologs. The DENVax-2 WVS and BVS produced plaques that were similar to the plaques of wt DENV-2 virus in Vero cells, but when tested in LLC-$MK_2$ cells all of the DENVax-2 manufactured seeds produced plaques that were somewhat smaller than those of the wt DENV-2 (1.4±0.4) and similar to the lab derived D2 PDK-53-VV45R (1.0±0.3) (FIG. 6).

Evaluation of the phenotypic markers of viral attenuation, including small plaque phenotype, temperature sensitivity, reduced replication in mosquito cells, reduced infection/dissemination/transmission by mosquitoes, and reduced neurovirulence in newborn ICR mice, were assessed for the compositions of MVS stocks. Results indicated that all of the DENVax retained the expected attenuation phenotypes similar to the original research-grade vaccine viruses. Given the mutations responsible for attenuation are conserved in all MVS, WVS and BV, it can be expected the attenuated phenotypes to be retained in the material manufactured for human clinical testing.

FIG. 6 represents an exemplary histogram illustrating plaque size of the DENVax MVS, WVS, and BVS. Mean plaque diameters±SD (error bars) of the virus plaques in Vero or LLC-$MK_2$ cells under agarose overlay measured on day 9 pi. The wt DENVs and previously published research-grade vaccine candidate viruses were included for control and comparison.

Virus Replication in Mosquito C6/36 Cells

Figure 7:
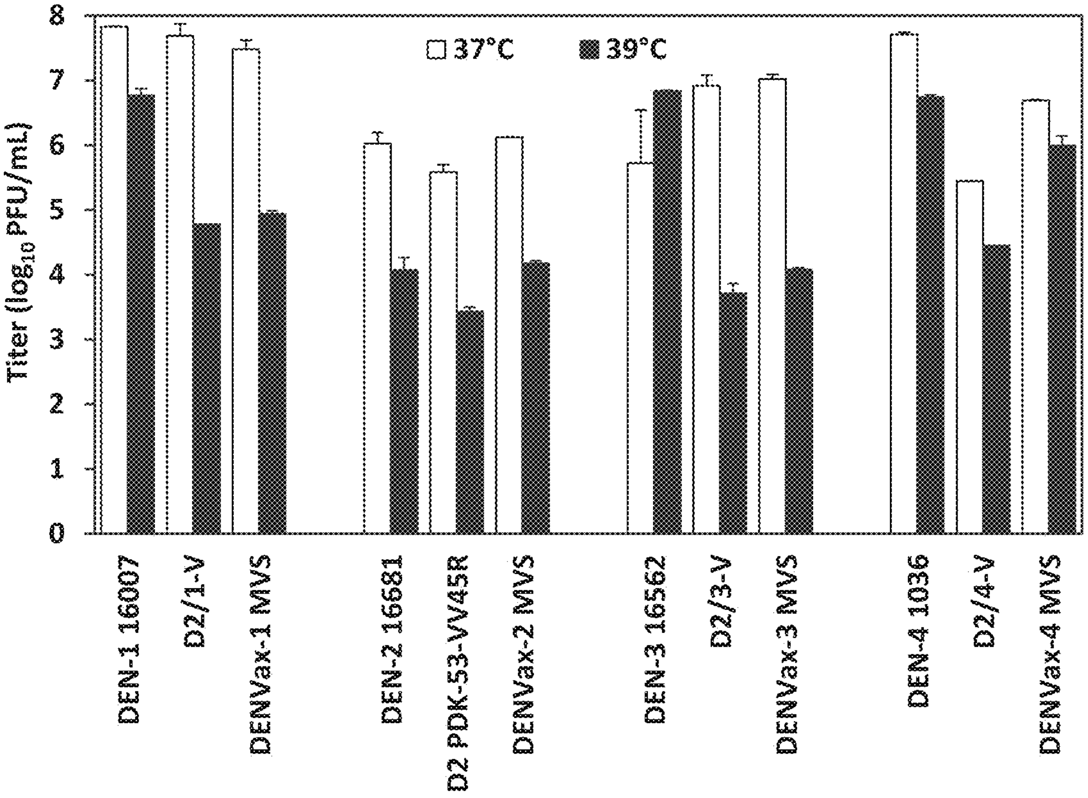
FIG. 7 represents an exemplary histogram plot illustrating growth of DENVax MSV, WVS, and BVS in C6/36 cells at two incubation temperatures to verify their retention of this in vitro attenuation marker after large scale manufacturing.

Previous studies demonstrated that the research-grade PDK-53-based chimeric vaccine viruses retained the attenuation phenotype of the backbone DENV-2 PDK53 virus in C6/36 cells. In some exemplary methods, the DENVax MSV, WVS, and BVS were grown in C6/36 cells to verify their retention of this in vitro attenuation marker after large scale manufacturing. Compared to the wt Dengue viruses, except for DENVax-3, the manufactured seeds showed marked growth reduction (at least 3 $\log_{10}$ PFU/ml reduction) in C6/36 cells on day 6 pi (FIG. 7). The DENVax-3 seeds also exhibited reduced growth compared to the wt DENV-3 16562, but the reduction was not as marked (1-2 $\log_{10}$ PFU/ml reduction). However, the titers of the DENVax-3 seed lots were similar (within 1 $\log_{10}$ PFU/ml difference) to the original research-grade chimeric D2/3-V vaccine virus.

Figure 8:
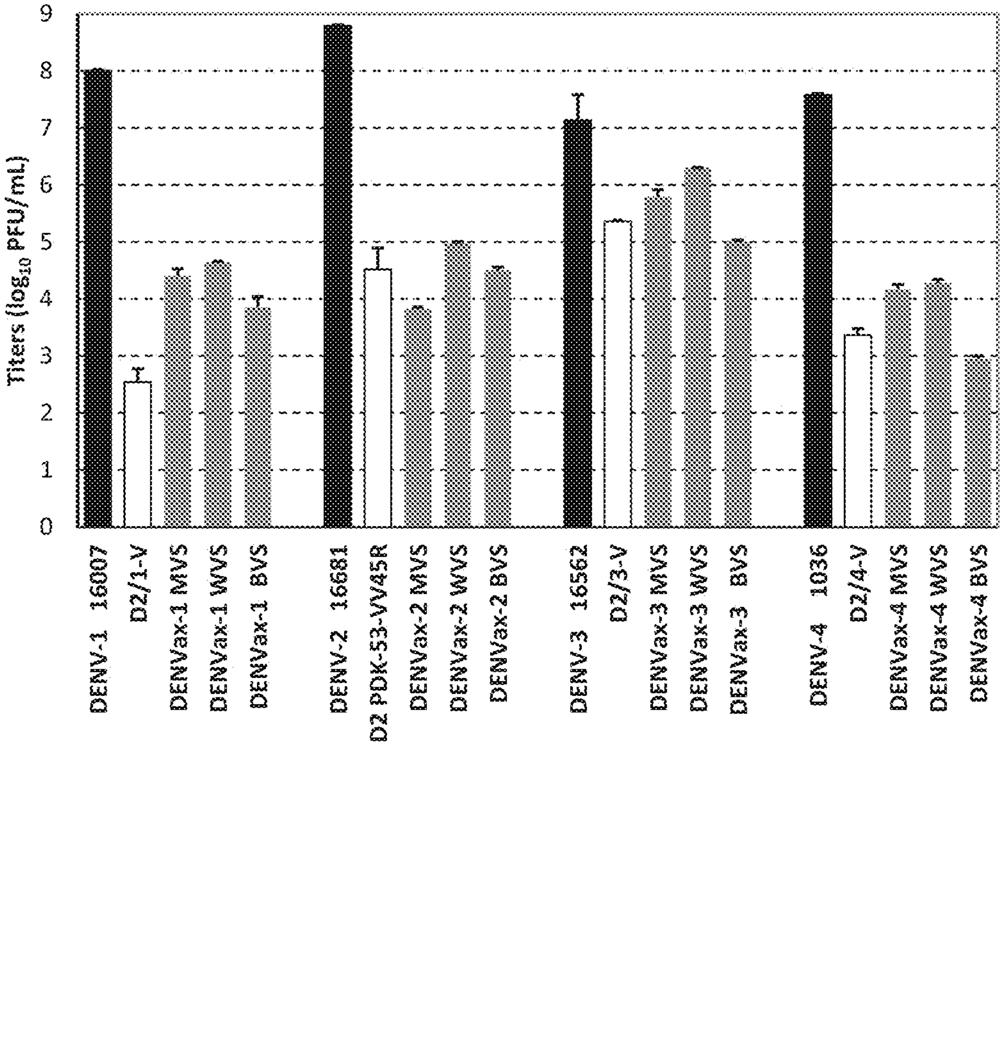
FIG. 8 represents an exemplary histogram plotting restricted growth of DENVax MVS, WVS, and BVS in C6/36 cells. Mean titers±SD (error bars) of the viruses replicated in C6/36 cells 7 days pi. The wt Dengue viruses and previously published research-grade vaccine candidate viruses were included for comparison.

FIG. 8 represents an exemplary histogram plotting restricted growth of DENVax MVS, WVS, and BVS in C6/36 cells. Mean titers±SD (error bars) of the viruses replicated in C6/36 cells 7 days pi. The wt Dengue viruses and previously published research-grade vaccine candidate viruses were included for comparison.

Neurovirulence in Suckling Mice

Additional experiments were performed to analyze neurovirulence in newborn ICR mice. At an intracranial dose of $10^4$ PFU, the survival rates for wt DENV-2 16681 and the D2 PDK-53-VV45R were 0% and 18.8%, respectively (FIG. 9A) in the ICR mice, but were about 20% for wt DENV-2 16681 and 100% for the D2 PDK-53-VV45R in the CDC ICR, mice. In this study, DENVax-1 and DENVax-3 MVS were attenuated (100% survival) for the mice at a dose of $10^4$ PFU, but the MVS of DENVax-2 and DENVax-4 caused 100% mortality at the dose of over $10^4$ PFU (FIG. 5A). However, when tested at a dose of $10^3$ PFU of virus, the DENVax-2 (31.3% survival) and DENVax-4 (81.3% survival) showed reduced neurovirulence relative to wt Dengue virus serotype-2 16681 (0% survival), and their survival rates were similar to those of the research-grade vaccine candidates D2 PKD-53-VV45R (32.3%) and D2/4-V (100/), respectively (FIG. 91). Although, wt DENV-1, -3, or -4 were not included for comparison in this study, previous work demonstrated that wt DENV-1 16007 was attenuated in the CDC-ICR mice by the ic route, while both wt DENV-3 16562 and DENV-4 1036 were highly virulent (0% survival) for the CDC-ICR mice. It is likely that these 3 wt DENV would exhibit similar or greater virulence in the more susceptible Taconic ICR mice. Therefore, inclusion of these wt Dengue viruses for comparison with their homologous DENVax MVSs was considered to be uninformative. This study indicated that all 4 DENVax MVSs and original laboratory derived candidate vaccine viruses exhibit comparable mouse attenuation phenotypes relative to the wt DENV-2 16681.

Figure 9A:
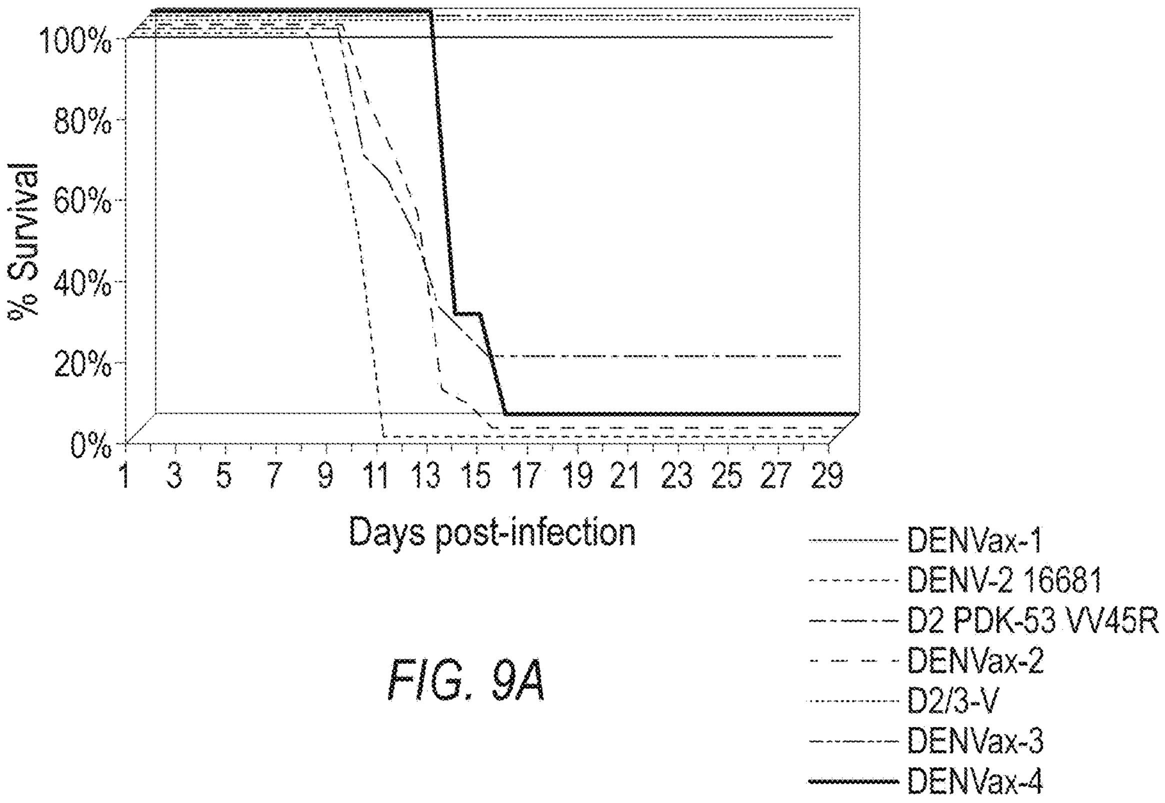
FIGS. 9A-9B represent exemplary graphs of data of neurovirulence of DENVax MVS in newborn ICR mice.
Figure 9B:
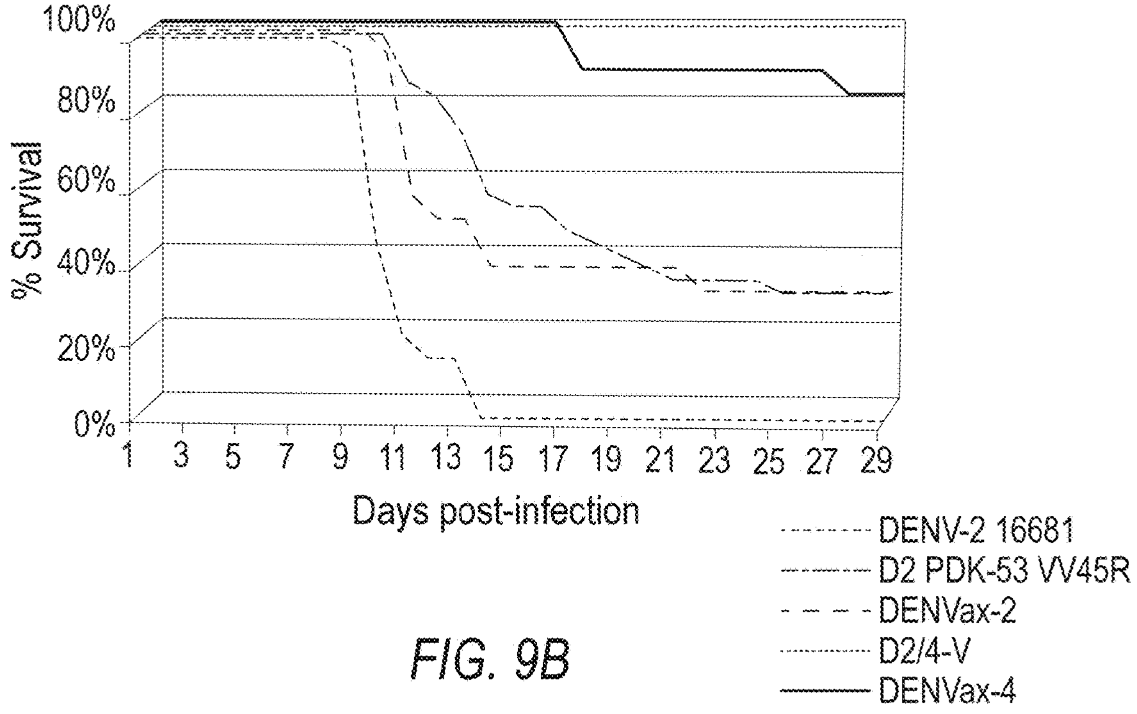

FIGS. 9A-9B represent exemplary graphs of data of neurovirulence of DENVax MVS in newborn ICR mice. (A) IC inoculations of the virus at dose of $10^4$ PFU. (B) IC inoculation of the virus at dose of $10^3$ PFU All seed lots of the DENVax were tested for the identity, sterility, and freedom from undesirable agents. Full-genome sequence analysis revealed that one extra amino acid mutation evolved in the DENVax-4 MVS, while the other 3 DENVax MVSs retained the consensus genome sequence of their pre-master seeds. In WVS lots, the DENVax-3 acquired an extra amino acid mutation and the other 3 serotypes accumulated 2 extra amino acid substitutions, relative to their pre-master seeds. Genome sequences of all the 4 BVS lots were identical to their WVS lots. Overall from the P2 seeds to the pre-master (P7) seeds, only 1 or 2 non-silent mutations occurred in a given seed. Between pre-master and BCS (P10) seeds, only 1 to 2 nucleotide substitutions were observed, all of which occurred in NS2A, 4A, or 4B, with the exception of single nucleotide change resulting in a conserved glycine and alanine at residue E-483. From P2 to BVS (P10) seeds, total 3 to 8 nucleotide substitutions were identified in any given DENVax seed, and only 2 to 4 of these substitutions resulted in amino acid changes. None of the silent mutations in the BVS were within the 5'- or 3'-NCR region which may affects virus replication. These results suggest that the DENVax viruses were genetically highly stable during manufacture. The three defined DENV-2 PDK-53 attenuation loci located in 5'NCR, NS1-53, and NS3-250 remained unchanged in the consensus genome sequence upon serial passage of the DENVax to generate BVS stocks. The highly sensitive TaqMAMA of the 5'-NCR-57 locus showed minimal or undetectable reversion in the MVS, WVS, and BVS of DENVax. The highest reversion rate of 0.21% was identified in the DENVax-2 BVS. The reversion rates of the P10-equivalent BVS (<0.07% to 0.21%) were significantly lower than the reversion rates that evolved in other vaccine candidates after serial passages in Vero cells (4-74% reversion by P10). This suggests that this strategy for large scale manufacturing of the DENVax seeds is successful, regarding maintaining genetic stability and retention of attenuation markers in the candidate vaccine viruses.

Since MVS stocks disclosed herein will be used for future manufacturing of WVS and BVS lots, full panels of virus attenuation phenotype evaluations, including small plaque phenotype, temperature sensitivity, reduced replication in mosquito cells, reduced infection/dissemination/transmission in whole mosquitoes, and reduced neurovirulence in newborn ICR mice, were conducted for all MVS or their equivalent surrogate stocks. For the WVS and BVS stocks, plaque size, infectivity in mosquito cells, were also performed to confirm their attenuations. Results indicated that all the MVS stocks of the 4 serotypes of DENVax retained the expected attenuation phenotypes, such as small plaques, reduced replication in C6/36 cells, and reduced mouse neurovirulence, similar to the original lab-derived vaccine viruses (FIGS. 6, 8, and 9). Except for the DENVax-4, all other 3 MVS stocks of DENVax were TS at 39° C. as shown in FIGS. 3 and 7.

For the WVS and BVS stocks, two attenuation phenotypes, small plaques and restricted replication in C6/36 cells, were analyzed and confirmed. Since there are very little genetic changes between the MVS and BVS, it was expected that they would retain the attenuation phenotypes as MVS. In addition to the experiments described in this report, safety and immunogenicity of the manufactured DENVax in Ag129 mice and nonhuman primate have been tested.

Exemplary methods are provided herein to demonstrate manufacture of DENVax MVS, WVS, and BVS stocks under cGMP. The BVS stocks were used to formulate the tetravalent DENVax currently in human clinical trial evaluations. A unique manufacture strategy to optimize the genetic stability and safety of the manufactured MVS was provided in some exemplary methods. Since the main attenuation loci of the DENVax have been well characterized previously and a highly sensitive and quantifiable SNP assay, TaqMAMA was developed to integrate genome sequence and the TaqMAMA to identify optimal pre-master seeds for making the MVS. The genetic and phenotypic characterizations of the MVS were fully analyzed to confirm that these viruses retained desirable attenuations for safety of the vaccine. This may be the only live, attenuated viral vaccine that can be efficiently analyzed for all the major attenuation genetic loci during manufacturing from pre-master all the way to BVS stocks. Results provided herein exemplified the advantage of strategically designed live-attenuated vaccines in vaccine safety.

FIG. 10 represents an exemplary table comparing new live, attenuated viruses to previously generated live, attenuated dengue viruses. Mutations are indicated where different from a control virus (e.g. 16681), or other live, attenuated dengue-2 viruses.

Materials and Methods

Viruses and Cells

DENV-1 16007, DENV-2 16681, DENV-3 16562, and DENV-4 1034 served as wild-type (wt) DENV controls, and they were the parental genotype viruses for the four recombinant DENVax vaccine candidates. DENVax progenitor research-grade viruses, designated as D2/1-V, D2 PDK-53-VV45R, D2/3-V, and D2/4-V, were prepared and characterized previously. Vero (African green monkey kidney) cells used for making the master and working cell banks for vaccine production were originated from the American Type Culture Collection (ATCC) CCL81 cell line that has been characterized by the World Health Organization (WHO) for vaccine manufacture (WCB-Vero cells).

Derivation of Live Recombinant DENVax Viruses from cDNA Clones

To re-derive the candidate vaccine viruses under cGMP manufacturing conditions, the previously engineered DENV infectious cDNA clones, pD2-PDK-53-VV45R, pD2/1-V, pD2/4-V, and in vitro-ligated pD2/3-V containing the fill genome-length viral cDNAs were used to make fresh viral RNA transcripts by in vitro transcription as described previously. Briefly, XbaI-linearized DENV genomic cDNAs were treated with proteinase K, extracted with phenol/chloroform and precipitated in ethanol to remove any residual proteins, and then suspended in RNase-free Tris-EDTA buffer prior to transcription. The in vitro transcription was conducted using the AmpliScribe T7 High Yield Transcription kit (Epicentre Technologies) following the manufacturer's recommended protocol. The RNA A-cap analog, m7G(5')ppp(5') A (New England BioLabs), was incorporated during the 2-hr transcription reaction to add the 5'-terminal A-cap to the RNA transcript. The samples were then treated with DNase 1 to digest the template cDNA, followed by low pH phenol/chloroform extraction and ethanol precipitation to remove residual DNA and proteins. The purified RNA transcripts, suspended in RNase-free water, were distributed in 20-μl aliquots and stored at −80° C. until ready for transfection of cells. The integrity and concentration of the RNA transcripts were analyzed by agarose gel electrophoresis. Each 20-μl aliquot was estimated to contain sufficient genome-length viral RNA to permit transfection of $0.4\text{-}1\times10^7$ production-certified Vero cells by electroporation.

Transfection of each RNA transcript into WCB-Vero cells was performed in the cGMP facility at Shantha Biotechnics. DENVax RNA transcripts were thawed, mixed with 400 μl of the Vero cell suspension ($1\times10^7$ cells/ml), and transferred to a pre-chilled sterile electroporation cuvette (4-mm gap) for electroporation by a Gene Pulser Xcell total system (BioRad Laboratories). Each sample was pulsed once at 250V/∞Ohms/500 μF, incubated for 10-15 min at room temperature, transferred to a 75-$cm^2$ flask containing 30 ml of cell growth medium (MEM with 10% FBS), and incubated at 36° C.±1° C., 5% $CO_2$ for 6 to 11 days. The culture medium was harvested, clarified by centrifugation, stabilized, and stored in small aliquots below −60° C. The viral titers of candidate vaccine stocks (termed P1 for passage level 1) resulting from transfection were determined by plaque titration assay in Vero cells and used for further propagation of the DENVax seeds.

Manufacture of DENVax Virus Seeds

P1 virus seeds were used to propagate DENVax pre-master, master, working, and bulk virus seed lots through a strategy designed to ensure the optimal genetic stability and safety of the manufactured lots. This strategy included three serial plaque purifications, as well as genetic analyses of viruses at various passage levels to select the optimal clonal virus population for continued seed production (Table 1). Briefly, the P1 seeds harvested from transfected cells were amplified once by infection of Vero cells at a MOI of 0.001 to generate the P2 seeds. Aliquots of the P2 seed stocks were evaluated by plaque morphology and complete viral genomic sequencing. The genetically confirmed P2 stocks were plated on Vero cell monolayers with overlay medium as described in the plaque titration section below to generate well-isolated plaques. After visualization with neutral red, six individual plaques from each of the 4 serotypes of vaccine viruses were isolated (plaque clones A to F) and mixed into 0.5 ml of culture medium (passage P3). Each of the six plaque suspensions was subjected to two additional rounds of plaque purification, resulting in twice- and thrice-plaque purified virus seeds at passages P4 and P5, respectively. The P5 viruses were amplified through two sequential Vero passages to produce P7 seed stocks.

Genetic analysis of the three major DENVax attenuation loci using spot sequencing and/or Taqman-based mismatched amplification mutation assay (TaqMAMA) as previously disclosed, and plaque phenotype analysis were conducted to screen all 24 P7 seeds. Seeds possessing appropriate initial characteristics were then further characterized by full genomic sequencing. As a result of these analyses, one of the 6 (clone A-F) P7 seeds of each DENVax serotype was selected to be the pre-master seed, based on the presence of the DENV-2 PDK-53 attenuating mutations, minimal genomic sequence alterations, and expected plaque phenotype. Each selected pre-master seed was expanded to master virus seed (MVS or P8) by a one-time passage of the virus at MOI of 0.001 in multiple 175 $cm^2$ flasks of Vero cells. Except for the DENVax-4 MVS, the master virus seeds were harvested at 8-10 days post infection (pi). The MVS stocks were harvested at 6-10 days post infection (pi), clarified by centrifugation, stabilized by the addition of sucrose/phosphate/glutamate solution (final concentration 7.5% sucrose, 3.4 mM potassium dihydrogen phosphate, 7.2 mM dipotassium hydrogen phosphate, 5.4 mM monosodium glutamate, respectively) and 0.95 to 1.90% FBS (final concentration). DENVax-4 MVS was prepared differently to optimize its yield. Briefly, multiple flasks of cells were infected with DENVax-4 pre-master seed at a MOI of 0.001 in the presence of 0.1% F-127T', poloxamer 407, (other EO-PO block copolymers have been assessed and may substitute here, see issued patent) that have been demonstrated to enhance DENV virus thermal stability. Infectious media was harvested days 6-10 pi, and stabilized with 17% FBS (final concentration), pooled, and frozen. All four DENVax MVS stocks were stored as 1-mi aliquots below −60° C.

The DENVax working virus seeds (WVS) were prepared by one-time passage in Vero cell culture of the MVS at a MOI of 0.001. The procedures were similar to the production of MVS, except they were cultured in multiple-layer cell factories (6360 $cm^2$). The WVS stocks were filtered through 10 μM and 0.45 μM filters, stabilized with the same stabilizers used for the MVS, aliquoted into 30 ml PETG bottles or 2.0 ml cryovials, and stored below −60° C.

In certain methods, bulk virus seeds (BVS) were produced by infecting multiple cell factories (6360 $cm^2$ each) of confluent Vero cells with 90 mL of diluted WVS to attain a MOI of 0.001. A media used for dilution of the WVS inocula contained 0.1% F-127™ without scrum. After 1.5 hr adsorption, cells were washed 3 times with PBS, and 800 ml of serum-free DMEM medium was added to each cell factory, and the factories were incubated at 36(±1)° C. in 5(±0.5)% $CO_2$. After incubation for four days, small aliquots of medium were collected for sterility testing. Viruses were harvested between day 5 and day 10 pi, and immediately clarified by filtration through a 0.45 um pore size filter, and 1 L of each clarified virus pool was stabilized by addition of 500 ml of 3× FTA buffer (final concentrations of 15% trehalose, 1.0% Pluronic® F-127™ poloxamer 407, 0.1% human albumin USP in PBS, pi 7.4). The stabilized virus was distributed into I-L PETG bottles and stored frozen below −60° C. for subsequent pooling and quality control testing. All stabilized virus harvests with a virus titer above $10^5$ PFU/ml and an acceptable level of residual DNA were rapidly thawed in a water bath at 32° C., then aseptically pooled and mixed. Each pooled monovalent BVS was distributed into labeled PETG containers and stored at below −60° C. until further use.

Manufacture Product Quality Controls

The MVS, WVS, and BVS seeds were tested for identity, sterility, and detectable adventitious agents. The identity of each vaccine stock was confirmed by RT-PCR with DENVax serotype-specific primers. The amplified cDNA fragments contained the E/NS1 chimeric junction site to permit identification of each of the four DENVax serotypes. Each seed was tested in all 4 serotype-specific RT-PCR reactions to confirm viral identity and freedom from cross contamination with heterologous DENVax serotypes. Sterility testing was performed in accordance with USP 71 (United States Pharmacopeia, section 71). *Mycoplasma* testing was performed.

The following in vitro and in vivo tests for viral contamination were all performed using unclarified, unstabilized DENVax harvests collected during manufacture of the seeds. Harvested infectious media were first neutralized with DENV rabbit polyclonal antiserum (Inviragen) at 36±1° C. for 1 hr to inactivate the DENV. For in vitro test, the neutralized seeds were inoculated into three indicator cells lines, MRC5. VERO and MA 104, in 25 $cm^2$ flasks. Echo virus (CPE control) or mumps virus (hemadsorption control) were used as positive CPE or hemadsorption control, respectively. All cells were monitored daily for CPE for a total of 14 days. At the end of 14 days, the culture supernatant was removed and replaced with 10 mL of a guinea pig red blood cell (RBC) solution (3 mL of 0.5% guinea pig RBC in phosphate buffered saline, made up to 10 mL with cell growth medium). The flasks were then incubated at 5±3° C. for 30 minutes followed by incubation at room temperature for 30 minutes. The monolayers were washed with PBS and observed under 10× magnification for the presence of any star-shaped clumps of RBCs for hemadsorption.

In vivo tests for adventitious agents were performed in suckling mice, post-weaning mice and guinea pigs. Suckling mice were inoculated with 0.1 ml or 0.01 ml (10 mice in each dose group) of the DENV-antiserum neutralized seed sample through intraperitoneal (ip) injection. Similarly, 10 post-weaning mice were each inoculated ip with 0.5 ml or 0.03 ml of the sample. Guinea pigs (5/group) were each inoculated ip with 5.0 mL. Suckling mice were observed daily for morbidity and mortality for a total of 14 days following inoculation. Post-weaning mice were observed for a total of 28 days, and guinea pigs were observed for a total of 42 days following inoculation. The test articles met the acceptance criterion if ≥80% of the inoculated animals remained healthy throughout the observation period.

The in vivo testing for contaminants was also performed in embryonated chicken eggs and was conducted. For every sample, 10 embryonated hen eggs (9 days old) were each inoculated with 0.5 mL of the DENV antiserum-neutralized sample into the allantoic fluid and incubated at 35° C. for 3 days. The allantoic fluids from these 10 eggs were harvested, pooled and passaged into the allantoic fluid of 10 fresh embryonated eggs (10-11 days old; 0.5 mL/egg) and incubated at 35° C. for a further 3 days. Similarly, for each sample, 10 embryonated eggs (6-7 days old) were each inoculated with 0.5 mL per egg (DENVax-2 monovalent BVS) or 0.25 mL per egg (DENVax-1, DENVax-3 and DENVax-4 BVS) by injection into the yolk sac and incubated at 35° C. for 9 days. The yolk sacs from these 10 eggs were harvested and pooled, and a 10% suspension was passaged into the yolk sacs of 10 fresh embryonated eggs (6-7 days old; 0.5 mL/egg) and incubated at 35° C. for a further 9 days. Eggs inoculated into the allantoic fluid (both initial and passage inoculations) were observed for viability after 3 days incubation. Both pools of allantoic fluid were tested for hemagglutination activity using chicken, guinea pig and human type O erythrocytes at 4° C. and 25° C. Eggs inoculated into the yolk sack (both initial and passage inoculations) were observed for viability after 9 days of incubation.

Virus Plaque Assay and Immunofocus Assay

Virus titers were measured by plaque assay or immunofocus assay using Vero cells. Plaque assays were performed in double agarose overlays in six-well plates of confluent Vero cells as previously described, and they were also used to evaluate the plaque phenotypes of the DENVax seeds. For accurate comparison, plaque sizes of all viruses were measured and compared in the same experiment. After visualization with neutral red on day 9 pi, up to 10 well isolated plaques for each virus were measured for mean plaque size calculation. Fewer plaques were measured for wt DENV-1, -3, and -4, whose larger plaque sizes often did not permit measurement of 10 well-separated plaques.

Because tetravalent DENVax contains all four DENV serotypes, a DENV serotype-specific immunofocus assay was developed to quantitate each DENVax component in the tetravalent formulations. Immunofocus assays of each individual DENVax MVS were compared with the plaque assays to ensure virus titration results were comparable between the two assays. The immunofocus assay was conducted in 6-well plates of confluent Vero cells infected with serially diluted viruses. Cells were overlayed with a balanced salt medium (BSS/YE-LAH medium) containing 0.7% high viscosity carboxymethyl cellulose (Sigma) and incubated for 7 days at 37° C. with 5% $CO_2$. After removal of overlays, cell sheets were washed 3 times with PBS, fixed with cold 80% acetone for 30 min at −20° C., washed once with PBS, and blocked with a blocking buffer containing 2.5% (w/v) nonfat dry milk, 0.5% Triton X-100, 0.05% Tween-20 in PBS at 37° C. for 30 min. Blocked cells were incubated with diluted DENV serotype-specific MAbs, IF1 (DENV-1), 3H5 (DENV-2), 8A-1 (DENV-3), or 1H10 (DENV-4) in blocking buffer at 37° C. for 1 hour or 4° C. overnight, washed 3 times with washing buffer (0.05% Tween-20 in PBS), and incubated with alkaline phosphatase- or horse radish peroxidase (HRP)-conjugated affinity-pure goat anti-mouse IgG (Jackson Immuno Research Laboratories) at 37° C. for 45-60 min. Plates were washed 3 times before the appropriate substrate, 1-Step NBT/BCIP plus suppressor (Pierce) for alkaline phosphatase or Vector-VIP kit (Vector Labs) for HRP, was added for color development. Color development was stopped by rinsing with water when the foci were fully developed. Stained immunofoci were directly visualized and counted on a light box.

Genetic Sequence

Full length genomes of the MVS and WVS were sequenced (see below). Briefly, viral RNA was extracted from DENVax seeds by using the QIAamp viral RNA kit (Qiagen), and overlapping cDNA fragments covering the entire genome were amplified using the Titan One Tube RT-PCR kit (Roche Applied Science, Inc.). The amplified cDNA fragments were gel purified before sequencing with both forward and reverse primers using the BigDye Terminator v3.1 cycle sequencing kit (Applied Biosystems). Sequence reactions were cleaned using the BigDye XTerminator Purification kit (Applied Biosystems), and run on the 3130×1 Genetic analyzer (Applied Biosystems) at DVBD/CDC. The Lasergene SeqMan software (DNAStar, Inc) was used for genome analysis and comparison.

Taqman-Based Mismatch Amplification Nutation Assay (TaqMAMA)

TaqMAMA is a sensitive, quantitative single nucleotide polymorphism assay developed to permit finer assessment of the level of reversion at the 5'NC-57 locus of attenuation, and was further optimized for this study. Extracted viral RNA from MVS and WVS were analyzed by the TaqMAMA with both sets of primers/Taqman probe that are specific to wt or the vaccine 5'NC-57 region. The forward primers used to detect DENV-2 wt and vaccine sequences were D2-41-GC and D2-40-TT, respectively. The 3'-terminal nucleotide of each forward primer matched the specific 5'NCR-57 nucleotide for each virus, while the nucleotide adjacent to the 3'-terminal nucleotide in each primer differed from the DENV-2 viral genomic sequence to enhance the mismatch effect. The reverse primer, CD-207, and the Taqman probe, CD-169F, for both wt and vaccine sets were identical. Sequences of the primers and probe as well as cycling conditions were described previously. The real time RT-PCR was performed with the iQ5 or CFX-95 system (BioRad), using a BioRad iScript RT-PCR (for probes) kit, in a 25-μl reaction containing 5 μl of viral RNA template, 0.4 uM of each primer, and 0.2 uM of the probe. Triplicate reactions for each wt- and vaccine-specific assay were conducted for each sample. Genome copy numbers were determined relative to a standard curve prepared for each viral genotype, where the RNA standards were transcripts derived from plasmids containing nt 1-2670 of each genotype-specific cDNA. In addition, the specificity of the assay was confirmed by testing each RNA standard with the heterologous genotype primer/probe sets to ensure minimum cross-reactivity in every experiment. The results were reported as the percentage of viral genomes showing reversion. Previously, due to higher cross-reactive backgrounds that limited the input RNA levels for this assay, the original detection sensitivity was about 0.1% reversion (discrimination power). Since then, the assay has been further optimized using improved real-time PCR equipment and reaction kits, and the cross-reactive background was decreased considerably at much high levels (7-8 $\log_{10}$ copies) of RNA template input. This optimization resulted in significant improvement of the detection sensitivity, down to 0.01-0.07% reversion.

Virus Replication in Mosquito C6/36 Cells and Temperature Sensitivity in Mammalian Vero Cells The replication phenotypes of the four DENVax MVS stocks and wt DENV-1, -2, -3, and -4 viruses were evaluated in C6/36 mosquito cells (*Aedes albopictus*). C6/36 cells grown in 6-well plates were infected in duplicate with each virus at a MOI of 0.001 and incubated with 4 ml/well of DMEM medium containing 2% FBS in a 5% $CO_2$ incubator at 28° C. Small aliquots of the culture supernatant were collected for each virus on day 6 pi, mixed with an equal volume of medium containing 40% FBS, and stored at ~80° C. until ready for virus plaque titration.

Temperature sensitivity was conducted by comparing viral growth at 39° C. versus growth at 37° C. at five days pi of Vero cells in 6-well plates. Cells were infected in quadruplicate with each virus at a MOI of 0.001 at 37° C. Following adsorption of virus, the infected cultures were incubated with 4 mL/well of DMEM medium containing 2% FBS in 2 separate 5% $CO_2$ incubators, one set (duplicate plates) at 37° C. and the other at 39° C. Aliquots (50-μl) of the culture supernatant were collected on day 5 pi, mixed with an equal volume of DMEM containing 40% of FBS, and stored at −80° C. until ready for virus plaque titration. Incubator temperatures were calibrated with NIST-traceable factory-calibrated thermometers (−1 to 51° C.; ERTCO).

Mosquito Infection, Dissemination, and Transmission

*Aedes aegypti* mosquitoes used for the study were from a colony established in 2002 from a village near Mac Sot (16' N, 33' E), Thailand. After emerging from larvae, adult mosquitoes were maintained at 28° C. at a 16:8 (light:dark) photoperiod with 10% sucrose solution provided ad libitum. Five-to-seven day old female mosquitoes were used for infectious blood meal feeding or intrathoracic (IT) inoculations. Aliquots of freshly cultured DENVax and wt DENV were used immediately upon harvest (without any freeze-thaw cycle) to make virus blood meals as indicated below for oral infection. Remaining virus supernatants were supplemented with FBS to a final concentration of 20%, and aliquots were stored at −80° C. for future virus plaque titration and IT inoculation experiments. The freshly prepared DENVax seeds for these experiments were amplified from the pre-master seeds in Vero cells, and were considered DENVax MVS equivalents.

Infectious blood meals were prepared by mixing fresh virus at a ratio of 1:1 with defribrinated chicken blood (Colorado Serum Company) on the day of oral infection.

Mosquitoes were sugar-starved overnight and then offered the virus:blood mixture for 1 hour using a Hemotek membrane feeding system (Discovery Workshops). A 50-μl aliquot of the blood meal was retained at −80° C. for back-titration of virus doses. Fully-engorged females were sorted under cold anesthesia and placed into cartons with 10% sucrose solution provided ad libitum. Cartons were placed at 28° C. with a photoperiod of 16:8 h (light:dark). After 14 days, 25-30 mosquitoes from each virus group were anesthetized via exposure to triethylamine (Flynap®, Carolina Biological Supply Company) and one hind leg was removed and placed in 0.5 ml of DMEM with 10% FBS and 5% penicillin/streptomycin (100 U/ml and 100 μg/ml respectively). Saliva was collected by inserting the proboscis of the anesthetized mosquito into a capillary tube containing 2.5% FBS and 25% sucrose solution. Mosquitoes were allowed to salivate for at least 15 minutes and then capillary tubes and bodies were placed into separate tubes containing DMEM. Mosquito bodies, legs and saliva were stored at −80° C. until they were triturated and assayed for infectious virus. For IT inoculation, mosquitoes were cold-anesthetized and inoculated with approximately 50 pfu of virus in 0.34 μl inoculum. Inoculated mosquitoes were kept for 7 days in the same conditions as described above. Mosquitoes were then anesthetized, and their saliva and bodies were collected as described above. Samples were stored at −80° C. until further processing.

To process the samples for virus titration, body and leg samples were homogenized with copper coated BBs (Crossman Corporation, NY) at 24 cycles/second for 4 min using a mixer mill, and then clarified by centrifuging at 3,000×g for 3 min. Saliva samples were centrifuged at 3,000× g for 3 minute, to expel fluid from capillary tubes. Ten-fold dilutions of the body and leg homogenates and saliva samples were tested for presence of infectious virus by plaque assay. Results from bodies, legs, and saliva were used for determining the infection, dissemination, and transmission rates, respectively.

Mouse Neurovirulence

Timed pregnant female ICR mice were obtained from Taconic Labs, and monitored several times each day to determine approximate birth times of pup litters. In a given experiment, approximately 12-24 hours after birth, two litters of eight pups per virus (n=16), was challenged with $10^3$ to $10^4$ pfu of virus in 20 μl of diluent by intracranial (ic) inoculation using a 30-gauge needle. Animals were monitored at least 3 times daily for at least 32 days following challenge. At the first sign of illness (rough fur, hunched back, weight loss, abnormal movement, paralysis, or lethargy) animals were euthanized by lethal anesthetization with isoflurane gas, followed by cervical dislocation. The post-infection day of euthanasia represented the "time to illness/morbidity" or "survival time" for the animal. The animal experiments were conducted following a DVBD/CDC IACUC-approved animal protocol.

Derivation of Master Seed Viruses

DENvax-1 Master Virus Seed (MVS)

Nucleotide sequence of the chimeric viral genome and deduced amino acid sequence of the translated protein are provided herein. Most of the prM-E gene (nt 457 to -2379, underlined) is wild-type (wt) DEN-1 16007 virus specific; the remaining genome is DEN-2 PDK-53 virus specific. All engineered substitutions differ from wt virus (D1 16007 or D2 16681), as well as extra mutations (changes from engineered cDNA clone) detected in the MVS are marked.

Substitutions Included in the Genome and Protein:

Junction sites between D1 (prM-E) and D2 backbone:

a. MluI (nt 451-456): engineered silent mutation, nt-453 A-to-G b. NgoMIV (nt 2380-2385): engineered mutations, nt-2381/2382 TG-to-CC (resulted in E-482 Val-to-Ala change)

D2 PDK-53 virus backbone (change from wt D2 16681): all in bold a. 5'-noncoding region (NCR)-57 (nt-57 C-to-T): major attenuation locus (in red)

b. NS1-53 Gly-to-Asp (nt-2579 G-to-A): major attenuation locus (in red)

c. NS2A-181 Leu-to-Phe (nt-4018 C-to-T)

d. NS3-250 Glu-to-Val (nt-5270 A-to-T): major attenuation locus (in red)

e. nt-5547 (NS3 gene) T-to-C silent mutation f. NS4A-75 Gly-to-Ala (nt-6599 G-to-C)

* nt-8571 C-to-T silent mutation of PDK-53 is not engineered in the vaccine virus DEN-1 prM-E (change from wt D1 16007)

a. Engineered nt-1575 T-to-C silent mutation to remove native XbaI site

Additional substitutions found in vaccine seed (0.03% nt different from original clone)

a. NS2A-116 Ile-to-Leu (nt-3823 A-to-C, in bold)

b. NS2B-92 Glu-to-Asp (nt-4407 A-to-T, in bold)

c. nt-7311 A-to-G silent mutation (in bold)

```
                                         NCR-57-T, D2 PDK-53 attenuation locus (wt D2 16681: C)
>5'-Noncoding Region                                    |                                        >C
        10        20        30        40        50        60        70        80        90       100
AGTTGTTAGTCTACGTGGACCGACAAAGACAGATTCTTTGAGGGAGCTAAGCTCAATGTAGTTCTAACAGTTTTTTAATTAGAGAGGAGATCTCTGATGA
                                                                                                M  N

       110       120       130       140       150       160       170       180       190       200
ATAACCAACGGAAAAAGGCGAAAAACACGCCTTTCAATATGCTGAAACGCGAGAGAAACCGCGTGTCGACTGTGCAACAGCTGACAAAGAGATTCTCACT
  N  Q  R  K  K  A  K  N  T  P  F  N  M  L  K  R  E  R  N  R  V  S  T  V  Q  Q  L  T  K  R  F  S  L

       210       220       230       240       250       260       270       280       290       300
TGGAATGCTGCAGGGACGAGGACCATTAAAACTGTTCATGGCCCTGGTGGCGTTCCTTCGTTTCCTAACAATCCCACCAACAGGAGGGATATTGAAGAGA
 G  M  L  Q  G  R  G  P  L  K  L  F  M  A  L  V  A  F  L  R  F  L  T  T  P  P  T  A  G  I  L  K  R

       310       320       330       340       350       360       370       380       390       400
TGGGGAACAATTAAAAAATCAAAAGCTATTAATGTTTTGAGAGGGTTCAGGAAAGAGATTGGAAGGATGCTGAACATCTTGAATAGGAGACGCAGATCTG
W  G  T  I  K  K  S  K  A  I  N  V  L  R  G  F  R  K  E  I  G  R  M  L  N  I  L  N  R  R  R  R  S  A

                                        >prM                Beginning of D1 16007 sequence
       410       420       430       440       450       |460       470       480       490       500
CAGGCATGATCATTATGCTGATTCCAACAGTGATGGCGTTCCATTTAACCACGCGTGGGGGAGAGCCGCATATGATAGTTAGCAAGGAGGAAAGAGGAAA
  G  M  I  I  M  L  I  P  T  V  M  A  F  H  L  T  T  R  G  G  E  P  H  M  I  V  S  K  Q  E  R  G  K
```

-continued

```
    |
                                       Engineered MluI splicing site (nt-453 A-to-G silent)

       510        520        530        540        550        560        570        580        590        600
GTCACTTTTGTTCAAGACCTCTGCAGGTGTCAACATGTGCACCCTCATTGCGATGGATTTGGGAGAGTTGTGTGAGGACACGATGACCTACAAATGCCCC
 S  L  L  F  K  T  S  A  G  V  N  M  C  T  L  I  A  M  D  L  G  E  L  C  E  D  T  M  T  Y  K  C  P

       610        620        630        640        650        660        670        680        690        700
CGGATCACTGAGGCGGAACCAGATGACGTTGACTGTTGGTGCAATGCCACGGACACATGGGTGACCTATGGAACGTGCTCTCAAACTGGCGAACACCGAC
R  I  T  E  A  E  P  D  D  V  D  C  W  C  N  A  T  D  T  W  V  T  Y  G  T  C  S  Q  T  G  E  H  R  R

         >M
       710        720        730        740        750        760        770        780        790        800
GAGACAAACGTTCCGTCGCATTGGCCCCACACGTGGGGCTTGGCCTAGAAACAAGAGCCGAAACGTGGATGTCCTCTGAAGGTGCTTGGAAACAGATACA
  D  K  R  S  V  A  L  A  P  H  V  G  L  G  L  E  T  R  A  E  T  W  M  S  S  E  G  A  W  K  Q  I  Q

       810        820        830        840        850        860        870        880        890        900
AAAAGTAGAGACTTGGGCTCTGAGACATCCAGGATTCACGGTGATAGCCCTTTTTCTAGCACATGCCATAGGAACATCCATCACCCAGAAAGGGATCATT
 K  V  E  T  W  A  L  R  H  P  G  F  T  V  I  A  L  F  L  A  H  A  I  G  T  S  I  T  Q  K  G  I  I

                                          >E
       910        920        930        940        950        960        970        980        990       1000
TTCATTTTGCTGATGCTGGTAACACCATCTATGGCCATGCGATGCGTGGGAATAGGCAACAGAGACTTCGTGGAAGGACTGTCAGGAGCAACATGGGTGG
F  I  L  L  M  L  V  T  P  S  M  A  M  R  C  V  G  I  G  N  R  D  F  V  E  G  L  S  G  A  T  W  V  D

      1010       1020       1030       1040       1050       1060       1070       1080       1090       1100
ATGTGGTACTGGAGCATGGAAGTTGCGTCACCACCATGGCAAAAAACAAACCAACACTGGACATTGAACTCTTGAAGACGGAGGTCACAAACCCTGCAGT
  V  V  L  E  H  G  S  C  V  T  T  M  A  K  N  K  P  T  L  D  I  E  L  L  K  T  E  V  T  N  P  A  V

      1110       1120       1130       1140       1150       1160       1170       1180       1190       1200
TCTGCGTAAATTGTGCATTGAAGCTAAAATATCAAACACCACCACCGATTCGAGATGTCCAACACAAGGAGAAGCCACACTGGTGGAAGAACAAGACGCG
 L  R  K  L  C  I  E  A  K  I  S  N  T  T  T  D  S  R  C  P  T  Q  G  E  A  T  L  V  E  E  Q  D  A

      1210       1220       1230       1240       1250       1260       1270       1280       1290       1300
AACTTTGTGTGCCGACGAACGTTCGTGGACAGAGGCTGGGGCAATGGCTGTGGGCTATTCGGAAAAGGTAGTCTAATAACGTGTGCCAAGTTTAAGTGTG
N  F  V  C  R  R  T  F  V  D  R  G  W  G  N  G  C  G  L  F  G  K  G  S  L  I  T  C  A  K  F  K  C  V

      1310       1320       1330       1340       1350       1360       1370       1380       1390       1400
TGACAAAACTAGAAGGAAAGATAGTTCAATATGAAAACCTAAAATATTCAGTGATAGTCACCGTCCACACTGGAGATCAGCACCAGGTGGGAAATGAGAC
  T  K  L  E  G  K  I  V  Q  Y  E  N  L  K  Y  S  V  I  V  T  V  H  T  G  D  Q  H  Q  V  G  N  E  T

      1410       1420       1430       1440       1450       1460       1470       1480       1490       1500
TACAGAACATGGAACAACTGCAACCATAACACCTCAAGCTCCTACGTCGGAAATACAGCTGACCGACTACGGAACCCTTACATTAGATTGTTCACCTAGG
 T  E  H  G  T  T  A  T  I  T  P  Q  A  P  T  S  E  I  Q  L  T  D  Y  G  T  L  T  L  D  C  S  P  R

      1510       1520       1530       1540       1550       1560       1570       1580       1590       1600
ACAGGGCTAGATTTTAACGAGATGGTGTTGCTGACAATGAAAGAAAGATCATGGCTTGTCCACAAACAATGGTTCCTAGACTTACCACTGCCTTGGACCT
T  G  L  D  F  N  E  M  V  L  L  T  M  K  E  R  S  W  L  V  H  K  Q  W  F  L  D  L  P  L  P  W  T  S
                                                                              |
Engineered silent mutation (nt-1575 T-to-C): remove the native DEN-1 virus-specific xbaI site

      1610       1620       1630       1640       1650       1660       1670       1680       1690       1700
CTGGGGCTTCAACATCCCAAGAGACTTGGAACAGACAAGATTTACTGGTCACATTTAAGACAGCTCATGCAAAGAAGCAGGAAGTAGTCGTACTAGGATC
  G  A  S  T  S  Q  E  T  W  N  R  Q  D  L  L  V  T  F  K  T  A  H  A  K  K  Q  E  V  V  V  L  G  S

      1710       1720       1730       1740       1750       1760       1770       1780       1790       1800
ACAAGAAGGAGCAATGCACACTGCGCTGACTGGAGCGACAGAAATCCAAACGTCAGGAACGACAACAATTTTCGCAGGACACCTAAAATGCAGACTAAAA
 Q  E  G  A  M  H  T  A  L  T  G  A  T  E  I  Q  T  S  G  T  T  T  I  F  A  G  H  L  K  C  R  L  K

      1810       1820       1830       1840       1850       1860       1870       1880       1890       1900
ATGGACAAACTAACTTTAAAAGGGATGTCATATGTGATGTGCACAGGCTCATTCAAGTTAGAGAAAGAAGTGGCTGAGACCCAGCATGGAACTGTTCTGG
M  D  K  L  T  L  K  G  M  S  Y  V  M  C  T  G  S  F  K  L  E  K  E  V  A  E  T  Q  H  G  T  V  L  V

      1910       1920       1930       1940       1950       1960       1970       1980       1990       2000
TGCAGGTTAAATATGAAGGAACAGACGCACCATGCAAGATTCCCTTTTCGACCCAAGATGAGAAAGGAGCAACCCAGAATGGGAGATTAATAACAGCCAA
  Q  V  K  Y  E  G  T  D  A  P  C  K  I  P  F  S  T  Q  D  E  K  G  A  T  Q  N  G  R  L  I  T  A  N

      2010       2020       2030       2040       2050       2060       2070       2080       2090       2100
CCCCATAGTCACTGACAAAGAAAAACCAGTCAATATTGAGGCAGAACCACCCTTTGGTGAGAGCTACATCGTGGTAGGAGCAGGTGAAAAAGCTTTGAAA
 P  I  V  T  D  K  E  K  P  V  N  I  E  A  E  P  P  F  G  E  S  Y  I  V  V  G  A  G  E  K  A  L  K

      2110       2120       2130       2140       2150       2160       2170       2180       2190       2200
CTAAGCTGGTTCAAGAAAGGAAGCAGCATAGGGAAAATGTTTGAAGCAACTGCCCGAGGAGCACGAAGGATGGCCATTCTGGGAGACACCGCATGGGACT
L  S  W  F  K  K  G  S  S  I  G  K  M  F  E  A  T  A  R  G  A  R  R  M  A  I  L  G  D  T  A  W  D  F

      2210       2220       2230       2240       2250       2260       2270       2280       2290       2300
TCGGTTCTATAGGAGGAGTGTTCACGTCTATGGGAAAACTGGTACACCAGGTTTTTGGAACTGCATATGGAGTTTTGTTTAGCGGAGTTTCTTGGACCAT
  G  S  I  G  G  V  F  T  S  M  G  K  L  V  H  Q  V  F  G  T  A  Y  G  V  L  F  S  G  V  S  W  T  M
```

-continued

End of D1 16007 sequence 2310 2320 2330 2340 2350 2360 2370 2380 2390 2400
GAAAATAGGAATAGGGATTCTGCTGACATGGCTAGGATTAAATTCAAGGAACACGTCCCTTTCGATGATGTGCATCGCAGCCGGCATTGTGACACTGTAT
K I G I G I L L T W L G L N S R N T S L S M M C I A A G I V T L Y Engineered NgoMIV splicing site, E-482 Val-to-Ala (nt-2381/2382 TG-to-CC)

>NS1
2410 2420 2430 2440 2450 2460 2470 2480 2490 2500
TTGGGAGTCATGGTGCAGGCCGATAGTGGTTGCGTTGTGAGCTGGAAAAACAAAGAACTGAAATGTGGCAGTGGGATTTTCATCACAGACAACGTGCACA
L G V M V Q A D S G C V V S W K N K E L K C G S G I F I T D N V H T 2510 2520 2530 2540 2550 2560 2570 2580 2590 2600
CATGGACAGAACAATACAAGTTCCAACCAGAATCCCCTTCAAAACTAGCTTCAGCTATCCAGAAAGCCCATGAAGAGGACATTTGTGGAATCCGCTCAGT
W T E Q Y K F Q P E S P S K L A S A I Q K A H E E D I C G I R S V

D2 PDK-53 ns1-53-aSP attenuation locus (wt D2 16681: Gly, nt-2579-G)

2610 2620 2630 2640 2650 2660 2670 2680 2690 2700
AACAAGACTGGAGAATCTGATGTGGAAACAAATAACACCAGAATTGAATCACATTCTATCAGAAAATGAGGTGAAGTTAACTATTATGACAGGAGACATC
T R L E N L M W K Q I T P E L N H I L S E N E V K L T I M T G D I 2710 2720 2730 2740 2750 2760 2770 2780 2790 2800
AAAGGAATCATGCAGGCAGGAAAACGATCTCTGCGGCCTCAGCCCACTGAGCTGAAGTATTCATGGAAAACATGGGGCAAAGCAAAAATGCTCTCTACAG
K G I M Q A G K R S L R P Q P T E L K Y S W K T W G K A K M L S T E 2810 2820 2830 2840 2850 2860 2870 2880 2890 2900
AGTCTCATAACCAGACCTTTCTCATTGATGGCCCCGAAACAGCAGAATGCCCCAACACAAATAGAGCTTGGAATTCGTTGGAAGTTGAAGACTATGGCTT
S H N Q T F L I D G P E T A E C P N T N R A W N S L E V E D Y G F 2910 2920 2930 2940 2950 2960 2970 2980 2990 3000
TGGAGTATTCACCACCAATATATGGCTAAAATTGAAAGAAAAACAGGATGTATTCTGCGACTCAAAACTCATGTCAGCGGCCATAAAAGACAACAGAGCC
G V F T T N I W L K L K E K Q D V F C D S K L M S A A I K D N R A 3010 3020 3030 3040 3050 3060 3070 3080 3090 3100
GTCCATGCCGATATGGGTTATTGGATAGAAAGTGCACTCAATGACACATGGAAGATAGAGAAAGCCTCTTTCATTGAAGTTAAAAACTGCCACTGGCCAA
V H A D M G Y W I E S A L N D T W K I E K A S F I E V K N C H W P K 3110 3120 3130 3140 3150 3160 3170 3180 3190 3200
AATCACACACCCTCTGGAGCAATGGAGTGCTAGAAAGTGAGATGATAATTCCAAAGAATCTCGCTGGACCAGTGTCTCAACACAACTATAGACCAGGCTA
S H T L W S N G V L E S E M I I P K N L A G P V S C H N Y R P G Y 3210 3220 3230 3240 3250 3260 3270 3280 3290 3300
CCATACACAAATAACAGGACCATGGCATCTAGGTAAGCTTGAGATGGACTTTGATTTCTGTGATGGAACAACAGTGGTAGTGACTGAGGACTGCGGAAAT
H T Q I T G P W H L G K L E M D F D F C D G T T V V V T E D C G N 3310 3320 3330 3340 3350 3360 3370 3380 3390 3400
AGAGGACCCTCTTTGAGAACAACCACTGCCTCTGGAAAACTCATAACAGAATGGTGCTGCCGATCTTGCACATTACCACCGCTAAGATACAGAGGTGAGG
R G P S L R T T T A S G K L I T E W C C R S C T L P P L R Y R G E D

>NS2A
3410 3420 3430 3440 3450 3460 3470 3480 3490 3500
ATGGGTGCTGGTACGGGATGGAAATCAGACCATTGAAGGAGAAAGAAGAGAATTTGGTCAACTCCTTGGTCACAGCTGGACATGGGCAGGTCGACAACTT
G C W Y G M E I R P L K E K E E N L V N S L V T A G H G Q V D N F 3510 3520 3530 3540 3550 3560 3570 3580 3590 3600
TTCACTAGGAGTCTTGGGAATGGCATTGTTCCTGGAGGAAATGCTTAGGACCCGAGTAGGAACGAAACATGCAATACTACTAGTTGCAGTTTCTTTTGTG
S L G V L G M A L F L E E M L R T R V G T K H A I L L V A V S F V 3610 3620 3630 3640 3650 3660 3670 3680 3690 3700
ACATTGATCACAGGGAACATGTCCTTTAGAGACCTGGGAAGAGTGATGGTTATGGTAGGCGCCACTATGACGGATGACATAGGTATGGGCGTGACTTATC
T L I T G N M S F R D L G R V M V M V G A T M T D D I G M G V T Y L 3710 3720 3730 3740 3750 3760 3770 3780 3790 3800
TTGCCCTACTAGCAGCCTTCAAAGTCAGACCAACTTTTGCAGCTGGACTACTCTTGAGAAAGCTGACCTCCAAGGAATTGATGATGACTACTATAGGAAT
A L L A A F K V R P T F A A G L L L R K L T S K E L M M T T I G I 3810 3820 3830 3840 3850 3860 3870 3880 3890 3900
TGTACTCCTCTCCCAGAGCACCCTACCAGAGACCATTCTTGAGTTGACTGATGCGTTAGCCTTAGGCATGATGGTCCTCAAAATGGTGAGAAATATGGAA
V L L S Q S T L P E T I L E L T D A L A L G M M V L K M V R N M E

Additional NS2A-116 Ile-to-Leu (nt3823 A-to-C) mutation in master and pre-master seed 3910 3920 3930 3940 3950 3960 3970 3980 3990 4000
AAGTATCAATTGGCAGTGACTATCATGGCTATCTTGTGCGTCCCAAACGCAGTGATATTACAAAACGCATGGAAAGTGAGTTGCACAATATTGGCAGTGG
K Y C L A V T I M A I L C V P N A V I L Q N A W K V S C T I L A V V -continued

```
      4010       4020       4030       4040       4050       4060       4070       4080       4090       4100
TGTCCGTTTCCCCACTGTTCTTAACATCCTCACAGCAAAAAACAGATTGGATACCATTAGCATTGACGATCAAAGGTCTCAATCCAACAGCTATTTTTCT
 S  V  S  P  L  F  L  T  S  S  Q  Q  K  T  D  W  I  P  L  A  L  T  I  K  G  L  N  P  T  A  I  F  L
                |
D2 PDK-53 specific NS2A-181-Phe (wt D2 16681: Leu, nt-4018-C)

                                            >NS2B
      4110       4120       4130       4140       4150       4160       4170       4180       4190       4200
AACAACCCTCTCAAGAACCAGCAAGAAAAGGAGCTGGCCATTAAATGAGGCTATCATGGCAGTCGGGATGGTGAGCATTTTAGCCAGTTCTCTCCTAAAA
 T  T  L  S  R  T  S  K  K  R  S  W  P  L  N  E  A  I  M  A  V  G  M  V  S  I  L  A  S  S  L  L  K

      4210       4220       4230       4240       4250       4260       4270       4280       4290       4300
AATGATATTCCCATGACAGGACCATTAGTGGCTGGAGGGCTCCTCACTGTGTGCTACGTGCTCACTGGACGATCGGCCGATTTGGAACTGGAGAGAGCAG
N  D  I  P  M  T  G  P  L  V  A  G  G  L  L  T  V  C  Y  V  L  T  G  R  S  A  D  L  E  L  E  R  A  A

      4310       4320       4330       4340       4350       4360       4370       4380       4390       4400
CCGATGTCAAATGGGAAGACCAGGCAGAGATATCAGGAAGGAGTCCAATCCTGTCAATAACAATATCAGAAGATGGTAGCATGTCGATAAAAAATGAAGA
  D  V  K  W  E  D  Q  A  E  I  S  G  S  S  P  I  L  S  I  T  I  S  E  D  G  S  M  S  I  K  N  E  E

      4410       4420       4430       4440       4450       4460       4470       4480       4490       4500
GGAAGATTCAAACACTGACCATACTCATTAGAACAGGATTGCTGGTGATCTCAGGACTTTTTCCTGTATCAATACCAATCACGGCAGGAGCATGGTACCTG
 E  D  Q  T  L  T  I  L  I  R  T  G  L  L  V  I  S  G  L  F  P  V  S  I  P  I  T  A  A  A  W  Y  L
|
Additional NS2B-92 Glu-to-Asp (nt-4407 A-to-T) mutation (in master and pre-master seed)

                              >NS3
      4510       4520       4530       4540       4550       4560       4570       4580       4590       4600
TGGGAAGTGAAGAAACAACGGGCCGGAGTATTGTGGGATGTTCCTTCACCCCCACCCATGGGAAAGGCTGAACTGGAAGATGGAGCCTATAGAATTAAGC
W  E  V  K  K  Q  R  A  G  V  L  W  D  V  P  S  P  P  P  M  G  K  A  E  L  E  D  G  A  Y  R  I  K  Q

      4610       4620       4630       4640       4650       4660       4670       4680       4690       4700
AAAAAGGGATTCTTGGATATTCCCAGATCGGAGCCGGAGTTTACAAAGAAGGAACATTCCATACAATGTGGCATGTCACACGTGGCGCTGTTCTAATGCA
  K  G  I  L  G  Y  S  Q  I  G  A  G  V  Y  K  E  G  T  F  H  T  M  W  H  V  T  R  G  A  V  L  M  H

      4710       4720       4730       4740       4750       4760       4770       4780       4790       4800
TAAAGGAAAGAGGATTGAACCATCATGGGCGGACGTCAAGAAAGACCTAATATCATATGGAGGAGGCTGGAAGTTAGAAGGAGAATGGAAGGAAGGAGAA
 K  G  K  R  I  E  P  S  W  A  D  V  K  K  D  L  I  S  Y  G  G  G  W  K  L  E  G  E  W  K  E  G  E

      4810       4820       4830       4840       4850       4860       4870       4880       4890       4900
GAAGTCCAGGTATTGGCACTGGAGCCTGGAAAAAATCCAAGAGCCGTCCAAACGAAACCTGGTCTTTTCAAAACCAACGCCGGAACAATAGGTGCTGTAT
E  V  Q  V  L  A  L  E  P  G  K  N  P  R  A  V  Q  T  K  P  G  L  F  K  T  N  A  G  T  I  G  A  V  S

      4910       4920       4930       4940       4950       4960       4970       4980       4990       5000
CTCTGGACTTTTCTCCTGGAACGTCAGGATCTCCAATTATCGACAAAAAAGGAAAAGTTGTGGGTCTTTATGGTAATGGTGTTGTTACAAGGAGTGGAGC
  L  D  F  S  P  G  T  S  G  S  P  I  I  D  K  K  G  K  V  V  G  L  Y  G  N  G  V  V  T  R  S  G  A

      5010       5020       5030       5040       5050       5060       5070       5080       5090       5100
ATATGTGAGTGCTATAGCCCAGACTGAAAAAAGCATTGAAGACAACCCAGAGATCGAAGATGACATTTTCCGAAAGAGAAGACTGACCATCATGGACCTC
 Y  V  S  A  I  A  Q  T  E  K  S  I  E  D  N  P  E  I  E  D  D  I  F  R  K  R  R  L  T  I  M  D  L

      5110       5120       5130       5140       5150       5160       5170       5180       5190       5200
CACCCAGGAGCGGGAAAGACGAAGAGATACCTTCCGGCCATAGTCAGAGAAGCTATAAAACGGGGTTTGAGAACATTAATCTTGGCCCCCACTAGAGTTG
H  P  G  A  G  K  T  K  R  Y  L  P  A  I  V  R  E  A  I  K  R  G  L  R  T  L  I  L  A  P  T  R  V  V

      5210       5220       5230       5240       5250       5260       5270       5280       5290       5300
TGGCAGCTGAAATGGAGGAAGCCCTTAGAGGACTTCCAATAAGATACCAGACCCCAGCCATCAGAGCTGTGCACACCGGGCGGGAGATTGTGGACCTAAT
  A  A  E  M  E  E  A  L  R  G  L  P  I  R  Y  Q  T  P  A  I  R  A  V  H  T  G  R  E  I  V  D  L  M
                                                                    |
                                    D2 PDK-53 NS3-250-Val attenuation locus (wt D2 16681: Glu, nt-5270-A)

      5310       5320       5330       5340       5350       5360       5370       5380       5390       5400
GTGTCATGCCACATTTACCATGAGGCTGCTATCACCAGTTAGAGTGCCAAACTACAACCTGATTATCATGGACGAAGCCCATTTCACAGACCCAGCAAGT
 C  H  A  T  F  T  M  R  L  L  S  P  V  R  V  P  N  Y  N  L  I  I  M  D  E  A  H  F  T  D  P  A  S

      5410       5420       5430       5440       5450       5460       5470       5480       5490       5500
ATAGGAGCTAGAGGATACATCTCAACTCGAGTGGAGATGGGTGAGGCAGCTGGGATTTTTATGACAGCCACTCCCCCGGGAAGGAGAGACCCATTTCCTC
I  A  A  R  G  Y  I  S  T  R  V  E  M  G  E  A  A  G  I  F  M  T  A  T  P  P  G  S  R  D  P  F  P  Q

      5510       5520       5530       5540       5550       5560       5570       5580       5590       5600
AGAGCAATGCACCAATCATAGATGAAGAAAGAGAAATCCCTGAACGCTCGTGGAATTCCGGACATGAATGGGTCACGGATTTTAAAGGGAAGACTGTTTG
  S  N  A  P  I  I  D  E  E  R  E  I  P  E  R  S  W  N  S  G  H  E  W  V  T  D  F  K  G  K  T  V  W
                                                 |
                                   D2 PDK-53 silent mutation nt-5547-C (wt D2 16681: T)

      5610       5620       5630       5640       5650       5660       5670       5680       5690       5700
GTTCGTTCCAAGTATAAAAGGAGGAAATGATATAGGAGCTTGCCTGAGGAAAAATGGAAAGAAAGTGATACAACTCAGTAGGAAGACCTTTGATTCTGAG
 F  V  P  S  I  K  A  G  N  D  I  A  A  C  L  R  K  N  G  K  K  V  I  Q  L  S  R  K  T  F  D  S  E
```

-continued 5710 5720 5730 5740 5750 5760 5770 5780 5790 5800
TATGTCAAGACTAGAACCAATGATTGGGACTTCGTGGTTACAACTGACATTTCAGAAATGGGTGCCAATTTCAAGGCTGAGAGGGTTATAGACCCCAGAC
Y V K T R T N D W D F V V T T D I S E M G A N F K A E R V I D P R R 5810 5820 5830 5840 5850 5860 5870 5880 5890 5900
GCTGCATGAAACCAGTCATACTAACAGATGGTGAAGAGCGGGTGATTCTGGCAGGACCTATGCCAGTGACCCACTCTAGTGCAGCACAAAGAAGAGGGAG
C M K P V I L T D G E E R V I L A G P M P V T H S S A A Q R R G R 5910 5920 5930 5940 5950 5960 5970 5980 5990 6000
AATAGGAAGAAATCCAAAAAATGAGAATGACCAGTACATATACATGGGGGAACCTCTGGAAAATGATGAAGACTGTGCACACTGGAAAGAAGCTAAAATG
I G R N P K N E N D Q Y I Y M G E P L E N D E D C A H W K E A K M 6010 6020 6030 6040 6050 6060 6070 6080 6090 6100
CTCCTAGATAACATCAACACGCCAGAAGGAATCATTCCTAGCATGTTCGAACCAGAGCGTGAAAAGGTGGATGCCATTGATGGCGAATACCGCTTGAGAG
L L D N I N T P E G I I P S M F E P E R E K V D A I D G E Y R L R G 6110 6120 6130 6140 6150 6160 6170 6180 6190 6200
GAGAAGCAAGGAAAACCTTTGTAGACTTAATGAGAAGAGGAGACCTACCAGTCTGGTTGGCCTACAGAGTGGCAGCTGAAGGCATCAACTACGCAGACAG
E A R K T F V D L M R R G D L P V W L A Y R V A A E G I N Y A D R 6210 6220 6230 6240 6250 6260 6270 6280 6290 6300
AAGGTGGTGTTTTGATGGAGTCAAGAACAACCAAATCCTAGAAGAAAACGTGGAAGTTGAAATCTGGACAAAAGAAGGGGAAAGGAAGAAATTGAAACCC
R W C F D G V K N N Q I L E E N V E V E I W T K E G E R K K L K P >NS4A
6310 6320 6330 6340 6350 6360 6370 6380 6390 6400
AGATGGTTGGATGCTAGGATCTATTCTGACCCACTGGCGCTAAAAGAATTTAAGGAATTTGCAGCCGGAAGAAAGTCTCTGACCCTGAACCTAATCACAG
R W L D A R I Y S D P L A L K E F K E F A A G R K S L T L N L I T E 6410 6420 6430 6440 6450 6460 6470 6480 6490 6500
AAATGGGTAGGCTCCCAACCTTCATGACTCAGAAGGCAAGAGACGCACTGGACAACTTAGCAGTGCTGCACACGGCTGAGGCAGGTGGAAGGGCGTACAA
M G R L P T F M T Q K A R D A L D N L A V L H T A E A G G R A Y N 6510 6520 6530 6540 6550 6560 6570 6580 6590 6600
CCATGCTCTCAGTGAACTGCCGGAGACCCTGGAGACATTGCTTTTACTGACACTTCTGGCTACAGTCACGGGAGGGATCTTTTTATTCTTGATGAGCGCA
H A L S E L P E T L E T L L L L T L L A T V T G G I F L F L M S A
|
D2 PDK-53 specific NS4A-75-Ala (wt D2 16681: Gly, nt-6599-G)

6610 6620 6630 6640 6650 6660 6670 6680 6690 6700
AGGGGCATAGGGAAGATGACCCTGGGAATGTGCTGCATAATCACGGCTAGCATCCTCCTATGGTACGCACAAATACAGCCACACTGGATAGCAGCTTCAA
R G I G K M T L G M C C I I T A S I L L W Y A Q I Q P H W I A A S I 6710 6720 6730 6740 6750 6760 6770 6780 6790 6800
TAATACTGGAGTTTTTCTCATAGTTTTGCTTATTCCAGAACCTGAAAAACAGAGAACACCCCAAGACAACCAACTGACCTACGTTGTCATAGCCATCCT
I L E F F L I V L L I P E P E K Q R T P Q D N Q L T Y V V I A I L

>NS4B
6810 6820 6830 6840 6850 6860 6870 6880 6890 6900
CACAGTGGTGGCCGCAACCATGGCAAACGAGATGGGTTTCCTAGAAAAAACGAAGAAAGATCTCGGATTGGGAAGCATTGCAACCCAGCAACCCGAGAGC
T V V A A T M A N E M G F L E K T K K D L G L G S I A T Q Q P E S 6910 6920 6930 6940 6950 6960 6970 6980 6990 7000
AACATCCTGGACATAGATCTACGTCCTGCATCAGCATGGACGCTGTATGCCGTGGCCACAACATTTGTTACACCAATGTTGAGACATAGCATTGAAAATT
N I L D I D L R P A S A W T L Y A V A T T F V T P M L R H S I E N S 7010 7020 7030 7040 7050 7060 7070 7080 7090 7100
CCTCAGTGAATGTGTCCCTAACAGCTATAGCCAACCAAGCCACAGTGTTAATGGGTCTCGGGAAAGGATGGCCATTGTCAAAGATGGACATCGGAGTTCC
S V N V S L T A I A N Q A T V L M G L G K G W P L S K M D I G V P 7110 7120 7130 7140 7150 7160 7170 7180 7190 7200
CCTTCTCGCCATTGGATGCTACTCACAAGTCAACCCCATAACTCTCACAGGAGCTCTTTTCTTATTGGTAGCACATTATGCCATCATAGGGCCAGGACTC
L L A I G C Y S Q V N P I T L T A A L F L L V A H Y A I I G P G L 7210 7220 7230 7240 7250 7260 7270 7280 7290 7300
CAAGCAAAAGCAACCAGAGAAGCTCAGAAAAGAGGAGCGGCGGGCATCATGAAAAACCCAACTGTCGATGGAATAACAGTGATTGACCTAGATCCAATAC
Q A K A T R E A Q K R A A A G I M K N P T V D G I T V I D L D P I P 7310 7320 7330 7340 7350 7360 7370 7380 7390 7400
CTTATGATCCGAAGTTTGAAAAGGAGTTGGGACAAGTAATGCTCCTAGTCCTCTGCGTGACTCAAGTATTGATGATGAGGACTACATGGGCTCTGTGTGA
Y D P K F E K Q L G Q V M L L V L C V T Q V L M M R T T W A L C E
|
Additional silent mutation (nt-7311 A-to-G, in master and pre-master seed)

7410 7420 7430 7440 7450 7460 7470 7480 7490 7500
GGCTTTAACCTTAGCTACCGGGCCCATCTCCACATTGTGGGAAGGAAATCCAGGGAGGTTTTGGAACACTACCATTGCGGTGTCAATGGCTAACATTTTT
A L T L A T G P I S T L W E G N P G R F W N T T I A V S M A N I F

-continued

```
                                                                  >NS5
      7510       7520       7530       7540       7550       7560       7570       7580       7590       7600
AGAGGGAGTTACTTGGCCGGAGCTGGACTTCTCTTTTCTATTATGAAGAACACAACCAACACAAGAAGGGGAACTGGCAACATAGGAGAGACGCTTGGAG
R  G  S  Y  L  A  G  A  G  L  L  F  S  I  M  K  N  T  T  N  T  R  R  G  T  G  N  I  G  E  T  L  G  E

      7610       7620       7630       7640       7650       7660       7670       7680       7690       7700
AGAAATGGAAAAGCCGATTGAACGCATTGGGAAAAAGTGAATTCCAGATCTACAAGAAAAGTGGAATCCAGGAAGTGGATAGAACCTTAGCAAAAGAAGG
 K  W  K  S  R  L  N  A  L  G  K  S  E  F  Q  I  Y  K  K  S  G  I  Q  E  V  D  R  T  L  A  K  E  G

      7710       7720       7730       7740       7750       7760       7770       7780       7790       7800
CATTAAAAGAGGAGAAACGGACCATCACGCTGTGTCGCGAGGCTCAGCAAAACTGAGATGGTTCGTTGAGAGAAACATGGTCACACCAGAAGGGAAAGTA
 I  K  R  G  E  T  D  H  H  A  V  S  R  G  S  A  K  L  R  W  F  V  E  R  N  M  V  T  P  E  G  K  V

      7810       7820       7830       7840       7850       7860       7870       7880       7890       7900
GTGGACCTCGGTTGTGGCAGAGGAGGCTGGTCATACTATTGTGGAGGACTAAAGAATGTAAGAGAAGTCAAAGGCCTAACAAAAGGAGGACCAGGACACG
V  D  L  G  C  G  R  G  G  W  S  Y  Y  C  G  G  L  K  N  V  R  E  V  K  G  L  T  K  G  G  P  G  H  E

      7910       7920       7930       7940       7950       7960       7970       7980       7990       8000
AAGAACCCATCCCCATGTCAACATATGGGTGGAATCTAGTGCGTCTTCAAAGTGGAGTTGACGTTTTCTTCATCCCGCCAGAAAAGTGTGACACATTATT
 E  P  I  P  M  S  T  Y  G  W  N  L  V  R  L  Q  S  G  V  D  V  F  F  I  P  P  E  K  C  D  T  L  L

      8010       8020       8030       8040       8050       8060       8070       8080       8090       8100
GTGTGACATAGGGGAGTCATCACCAAATCCCACAGTGGAAGCAGGACGAACACTCAGAGTCCTTAACTTAGTAGAAAATTGGTTGAACAACAACACTCAA
 C  D  I  G  E  S  S  P  N  P  T  V  E  A  G  R  T  A  R  V  L  N  A  V  E  N  W  L  N  N  N  T  Q

      8110       8120       8130       8140       8150       8160       8170       8180       8190       8200
TTTTGCATAAAGGTTCTCAACCCATATATGCCCTCAGTCATAGAAAAAATGGAAGCACTACAAAGGAAATATGGAGGAGCCTTAGTGAGGAATCCACTCT
F  C  I  K  V  L  N  P  Y  M  P  S  V  I  E  K  M  E  A  L  Q  R  K  Y  G  G  A  L  V  R  N  P  L  S

      8210       8220       8230       8240       8250       8260       8270       8280       8290       8300
CACGAAACTCCACACATGAGATGTACTGGGTATCCAATGCTTCCGGGAACATAGTGTCATCAGTGAACATGATTTCAAGGATGTTGATCAACAGATTTAC
 R  N  S  T  H  E  M  Y  W  V  S  N  A  S  G  N  I  V  S  S  V  N  M  I  S  R  M  L  I  N  R  F  T

      8310       8320       8330       8340       8350       8360       8370       8380       8390       8400
AATGAGATACAAGAAAGCCACTTACGAGCCGGATGTTGACCTCGGAAGCGGAACCCGTAACATCGGGATTGAAAGTGAGATACCAAACCTAGATATAATT
 M  R  Y  K  K  A  T  Y  E  P  D  V  D  L  G  S  G  T  R  N  I  G  I  E  S  E  I  P  N  L  D  I  I

      8410       8420       8430       8440       8450       8460       8470       8480       8490       8500
GGGAAAAGAATAGAAAAAATAAAGCAAGAGCATGAAACATCATGGCACTATGACCAAGACCACCCATACAAAACGTGGGCATACCATGGTAGCTATGAAA
G  K  R  I  E  K  I  K  Q  E  H  E  T  S  W  H  Y  D  Q  D  H  P  Y  K  T  W  A  Y  H  G  S  Y  E  T

      8510       8520       8530       8540       8550       8560       8570       8580       8590       8600
CAAAACAGACTGGATCAGCATCATCCATGGTCAACGGAGTGGTCAGGCTGCTGACAAAACCTTGGGACGTCGTCCCCATGGTGACACAGATGGCAATGAC
 K  Q  T  G  S  A  S  S  M  V  N  G  V  V  R  L  L  T  K  P  W  D  V  V  P  M  V  T  Q  M  A  M  T

      8610       8620       8630       8640       8650       8660       8670       8680       8690       8700
AGACACGACTCCATTTGGACAACAGCGCGTTTTTAAAGAGAAAGTGGACACGAGAACCCAAGAACCGAAAGAAGGCACGAAGAAACTAATGAAAATAACA
 D  T  T  P  F  G  Q  Q  R  V  F  K  E  K  V  D  T  R  T  Q  E  P  K  E  G  T  K  K  L  M  K  I  T

      8710       8720       8730       8740       8750       8760       8770       8780       8790       8800
GCAGAGTGGCTTTGGAAAGAATTAGGGAAGAAAAAGACACCCAGGATGTGCACCAGAGAAGAATTCACAAGAAAGGTGAGAAGCAATGCAGCCTTGGGGG
A  E  W  L  W  K  E  L  G  K  K  K  T  P  R  M  C  T  R  E  E  F  T  R  K  V  R  S  N  A  A  L  G  A

      8810       8820       8830       8840       8850       8860       8870       8880       8890       8900
CCATATTCACTGATGAGAACAAGTGGAAGTCGGCACGTGAGGCTGTTGAAGATAGTAGGTTTTGGGAGCTGGTTGACAAGGAAAGGAATCTCCATCTTGA
 I  F  T  D  E  N  K  W  K  S  A  R  E  A  V  E  D  S  R  F  W  E  L  V  D  K  E  R  N  L  H  L  E

      8910       8920       8930       8940       8950       8960       8970       8980       8990       9000
AGGAAAGTGTGAAACATGTGTGTACAACATGATGGGAAAAAGAGAGAAGAAGCTAGGGGAATTCGGCAAGGCAAAAGGCAGCAGAGCCATATGGTACATG
 G  K  C  E  T  C  V  Y  N  M  M  G  K  R  E  K  K  L  G  E  F  G  K  A  K  G  S  R  A  I  W  Y  M

      9010       9020       9030       9040       9050       9060       9070       9080       9090       9100
TGGCTTGGAGCACGCTTCTTAGAGTTTGAAGCCCTAGGATTCTTAAATGAAGATCACTGGTTCTCCAGAGAGAACTCCCTGAGTGGAGTGGAAGGAGAAG
W  L  G  A  R  F  L  E  F  E  A  L  G  F  L  N  E  D  H  W  F  S  R  E  N  S  L  S  G  V  E  G  E  G

      9110       9120       9130       9140       9150       9160       9170       9180       9190       9200
GGCTGCACAAGCTAGGTTACATTCTAAGAGACGTGAGCAAGAAAGAGGGAGGAGCAATGTATGCCGATGACACCGCAGGATGGGATACAAGAATCACACT
 L  H  K  L  G  Y  I  L  R  D  V  S  K  K  E  G  G  A  M  Y  A  D  D  T  A  G  W  D  T  R  I  T  L

      9210       9220       9230       9240       9250       9260       9270       9280       9290       9300
AGAAGACCTAAAAAATGAAGAAATGGTAACAAACCACATGGAAGGAGAACACAAGAAACTAGCCGAGGCCATTTTCAAACTAACGTACCAAAACAAGGTG
 E  D  L  K  N  E  E  M  V  T  N  H  M  E  G  E  H  K  K  L  A  E  A  I  F  K  L  T  Y  Q  N  K  V

      9310       9320       9330       9340       9350       9360       9370       9380       9390       9400
GTGCGTGTGCAAAGACCAACACCAAGAGGCACAGTAATGGACATCATATCGAGAAGAGACCAAAGAGGTAGTGGACAAGTTGGCACCTATGGACTCAATA
V  R  V  Q  R  P  T  P  R  G  T  V  M  D  I  I  S  R  R  D  Q  R  G  S  G  Q  V  G  T  Y  G  L  N  T

      9410       9420       9430       9440       9450       9460       9470       9480       9490       9500
CTTTCACCAATATGGAAGCCCAACTAATCAGACAGATGGAGGGAGAAGGAGTCTTTAAAAGCATTCAGCACCTAACAATCACAGAAGAAATCGCTGTGCA
 F  T  N  M  E  A  Q  L  I  R  Q  M  E  G  E  G  V  F  K  S  I  Q  H  L  T  I  T  E  E  I  A  V  Q
```

-continued

```
      9510      9520      9530      9540      9550      9560      9570      9580      9590      9600
AAACTGGTTAGCAAGAGTGGGGCGCGAAAGGTTATCAAGAATGGCCATCAGTGGAGATGATTGTGTTGTGAAACCTTTAGATGACAGGTTCGCAAGCGCT
 N  W  L  A  R  V  G  R  E  R  L  S  R  M  A  I  S  G  D  D  C  V  V  K  P  L  D  D  R  F  A  S  A

      9610      9620      9630      9640      9650      9660      9670      9680      9690      9700
TTAACAGCTCTAAATGACATGGGAAAGATTAGGAAAGACATACAACAATGGGAACCTTCAAGAGGATGGAATGATTGGACACAAGTGCCCTTCTGTTCAC
L  T  A  L  N  D  M  G  K  I  R  K  D  I  Q  Q  W  E  P  S  R  G  W  N  D  W  T  Q  V  P  F  C  S  H

      9710      9720      9730      9740      9750      9760      9770      9780      9790      9800
ACCATTTCCATGAGTTAATCATGAAAGACGGTCGCGTACTCGTTGTTCCATGTAGAAACCAAGATGAACTGATTGGCAGAGCCCGAATCTCCCAAGGAGC
  H  F  H  E  L  I  M  K  D  G  R  V  L  V  V  P  C  R  N  Q  D  E  L  I  G  R  A  R  I  S  Q  G  A

      9810      9820      9830      9840      9850      9860      9870      9880      9890      9900
AGGGTGGTCTTTGCGGGAGACGGCCTGTTTGGGGAAGTCTTACGCCCAAATGTGGAGCTTGATGTACTTCCACAGACGCGACCTCAGGCTGGCGGCAAAT
 G  W  S  L  R  E  T  A  C  L  G  K  S  Y  A  Q  M  W  S  L  M  Y  F  H  R  R  D  L  R  L  A  A  N

      9910      9920      9930      9940      9950      9960      9970      9980      9990     10000
GCTATTTGCTCGGCAGTACCATCACATTGGGTTCCAACAAGTCGAACAACCTGGTCCATACATGCTAAACATGAATGGATGACAACGGAAGACATGCTGA
A  I  C  S  A  V  P  S  H  W  V  P  T  S  R  T  T  W  S  I  H  A  K  H  E  W  M  T  T  E  D  M  L  T

     10010     10020     10030     10040     10050     10060     10070     10080     10090     10100
CAGTCTGGAACAGGGTGTGGATTCAAGAAAACCCATGGATGGAAGACAAAACTCCAGTGGAATCATGGGAGGAAATCCCATACTTGGGGAAAAGAGAAGA
  V  W  N  R  V  W  I  Q  E  N  P  W  M  E  D  K  T  P  V  E  S  W  E  E  I  P  Y  L  G  K  R  E  D

     10110     10120     10130     10140     10150     10160     10170     10180     10190     10200
CCAATGGTGCGGCTCATTGATTGGGTTAACAAGGAGGGCCACCTGGGCAAAGAACATCCAAGGAGCAATAAATCAAGTTAGATCCCTTATAGGCAATGAA
 Q  W  C  G  S  L  I  G  L  T  S  R  A  T  W  A  K  N  I  Q  A  A  I  N  Q  V  R  S  L  I  G  N  E

                                                                            >3'-Noncoding Region
     10210     10220     10230     10240     10250     10260     10270     10280     10290     10300
GAATACACAGATTACATGCCATCCATGAAAAGATTCAGAAGAGAAGAGGAAGAAGGAGGAGTTCTGTGGTAGAAAGCAAAACTAACATGAAACAAGGCTA
E  Y  T  D  Y  M  P  S  M  K  R  F  R  R  E  E  E  E  A  G  V  L  W  *

     10310     10320     10330     10340     10350     10360     10370     10380     10390     10400
GAAGTCAGGTCGGATTAAGCCATAGTACGGAAAAAACTATGCTACCTGTGAGCCCCGTCCAAGGACGTTAAAAGAAGTCAGGCCATCATAAATGCCATAG

     10410     10420     10430     10440     10450     10460     10470     10480     10490     10500
CTTGAGTAAACTATGCAGCCTGTAGCTCCACCTGAGAAGGTGTAAAAAATCCGGGAGGCCACAAACCATGGAAGCTGTACGCATGGCGTAGTGGACTAGC

     10510     10520     10530     10540     10550     10560     10570     10580     10590     10600
GGTTAGAGGAGACCCCTCCCTTACAAATCGCAGCAACAATGGGGGCCCAAGGCGAGATGAAGCTGTAGTCTCGCTGGAAGGACTAGAGGTTAGAGGAGAC

     10610     10620     10630     10640     10650     10660     10670     10680     10690     10700
CCCCCCGAAACAAAAAACAGCATATTGACGCTGGGAAAGACCAGAGATCCTGCTGTCTCCTCAGCATCATTCCAGGCACAGAACGCCAGAAAATGGAATG

     10710     10720
GTGCTGTTGAATCAACAGGTTCT
```

DENvax-2 Master Virus Seed (MVS)

Nucleotide sequence of the recombinant viral genome and deduced amino acid sequence of the translated protein are provided herein. The engineered virus is based on D2 PDK-53 virus. All engineered substitutions that are different from wild-type DEN-2 16681 virus (also the parental virus for PDK-53), as well as extra mutations (changes from engineered cDNA clone) detected in the MVS are marked.

Substitutions Included in the Genome and Protein:

D2 PDK-53 virus backbone (change from wt D2 16681): all in bold a. 5'-noncoding region (NCR)-57 (nt-57 C-to-T): major attenuation locus (in red)
b. prM-29 Asp-to-Val (nt-524 A-to-T)
c. nt-2055 C-to-T (E gene) silent mutation
d. NS1-53 Gly-to-Asp (nt-2579 G-to-A): major attenuation locus (in red)
e. NS2A-181 Leu-to-Phe (nt-4018 C-to-T)
f. NS3-250 Glu-to-Val (nt-5270 A-to-T): major attenuation locus (in red)
g. nt-5547 (NS3 gene) T-to-C silent mutation
h. NS4A-75 Gly-to-Ala (nt-6599 G-to-C)

* nt-8571 C-to-T silent mutation of PDK-53 is not engineered in the vaccine virus Engineered clone marker (silent mutation):

a. nt-900 T-to-C silent mutation: infectious clone marker

Additional substitutions found in vaccine seed (0.02% nt different from original clone)

a. prM-52 Lys-to-Glu (nt-592 A-to-G), in bold
b. NS5-412 Ile-to-Val (nt-8803 A-to-G), in bold

```
                                      NCR-57-T, D2 PDK-53 attenuation locus (wt D2 16681: C)
>5'-NC                                                       |                                  >C
         10        20        30        40        50        60        70        80        90       100       110       120
AGTTGTTAGTCTACGTGGACCGACAAAGACAGATTCTTTGAGGGAGCTAAGCTCAATGTAGTTCTAACAGTTTTTTAATTAGAGAGCAGATCTCTGATGAATAACCAACGGAAAAAGGCG
                                                                                                M  N  N  Q  R  K  K  A

        130       140       150       160       170       180       190       200       210       220       230       240
AAAAACACGCCTTTCAATATGCTGAAACGCGAGAGAAACCGCGTGTCGACTGTGCAACAGCTGACAAAGAGATTCTCACTTGGAATGCTGCAGGGACGAGGACCATTAAAACTGTTCATG
K  N  T  P  F  N  M  L  K  R  E  R  N  A  V  S  T  V  Q  Q  L  T  K  R  F  S  L  G  M  L  Q  G  R  G  P  L  K  L  F  M

        250       260       270       280       290       300       310       320       330       340       350       360
GCCCTGGTGGCGTTCCTTCGTTTCCTAACAATCCCACCAACAGCAGGGATATTGAAGAGATGGGGAACAATTAAAAAATCAAAAGCTATTAATGTTTTGAGAGGGTTCAGGAAAGAGATT
A  L  V  A  F  L  R  F  L  T  I  P  P  T  A  G  I  L  K  R  W  G  T  I  K  K  S  K  A  I  N  V  L  R  G  F  R  K  E  I

                                                                                  >prM
        370       380       390       400       410       420       430       440       450       460       470       480
GGAAGGATGCTGAACATCTTGAATAGGAGACGCAGATCTGCAGGCATGATCATTATGCTGATTCCAACAGTGATGGCGTTCCATTTAACCACACGTAACGGAGAACCACACATGATCGTC
G  R  M  L  N  I  L  N  R  R  R  R  S  A  G  M  I  I  M  L  I  P  T  V  M  A  F  H  L  T  T  R  N  G  E  P  H  M  I  V

        490       500       510       520       530       540       550       560       570       580       590       600
AGCAGACAAGAGAAAGGGAAAAGTCTTCTGTTTAAAACAGAGGTTGGCGTGAACATGTGTACCCTCATGGCCATGGACCTTGGTGAATTGTGTGAAGACACAATCACGTACGAGTGTCCC
S  R  Q  E  K  G  K  S  L  L  F  K  T  E  V  G  V  N  M  C  T  L  M  A  M  D  L  G  E  L  C  E  D  T  I  T  Y  E  C  P
                                          |                                                                        |
D2 PDK-53 specific prM-29 Val (wt D2 16681 Asp, nt-524-A)    Additional prM-52 Lys-to-Glu mutation (nt-592 A-to-G)

                                                                                                                   >M
        610       620       630       640       650       660       670       680       690       700       710       720
CTTCTCAGGCAGAATGAGCCAGAAGACATAGACTGTTGGTGCAACTCTACGTCCACGTGGGTAACTTATGGGACGTGTACCACCATGGGAGAACATAGAAGAGAAAAAAGATCAGTGGCA
L  L  R  Q  N  E  P  E  D  I  D  C  W  C  N  S  T  S  T  W  V  T  Y  G  T  C  T  T  M  G  E  H  R  R  E  K  R  S  V  A

        730       740       750       760       770       780       790       800       810       820       830       840
CTCGTTCCACATGTGGGAATGGGACTGGAGACACGAACTGAAACATGGATGTCATCAGAAGGGGCCTGGAAACATGTCCAGAGAATTGAAACTTGGATCTTGAGACATCCAGGCTTCACC
L  V  P  H  V  G  M  G  L  E  T  R  T  E  T  W  M  S  S  E  G  A  W  K  H  V  Q  R  I  E  T  W  I  L  R  H  P  G  F  T

>E
        850       860       870       880       890       900       910       920       930       940       950       960
ATGATGGCAGCAATCCTGGCATACACCATAGGAACGACACATTTCCAAAGAGCCCTGATCTTCATCTTACTGACAGCTGTCACTCCTTCAATGACAATGCGTTGCATAGGAATGTCAAAT
M  M  A  A  I  L  A  Y  T  I  G  T  T  H  F  Q  R  A  L  I  F  I  L  L  T  A  V  T  P  S  M  T  M  R  C  I  G  M  S  N
                                                            |
                                             Engineered silent clone marker: nt-900 T-to-C silent mutation

        970       980       990      1000      1010      1020      1030      1040      1050      1060      1070      1080
AGAGACTTTGTGGAAGGGGTTTCAGGAGGAAGCTGGGTTGACATAGTCTTAGAACATGGAAGCTGTGTGACGACGATGGCAAAAAACAAACCAACATTGGATTTTGAACTGATAAAAACA
R  D  F  V  E  G  V  S  G  G  S  W  V  D  I  V  L  E  H  G  S  C  V  T  T  M  A  K  N  K  P  T  L  D  F  E  L  I  K  T

       1090      1100      1110      1120      1130      1140      1150      1160      1170      1180      1190      1200
GAAGCCAAACAGCCTGCCACCCTAAGGAAGTACTGTATAGAGGCAAAGCTAACCAACACAACAACAGAATCTCGCTGCCCAACACAAGGGGAACCCAGCCTAAATGAAGAGCAGGACAAA
E  A  K  Q  P  A  T  L  R  K  Y  C  I  E  A  K  L  T  N  T  T  T  E  S  R  C  P  T  Q  G  E  P  S  L  N  E  E  Q  D  K

       1210      1220      1230      1240      1250      1260      1270      1280      1290      1300      1310      1320
AGGTTCGTCTGCAAACACTCCATGGTAGACAGAGGATGGGGAAATGGATGTGGACTATTTGGAAAGGGAGGCATTGTGACCTGTGCTATGTTCAGATGCAAAAAGAACATGGAAGGAAAA
R  F  V  C  K  H  S  M  V  D  R  G  W  G  N  G  C  G  L  F  G  K  G  G  I  V  T  C  A  M  F  R  C  K  K  N  M  E  G  K
```

-continued

```
      1330      1340      1350      1360      1370      1380      1390      1400      1410      1420      1430      1440
GTTGTGCAACCAGAAAACTTGGAATACACCATTGTGATAACACCTCACTCAGGGGAAGAGCATGCAGTCGGAAATGACACAGGAAAACATGGCAAGGAAATCAAAATAACACCACAGAGT
V  V  Q  P  E  N  L  E  Y  T  I  V  I  T  P  H  S  G  E  E  H  A  V  G  N  D  T  G  K  H  G  K  E  I  K  I  T  P  Q  S

      1450      1460      1470      1480      1490      1500      1510      1520      1530      1540      1550      1560
TCCATCACAGAAGCAGAATTGACAGGTTATGGCACTGTCACAATGGAGTGCTCTCCAAGAACGGGCCTCGACTTCAATGAGATGGTGTTGCTGCAGATGGAAAATAAAGCTTGGCTGGTG
S  I  T  E  A  E  L  T  G  Y  G  T  V  T  M  E  C  S  P  R  T  G  L  D  F  N  E  M  V  L  L  Q  M  E  N  K  A  W  L  V

      1570      1580      1590      1600      1610      1620      1630      1640      1650      1660      1670      1680
CACAGGCAATGGTTCCTAGACCTGCCGTTACCATGGTTGCCCGGAGCGGACACACAAGGGTCAAATTGGATACAGAAAGAGACATTGGTCACTTTCAAAAATCCCCATGCGAAGAAACAG
H  R  Q  W  F  L  D  L  P  L  P  W  L  P  G  A  D  T  Q  G  S  N  W  I  Q  K  E  T  L  V  T  F  K  N  P  H  A  K  K  Q

      1690      1700      1710      1720      1730      1740      1750      1760      1770      1780      1790      1800
GATGTTGTTGTTTTAGGATCCCAAGAAGGGGCCATGCACACAGCACTTACAGGGGCCACAGAAATCCAAATGTCATCAGGAAACTTACTCTTCACAGGACATCTCAAGTGCAGGCTGAGA
D  V  V  V  L  G  S  Q  E  G  A  M  H  T  A  L  T  G  A  T  E  I  Q  M  S  S  G  N  L  L  F  T  G  H  L  K  C  R  L  R

      1810      1820      1830      1840      1850      1860      1870      1880      1890      1900      1910      1920
ATGGACAAGCTACAGCTCAAAGGAATGTCATACTCTATGTGCACAGGAAAGTTTAAAGTTGTGAAGGAAATAGCAGAAACACAACATGGAACAATAGTTATCAGAGTGCAATATGAAGGG
M  D  K  L  Q  L  K  G  M  S  Y  S  M  C  T  G  K  F  K  V  V  K  E  I  A  E  T  Q  H  G  T  I  V  I  R  V  Q  Y  E  G

      1930      1940      1950      1960      1970      1980      1990      2000      2010      2020      2030      2040
GACGGCTCTCCATGCAAGATCCCTTTTGAGATAATGGATTTGGAAAAAAGACATGTCTTAGGTCGCCTGATTACAGTCAACCCAATTGTGACAGAAAAAGATAGCCCAGTCAACATAGAA
D  G  S  P  C  K  I  P  F  E  I  M  D  L  E  K  R  H  V  L  G  R  L  I  T  V  N  P  I  V  T  E  K  D  S  P  V  N  I  E

      2050      2060      2070      2080      2090      2100      2110      2120      2130      2140      2150      2160
GCAGAACCTCCATTTGGAGACAGCTACATCATCATAGGAGTAGAGCCGGGACAACTGAAGCTCAACTGGTTTAAGAAAGGAAGTTCTATCGGCCAAATGTTTGAGACAACAATGAGGGGG
A  E  P  P  F  G  D  S  Y  I  I  I  G  V  E  P  G  Q  L  K  L  N  W  F  K  K  G  S  S  I  G  Q  M  F  E  T  T  M  R  G
               |
D2 PDK-53 nt-2055-T silent mutation (D2 16681: C)

      2170      2180      2190      2200      2210      2220      2230      2240      2250      2260      2270      2280
GCGAAGAGAATGGCCATTTTAGGTGACACAGCCTGGGATTTTGGATCCTTGGGAGGAGTGTTTACATCTATAGGAAAGGCTCTCCACCAAGTCTTTGGAGCAATCTATGGAGCTGCCTTC
A  K  R  M  A  I  L  G  D  T  A  W  D  F  G  S  L  G  G  V  F  T  S  I  G  K  A  L  H  Q  V  F  G  A  I  Y  G  A  A  F

      2290      2300      2310      2320      2330      2340      2350      2360      2370      2380      2390      2400
AGTGGGGTTTCATGGACTATGAAAATCCTCATAGGAGTCATTATCACATGGATAGGAATGAATTCACGCAGCACCTCACTGTCTGTGACACTAGTATTGGTGGGAATTGTGACACTGTAT
S  G  V  S  W  T  M  K  I  L  I  G  V  I  I  T  W  I  G  M  N  S  R  S  T  S  L  S  V  T  L  V  L  V  G  I  V  T  L  Y

                        >NS1
      2410      2420      2430      2440      2450      2460      2470      2480      2490      2500      2510      2520
TTGGGAGTCATGGTGCAGGCCGATAGTGGTTGCGTTGTGAGCTGGAAAAACAAAGAACTGAAATGTGGCAGTGGGATTTTCATCACAGACAACGTGCACACATGGACAGAACAATACAAG
L  G  V  M  V  Q  A  D  S  G  C  V  V  S  W  K  N  K  E  L  K  C  G  S  G  I  F  I  T  D  N  V  H  T  W  T  E  Q  Y  K

      2530      2540      2550      2560      2570      2580      2590      2600      2610      2620      2630      2640
TTCCAACCAGAATCCCCTTCAAAACTAGCTTCAGCTATCCAGAAAGCCCATGAAGAGGACATTTGTGGAATCCGCTCAGTAACAAGACTGGAGAATCTGATGTGGAAACAAATAACACCA
F  Q  P  E  S  P  S  K  L  A  S  A  I  Q  K  A  H  E  E  D  I  C  G  I  R  S  V  T  R  L  E  N  L  M  W  K  Q  I  T  P
                                                           |
                                                        D2 PDK-53 NS1-53-Asp attenuation locus (wt D2 16681: Gly, nt-2579-G)

      2650      2660      2670      2680      2690      2700      2710      2720      2730      2740      2750      2760
GAATTGAATCACATTCTATCAGAAAATGAGGTGAAGTTAACTATTATGACAGGAGACATCAAAGGAATCATGCAGGCAGGAAAACGATCTCTGCGGCCTCAGCCCACTGAGCTGAAGTAT
E  L  N  H  I  L  S  E  N  E  V  K  L  T  I  M  T  G  D  I  K  G  I  M  Q  A  G  K  R  S  L  R  P  Q  P  T  E  L  K  Y
```

-continued

```
      2770      2780      2790      2800      2810      2820      2830      2840      2850      2860      2870      2880
TCATGGAAAACATGGGGCAAAGCAAAAATGCTCTCTACAGAGTCTCATAACCAGACCTTTCTCATTGATGGCCCCGAAACAGCAGAATGCCCCAACACAAATAGAGCTTGGAATTCGTTG
S  W  K  T  W  G  K  A  K  M  L  S  T  E  S  H  N  Q  T  F  L  I  D  G  P  E  T  A  E  C  P  N  T  N  R  A  W  N  S  L

      2890      2900      2910      2920      2930      2940      2950      2960      2970      2980      2990      3000
GAAGTTGAAGACTATGGCTTTGGAGTATTCACCACCAATATATGGCTAAAATTGAAAGAAAAACAGGATGTATTCTGCGACTCAAAACTCATGTCAGCGGCCATAAAAGACAACAGAGCC
E  V  E  D  Y  G  F  G  V  F  T  T  N  I  W  L  K  L  K  E  K  Q  D  V  F  C  D  S  K  L  M  S  A  A  I  K  D  N  R  A

      3010      3020      3030      3040      3050      3060      3070      3080      3090      3100      3110      3120
GTCCATGCCGATATGGGTTATTGGATAGAAAGTGCACTCAATGACACATGGAAGATAGAGAAAGCCTCTTTCATTGAAGTTAAAAACTGCCACTGGCCAAAATCACACACCCTCTGGAGC
V  H  A  D  M  G  Y  W  I  E  S  A  L  N  D  T  W  K  I  E  K  A  S  F  I  E  V  K  N  C  H  W  P  K  S  H  T  L  W  S

      3130      3140      3150      3160      3170      3180      3190      3200      3210      3220      3230      3240
AATGGAGTGCTAGAAAGTGAGATGATAATTCCAAAGAATCTCGCTGGACCAGTGTCTCAACACAACTATAGACCAGGCTACCATACACAAATAACAGGACCATGGCATCTAGGTAAGCTT
N  G  V  L  E  S  E  M  I  I  P  K  N  L  A  G  P  V  S  Q  H  N  Y  R  P  G  Y  H  T  Q  I  T  G  P  W  H  L  G  K  L

      3250      3260      3270      3280      3290      3300      3310      3320      3330      3340      3350      3360
GAGATGGACTTTGATTTCTGTGATGGAACAACAGTGGTAGTGACTGAGGACTGCGGAAATAGAGGACCCTCTTTGAGAACAACCACTGCCTCTGGAAAACTCATAACAGAATGGTGCTGC
E  M  D  F  D  F  C  D  G  T  T  V  V  V  T  E  D  C  G  N  R  G  P  S  L  R  T  T  T  A  S  G  K  L  I  T  E  W  C  C

                                                                                                                      >NS2A
      3370      3380      3390      3400      3410      3420      3430      3440      3450      3460      3470      3480
CGATCTTGCACATTACCACCGCTAAGATACAGAGGTGAGGATGGGTGCTGGTACGGGATGGAAATCAGACCATTGAAGGAGAAAGAAGAGAATTTGGTCAACTCCTTGGTCACAGCTGGA
R  S  C  T  L  P  P  L  R  Y  R  G  E  D  G  C  W  Y  G  M  E  I  R  P  L  K  E  K  E  E  N  L  V  N  S  L  V  T  A  G

      3490      3500      3510      3520      3530      3540      3550      3560      3570      3580      3590      3600
CATGGGCAGGTCGACAACTTTTCACTAGGAGTCTTGGGAATGGCATTGTTCCTGGAGGAAATGCTTAGGACCCGAGTAGGAACGAAACATGCAATACTACTAGTTGCAGTTTCTTTTGTG
H  G  Q  V  D  N  F  S  L  G  V  L  G  M  A  L  F  L  E  E  M  L  R  T  R  V  G  T  K  H  A  I  L  L  V  A  V  S  F  V

      3610      3620      3630      3640      3650      3660      3670      3680      3690      3700      3710      3720
ACATTGATCACAGGGAACATGTCCTTTAGAGACCTGGGAAGAGTGATGGTTATGGTAGGCGCCACTATGACGGATGACATAGGTATGGGCGTGACTTATCTTGCCCTACTAGCAGCCTTC
T  L  I  T  G  N  M  S  F  R  D  L  G  R  V  M  V  M  V  G  A  T  M  T  D  D  I  G  M  G  V  T  Y  L  A  L  L  A  A  F

      3730      3740      3750      3760      3770      3780      3790      3800      3810      3820      3830      3840
AAAGTCAGACCAACTTTTGCAGCTGGACTACTCTTGAGAAAGCTGACCTCCAAGGAATTGATGATGACTACTATAGGAATTGTACTCCTCTCCCAGAGCACCATACCAGAGACCATTCTT
K  V  R  P  T  F  A  A  G  L  L  L  R  K  L  T  S  K  E  L  M  M  T  T  I  G  I  V  L  L  S  Q  S  T  I  P  E  T  I  L

      3850      3860      3870      3880      3890      3900      3910      3920      3930      3940      3950      3960
GAGTTGACTGATGCGTTAGCCTTAGGCATGATGGTCCTCAAAATGGTGAGAAATATGGAAAAGTATCAATTGGCAGTGACTATCATGGCTATCTTGTGCGTCCCAAACGCAGTGATATTA
E  L  T  D  A  L  A  L  G  M  M  V  L  K  M  V  R  N  M  E  K  Y  Q  L  A  V  T  I  M  A  I  L  C  V  P  N  A  V  I  L

      3970      3980      3990      4000      4010      4020      4030      4040      4050      4060      4070      4080
CAAAACGCATGGAAAGTGAGTTGCACAATATTGGCAGTGGTGTCCGTTTCCCCACTGTTCTTAACATCCTCACAGCAAAAAACAGATTGGATACCATTAGCATTGACGATCAAAGGTCTC
Q  N  A  W  K  V  S  C  T  I  L  A  V  V  S  V  S  P  L  F  L  T  S  S  Q  Q  K  T  D  W  I  P  L  A  L  T  I  K  G  L
                                                           |
                                                 D2 PDK-53 specific NS2A-181-Phe (wt D2 16681: Leu, nt-4018-C)

                                                 >NS2B
      4090      4100      4110      4120      4130      4140      4150      4160      4170      4180      4190      4200
AATCCAACAGCTATTTTTCTAACAACCCTCTCAAGAACCAGCAAGAAAAGGAGCTGGCCATTAAATGAGGCTATCATGGCAGTCGGGATGGTGAGCATTTTAGCCAGTTCTCTCCTAAAA
N  P  T  A  I  F  L  T  T  L  S  R  T  S  K  K  R  S  W  P  L  N  E  A  I  M  A  V  G  M  V  S  I  L  A  S  S  L  L  K
```

-continued

```
      4210      4220      4230      4240      4250      4260      4270      4280      4290      4300      4310      4320
AATGATATTCCCATGACAGGACCATTAGTGGCTGGAGGGCTCCTCACTGTGTGCTACGTGCTCACTGGACGATCGGCCGATTTGGAACTGGAGAGAGCAGCCGATGTCAAATGGGAAGAC
N  D  I  P  M  T  G  P  L  V  A  G  G  L  L  T  V  C  Y  V  L  T  G  R  S  A  D  L  E  L  E  R  A  A  D  V  K  W  E  D

      4330      4340      4350      4360      4370      4380      4390      4400      4410      4420      4430      4440
CAGGCAGAGATATCAGGAAGCAGTCCAATCCTGTCAATAACAATATCAGAAGATGGTAGCATGTCGATAAAAAATGAAGAGGAAGAACAAACACTGACCATACTCATTAGAACAGGATTG
Q  A  E  I  S  G  S  S  P  I  L  S  I  T  I  S  E  D  G  S  M  S  I  K  N  E  E  E  E  Q  T  L  T  I  L  I  R  T  G  L

                                                                                 >NS3
      4450      4460      4470      4480      4490      4500      4510      4520      4530      4540      4550      4560
CTGGTGATCTCAGGACTTTTTCCTGTATCAATACCAATCACGGCAGCAGCATGGTACCTGTGGGAAGTGAAGAAACAACGGGCCGGAGTATTGTGGGATGTTCCTTCACCCCCACCCATG
L  V  I  S  G  L  F  P  V  S  I  P  I  T  A  A  A  W  Y  L  W  E  V  K  K  Q  R  A  G  V  L  W  D  V  P  S  P  P  P  M

      4570      4580      4590      4600      4610      4620      4630      4640      4650      4660      4670      4680
GGAAAGGCTGAACTGGAAGATGGAGCCTATAGAATTAAGCAAAAAGGGATTCTTGGATATTCCCAGATCGGAGCCGGAGTTTACAAAGAAGGAACATTCCATACAATGTGGCATGTCACA
G  K  A  E  L  E  D  G  A  Y  R  I  K  Q  K  G  I  L  G  Y  S  Q  I  G  A  G  V  Y  K  E  G  T  F  H  T  M  W  H  V  T

      4690      4700      4710      4720      4730      4740      4750      4760      4770      4780      4790      4800
CGTGGCGCTGTTCTAATGCATAAAGGAAAGAGGATTGAACCATCATGGGCGGACGTCAAGAAAGACCTAATATCATATGGAGGAGGCTGGAAGTTAGAAGGAGAATGGAAGGAAGGAGAA
R  G  A  V  L  M  H  K  G  K  R  I  E  P  S  W  A  D  V  K  K  D  L  I  S  Y  G  G  G  W  K  L  E  G  E  W  K  E  G  E

      4810      4820      4830      4840      4850      4860      4870      4880      4890      4900      4910      4920
GAAGTCCAGGTATTGGCACTGGAGCCTGGAAAAAATCCAAGAGCCGTCCAAACGAAACCTGGTCTTTTCAAAACCAACGCCGGAACAATAGGTGCTGTATCTCTGGACTTTTCTCCTGGA
E  V  Q  V  L  A  L  E  P  G  K  N  P  R  A  V  Q  T  K  P  G  L  F  K  T  N  A  G  T  I  G  A  V  S  L  D  F  S  P  G

      4930      4940      4950      4960      4970      4980      4990      5000      5010      5020      5030      5040
ACGTCAGGATCTCCAATTATCGACAAAAAAGGAAAAGTTGTGGGTCTTTATGGTAATGGTGTTGTTACAAGGAGTGGAGCATATGTGAGTGCTATAGCCCAGACTGAAAAAAGCATTGAA
T  S  G  S  P  I  I  D  K  K  G  K  V  V  G  L  Y  G  N  G  V  V  T  R  S  G  A  Y  V  S  A  I  A  Q  T  E  K  S  I  E

      5050      5060      5070      5080      5090      5100      5110      5120      5130      5140      5150      5160
GACAACCCAGAGATCGAAGATGACATTTTCCGAAAGAGAAGACTGACCATCATGGACCTCCACCCAGGAGCGGGAAAGACGAAGAGATACCTTCCGGCCATAGTCAGAGAAGCTATAAAA
D  N  P  E  I  E  D  D  I  F  R  K  R  A  L  T  I  M  D  L  H  P  G  A  G  K  T  K  R  Y  L  P  A  I  V  R  E  A  I  K

      5170      5180      5190      5200      5210      5220      5230      5240      5250      5260      5270      5280
CGGGGTTTGAGAACATTAATCTTGGCCCCCACTAGAGTTGTGGCAGCTGAAATGGAGGAAGCCCTTAGAGGACTTCCAATAAGATACCAGACCCCAGCCATCAGAGCTGTGCACACCGGG
R  G  L  R  T  L  I  L  A  P  T  R  V  V  A  A  E  M  E  E  A  L  R  G  L  P  I  R  Y  Q  T  P  A  I  R  A  V  H  T  G
                                                                                                    |
                                        D2 PDK-53 WS3-250-Val attenuation locus (D2 16681: Glu, nt-5270-A)

      5290      5300      5310      5320      5330      5340      5350      5360      5370      5380      5390      5400
CGGGAGATTGTGGACCTAATGTGTCATGCCACATTTACCATGAGGCTGCTATCACCAGTTAGAGTGCCAAACTACAACCTGATTATCATGGACGAAGCCCATTTCACAGACCCAGCAAGT
R  E  I  V  D  L  M  C  H  A  T  F  T  M  R  L  L  S  P  V  R  V  P  N  Y  N  L  I  I  M  D  E  A  H  F  T  D  P  A  S

      5410      5420      5430      5440      5450      5460      5470      5480      5490      5500      5510      5520
ATAGCAGCTAGAGGATACATCTCAACTCGAGTGGAGATGGGTGAGGCAGCTGGGATTTTTATGACAGCCACTCCCCCGGGAAGCAGAGACCCATTTCCTCAGAGCAATGCACCAATCATA
I  A  A  R  G  Y  I  S  T  R  V  E  M  G  E  A  A  G  I  F  M  T  A  T  P  P  G  S  R  D  P  F  P  Q  S  N  A  P  I  I

      5530      5540      5550      5560      5570      5580      5590      5600      5610      5620      5630      5640
GATGAAGAAAGAGAAATCCCTGAACGCTCGTGGAATTCCGGACATGAATGGGTCACGGATTTTAAAGGGAAGACTGTTTGGTTCGTTCCAAGTATAAAAGCAGGAAATGATATAGCAGCT
D  E  E  R  E  I  P  E  R  S  W  N  S  G  H  E  W  V  T  D  F  K  G  K  T  V  W  F  V  P  S  I  K  A  G  N  D  I  A  A
```

-continued

```
                                    |
                                  D2 PDK-53 silent mutation nt-5547-C (D2 16681: T)

     5650      5660      5670      5680      5690      5700      5710      5720      5730      5740      5750      5760
TGCCTGAGGAAAAATGGAAAGAAAGTGATACAACTCAGTAGGAAGACCTTTGATTCTGAGTATGTCAAGACTAGAACCAATGATTGGGACTTCGTGGTTACAACTGACATTTCAGAAATG
C  L  R  K  N  G  K  K  V  I  Q  L  S  R  K  T  F  D  S  E  Y  V  K  T  R  I  N  D  W  D  F  V  V  I  T  D  I  S  E  M

     5770      5780      5790      5800      5810      5820      5830      5840      5850      5860      5870      5880
GGTGCCAATTTCAAGGCTGAGAGGGTTATAGACCCCAGACGCTGCATGAAACCAGTCATACTAACAGATGGTGAAGAGCGGGTGATTCTGGCAGGACCTATGCCAGTGACCCACTCTAGT
G  A  N  F  K  A  E  R  V  I  D  P  R  A  C  M  K  P  V  I  L  T  D  G  E  E  R  V  I  L  A  G  P  M  P  V  T  H  S  S

     5890      5900      5910      5920      5930      5940      5950      5960      5970      5980      5990      6000
GCAGCACAAAGAAGAGGGAGAATAGGAAGAAATCCAAAAAATGAGAATGACCAGTACATATACATGGGGGAACCTCTGGAAAATGATGAAGACTGTGCACACTGGAAAGAAGCTAAAATG
A  A  Q  R  R  G  R  I  G  R  N  P  K  N  E  N  D  Q  Y  I  Y  M  G  E  P  L  E  N  D  E  D  C  A  H  W  K  E  A  K  M

     6010      6020      6030      6040      6050      6060      6070      6080      6090      6100      6110      6120
CTCCTAGATAACATCAACACGCCAGAAGGAATCATTCCTAGCATGTTCGAACCAGAGCGTGAAAAGGTGGATGCCATTGATGGCGAATACCGCTTGAGAGGAGAAGCAAGGAAAACCTTT
L  L  D  N  I  N  T  P  E  G  I  I  P  S  M  F  E  P  E  R  E  K  V  D  A  I  D  G  E  Y  R  L  R  G  E  A  R  K  T  F

     6130      6140      6150      6160      6170      6180      6190      6200      6210      6220      6230      6240
GTAGACTTAATGAGAAGAGGAGACCTACCAGTCTGGTTGGCCTACAGAGTGGCAGCTGAAGGCATCAACTACGCAGACAGAAGGTGGTGTTTTGATGGAGTCAAGAACAACCAAATCCTA
V  D  L  M  A  R  G  D  L  P  V  W  L  A  Y  R  V  A  A  E  G  I  N  Y  A  D  R  A  W  C  F  D  G  V  K  N  N  Q  I  L

     6250      6260      6270      6280      6290      6300      6310      6320      6330      6340      6350      6360
GAAGAAAACGTGGAAGTTGAAATCTGGACAAAAGAAGGGGAAAGGAAGAAATTGAAACCCAGATGGTTGGATGCTAGGATCTATTCTGACCCACTGGCGCTAAAAGAATTTAAGGAATTT
E  E  N  V  E  V  E  I  W  T  K  E  G  E  R  K  K  L  K  P  R  W  L  D  A  R  I  Y  S  D  P  L  A  L  K  E  F  K  E  F

              >NS4A
     6370      6380      6390      6400      6410      6420      6430      6440      6450      6460      6470      6480
GCAGCCGGAAGAAAGTCTCTGACCCTGAACCTAATCACAGAAATGGGTAGGCTCCCAACCTTCATGACTCAGAAGGCAAGAGACGCACTGGACAACTTAGCAGTGCTGCACACGGCTGAG
A  A  G  R  K  S  L  T  L  N  L  I  T  E  M  G  R  L  P  T  F  M  T  Q  K  A  R  D  A  L  D  N  L  A  V  L  H  T  A  E

     6490      6500      6510      6520      6530      6540      6550      6560      6570      6580      6590      6600
GCAGGTGGAAGGGCGTACAACCATGCTCTCAGTGAACTGCCGGAGACCCTGGAGACATTGCTTTTACTGACACTTCTGGCTACAGTCACGGGAGGGATCTTTTTATTCTTGATGAGCGCA
A  G  G  R  A  Y  N  H  A  L  S  E  L  P  E  T  L  E  T  L  L  L  L  T  L  L  A  T  V  T  G  G  I  F  L  F  L  M  S  A
             |
                                                                            D2 PDK-53 specific NS4A-75-Ala (wt D2 16681: Gly, nt-6599-G)

     6610      6620      6630      6640      6650      6660      6670      6680      6690      6700      6710      6720
AGGGGCATAGGGAAGATGACCCTGGGAATGTGCTGCATAATCACGGCTAGCATCCTCCTATGGTACGCACAAATACAGCCACACTGGATAGCAGCTTCAATAATACTGGAGTTTTTCTC
R  G  I  G  K  M  T  L  G  M  C  C  I  I  T  A  S  I  L  L  W  Y  A  Q  I  Q  P  H  W  I  A  A  S  I  I  L  E  F  F  L

                                                                                                             >NS4B
     6730      6740      6750      6760      6770      6780      6790      6800      6810      6820      6830      6840
ATAGTTTTGCTTATTCCAGAACCTGAAAAACAGAGAACACCCCAAGACAACCAACTGACCTACGTTGTCATAGCCATCCTCACAGTGGTGGCCGCAACCATGGCAAACGAGATGGGTTTC
I  V  L  L  I  P  E  P  E  K  Q  R  T  P  Q  D  N  Q  L  T  Y  V  V  I  A  I  L  T  V  V  A  A  T  M  A  N  E  M  G  F

     6850      6860      6870      6880      6890      6900      6910      6920      6930      6940      6950      6960
CTAGAAAAAACGAAGAAAGATCTCGGATTGGGAAGCATTGCAACCCAGCAACCCGAGAGCAACATCCTGGACATAGATCTACGTCCTGCATCAGCATGGACGCTGTATGCCGTGGCCACA
L  E  K  T  K  K  D  L  G  L  G  S  I  A  T  Q  Q  P  E  S  N  I  L  D  I  D  L  R  P  A  S  A  W  T  L  Y  A  V  A  T

     6970      6980      6990      7000      7010      7020      7030      7040      7050      7060      7070      7080
ACATTTGTTACACCAATGTTGAGACATAGCATTGAAAATTCCTCAGTGAATGTGTCCCTAACAGCTATAGCCAACCAAGCCACAGTGTTAATGGGICTCGGGAAAGGATGGCCATTGICA
T  F  V  T  P  M  L  R  H  S  I  E  N  S  S  V  N  V  S  L  T  A  I  A  N  Q  A  T  V  L  M  G  L  G  K  G  W  P  L  S
```

-continued

```
      7090      7100      7110      7120      7130      7140      7150      7160      7170      7180      7190      7200
AAGATGGACATCGGAGTTCCCCTTCTCGCCATTGGATGCTACTCACAAGTCAACCCCATAACTCTCACAGCAGCTCTTTTCTTATTGGTAGCACATTATGCCATCATAGGGCCAGGACTC
K  M  D  I  G  V  P  L  L  A  I  G  C  Y  S  Q  V  N  P  I  T  L  T  A  A  L  F  L  L  V  A  H  Y  A  I  I  G  P  G  L

      7210      7220      7230      7240      7250      7260      7270      7280      7290      7300      7310      7320
CAAGCAAAAGCAACCAGAGAAGCTCAGAAAAGAGCAGCGGCGGGCATCATGAAAAACCCAACTGTCGATGGAATAACAGTGATTGACCTAGATCCAATACCTTATGATCCAAAGTTTGAA
Q  A  K  A  T  R  E  A  Q  K  R  A  A  A  G  I  M  K  N  P  T  V  D  G  I  T  V  I  D  L  D  P  I  P  Y  D  P  K  F  E

      7330      7340      7350      7360      7370      7380      7390      7400      7410      7420      7430      7440
AAGCAGTTGGGACAAGTAATGCTCCTAGTCCTCTGCGTGACTCAAGTATTGATGATGAGGACTACATGGGCTCTGTGTGAGGCTTTAACCTTAGCTACCGGGCCCATCTCCACATTGTGG
K  Q  L  G  Q  V  M  L  L  V  L  C  V  T  Q  V  L  M  M  R  T  T  W  A  L  C  E  A  L  T  L  A  T  G  P  I  S  T  L  W

      7450      7460      7470      7480      7490      7500      7510      7520      7530      7540      7550      7560
GAAGGAAATCCAGGGAGGTTTTGGAACACTACCATTGCGGTGTCAATGGCTAACATTTTTAGAGGGAGTTACTTGGCCGGAGCTGGACTTCTCTTTTCTATTATGAAGAACACAACCAAC
E  G  N  P  G  R  F  W  N  T  T  I  A  V  S  M  A  N  I  F  R  G  S  Y  L  A  G  A  G  L  L  F  S  I  M  K  N  T  T  N

         >NS5
      7570      7580      7590      7600      7610      7620      7630      7640      7650      7660      7670      7680
ACAAGAAGGGGAACTGGCAACATAGGAGAGACGCTTGGAGAGAAATGGAAAAGCCGATTGAACGCATTGGGAAAAAGTGAATTCCAGATCTACAAGAAAAGTGGAATCCAGGAAGTGGAT
T  R  R  G  T  G  N  I  G  E  T  L  G  E  K  W  K  S  R  L  N  A  L  G  K  S  E  F  Q  I  Y  K  K  S  G  I  Q  E  V  D

      7690      7700      7710      7720      7730      7740      7750      7760      7770      7780      7790      7800
AGAACCTTAGCAAAAGAAGGCATTAAAAGAGGAGAAACGGACCATCACGCTGTGTCGCGAGGCTCAGCAAAACTGAGATGGTTCGTTGAGAGAAACATGGTCACACCAGAAGGGAAAGTA
R  T  L  A  K  E  G  I  K  R  G  E  T  D  H  H  A  V  S  R  G  S  A  K  L  R  W  F  V  E  R  N  M  V  T  P  E  G  K  V

      7810      7820      7830      7840      7850      7860      7870      7880      7890      7900      7910      7920
GTGGACCTCGGTTGTGGCAGAGGAGGCTGGTCATACTATTGTGGAGGACTAAAGAATGTAAGAGAAGTCAAAGGCCTAACAAAAGGAGGACCAGGACACGAAGAACCCATCCCCATGTCA
V  D  L  G  C  G  R  G  G  W  S  Y  Y  C  G  G  L  K  N  V  R  E  V  K  G  L  T  K  G  G  P  G  H  E  E  P  I  P  M  S

      7930      7940      7950      7960      7970      7980      7990      8000      8010      8020      8030      8040
ACATATGGGTGGAATCTAGTGCGTCTTCAAAGTGGAGTTGACGTTTTCTTCATCCCGCCAGAAAAGTGTGACACATTATTGTGTGACATAGGGGAGTCATCACCAAATCCCACAGTGGAA
T  Y  G  W  N  L  V  R  L  Q  S  G  V  D  V  F  F  I  P  P  E  K  C  D  T  L  L  C  D  I  G  E  S  S  P  N  P  T  V  E

      8050      8060      8070      8080      8090      8100      8110      8120      8130      8140      8150      8160
GCAGGACGAACACTCAGAGTCCTTAACTTAGTAGAAAATTGGTTGAACAACAACACTCAATTTTGCATAAAGGTTCTCAACCCATATATGCCCTCAGTCATAGAAAAAATGGAAGCACTA
A  G  R  T  L  R  V  L  N  L  V  E  N  W  L  N  N  N  T  Q  F  C  I  K  V  L  N  P  Y  M  P  S  V  I  E  K  M  E  A  L

      8170      8180      8190      8200      8210      8220      8230      8240      8250      8260      8270      8280
CAAAGGAAATATGGAGGAGCCTTAGTGAGGAATCCACTCTCACGAAACTCCACACATGAGATGTACTGGGTATCCAATGCTTCCGGGAACATAGTGTCATCAGTGAACATGATTTCAAGG
Q  R  K  Y  G  G  A  L  V  R  N  P  L  S  R  N  S  T  H  E  M  Y  W  V  S  N  A  S  G  N  I  V  S  S  V  N  M  I  S  R

      8290      8300      8310      8320      8330      8340      8350      8360      8370      8380      8390      8400
ATGTTGATCAACAGATTTACAATGAGATACAAGAAAGCCACTTACGAGCCGGATGTTGACCTCGGAAGCGGAACCCGTAACATCGGGATTGAAAGTGAGATACCAAACCTAGATATAATT
M  L  I  N  R  F  T  M  R  Y  K  K  A  T  Y  E  P  D  V  D  L  G  S  G  T  R  N  I  G  I  E  S  E  I  P  N  L  D  I  I

      8410      8420      8430      8440      8450      8460      8470      8480      8490      8500      8510      8520
GGGAAAAGAATAGAAAAAATAAAGCAAGAGCATGAAACATCATGGCACCATGACCAAGACCACCCATACAAAACGTGGGCATACCATGGTAGCTATGAAACAAAACAGACTGGATCAGCA
G  K  R  I  E  K  I  K  Q  E  H  E  T  S  W  H  Y  D  Q  D  H  P  Y  K  T  W  A  Y  H  G  S  Y  E  T  K  Q  T  G  S  A

      8530      8540      8550      8560      8570      8580      8590      8600      8610      8620      8630      8640
TCATCCATGGTCAACGGAGTGGTCAGGCTGCTGACAAAACCTTGGGACGTCGTCCCCATGGTGACACAGATGGCAATGACAGACACGACTCCATTTGGACAACAGCGCGTTTTTAAAGAG
S  S  M  V  N  G  V  V  R  L  L  T  K  P  W  D  V  V  P  M  V  T  Q  M  A  M  T  D  T  T  P  F  G  Q  Q  R  V  F  K  E
```

-continued

```
      8650      8660      8670      8680      8690      8700      8710      8720      8730      8740      8750      8760
AAAGTGGACACGAGAACCCAAGAACCGAAAGAAGGCACGAAGAAACTAATGAAAATAACAGCAGAGTGGCTTTGGAAAGAATTAGGGAAGAAAAAGACACCCAGGATGTGCACCAGAGAA
K  V  D  T  R  T  Q  E  P  K  E  G  T  K  K  L  M  K  I  T  A  E  W  L  W  K  E  L  G  K  K  K  T  P  R  M  C  T  R  E

      8770      8780      8790      8800      8810      8820      8830      8840      8850      8860      8870      8880
GAATTCACAAGAAAGGTGAGAAGCAATGCAGCCTIGGGGGCCGTATTCACTGATGAGAACAAGTGGAAGTCGGCACGTGAGGCTGTTGAAGATAGTAGGTTTIGGGAGCTGGTTGACAAG
E  F  T  R  K  V  A  S  N  A  A  L  G  A  V  F  T  D  E  N  K  W  K  S  A  R  E  A  V  E  D  S  R  F  W  E  L  V  D  K
                                             |
                                 Additional NS5-412 Ile-to-Val (nt-8803 A-to-G) mutation in master and pre-master seed

      8890      8900      8910      8920      8930      8940      8950      8960      8970      8980      8990      9000
GAAAGGAATCTCCATCTTGAAGGAAAGTGTGAAACATGTGTGTACAACATGATGGGAAAAAGAGAGAAGAAGCTAGGGGAATTCGGCAAGGCAAAAGGCAGCAGAGCCATATGGTACATG
E  R  N  L  H  L  E  G  K  C  E  T  C  V  Y  N  M  M  G  K  R  E  K  K  L  G  E  F  G  K  A  K  G  S  R  A  I  W  Y  M

      9010      9020      9030      9040      9050      9060      9070      9080      9090      9100      9110      9120
TGGCTIGGAGCACGCTTCTTAGAGTTTGAAGCCCTAGGATTCTTAAATGAAGATCACTGGTTCTCCAGAGAGAACTCCCTGAGTGGAGTGGAAGGAGAAGGGCTGCACAAGCTAGGTTAC
W  L  G  A  R  F  L  E  F  E  A  L  G  F  L  N  E  D  H  W  F  S  R  E  N  S  L  S  G  V  E  G  E  G  L  H  K  L  G  Y

      9130      9140      9150      9160      9170      9180      9190      9200      9210      9220      9230      9240
ATTCTAAGAGACGTGAGCAAGAAAGAGGGAGGAGCAATGTATGCCGATGACACCGCAGGATGGGATACAAGAATCACACTAGAAGACCTAAAAAATGAAGAAATGGTAACAAACCACATG
I  L  R  D  V  S  K  K  E  G  G  A  M  Y  A  D  D  T  A  G  W  D  T  R  I  T  L  E  D  L  K  N  E  E  M  V  T  N  H  M

      9250      9260      9270      9280      9290      9300      9310      9320      9330      9340      9350      9360
GAAGGAGAACACAAGAAACTAGCCGAGGCCATTTTCAAACTAACGTACCAAAACAAGGTGGTGCGTGTGCAAAGACCAACACCAAGAGGCACAGTAATGGACATCATATCGAGAAGAGAC
E  G  E  H  K  K  L  A  E  A  I  F  K  L  T  Y  Q  N  K  V  V  R  V  Q  R  P  T  P  R  G  T  V  M  D  I  I  S  R  R  D

      9370      9380      9390      9400      9410      9420      9430      9440      9450      9460      9470      9480
CAAAGAGGTAGTGGACAAGTTGGCACCTATGGACTCAATACTTTCACCAATATGGAAGCCCAACTAATCAGACAGATGGAGGGAGAAGGAGTCTTTAAAAGCATTCAGCACCTAACAATC
Q  R  G  S  G  Q  V  G  T  Y  G  L  N  T  F  T  N  M  E  A  Q  L  I  R  Q  M  E  G  E  G  V  F  K  S  I  Q  H  L  T  I

      9490      9500      9510      9520      9530      9540      9550      9560      9570      9580      9590      9600
ACAGAAGAAATCGCTGTGCAAAACTGGTTAGCAAGAGTGGGGCGCGAAAGGTTATCAAGAATGGCCATCAGTGGAGATGATTGTGTTGTGAAACCTTTAGATGACAGGTTCGCAAGCGCT
T  E  E  I  A  V  Q  N  W  L  A  R  V  G  R  E  R  L  S  R  M  A  I  S  G  D  D  C  V  V  K  P  L  D  D  R  F  A  S  A

      9610      9620      9630      9640      9650      9660      9670      9680      9690      9700      9710      9720
TTAACAGCTCTAAATGACATGGGAAAGATTAGGAAAGACATACAACAATGGGAACCTTCAAGAGGATGGAATGATTGGACACAAGTGCCCTTCTGTTCACACCATTTCCATGAGTTAATC
L  T  A  L  N  D  M  G  K  I  R  K  D  I  Q  Q  W  E  P  S  R  G  W  N  D  W  T  Q  V  P  F  C  S  H  H  F  H  E  L  I

      9730      9740      9750      9760      9770      9780      9790      9800      9810      9820      9830      9840
ATGAAAGACGGTCGCGTACTCGTTGTTCCATGTAGAAACCAAGATGAACTGATTGGCAGAGCCCGAATCTCCCAAGGAGCAGGGTGGTCTTTGCGGGAGACGGCCTGTTTGGGGAAGTCT
M  K  D  G  R  V  L  V  V  P  C  R  N  Q  D  E  L  I  G  R  A  R  I  S  Q  G  A  G  W  S  L  R  E  T  A  C  L  G  K  S

      9850      9860      9870      9880      9890      9900      9910      9920      9930      9940      9950      9960
TACGCCCAAATGTGGAGCTTGATGTACTTCCACAGACGCGACCTCAGGCTGGCGGCAAATGCTATTTGCTCGGCAGTACCATCACATTGGGTTCCAACAAGTCGAACAACCTGGTCCATA
Y  A  Q  M  W  S  L  M  Y  F  H  R  R  D  L  R  L  A  A  N  A  I  C  S  A  V  P  S  H  W  V  P  T  S  R  T  T  W  S  I

      9970      9980      9990     10000     10010     10020     10030     10040     10050     10060     10070     10080
CATGCTAAACATGAATGGATGACAACGGAAGACATGCTGACAGTCTGGAACAGGGTGTGGATTCAAGAAAACCCATGGATGGAAGACAAAACTCCAGTGGAATCATGGGAGGAAATCCCA
H  A  K  H  E  W  M  T  T  E  D  M  L  T  V  W  N  R  V  W  I  Q  E  N  P  W  M  E  D  K  T  P  V  E  S  W  E  E  I  P

     10090     10100     10110     10120     10130     10140     10150     10160     10170     10180     10190     10200
TACTTGGGGAAAAGAGAAGACCAATGGTGCGGCTCATTGATTGGGTTAACAAGCAGGGCCACCTGGGCAAAGAACATCCAAGCAGCAATAAATCAAGTTAGATCCCTTATAGGCAATGAA
Y  L  G  K  R  E  D  Q  W  C  G  S  L  I  G  L  T  S  R  A  T  W  A  K  N  I  Q  A  A  I  N  Q  V  R  S  L  I  G  N  E
```

-continued

```
                                                                    >3'-NC
     10210      10220      10230      10240      10250      10260      10270      10280      10290      10300      10310      10320
GAATACACAGATTACATGCCATCCATGAAAAGATTCAGAAGAGAAGAGGAAGAAGCAGGAGTTCTGTGGTAGAAAGCAAAACTAACATGAAACAAGGCTAGAAGTCAGGICGGATTAAGC
E  Y  T  D  Y  M  P  S  M  K  R  F  R  R  E  E  E  E  A  G  V  L  W

     10330      10340      10350      10360      10370      10380      10390      10400      10410      10420      10430      10440
CATAGTACGGAAAAAACTATGCTACCTGTGAGCCCCGTCCAAGGACGTTAAAAGAAGTCAGGCCATCATAAATGCCATAGCTTGAGTAAACTATGCAGCCTGTAGCTCCACCTGAGAAGG

     10450      10460      10470      10480      10490      10500      10510      10520      10530      10540      10550      10560
TGTAAAAAATCCGGGAGGCCACAAACCATGGAAGCTGTACGCATGGCGTAGTGGACTAGCGGTTAGAGGAGACCCCTCCCTTACAAATCGCAGCAACAATGGGGGCCCAAGGCGAGATGA

     10570      10580      10590      10600      10610      10620      10630      10640      10650      10660      10670      10680
AGCTGTAGTCTCGCTGGAAGGACTAGAGGTTAGAGGAGACCCCCCCGAAACAAAAAACAGCATATTGACGCTGGGAAAGACCAGAGATCCTGCTGICTCCTCAGCATCATTCCAGGCACA

     10690      10700      10710      10720
GAACGCCAGAAAATGGAATGGTGCTGTTGAATCAACAGGTTCT
```

DENvax-3 Master Virus Seed (MVS)

Nucleotide sequence of the chimeric viral genome and deduced amino acid sequence of the translated protein are provided herein. Most of the prM-E gene (nt-457 to –2373, underlined) is wild-type (wt) DEN-3 16562 virus-specific; the remaining nucleotide sequence is DEN-2 PDK-53 virus-specific. The E protein of DEN-3 virus has two fewer amino acids than the E protein of DEN-2. Therefore, nt position starting from NgoMIV is 6 nt less than the original DEN-2 PDK-53 nt position. All engineered substitutions differ from wt virus (DEN-3 16562 or DEN-2 16681), as well as extra mutations (changes from engineered cDNA clone) are marked.

Substitutions Included in the Genome and Protein:

Junction sites:

a. MluI (nt 451-456): engineered silent mutation, nt-453 A-to-G b. NgoMIV (nt 2374-2379): engineered mutations, nt-2375/2376 TG-to-CC (resulted in E-480 Val-to-Ala change)

D2 PDK-53 virus backbone (change from wt D2 16681): in bold a. 5'-noncoding region (NCR)-57 (nt-57 C-to-T): major attenuation locus (in red)

b. NS1-53 Gly-to-Asp (nt-2573 G-to-A): major attenuation locus (in red)

c. NS2A-181 Leu-to-Phe (nt-4012 C-to-T)

d. NS3-250 Glu-to-Val (nt-5264 A-to-T): major attenuation locus (in red)

e. nt-5541 (NS3 gene) T-to-C silent mutation f. NS4A-75 Gly-to-Ala (nt-6593 G-to-C)

* nt-8565 C-to-T silent mutation of PDK-53 is not engineered in the vaccine virus Engineered mutation in DEN-3 prM-E (change from wt D3 16562)

a. Engineered nt-552 C-to-T silent mutation: clone marker b. Engineered E-345 His-to-Leu (nt-1970 A-to-T) for efficient replication in cultures Additional substitutions found in vaccine seed (0.02% nt different from original clone)

a. E-223 Thr-to-Ser mutation (nt-1603 A-to-T, in bold)

b. nt-7620 A-to-G silent mutation (in bold)

```
                       NCR-57-T, D2 PDK-53 attenuation locus (wt D2 16681:C)
>5'-Noncoding Region                                |                                        > C
        10        20        30        40        50        60        70        80        90       100
AGTTGTTAGTCTACGTGGACCGACAAAGACAGATTCTTTGAGGGAGCTAAGCTCAATGTAGTTCTAACAGTTTTTTAATTAGAGAGCAGATCTCTGATGA
                                                                                                 M  N

       110       120       130       140       150       160       170       180       190       200
ATAACCAACGGAAAAAGGCGAAAAACACGCCTTTCAATATGCTGAAACGCGAGAGAAACCGCGTGTCGACTGTGCAACAGCTGACAAAGAGATTCTCACT
  N  Q  R  K  K  A  K  N  T  P  F  N  M  L  K  R  E  R  N  R  V  S  T  V  Q  Q  L  T  K  R  F  S  L

       210       220       230       240       250       260       270       280       290       300
TGGAATGCTGCAGGGACGAGGACCATTAAAACTGTTCATGGCCCTGGTGGCGTTCCTTCGTTTCCTAACAATCCCACCAACAGGAGGGATATTGAAGAGA
 G  M  L  Q  G  R  G  P  L  K  L  F  M  A  L  V  A  F  L  R  F  L  T  I  P  P  T  A  G  I  L  K  R

       310       320       330       340       350       360       370       380       390       400
TGGGGAACAATTAAAAAATCAAAAGCTATTAATGTTTTGAGAGGGTTCAGGAAAGAGATTGGAAGGATGCTGAACATCTTGAATAGGAGACGCAGATCTG
W  G  T  I  K  K  S  K  A  I  N  V  L  R  G  F  R  K  E  I  G  R  M  L  N  I  L  N  R  R  R  R  S  A

                                       > prM            Beginning of D3 16562 sequence
       410       420       430       440       450       |460       470       480       490       500
CAGGCATGATCATTATGCTGATTCCAACAGTGATGGCGTTCCATTTAACCACGCGTGATGGAGAGCCGCGCATGATTGTGGGGAAGAATGAAAGAGGAAA
  G  M  I  I  M  L  I  P  T  V  M  A  F  H  L  T  T  R  D  G  E  P  R  M  I  V  G  K  N  E  R  G  K
                                                       |
                                     Engineered MluI splicing site (nt-453 A-to-G silent mutation)

       510       520       530       540       550       560       570       580       590       600
ATCCCTACTTTTCAAGACAGCCTCTGGAATCAACATGTGCACACTCATAGCTATGGATCTGGGAGAGATGTGTGATGACACGGTCACTTACAAATGCCCC
  S  L  L  F  K  T  A  S  G  I  N  M  C  T  L  I  A  M  D  L  G  E  M  C  D  D  T  V  T  Y  K  C  P
                                                      |
                                                Silent C-to-T nt mutation as clone marker

       610       620       630       640       650       660       670       680       690       700
CACATTACCGAAGTGGAGCCTGAAGACATTGACTGCTGGTGCAACCTTACATCGACATGGGTGACTTATGGAACATGCAATCAAGCTGGAGAGCATAGAC
H  I  T  E  V  E  P  E  D  I  D  C  W  C  N  L  T  S  T  W  V  T  Y  G  T  C  N  Q  A  G  E  H  R  R

           > M
       710       720       730       740       750       760       770       780       790       800
GCGATAAGAGATCAGTGGCGTTAGCTCCCCATGTTGGCATGGGACTGGACACACGCACTCAAACCTGGATGTCGGCTGAAGGAGCTTGGAGACAAGTCGA
  D  K  R  S  V  A  L  A  P  H  V  G  M  G  L  D  T  R  T  Q  T  W  M  S  A  E  G  A  W  R  Q  V  E

       810       820       830       840       850       860       870       880       890       900
GAAGGTAGAGACATGGGCCCTTAGGCACCCAGGGTTTACCATACTAGCCCTATTTCTTGCCCATTACATAGGCACTTCCTTGACCCAGAAAGTGGTTATT
 K  V  E  T  W  A  L  R  H  P  G  F  T  I  L  A  L  F  L  A  H  Y  I  G  T  S  L  T  Q  K  V  V  I

                                       > E
       910       920       930       940       950       960       970       980       990      1000
TTTATACTATTAATGCTGGTTACCCCATCCATGACAATGAGATGTGTAGGAGTAGGAAACAGAGATTTTGTGGAAGGCCTATCGGGAGCTACGTGGGTTG
F  I  L  L  M  L  V  T  P  S  M  T  M  R  C  V  G  V  G  N  R  D  F  V  E  G  L  S  G  A  T  W  V  D

      1010      1020      1030      1040      1050      1060      1070      1080      1090      1100
ACGTGGTGCTCGAGCACGGTGGGTGTGTGACTACCATGGCTAAGAACAAGCCCACGCTGGACATAGAGCTTCAGAAGACCGAGGCCACCCAACTGGCGAC
  V  V  L  E  H  G  G  C  V  T  T  M  A  K  N  K  P  T  L  D  I  E  L  Q  K  T  E  A  T  Q  L  A  T
```

-continued

```
      1110      1120      1130      1140      1150      1160      1170      1180      1190      1200
CCTAAGGAAGCTATGCATTGAGGGAAAAATTACCAACATAACAACCGACTCAAGATGTCCCACCCAAGGGGAAGCGATTTTACCTGAGGAGCAGGACCAG
 L  R  K  L  C  I  E  G  K  I  T  N  I  T  T  D  S  R  C  P  T  Q  G  E  A  I  L  P  E  E  Q  D  Q

      1210      1220      1230      1240      1250      1260      1270      1280      1290      1300
AACTACGTGTGTAAGCATACATACGTGGACAGAGGCTGGGGAAACGGTTGTGGTTTGTTTGGCAAGGGAAGCTTGGTGACATGCGCGAAATTTCAATGTT
N  Y  V  C  K  H  T  Y  V  D  R  G  W  G  N  G  C  G  L  F  G  K  G  S  L  V  T  C  A  K  F  Q  C  L

      1310      1320      1330      1340      1350      1360      1370      1380      1390      1400
TAGAATCAATAGAGGGAAAAGTGGTGCAACATGAGAACCTCAAATACACCGTCATCATCACAGTGCACACAGGAGACCAACACCAGGTGGGAAATGAAAC
  E  S  I  E  G  K  V  V  Q  H  E  N  L  K  Y  T  V  I  I  T  V  H  T  G  D  Q  H  Q  V  G  N  E  T

      1410      1420      1430      1440      1450      1460      1470      1480      1490      1500
GCAGGGAGTCACGGCTGAGATAACACCCCAGGCATCAACCGCTGAAGCCATTTTACCTGAATATGGAACCCTCGGGCTAGAATGCTCACCACGGACAGGT
 Q  G  V  T  A  E  I  T  P  Q  A  S  T  A  E  A  I  L  P  E  Y  G  T  L  G  L  E  C  S  P  R  T  G

      1510      1520      1530      1540      1550      1560      1570      1580      1590      1600
TTGGATTTCAATGAAATGATCTCATTGACAATGAAGAACAAAGCATGGATGGTACATAGACAATGGTTCTTTGACTTACCCCTACCATGGACATCAGGAG
L  D  F  N  E  M  I  S  L  T  M  K  N  K  A  W  M  V  H  R  Q  W  F  F  D  L  P  L  P  W  T  S  G  A

      1610      1620      1630      1640      1650      1660      1670      1680      1690      1700
CTTCAGGAGAAACACCAACTTGGAACAGGAAAGAGCTTCTTGTGACATTTAAAAATGCACATGCAAAAAAGCAAGAAGTAGTTGTTCTTGGATCACAAGA
  S  A  E  T  P  T  W  N  R  K  E  L  L  V  T  F  K  N  A  H  A  K  K  Q  E  V  V  V  L  G  S  Q  E
  |
Additional E-233 Thr-to-Ser mutation (wt D3 16562: nt-1603 A) in master and pre-master seed

      1710      1720      1730      1740      1750      1760      1770      1780      1790      1800
GGGAGCAATGCATACAGCACTGACAGGAGCTACAGAGATCCAAACCTCAGGAGGCACAAGTATCTTTGCGGGGCACTTAAAATGTAGACTCAAGATGGAC
 G  A  M  H  T  A  L  T  G  A  T  E  I  Q  T  S  G  G  T  S  I  F  A  G  H  L  K  C  R  L  K  M  D

      1810      1820      1830      1840      1850      1860      1870      1880      1890      1900
AAATTGGAACTCAAGGGGATGAGCTATGCAATGTGCTTGAGTAGCTTTGTGTTGAAGAAAGAAGTCTCCGAAACGCAGCATGGGACAATACTCATTAAGG
K  L  E  L  K  G  M  S  K  A  M  C  L  S  S  F  V  L  K  K  E  V  S  E  T  Q  H  G  T  I  L  I  K  V

      1910      1920      1930      1940      1950      1960      1970      1980      1990      2000
TTGAGTACAAAGGGGAAGATGCACCCTGCAAGATTCCTTTCTCCACGGAGGATGGACAAGGAAAAGCTCTCAATGGCAGACTGATCACAGCCAATCCAGT
  E  Y  K  G  E  D  A  P  C  K  I  P  F  S  T  E  D  G  Q  G  K  A  L  N  G  R  L  I  T  A  N  P  V
                                                                    |
                    Engineered E-345 His-to-Leu (wt D3 16562: nt-1970-A) for efficient growth

      2010      2020      2030      2040      2050      2060      2070      2080      2090      2100
GGTGACCAAGAAGGAGGAGCCTGTCAACATTGAGGCTGAACCTCCTTTTGGAGAAAGTAACATAGTAATTGGAATTGGAGACAAAGCCCTGAAAATCAAC
 V  T  K  K  E  E  P  V  N  I  E  A  E  P  P  F  G  E  S  N  I  V  I  G  I  G  D  K  A  L  K  I  N

      2110      2120      2130      2140      2150      2160      2170      2180      2190      2200
TGGTACAAGAAGGGAAGCTCGATTGGGAAGATGTTCGAGGCCACTGCCAGAGGTGCAAGGCGCATGGCCATCTTGGGAGACACAGCCTGGGACTTTGGAT
W  Y  K  K  G  S  S  I  G  K  M  F  E  A  T  A  R  G  A  R  R  M  A  I  L  G  D  T  A  W  D  F  G  S

      2210      2220      2230      2240      2250      2260      2270      2280      2290      2300
CAGTGGGTGGTGTTTTGAATTCATTAGGGAAAATGGTCCACCAAATATTTGGGAGTGCTTACACAGCCCTATTTGGTGGAGTCTCCTGGATGATGAAAAT
  V  G  G  V  L  N  S  L  G  K  M  V  H  Q  I  F  G  S  A  Y  T  A  L  F  G  G  V  S  W  M  M  K  I

                                                                   End of D3 16562 sequence
      2310      2320      2330      2340      2350      2360      2370  |   2380      2390      2400
TGGAATAGGTGTCCTCTTAACCTGGATAGGGTTGAACTCAAAAAATACTTCTATGTCATTTTCATGCATCGCGGCCGGCATTGTGACACTGTATTTGGGA
 G  I  G  V  L  L  T  W  I  G  L  N  S  K  N  T  S  M  S  F  S  C  I  A  A  G  I  V  T  L  Y  L  G
                                                                       |
                  Engineered NgoMIV splicing site, E-480 Val-to-Ala (nt-2375/2376 TG-to-CC)

              > NS1
      2410      2420      2430      2440      2450      2460      2470      2480      2490      2500
GTCATGGTGCAGGCCGATAGTGGTTGCGTTGTGAGCTGGAAAAACAAAGAACTGAAATGTGGCAGTGGGATTTTCATCACAGACAACGTGCACACATGGA
V  M  V  Q  A  D  S  G  C  V  V  S  W  K  N  K  E  L  K  C  G  S  G  I  F  I  T  D  N  V  H  T  W  T

      2510      2520      2530      2540      2550      2560      2570      2580      2590      2600
CAGAACAATACAAGTTCCAACCAGAATCCCCTTCAAAACTAGCTTCAGCTATCCAGAAAGCCCATGAAGAGRACATTTGTGGAATCCGCTCAGTAACAAG
  E  Q  Y  K  F  Q  P  E  S  P  S  K  L  A  S  A  I  Q  K  A  H  E  E  D  I  C  G  I  R  S  V  T  R
                                                                       |
                       D2 PDK-53 NS1-53-Asp atteniation locus (wt D2 16681: Gly, no-2573-G)

      2610      2620      2630      2640      2650      2660      2670      2680      2690      2700
ACTGGAGAATCTGATGTGGAAACAAATAACACCAGAATTGAATCACATTCTATCAGAAAATGAGGTGAAGTTAACTATTATGACAGGAGACATCAAAGGA
 L  E  N  L  M  W  K  Q  I  T  P  E  L  N  H  I  L  S  E  N  E  V  K  L  T  I  M  T  G  D  I  K  G

      2710      2720      2730      2740      2750      2760      2770      2780      2790      2800
ATCATGCAGGCAGGAAAACGATCTCTGCGGCCTCAGCCCACTGAGCTGAAGTATTCATGGAAAACATGGGGCAAAGCAAAAATGCTCTCTACAGAGTCTC
I  M  Q  A  G  K  R  S  L  R  P  Q  P  T  E  L  K  Y  S  W  K  T  W  G  K  A  K  M  L  S  T  E  S  H
```

-continued

```
       2810      2820      2830      2840      2850      2860      2870      2880      2890      2900
ATAACCAGACCTTTCTCATTGATGGCCCCGAAACAGGAGAATGCCCCAACACAAATAGAGCTTGGAATTCGTTGGAAGTTGAAGACTATGGCTTTGGAGT
 N  Q  T  F  L  I  D  G  P  E  T  A  E  C  P  N  T  N  R  A  W  N  S  L  E  V  E  D  Y  G  F  G  V

       2910      2920      2930      2940      2950      2960      2970      2980      2990      3000
ATTCACCACCAATATATGGCTAAAATTGAAAGAAAAACAGGATGTATTCTGCGACTCAAAACTCATGTCAGCGGCCATAAAAGACAACAGAGCCGTCCAT
 F  T  T  N  I  W  L  K  L  K  E  K  Q  D  V  F  C  D  S  K  L  M  S  A  A  I  K  D  N  R  A  V  H

       3010      3020      3030      3040      3050      3060      3070      3080      3090      3100
GCCGATATGGGTTATTGGATAGAAAGTGCACTCAATGACACATGGAAGATAGAGAAAGCCTCTTTCATTGAAGTTAAAAACTGCCACTGGCCAAAATCAC
A  D  M  G  Y  W  I  E  S  A  L  N  D  T  W  K  I  E  K  A  S  F  I  E  V  K  N  C  H  W  P  K  S  H

       3110      3120      3130      3140      3150      3160      3170      3180      3190      3200
ACACCCTCTGGAGCAATGGAGTGCTAGAAAGTGAGATGATAATTCCAAAGAATCTCGCTGGACCAGTGTCTCAACACAACTATAGACCAGGCTACCATAC
 T  L  W  S  N  G  V  L  E  S  E  M  I  I  P  K  N  L  A  G  P  V  S  Q  H  N  Y  R  P  G  Y  H  T

       3210      3220      3230      3240      3250      3260      3270      3280      3290      3300
ACAAATAACAGGACCATGGCATCTAGGTAAGCTTGAGATGGACTTTGATTTCTGTGATGGAACAACAGTGGTAGTGACTGAGGACTGCGGAAATAGAGGA
 Q  I  T  G  P  W  H  L  G  K  L  E  M  D  F  D  F  C  D  G  T  T  V  V  V  T  E  D  C  G  N  R  G

       3310      3320      3330      3340      3350      3360      3370      3380      3390      3400
CCCTCTTTGAGAACAACCACTGCCTCTGGAAAACTCATAACAGAATGGTGCTGCCGATCTTGCACATTACCACCGCTAAGATACAGAGGTGAGGATGGGT
P  S  L  R  T  T  T  A  S  G  K  L  I  T  E  W  C  C  R  S  C  T  L  P  P  L  R  Y  R  G  E  D  G  C

                                                                      > NS2A
       3410      3420      3430      3440      3450      3460      3470      3480      3490      3500
GCTGGTACGGGATGGAAATCAGACCATTGAAGGAGAAAGAAGAGAATTTGGTCAACTCCTTGGTCACAGCTGGACATGGGCAGGTCGACAACTTTTCACT
 W  Y  G  M  E  I  R  P  L  K  E  K  E  E  N  L  V  N  S  L  V  T  A  G  H  G  Q  V  D  N  F  S  L

       3510      3520      3530      3540      3550      3560      3570      3580      3590      3600
AGGAGTCTTGGGAATGGCATTGTTCCTGGAGGAAATGCTTAGGACCCGAGTAGGAACGAAACATGCAATACTACTAGTTGCAGTTTCTTTTGTGACATTG
 G  V  L  G  M  A  L  F  L  E  E  M  L  R  T  R  V  G  T  K  H  A  I  L  L  V  A  V  S  F  V  T  L

       3610      3620      3630      3640      3650      3660      3670      3680      3690      3700
ATCACAGGGAACATGTCCTTTAGAGACCTGGGAAGAGTGATGGTTATGGTAGGCGCCACTATGACGGATGACATAGGTATGGGCGTGACTTATCTTGCCC
I  T  G  N  M  S  F  R  D  L  G  R  V  M  V  M  V  G  A  T  M  T  D  D  I  G  M  G  V  T  Y  L  A  L

       3710      3720      3730      3740      3750      3760      3770      3780      3790      3800
TACTAGCAGCCTTCAAAGTCAGACCAACTTTTGCAGCTGGACTACTCTTGAGAAAGCTGACCTCCAAGGAATTGATGATGACTACTATAGGAATTGTACT
 L  A  A  F  K  V  R  P  T  F  A  A  G  L  L  L  R  K  L  T  S  K  E  L  M  M  T  T  I  G  I  V  L

       3810      3820      3830      3840      3850      3860      3870      3880      3890      3900
CCTCTCCCAGAGCACCATACCAGAGACCATTCTTGAGTTGACTGATGCGTTAGCCTTAGGCATGATGGTCCTCAAAATGGTGAGAAATATGGAAAAGTAT
 L  S  Q  S  T  I  P  E  T  I  L  E  L  T  D  A  L  A  L  G  M  M  V  L  K  M  V  R  N  M  E  K  Y

       3910      3920      3930      3940      3950      3960      3970      3980      3990      4000
CAATTGGCAGTGACTATCATGGCTATCTTGTGCGTCCCAAACGCAGTGATATTACAAAACGCATGGAAAGTGAGTTGCACAATATTGGCAGTGGTGTCCG
Q  L  A  V  T  I  M  A  I  L  C  V  P  N  A  V  I  L  Q  N  A  W  K  V  S  C  T  I  L  A  V  V  S  V

       4010      4020      4030      4040      4050      4060      4070      4080      4090      4100
TTTCCCCACTGTTCTTAACATCCTCACAGCAAAAAACAGATTGGATACCATTAGCATTGACGATCAAAGGTCTCAATCCAACAGCTATTTTTCTAACAAC
 S  P  L  F  L  T  S  S  Q  Q  K  T  D  W  I  P  L  A  L  T  I  K  G  L  N  P  T  A  I  F  L  T  T
            |
      D2 PDK-53 specific NS2A-181-Phe (wt D2 16681: Leu, nt-4012-C)

                            > NS2B
       4110      4120      4130      4140      4150      4160      4170      4180      4190      4200
CCTCTCAAGAACCAGCAAGAAAAGGAGCTGGCCATTAAATGAGGCTATCATGGCAGTCGGGATGGTGAGCATTTTAGCCAGTTCTCTCCTAAAAAATGAT
 L  S  R  T  S  K  K  R  S  W  P  L  N  E  A  I  M  A  V  G  M  V  S  I  L  A  S  S  L  L  K  N  D

       4210      4220      4230      4240      4250      4260      4270      4280      4290      4300
ATTCCCATGACAGGACCATTAGTGGCTGGAGGGCTCCTCACTGTGTGCTACGTGCTCACTGGACGATCGGCCGATTTGGAACTGGAGAGAGCAGCCGATG
I  P  M  T  G  P  L  V  A  G  G  L  L  T  V  C  Y  V  L  T  G  R  S  A  D  L  E  L  E  R  A  A  D  V

       4310      4320      4330      4340      4350      4360      4370      4380      4390      4400
TCAAATGGGAAGACCAGGCAGAGATATCAGGAAGGAGTCCAATCCTGTCAATAACAATATCAGAAGATGGTAGCATGTCGATAAAAAATGAAGAGGAAGA
 K  W  E  D  Q  A  E  I  S  G  S  S  P  I  L  S  I  T  I  S  E  D  G  S  M  S  I  K  N  E  E  E  E

       4410      4420      4430      4440      4450      4460      4470      4480      4490      4500
ACAAACACTGACCATACTCATTAGAACAGGATTGCTGGTGATCTCAGGACTTTTTCCTGTATCAATACCAATCACGGCAGGAGCATGGTACCTGTGGGAA
 Q  T  L  T  I  L  I  R  T  G  L  L  V  I  S  G  L  F  P  V  S  I  P  I  T  A  A  A  W  Y  L  W  E

                > NS3
       4510      4520      4530      4540      4550      4560      4570      4580      4590      4600
GTGAAGAAACAACGGGCCGGAGTATTGTGGGATGTTCCTTCACCCCCACCCATGGGAAAGGCTGAACTGGAAGATGGAGCCTATAGAATTAAGCAAAAAG
V  K  K  Q  R  A  G  V  L  W  D  V  P  S  P  P  P  M  G  K  A  E  L  E  D  G  A  Y  R  I  K  Q  K  G

       4610      4620      4630      4640      4650      4660      4670      4680      4690      4700
GGATTCTTGGATATTCCCAGATCGGAGCCGGAGTTTACAAAGAAGGAACATTCCATACAATGTGGCATGTCACACGTGGCGCTGTTCTAATGCATAAAGG
 I  L  G  Y  S  Q  I  G  A  G  V  Y  K  E  G  T  F  H  T  M  W  H  V  T  R  G  A  V  L  M  H  K  G
```

-continued

```
     4710      4720      4730      4740      4750      4760      4770      4780      4790      4800
AAAGAGGATTGAACCATCATGGGCGGACGTCAAGAAAGACCTAATATCATATGGAGGAGGCTGGAAGTTAGAAGGAGAATGGAAGGAAGGAGAAGAAGTC
 K  R  I  E  P  S  W  A  D  V  K  K  D  L  I  S  Y  G  G  G  W  K  L  E  G  E  W  K  E  G  E  E  V

     4810      4820      4830      4840      4850      4860      4870      4880      4890      4900
CAGGTATTGGCACTGGAGCCTGGAAAAAATCCAAGAGCCGTCCAAACGAAACCTGGTCTTTTCAAAACCAACGCCGGAACAATAGGTGCTGTATCTCTGG
Q  V  L  A  L  E  P  G  K  N  P  R  A  V  Q  T  K  P  G  L  F  K  T  N  A  G  T  I  G  A  V  S  L  D

     4910      4920      4930      4940      4950      4960      4970      4980      4990      5000
ACTTTTCTCCTGGAACGTCAGGATCTCCAATTATCGACAAAAAAGGAAAAGTTGTGGGTCTTTATGGTAATGGTGTTGTTACAAGGAGTGGAGCATATGT
  F  S  P  G  T  S  G  S  P  I  I  D  K  K  G  K  V  V  G  L  Y  G  N  G  V  V  T  R  S  G  A  Y  V

     5010      5020      5030      5040      5050      5060      5070      5080      5090      5100
GAGTGCTATAGCCCAGACTGAAAAAAGCATTGAAGACAACCCAGAGATCGAAGATGACATTTTCCGAAAGAGAAGACTGACCATCATGGACCTCCACCCA
 S  A  I  A  Q  T  E  K  S  I  E  D  N  P  E  I  E  D  D  I  F  R  K  R  R  L  T  I  M  D  L  H  P

     5110      5120      5130      5140      5150      5160      5170      5180      5190      5200
GGAGCGGGAAAGACGAAGAGATACCTTCCGGCCATAGTCAGAGAAGCTATAAAACGGGGTTTGAGAACATTAATCTTGGCCCCCACTAGAGTTGTGGCAG
G  A  G  K  T  K  R  Y  L  P  A  I  V  R  E  A  I  K  R  G  L  R  T  L  I  L  A  P  T  R  V  V  A  A

     5210      5220      5230      5240      5250      5260      5270      5280      5290      5300
CTGAAATGGAGGAAGCCCTTAGAGGACTTCCAATAAGATACCAGACCCCAGCCATCAGAGCTGTGCACACCGGGCGGGAGATTGTGGACCTAATGTGTCA
  E  M  E  E  A  L  R  G  L  P  I  R  Y  Q  T  P  A  I  R  A  V  H  T  G  R  E  I  V  D  L  M  C  H
                                                               |
                          D2 PDK-53 NS3-250-Val attenuation locus (D2 16681: Glu, nt-5270-A)

     5310      5320      5330      5340      5350      5360      5370      5380      5390      5400
TGCCACATTTACCATGAGGCTGCTATCACCAGTTAGAGTGCCAAACTACAACCTGATTATCATGGACGAAGCCCATTTCACAGACCCAGCAAGTATAGCA
 A  T  F  T  M  R  L  L  S  P  V  R  V  P  N  Y  N  L  I  I  M  D  E  A  H  F  T  D  P  A  S  I  A

     5410      5420      5430      5440      5450      5460      5470      5480      5490      5500
GCTAGAGGATACATCTCAACTCGAGTGGAGATGGGTGAGGCAGCTGGGATTTTTATGACAGCCACTCCCCCGGGAAGGAGAGACCCATTTCCTCAGAGCA
A  R  G  Y  I  S  T  R  V  E  M  G  E  A  A  G  I  F  M  T  A  T  P  P  G  S  R  D  P  F  P  Q  S  N

     5510      5520      5530      5540      5550      5560      5570      5580      5590      5600
ATGCACCAATCATAGATGAAGAAAGAGAAATCCCTGAACGCTCGTGGAATTCCGGACATGAATGGGTCACGGATTTTAAAGGGAAGACTGTTTGGTTCGT
  A  P  I  I  D  E  E  R  E  I  P  E  R  S  W  N  S  G  H  E  W  V  T  D  F  K  G  K  T  V  W  F  V
                                         |
                                  D2 PDK-53 silent mutation nt-5541-C (D2 16681: T)

     5610      5620      5630      5640      5650      5660      5670      5680      5690      5700
TCCAAGTATAAAAGGAGGAAATGATATAGGAGCTTGCCTGAGGAAAAATGGAAAGAAAGTGATACAACTCAGTAGGAAGACCTTTGATTCTGAGTATGTC
 P  S  I  K  A  G  N  D  I  A  A  C  L  R  K  N  G  K  K  V  I  Q  L  S  R  K  T  F  D  S  E  Y  V

     5710      5720      5730      5740      5750      5760      5770      5780      5790      5800
AAGACTAGAACCAATGATTGGGACTTCGTGGTTACAACTGACATTTCAGAAATGGGTGCCAATTTCAAGGCTGAGAGGGTTATAGACCCCAGACGCTGCA
K  T  R  T  N  D  W  D  F  V  V  T  T  D  I  S  E  M  G  A  N  F  K  A  E  R  V  I  D  P  R  R  C  M

     5810      5820      5830      5840      5850      5860      5870      5880      5890      5900
TGAAACCAGTCATACTAACAGATGGTGAAGAGCGGGTGATTCTGGCAGGACCTATGCCAGTGACCCACTCTAGTGCAGCACAAAGAAGAGGGAGAATAGG
  K  P  V  I  L  T  D  G  E  E  R  V  I  L  A  G  P  M  P  V  T  H  S  S  A  A  Q  R  R  G  R  I  G

     5910      5920      5930      5940      5950      5960      5970      5980      5990      6000
AAGAAATCCAAAAAATGAGAATGACCAGTACATATACATGGGGGAACCTCTGGAAAATGATGAAGACTGTGCACACTGGAAAGAAGCTAAAATGCTCCTA
 R  N  P  K  N  E  N  D  Q  Y  I  Y  M  G  E  P  L  E  N  D  E  D  C  A  H  W  K  E  A  K  M  L  L

     6010      6020      6030      6040      6050      6060      6070      6080      6090      6100
GATAACATCAACACGCCAGAAGGAATCATTCCTAGCATGTTCGAACCAGAGCGTGAAAAGGTGGATGCCATTGATGGCGAATACCGCTTGAGAGGAGAAG
D  N  I  N  T  P  E  G  I  I  P  S  M  F  E  P  E  R  E  K  V  D  A  I  D  G  E  Y  R  L  R  G  E  A

     6110      6120      6130      6140      6150      6160      6170      6180      6190      6200
CAAGGAAAACCTTTGTAGACTTAATGAGAAGAGGAGACCTACCAGTCTGGTTGGCCTACAGAGTGGCAGCTGAAGGCATCAACTACGCAGACAGAAGGTG
  R  K  T  F  V  D  L  M  R  R  G  D  L  P  V  W  L  A  Y  R  V  A  A  E  G  I  N  Y  A  D  R  R  W

     6210      6220      6230      6240      6250      6260      6270      6280      6290      6300
GTGTTTTGATGGAGTCAAGAACAACCAAATCCTAGAAGAAAACGTGGAAGTTGAAATCTGGACAAAAGAAGGGGAAAGGAAGAAATTGAAACCCAGATGG
 C  F  D  G  V  K  N  N  Q  I  L  E  E  N  V  E  V  E  I  W  T  K  E  G  E  R  K  K  L  K  P  R  W

                                                                         >NS4A
     6310      6320      6330      6340      6350      6360      6370      6380      6390      6400
TTGGATGCTAGGATCTATTCTGACCCACTGGCGCTAAAAGAATTTAAGGAATTTGCAGCCGGAAGAAAGTCTCTGACCCTGAACCTAATCACAGAAATGG
L  D  A  R  I  Y  S  D  P  L  A  L  K  E  F  K  E  F  A  A  G  R  K  S  L  T  L  N  L  I  T  E  M  G

     6410      6420      6430      6440      6450      6460      6470      6480      6490      6500
GTAGGCTCCCAACCTTCATGACTCAGAAGGCAAGAGACGCACTGGACAACTTAGCAGTGCTGCACACGGCTGAGGCAGGTGGAAGGGCGTACAACCATGC
  R  L  P  T  F  M  T  Q  K  A  R  D  A  L  D  N  L  A  V  L  H  T  A  E  A  G  G  R  A  Y  N  H  A

     6510      6520      6530      6540      6550      6560      6570      6580      6590      6600
TCTCAGTGAACTGCCGGAGACCCTGGAGACATTGCTTTTACTGACACTTCTGGCTACAGTCACGGGAGGGATCTTTTTATTCTTGATGAGCGCAAGGGGC
 L  S  E  L  P  E  T  L  E  T  L  L  L  L  T  L  L  A  T  V  T  G  G  I  F  L  F  L  M  S  A  R  G
```

-continued

```
                                                                                     |
                                         D2 PDK-53 specific NS4A-75-ALa (wt D2 16681: Gly, nt-6599-G)

      6610      6620      6630      6640      6650      6660      6670      6680      6690      6700
ATAGGGAAGATGACCCTGGGAATGTGCTGCATAATCACGGCTAGCATCCTCCTATGGTACGCACAAATACAGCCACACTGGATAGCAGCTTCAATAATAC
I  G  K  M  T  L  G  M  C  C  I  I  T  A  S  I  L  L  W  Y  A  Q  I  Q  P  H  W  I  A  A  S  I  I  L

      6710      6720      6730      6740      6750      6760      6770      6780      6790      6800
TGGAGTTTTTCTCATAGTTTTGCTTATTCCAGAACCTGAAAAACAGAGAACACCCCAAGACAACCAACTGACCTACGTTGTCATAGCCATCCTCACAGT
 E  F  F  L  I  V  L  L  I  P  E  P  E  K  Q  R  T  P  Q  D  N  Q  L  T  Y  V  V  I  A  I  L  T  V

                   > NS4B
      6810      6820      6830      6840      6850      6860      6870      6880      6890      6900
GGTGGCCGCAACCATGGCAAACGAGATGGGTTTCCTAGAAAAAACGAAGAAAGATCTCGGATTGGGAAGCATTGCAACCCAGCAACCCGAGAGCAACATC
 V  A  A  T  M  A  N  E  M  G  F  L  E  K  T  K  K  D  L  G  L  G  S  I  A  T  Q  Q  P  E  S  N  I

      6910      6920      6930      6940      6950      6960      6970      6980      6990      7000
CTGGACATAGATCTACGTCCTGCATCAGCATGGACGCTGTATGCCGTGGCCACAACATTTGTTACACCAATGTTGAGACATAGCATTGAAAATTCCTCAG
L  D  I  D  L  R  P  A  S  A  W  T  L  Y  A  V  A  T  T  F  V  T  P  M  L  R  H  S  I  E  N  S  S  V

      7010      7020      7030      7040      7050      7060      7070      7080      7090      7100
TGAATGTGTCCCTAACAGCTATAGCCAACCAAGCCACAGTGTTAATGGGTCTCGGGAAAGGATGGCCATTGTCAAAGATGGACATCGGAGTTCCCCTTCT
 N  V  S  L  T  A  I  A  N  Q  A  T  V  L  M  G  L  G  K  G  W  P  L  S  K  M  D  I  G  V  P  L  L

      7110      7120      7130      7140      7150      7160      7170      7180      7190      7200
CGCCATTGGATGCTACTCACAAGTCAACCCCATAACTCTCACAGGAGCTCTTTTCTTATTGGTAGCACATTATGCCATCATAGGGCCAGGACTCCAAGCA
 A  I  G  C  Y  S  Q  V  N  P  I  T  L  T  A  A  L  F  L  L  V  A  H  Y  A  I  I  G  P  G  L  Q  A

      7210      7220      7230      7240      7250      7260      7270      7280      7290      7300
AAAGCAACCAGAGAAGCTCAGAAAAGAGGAGCGGCGGGCATCATGAAAAACCCAACTGTCGATGGAATAACAGTGATTGACCTAGATCCAATACCTTATG
K  A  T  R  E  A  Q  K  R  A  A  A  G  I  M  K  N  P  T  V  D  G  I  T  V  I  D  L  D  P  I  P  Y  D

      7310      7320      7330      7340      7350      7360      7370      7380      7390      7400
ATCCAAAGTTTGAAAAGGAGTTGGGACAAGTAATGCTCCTAGTCCTCTGCGTGACTCAAGTATTGATGATGAGGACTACATGGGCTCTGTGTGAGGCTTT
 P  K  F  E  K  Q  L  G  Q  V  M  L  L  V  L  C  V  T  Q  V  L  M  M  R  T  T  W  A  L  C  E  A  L

      7410      7420      7430      7440      7450      7460      7470      7480      7490      7500
AACCTTAGCTACCGGGCCCATCTCCACATTGTGGGAAGGAAATCCAGGGAGGTTTTGGAACACTACCATTGCGGTGTCAATGGCTAACATTTTTAGAGGG
 T  L  A  T  G  P  I  S  T  L  W  E  G  N  P  G  R  F  W  N  T  T  I  A  V  S  M  A  N  I  F  R  G

                                                                   > NS5
      7510      7520      7530      7540      7550      7560      7570      7580      7590      7600
AGTTACTTGGCCGGAGCTGGACTTCTCTTTTCTATTATGAAGAACACAACCAACACAAGAAGGGGAACTGGCAACATAGGAGAGACGCTTGGAGAGAAAT
S  Y  L  A  G  A  G  L  L  F  S  I  M  K  N  T  T  N  T  R  R  G  T  G  N  I  G  E  T  L  G  E  K  W

      7610      7620      7630      7640      7650      7660      7670      7680      7690      7700
GGAAAAGCCGATTGAACGCGTTGGGAAAAAGTGAATTCCAGATCTACAAGAAAAGTGGAATCCAGGAAGTGGATAGAACCTTAGCAAAAGAAGGCATTAA
 K  S  R  L  N  A  L  G  K  S  E  F  Q  I  Y  K  K  S  G  I  Q  E  V  D  R  T  L  A  K  E  G  I  K
                   |
            Additional nt-7260 A-to-G silent mutation in master and pre-master seeds

      7710      7720      7730      7740      7750      7760      7770      7780      7790      7800
AAGAGGAGAAACGGACCATCACGCTGTGTCGCGAGGCTCAGCAAAACTGAGATGGTTCGTTGAGAGAAACATGGTCACACCAGAAGGGAAAGTAGTGGAC
 R  G  E  T  D  H  H  A  V  S  R  G  S  A  K  L  R  W  F  V  E  R  N  M  V  T  P  E  G  K  V  V  D

      7810      7820      7830      7840      7850      7860      7870      7880      7890      7900
CTCGGTTGTGGCAGAGGAGGCTGGTCATACTATTGTGGAGGACTAAAGAATGTAAGAGAAGTCAAAGGCCTAACAAAAGGAGGACCAGGACACGAAGAAC
L  G  C  G  R  G  G  W  S  Y  Y  C  G  G  L  K  N  V  R  E  V  K  G  L  T  K  G  G  P  G  H  E  E  P

      7910      7920      7930      7940      7950      7960      7970      7980      7990      8000
CCATCCCCATGTCAACATATGGGTGGAATCTAGTGCGTCTTCAAAGTGGAGTTGACGTTTTCTTCATCCCGCCAGAAAAGTGTGACACATTATTGTGTGA
 I  P  M  S  T  Y  G  W  N  L  V  R  L  Q  S  G  V  D  V  F  F  I  P  P  E  K  C  D  T  L  L  C  D

      8010      8020      8030      8040      8050      8060      8070      8080      8090      8100
CATAGGGGAGTCATCACCAAATCCCACAGTGGAAGGAGGACGAACACTCAGAGTCCTTAACTTAGTAGAAAATTGGTTGAACAACAACACTCAATTTTGC
 I  G  E  S  S  P  N  P  T  V  E  A  G  R  T  L  R  V  L  N  L  V  E  N  W  L  N  N  N  T  Q  F  C

      8110      8120      8130      8140      8150      8160      8170      8180      8190      8200
ATAAAGGTTCTCAACCCATATATGCCCTCAGTCATAGAAAAAATGGAAGCACTACAAAGGAAATATGGAGGAGCCTTAGTGAGGAATCCACTCTCACGAA
I  K  V  L  N  P  Y  M  P  S  V  I  E  K  M  E  A  L  Q  R  K  Y  G  G  A  L  V  R  N  P  L  S  R  N

      8210      8220      8230      8240      8250      8260      8270      8280      8290      8300
ACTCCACACATGAGATGTACTGGGTATCCAATGCTTCCGGGAACATAGTGTCATCAGTGAACATGATTTCAAGGATGTTGATCAACAGATTTACAATGAG
 S  T  H  E  M  Y  W  V  S  N  A  S  G  N  I  V  S  S  V  N  M  I  S  R  M  L  I  N  R  F  T  M  R

      8310      8320      8330      8340      8350      8360      8370      8380      8390      8400
ATACAAGAAAGCCACTTACGAGCCGGATGTTGACCTCGGAAGCGGAACCCGTAACATCGGGATTGAAAGTGAGATACCAAACCTAGATATAATTGGGAAA
 Y  K  K  A  T  Y  E  P  D  V  D  L  G  S  G  T  R  N  I  G  I  E  S  E  I  P  N  L  D  I  I  G  K
```

-continued

```
        8410       8420       8430       8440       8450       8460       8470       8480       8490       8500
AGAATAGAAAAAATAAAGCAAGAGCATGAAACATCATGGCACTATGACCAAGACCACCCATACAAAACGTGGGCATACCATGGTAGCTATGAAACAAAAC
R  I  E  K  I  K  Q  E  H  E  T  S  W  H  Y  D  Q  D  H  P  Y  K  T  W  A  Y  H  G  S  Y  E  T  K  Q

        8510       8520       8530       8540       8550       8560       8570       8580       8590       8600
AGACTGGATCAGCATCATCCATGGTCAACGGAGTGGTCAGGCTGCTGACAAAACCTTGGGACGTCGTCCCCATGGTGACACAGATGGCAATGACAGACAC
  T  G  S  A  S  S  M  V  N  G  V  V  R  L  L  T  K  P  W  D  V  V  P  M  V  T  Q  M  A  M  T  D  T

        8610       8620       8630       8640       8650       8660       8670       8680       8690       8700
GACTCCATTTGGACAACAGCGCGTTTTTAAAGAGAAAGTGGACACGAGAACCCAAGAACCGAAAGAAGGCACGAAGAAACTAATGAAAATAACAGGAGAG
 T  P  F  G  Q  Q  R  V  F  K  E  K  V  D  T  R  T  Q  E  P  K  E  G  T  K  K  L  M  K  I  T  A  E

        8710       8720       8730       8740       8750       8760       8770       8780       8790       8800
TGGCTTTGGAAAGAATTAGGGAAGAAAAAGACACCCAGGATGTGCACCAGAGAAGAATTCACAAGAAAGGTGAGAAGCAATGCAGCCTTGGGGGCCATAT
W  L  W  K  E  L  G  K  K  K  T  P  R  M  C  T  R  E  E  F  T  R  K  V  R  S  N  A  A  L  G  A  I  F

        8810       8820       8830       8840       8850       8860       8870       8880       8890       8900
TCACTGATGAGAACAAGTGGAAGTCGGCACGTGAGGCTGTTGAAGATAGTAGGTTTTGGGAGCTGGTTGACAAGGAAAGGAATCTCCATCTTGAAGGAAA
  T  D  E  N  K  W  K  S  A  R  E  A  V  E  D  S  R  F  W  E  L  V  D  K  E  R  N  L  H  L  E  G  K

        8910       8920       8930       8940       8950       8960       8970       8980       8990       9000
GTGTGAAACATGTGTGTACAACATGATGGGAAAAAGAGAGAAGAAGCTAGGGGAATTCGGCAAGGCAAAAGGCAGGAGAGCCATATGGTACATGTGGCTT
 C  E  T  C  V  Y  N  M  M  G  K  R  E  K  K  L  G  E  F  G  K  A  K  G  S  R  A  I  W  Y  M  W  L

        9010       9020       9030       9040       9050       9060       9070       9080       9090       9100
GGAGCACGCTTCTTAGAGTTTGAAGCCCTAGGATTCTTAAATGAAGATCACTGGTTCTCCAGAGAGAACTCCCTGAGTGGAGTGGAAGGAGAAGGGCTGC
G  A  R  F  L  E  F  E  A  L  G  F  L  N  E  D  H  W  F  S  R  E  N  S  L  S  G  V  E  G  E  G  L  H

        9110       9120       9130       9140       9150       9160       9170       9180       9190       9200
ACAAGCTAGGTTACATTCTAAGAGACGTGAGCAAGAAAGAGGGAGGAGCAATGTATGCCGATGACACCGCAGGATGGGATACAAGAATCACACTAGAAGA
  K  L  G  Y  I  L  R  D  V  S  K  K  E  G  G  A  M  Y  A  D  D  T  A  G  W  D  T  R  I  T  L  E  D

        9210       9220       9230       9240       9250       9260       9270       9280       9290       9300
CCTAAAAAATGAAGAAATGGTAACAAACCACATGGAAGGAGAACACAAGAAACTAGCCGAGGCCATTTTCAAACTAACGTACCAAAACAAGGTGGTGCGT
 L  K  N  E  E  M  V  T  N  H  M  E  G  E  H  K  K  L  A  E  A  I  F  K  L  T  Y  Q  N  K  V  V  R

        9310       9320       9330       9340       9350       9360       9370       9380       9390       9400
GTGCAAAGACCAACACCAAGAGGCACAGTAATGGACATCATATCGAGAAGAGACCAAAGAGGTAGTGGACAAGTTGGCACCTATGGACTCAATACTTTCA
V  Q  R  P  T  P  R  G  T  V  M  D  I  I  S  R  R  D  Q  R  G  S  G  Q  V  G  T  Y  G  L  N, T  F  T

        9410       9420       9430       9440       9450       9460       9470       9480       9490       9500
CCAATATGGAAGCCCAACTAATCAGACAGATGGAGGGAGAAGGAGTCTTTAAAAGCATTCAGCACCTAACAATCACAGAAGAAATCGCTGTGCAAAACTG
  N  M  E  A  Q  L  I  R  Q  M  E  G  E  G  V  F  K  S  I  Q  H  L  T  I  T  E  E  I  A  V  Q  N  W

        9510       9520       9530       9540       9550       9560       9570       9580       9590       9600
GTTAGCAAGAGTGGGGCGCGAAAGGTTATCAAGAATGGCCATCAGTGGAGATGATTGTGTTGTGAAACCTTTAGATGACAGGTTCGCAAGCGCTTTAACA
 L  A  R  V  G  R  E  R  L  S  R  M  A  I  S  G  D  D  C  V  V  K  P  L  D  D  R  F  A  S  A  L  T

        9610       9620       9630       9640       9650       9660       9670       9680       9690       9700
GCTCTAAATGACATGGGAAAGATTAGGAAAGACATACAACAATGGGAACCTTCAAGAGGATGGAAtgATTGGACACAAGTGCCCTTCTGTTCACACCATT
A  L  N  D  M  G  K  I  R  K  D  I  Q  Q  W  E  P  S  R  G  W  N  D  W  T  Q  V  P  F  C  S  H  H  F

        9710       9720       9730       9740       9750       9760       9770       9780       9790       9800
TCCATGAGTTAATCATGAAAGACGGTCGCGTACTCGTTGTTCCATGTAGAAACCAAGATGAACTGATTGGCAGAGCCCGAATCTCCCAAGGAGGAGGGTG
  H  E  L  I  M  K  D  G  R  V  L  V  V  P  C  R  N  Q  D  E  L  I  G  R  A  R  I  S  Q  G  A  G  W

        9810       9820       9830       9840       9850       9860       9870       9880       9890       9900
GTCTTTGCGGGAGACGGCCTGTTTGGGGAAGTCTTACGCCCAAATGTGGAGCTTGATGTACTTCCACAGACGCGACCTCAGGCTGGCGGCAAATGCTATT
 S  L  R  E  T  A  C  L  G  K  S  Y  A  Q  M  W  S  L  M  Y  F  H  R  R  D  L  R  L  A  A  N  A  I

        9910       9920       9930       9940       9950       9960       9970       9980       9990      10000
TGCTCGGCAGTACCATCACATTGGGTTCCAACAAGTCGAACAACCTGGTCCATACATGCTAAACATGAATGGATGACAACGGAAGACATGCTGACAGTCT
G  S  A  V  P  S  H  W  V  P  T  S  R  T  T  W  S  I  H  A  K  H  E  W  M  T  T  E  D  M  L  T  V  W

      10010      10020      10030      10040      10050      10060      10070      10080      10090      10100
GGAACAGGGTGTGGATTCAAGAAAACCCATGGATGGAAGACAAAACTCCAGTGGAATCATGGGAGGAAATCCCATACTTGGGGAAAAGAGAAGACCAATG
  N  R  V  W  I  Q  E  N  P  W  M  E  D  K  T  P  V  E  S  W  E  E  T  P  Y  L  G  K  R  E  D  Q  W

      10110      10120      10130      10140      10150      10160      10170      10180      10190      10200
GTGCGGCTCATTGATTGGGTTAACAAGGAGGGCCACCTGGGCAAAGAACATCCAAGGAGCAATAAATCAAGTTAGATCCCTTATAGGCAATGAAGAATAC
 C  G  S  L  I  G  L  T  S  R  A  T  W  A  K  N  I  Q  A  A  I  N  Q  V  R  S  L  I  G  N  E  E  Y

                                                            > 3'-Noncoding Region
      10210      10220      10230      10240      10250      10260      10270      10280      10290      10300
ACAGATTACATGCCATCCATGAAAAGATTCAGAAGAGAAGAGGAAGAAGGAGGAGTTCTGTGGTAGAAAGCAAAACTAACATGAAACAAGGCTAGAAGTC
T  D  Y  M  P  S  M  K  R  F  R  R  E  E  E  E  A  G  V  L  W  *

      10310      10320      10330      10340      10350      10360      10370      10380      10390      10400
AGGTCGGATTAAGCCATAGTACGGAAAAAACTATGCTACCTGTGAGCCCCGTCCAAGGACGTTAAAAGAAGTCAGGCCATCATAAATGCCATAGCTTGAG
```

-continued

```
     10410      10420      10430      10440      10450      10460      10470      10480      10490      10500
TAAACTATGCAGCCTGTAGCTCCACCTGAGAAGGTGTAAAAAATCCGGGAGGCCACAAACCATGGAAGCTGTACGCATGGCGTAGTGGACTAGCGGTTAG

     10510      10520      10530      10540      10550      10560      10570      10580      10590      10600
AGGAGACCCCTCCCTTACAAATCGCAGCAACAATGGGGGCCCAAGGCGAGATGAAGCTGTAGTCTCGCTGGAAGGACTAGAGGTTAGAGGAGACCCCCCC

     10610      10620      10630      10640      10650      10660      10670      10680      10690      10700
GAAACAAAAAACAGCATATTGACGCTGGGAAAGACCAGAGATCCTGCTGTCTCCTCAGCATCATTCCAGGCACAGAACGCCAGAAAATGGAATGGTGCTG

     10710
TTGAATCAACAGGTTCT
```

DENvax-4 Master Virus Seed (MVS)

Nucleotide sequence of the chimeric viral genome and deduced amino acid sequence of the translated protein. Most of the prM-E gene (nt-457 to -2379, underlined) is wild-type (wt) DEN-4 1036 virus-specific; the remaining nucleotide sequence is DEN-2 PDK-53 virus-specific. All engineered substitutions differ from wt virus (DEN-3 16562 or DEN-2 16681), as well as extra mutations (changes from engineered cDNA clone) are marked.

Substitutions Included in the Genome and Protein:

Junction Sites:

a. MluI (nt 451-456): engineered silent mutation, nt-453 A-to-G b. NgoMIV (nt 2380-2385): engineered mutations, nt-2381/2382 TG-to-CC (resulted in E-482 Val-to-Ala change)

D2 PDK-53 Virus Backbone (Change from Wt D2 16681)

a. 5'-noncoding region (NCR)-57 (nt-57 C-to-T): major attenuation locus (in red)

b. NS1-53 Gly-to-Asp (nt-2579 G-to-A): major attenuation locus (in red)

c. NS2A-181 Leu-to-Phe (nt-4018 C-to-T, in bold)

d. NS3-250 Glu-to-Val (nt-5270 A-to-T): major attenuation locus (in red)

e. nt-5547 (NS3 gene) T-to-C silent mutation (in bold)

f. NS4A-75 Gly-to-Ala (nt-6599 G-to-C, in bold)

* nt-8571 C-to-T silent mutation of PDK-53 is not engineered in the vaccine virus Engineered Substitutions in cDNA Clone a. Engineered C-100 Arg-to-Ser (nt-396 A-to-C): may improve viral replication in culture b. Engineered nt-1401 A-to-G silent mutation c. Engineered E-364 Ala-to-Val (nt-2027 C-to-T): may improve viral replication in culture d. Engineered E-447 Met-to-Leu (nt-2275 A-to-C): may improve viral replication in culture Additional substitutions found in vaccine seed (0.06% nt different from original clone)

a. nt-225 (C gene) A-to-T silent mutation (in bold)

b. NS2A-66 Asp-to-Gly (nt-3674 A-to-G) mutation (in bold)

c. NS2A-99 Lys-to-Lys/Arg mix (nt-3773 A-to-A/G mix, in bold)

d. nt-5391 C-to-T (NS3 gene) silent mutation (in bold)

e. NS4A-21 Ala-to-Val (nt-6437 C-to-T, in bold)

f. nt-7026 T-to-C/T mix silent mutation (in bold)

g. nt-9750 A-to-C silent mutation (in bold)

```
                                          NCR-57-T, D2 PDK-53 attenuation locus (wt D2 16681: C)
>5'-Noncoding Region                                   |                                          >C
        10         20         30         40         50         60         70         80         90        100
AGTTGTTAGTCTACGTGGACCGACAAAGACAGATTCTTTGAGGGAGCTAAGCTCAATGTAGTTCTAACAGTTTTTTAATTAGAGAGCAGATCTCTGATGA
                                                                                                   M  N

       110        120        130        140        150        160        170        180        190        200
ATAACCAACGGAAAAAGGCGAAAAACACGCCTTTCAATATGCTGAAACGCGAGAGAAACCGCGTGTCGACTGTGCAACAGCTGACAAAGAGATTCTCACT
  N  Q  R  K  K  A  K  N  T  P  F  N  M  L  K  R  E  R  N  R  V  S  T  V  Q  Q  L  T  K  R  F  S  L

       210        220        230        240        250        260        270        280        290        300
TGGAATGCTGCAGGGACGAGGACCTTTAAAACTGTTCATGGCCCTGGTGGCGTTCCTTCGTTTCCTAACAATCCCACCAACAGCAGGGATATTGAAGAGA
 G  M  L  Q  G  R  G  P  L  K  L  F  M  A  L  V  A  F  L  R  F  L  T  I  P  P  T  A  G  I  L  K  R
                         |
              Additional nt-225 A-to-T silent mutation in master and pre-master seeds

       310        320        330        340        350        360        370        380        390        400
TGGGGAACAATTAAAAAATCAAAAGCTATTAATGTTTTGAGAGGGTTCAGGAAAGAGATTGGAAGGATGCTGAACATCTTGAATAGGAGACGCAGCTCTG
W  G  T  I  K  K  S  K  A  I  N  V  L  R  G  F  R  K  E  I  G  R  M  L  N  I  L  N  R  R  R  S  S  A
                                                                                                |
                                                        Engineered C-100 Arg-to-Ser (nt 396 A-to-C)

                                         > prM                  Beginning of D4 1036 sequence
       410        420        430        440        450        |460        470        480        490        500
CAGGCATGATCATTATGCTGATTCCAACAGTGATGGCGTTCCATTTAACCACGCGTGATGGCGAACCCCTCATGATAGTGGCAAAACATGAAAGGGGGAG
  G  M  I  I  M  L  I  P  T  V  M  A  F  H  L  T  T  R  D  G  E  P  L  M  I  V  A  K  H  E  R  G  R
                                                     |
                                    Engineered MluI splicing site (nt-453 A-to-G silent)

       510        520        530        540        550        560        570        580        590        600
ACCTCTCTTGTTTAAGACAACAGAGGGGATCAACAAATGCACTCTCATTGCCATGGACTTGGGTGAAATGTGTGAGGACACTGTCACGTATAAATGCCCC
 P  L  L  F  K  T  T  E  G  I  N  K  C  T  L  I  A  M  D  L  G  E  M  C  E  D  T  V  T  Y  K  C  P
```

-continued

```
       610       620       630       640       650       660       670       680       690       700
TTACTGGTCAATACCGAACCTGAAGACATTGATTGCTGGTGCAATCTCACGTCTACCTGGGTCATGTATGGGACATGCACCCAGAGCGGAGAACGGAGAC
L  L  V  N  T  E  P  E  D  I  D  C  W  C  N  L  T  S  T  W  V  M  Y  G  T  C  T  Q  S  G  E  R  R  R

           > M
       710       720       730       740       750       760       770       780       790       800
GAGAGAAGCGCTCAGTAGCTTTAACACCACATTCAGGAATGGGATTGGAAACAAGAGCTGAGACATGGATGTCATCGGAAGGGGCTTGGAAGCATGCTCA
  E  K  R  S  V  A  L  T  P  H  S  G  M  G  L  E  T  R  A  E  T  W  M  S  S  E  G  A  W  K  H  A  Q

       810       820       830       840       850       860       870       880       890       900
GAGAGTAGAGAGCTGGATACTCAGAAACCCAGGATTCGCGCTCTTGGCAGGATTTATGGCTTATATGATTGGGCAAACAGGAATCCAGCGAACTGTCTTC
 R  V  E  S  W  I  L  R  N  P  G  F  A  L  L  A  G  F  M  A  Y  M  I  G  Q  T  G  I  Q  R  T  V  F

                                      > E
       910       920       930       940       950       960       970       980       990      1000
TTTGTCCTAATGATGCTGGTCGCCCCATCCTACGGAATGCGATGCGTAGGAGTAGGAAACAGAGACTTTGTGGAAGGAGTCTCAGGTGGAGCATGGGTCG
F  V  L  M  M  L  V  A  P  S  Y  G  M  R  C  V  G  V  G  N  R  D  F  V  E  G  V  S  G  G  A  W  V  D

      1010      1020      1030      1040      1050      1060      1070      1080      1090      1100
ATCTGGTGCTAGAACATGGAGGATGCGTCACAACCATGGCCCAGGGAAAACCAACCTTGGATTTTGAACTGACTAAGACAACAGCCAAGGAAGTGGCTCT
  L  V  L  E  H  G  G  C  V  T  T  M  A  Q  G  K  P  T  L  D  F  E  L  T  K  T  T  A  K  E  V  A  L

      1110      1120      1130      1140      1150      1160      1170      1180      1190      1200
GTTAAGAACCTATTGCATTGAAGCCTCAATATCAAACATAACCACGGCAACAAGATGTCCAACGCAAGGAGAGCCTTATCTAAAAGAGGAACAAGACCAA
 L  R  T  Y  C  I  E  A  S  I  S  N  I  T  T  A  T  R  C  P  T  Q  G  E  P  Y  L  K  E  E  Q  D  Q

      1210      1220      1230      1240      1250      1260      1270      1280      1290      1300
CAGTACATTTGCCGGAGAGATGTGGTAGACAGAGGGTGGGGCAATGGCTGTGGCTTGTTTGGAAAAGGAGGAGTTGTGACATGTGCGAAGTTTTCATGTT
Q  Y  I  C  R  R  D  V  V  D  R  G  W  G  N  G  C  G  L  F  G  K  G  G  V  V  T  C  A  K  F  S  C  S

      1310      1320      1330      1340      1350      1360      1370      1380      1390      1400
CGGGGAAGATAACAGGCAATTTGGTCCAAATTGAGAACCTTGAATACACAGTGGTTGTAACAGTCCACAATGGAGACACCCATGCAGTAGGAAATGACAC
  G  K  I  T  G  N  L  V  Q  I  E  N  L  E  Y  T  V  V  V  T  V  H  N  G  D  T  H  A  V  G  N  D  T

      1410      1420      1430      1440      1450      1460      1470      1480      1490      1500
GTCCAATCATGGAGTTACAGCCACGATAACTCCCAGGTCACCATCGGTGGAAGTCAAATTGCCGGACTATGGAGAACTAACACTCGATTGTGAACCCAGG
 S  N  H  G  V  T  A  T  I  T  P  R  S  P  S  V  E  V  K  L  P  D  Y  G  E  L  T  L  D  C  E  P  R
|
Silent nt-1401 A-to-G mutation in engineered clone

      1510      1520      1530      1540      1550      1560      1570      1580      1590      1600
TCTGGAATTGACTTTAATGAGATGATTCTGATGAAAATGAAAAAGAAAACATGGCTTGTGCATAAGCAATGGTTTTTGGATCTACCTCTACCATGGACAG
S  G  I  D  F  N  E  M  I  L  M  K  M  K  K  K  T  W  L  V  H  K  Q  W  F  L  D  L  P  L  P  W  T  A

      1610      1620      1630      1640      1650      1660      1670      1680      1690      1700
CAGGAGCAGACACATCAGAGGTTCACTGGAATTACAAAGAGAGAATGGTGACATTTAAGGTTCCTCATGCCAAGAGACAGGATGTGACAGTGCTGGGATC
  G  A  D  T  S  E  V  H  W  N  Y  K  E  R  M  V  T  F  K  V  P  H  A  K  R  Q  D  V  T  V  L  G  S

      1710      1720      1730      1740      1750      1760      1770      1780      1790      1800
TCAGGAAGGAGCCATGCATTCTGCCCTCGCTGGAGCCACAGAAGTGGACTCCGGTGATGGAAATCACATGTTTGCAGGACATCTCAAGTGCAAAGTCCGT
 Q  E  G  A  M  H  S  A  L  A  G  A  T  E  V  D  S  G  D  G  N  H  M  F  A  G  H  L  K  C  K  V  R

      1810      1820      1830      1840      1850      1860      1870      1880      1890      1900
ATGGAGAAATTGAGAATCAAGGGAATGTCATACACGATGTGTTCAGGAAAGTTCTCAATTGACAAAGAGATGGCAGAAACACAGCATGGGACAACAGTGG
M  E  K  L  R  I  K  G  M  S  Y  T  M  C  S  G  K  F  S  I  D  K  E  M  A  E  T  C  H  G  T  T  V  V

      1910      1920      1930      1940      1950      1960      1970      1980      1990      2000
TGAAAGTCAAGTATGAAGGTGCTGGAGCTCCGTGTAAAGTCCCCATAGAGATAAGAGATGTGAACAAGGAAAAAGTGGTTGGGCGTATCATCTCATCCAC
  K  V  K  Y  E  G  A  G  A  P  C  K  V  P  I  E  I  R  D  V  N  K  E  K  V  V  G  R  I  I  S  S  T

      2010      2020      2030      2040      2050      2060      2070      2080      2090      2100
CCCTTTGGCTGAGAATACCAACAGTGTAACCAACATAGAGTTAGAACCCCCCTTTGGGGACAGCTACATAGTGATAGGTGTTGGAAACAGTGCATTAACA
 P  L  A  E  N  T  N  S  V  T  N  I  E  L  E  P  P  F  G  D  S  Y  T  V  T  G  V  G  N  S  A  L  T
                         |
          Engineered E-364 Ala-to-Val (nt-2027 C-to-T) to improve viral growth in culture

      2110      2120      2130      2140      2150      2160      2170      2180      2190      2200
CTCCATTGGTTCAGGAAAGGGAGTTCCATTGGCAAGATGTTTGAGTCCACATACAGAGGTGCAAAACGAATGGCCATTCTAGGTGAAACAGCTTGGGATT
L  H  W  F  R  K  G  S  S  I  G  K  M  F  E  S  T  Y  R  G  A  K  R  M  A  T  L  G  E  T  A  W  D  F

      2210      2220      2230      2240      2250      2260      2270      2280      2290      2300
TTGGTTCCGTTGGTGGACTGTTCACATCATTGGGAAAGGCTGTGCACCAGGTTTTTGGAAGTGTGTATACAACCCTGTTTGGAGGAGTCTCATGGATGAT
  G  S  V  G  G  L  F  T  S  L  G  K  A  V  H  Q  V  F  G  S  V  Y  T  T  L  F  G  G  V  S  W  M  I
                                                                          |
                                        Engineered E-447 Met-to-Leu (nt-2275 A-to-C) mutation

                                                   End of D4 1036 sequence
      2310      2320      2330      2340      2350      2360      2370       |          2390      2400
TAGAATCCTAATTGGGTTCCTAGTGTTGTGGATTGGCACGAACTCAAGGAACACTTCAATGGCTATGACGTGCATAGCTGCCGGCATTGTGACACTGTAT
 R  I  L  I  G  F  L  V  L  W  I  G  T  N  S  R  N  T  S  M  A  M  T  C  I  A  A  G  I  V  T  L  Y
```

-continued

```
                                                                          |
                    Engineered NgoMIV splicing site, E-482 Val-to-Ala (nt-2381/2382 TG-to-CC)

                > NS1
      2410       2420       2430       2440       2450       2460       2470       2480       2490       2500
TTGGGGGTCATGGTGCAGGCCGATAGTGGTTGCGTTGTGAGCTGGAAAAACAAAGAACTGAAATGTGGCAGTGGGATTTTCATCACAGACAACGTGCACA
L  G  V  M  V  Q  A  D  S  G  C  V  V  S  W  K  N  K  E  L  K  C  G  S  G  I  F  I  T  D  N  V  H  T

      2510       2520       2530       2540       2550       2560       2570       2580       2590       2600
CATGGACAGAACAATACAAGTTCCAACCAGAATCCCCTTCAAAACTAGCTTCAGCTATCCAGAAAGCCCATGAAGAGGACATTTGTGGAATCCGCTCAGT
 W  T  E  Q  Y  K  F  Q  P  E  S  P  S  K  L  A  S  A  I  Q  K  A  H  E  E  D  I  C  G  I  R  S  V
                                                                                        |
                       D2 PDK-53 NS1-53-Asp attenuation locus (wt D2 16681: Gly, no-2579-G)

      2610       2620       2630       2640       2650       2660       2670       2680       2690       2700
AACAAGACTGGAGAATCTGATGTGGAAACAAATAACACCAGAATTGAATCACATTCTATCAGAAAATGAGGTGAAGTTAACTATTATGACAGGAGACATC
 T  R  L  E  N  L  M  W  K  Q  I  T  P  E  L  N  H  I  L  S  E  N  E  V  K  L  T  I  M  T  G  D  I

      2710       2720       2730       2740       2750       2760       2770       2780       2790       2800
AAAGGAATCATGCAGGCAGGAAAACGATCTCTGCGGCCTCAGCCCACTGAGCTGAAGTATTCATGGAAAACATGGGGCAAAGCAAAAATGCTCTCTACAG
K  G  I  M  C  A  G  K  R  S  L  R  P  Q  P  T  E  L  K  Y  S  W  K  T  W  G  K  A  K  M  L  S  T  E

      2810       2820       2830       2840       2850       2860       2870       2880       2890       2900
AGTCTCATAACCAGACCTTTCTCATTGATGGCCCCGAAACAGGAGAATGCCCCAACACAAATAGAGCTTGGAATTCGTTGGAAGTTGAAGACTATGGCTT
 S  H  N  Q  T  F  L  I  D  G  P  E  T  A  E  C  P  N  T  N  R  A  W  N  S  L  E  V  E  D  Y  G  F

      2910       2920       2930       2940       2950       2960       2970       2980       2990       3000
TGGAGTATTCACCACCAATATATGGCTAAAATTGAAAGAAAAACAGGATGTATTCTGCGACTCAAAACTCATGTCAGCGGCCATAAAAGACAACAGAGCC
 G  V  F  T  T  N  I  W  L  K  L  K  E  K  Q  D  V  F  C  D  S  K  L  M  S  A  A  I  K  D  N  R  A

      3010       3020       3030       3040       3050       3060       3070       3080       3090       3100
GTCCATGCCGATATGGGTTATTGGATAGAAAGTGCACTCAATGACACATGGAAGATAGAGAAAGCCTCTTTCATTGAAGTTAAAAACTGCCACTGGCCAA
V  H  A  D  M  G  Y  W  I  E  S  A  L  N  D  T  W  K  I  E  K  A  S  F  I  E  V  K  N  C  H  W  P  K

      3110       3120       3130       3140       3150       3160       3170       3180       3190       3200
AATCACACACCCTCTGGAGCAATGGAGTGCTAGAAAGTGAGATGATAATTCCAAAGAATCTCGCTGGACCAGTGTCTCAACACAACTATAGACCAGGCTA
 S  H  T  L  W  S  N  G  V  L  E  S  E  M  I  I  P  K  N  L  A  G  P  V  S  C  H  N  Y  R  P  G  Y

      3210       3220       3230       3240       3250       3260       3270       3280       3290       3300
CCATACACAAATAACAGGACCATGGCATCTAGGTAAGCTTGAGATGGACTTTGATTTCTGTGATGGAACAACAGTGGTAGTGACTGAGGACTGCGGAAAT
 H  T  Q  I  T  G  P  W  H  L  G  K  L  E  M  D  F  D  F  C  C  G  T  T  V  V  V  T  E  D  C  G  N

      3310       3320       3330       3340       3350       3360       3370       3380       3390       3400
AGAGGACCCTCTTTGAGAACAACCACTGCCTCTGGAAAACTCATAACAGAATGGTGCTGCCGATCTTGCACATTACCACCGCTAAGATACAGAGGTGAGG
R  G  P  S  L  R  T  T  T  A  S  G  K  L  I  T  E  W  C  C  R  S  C  T  L  P  P  L  R  Y  R  G  E  D

                                                                                 >NS2A
      3410       3420       3430       3440       3450       3460       3470       3480       3490       3500
ATGGGTGCTGGTACGGGATGGAAATCAGACCATTGAAGGAGAAAGAAGAGAATTTGGTCAACTCCTTGGTCACAGCTGGACATGGGCAGGTCGACAACTT
 G  C  W  Y  G  M  E  I  R  P  L  K  E  K  E  E  N  L  V  N  S  L  V  T  A  G  H  G  Q  V  D  N  F

      3510       3520       3530       3540       3550       3560       3570       3580       3590       3600
TTCACTAGGAGTCTTGGGAATGGCATTGTTCCTGGAGGAAATGCTTAGGACCCGAGTAGGAACGAAACATGCAATACTACTAGTTGCAGTTTCTTTTGTG
 S  L  G  V  L  G  M  A  L  F  L  E  E  M  L  R  T  R  V  G  T  K  H  A  I  L  L  V  A  V  S  F  V

      3610       3620       3630       3640       3650       3660       3670       3680       3690       3700
ACATTGATCACAGGGAACATGTCCTTTAGAGACCTGGGAAGAGTGATGGTTATGGTAGGCGCCACTATGACGGGTGACATAGGTATGGGCGTGACTTATC
T  L  I  T  G  N  M  S  F  R  D  L  G  R  V  M  V  M  V  G  A  T  M  T  G  D  I  G  M  G  V  T  Y  L
                                                                            |
            Additional NS2A-66 Asp-to-Gly (nt-3674 A-to-G mutation) in master and pre-master seeds

      3710       3720       3730       3740       3750       3760       3770       3780       3790       3800
TTGCCCTACTAGCAGCCTTCAAAGTCAGACCAACTTTTGCAGCTGGACTACTCTTGAGAAAGCTGACCTCCAGGGAATTGATGATGACTACTATAGGAAT
 A  L  L  A  A  F  K  V  R  P  T  F  A  A  G  L  L  L  R  K  L  T  S  K  E  L  M  M  T  T  I  G  I
                                                                           |
                    Additional NS2A-99 K to R/K (mix) (nt-3773 A-to-G/A) mutation in master seed

      3810       3820       3830       3840       3850       3860       3870       3880       3890       3900
TGTACTCCTCTCCCAGAGCACCATACCAGAGACCATTCTTGAGTTGACTGATGCGTTAGCCTTAGGCATGATGGTCCTCAAAATGGTGAGAAATATGGAA
 V  L  L  S  Q  S  T  I  P  E  T  I  L  E  L  T  D  A  L  A  L  G  M  M  V  L  K  M  V  R  N  M  E

      3910       3920       3930       3940       3950       3960       3970       3980       3990       4000
AAGTATCAATTGGCAGTGACTATCATGGCTATCTTGTGCGTCCCAAACGCAGTGATATTACAAAACGCATGGAAAGTGAGTTGCACAATATTGGCAGTGG
K  Y  Q  L  A  V  T  I  M  A  I  L  C  V  P  N  A  V  I  L  Q  N  A  W  K  V  S  C  T  I  L  A  V  V

      4010       4020       4030       4040       4050       4060       4070       4080       4090       4100
TGTCCGTTTCCCCACTGTTCTTAACATCCTCACAGCAAAAAACAGATTGGATACCATTAGCATTGACGATCAAAGGTCTCAATCCAACAGCTATTTTTCT
 S  V  S  P  L  F  L  T  S  S  Q  Q  K  T  D  W  I  P  L  A  L  T  I  K  G  L  N  P  T  A  I  F  L
```

-continued

```
                          |
 D2 PDK-53 specific NS2A-181-Phe (wt D2 16681: Leu, nt-4018-C)

                               > NS2B
      4110       4120       4130       4140       4150       4160       4170       4180       4190       4200
AACAACCCTCTCAAGAACCAGCAAGAAAAGGAGCTGGCCATTAAATGAGGCTATCATGGCAGTCGGGATGGTGAGCATTTTAGCCAGTTCTCTCCTAAAA
 T  T  L  S  R  T  S  K  K  R  S  W  P  L  N  E  A  I  M  A  V  G  M  V  S  I  L  A  S  S  L  L  K

      4210       4220       4230       4240       4250       4260       4270       4280       4290       4300
AATGATATTCCCATGACAGGACCATTAGTGGCTGGAGGGCTCCTCACTGTGTGCTACGTGCTCACTGGACGATCGGCCGATTTGGAACTGGAGAGAGCAG
N  D  I  P  M  T  G  P  L  V  A  G  G  L  L  T  V  C  Y  V  L  T  G  R  S  A  D  L  E  L  E  R  A  A

      4310       4320       4330       4340       4350       4360       4370       4380       4390       4400
CCGATGTCAAATGGGAAGACCAGGCAGAGATATCAGGAAGGAGTCCAATCCTGTCAATAACAATATCAGAAGATGGTAGCATGTCGATAAAAAATGAAGA
  D  V  K  W  E  D  Q  A  E  I  S  G  S  S  P  I  L  S  I  T  I  S  E  D  G  S  M  S  I  K  N  E  E

      4410       4420       4430       4440       4450       4460       4470       4480       4490       4500
GGAAGAACAAACACTGACCATACTCATTAGAACAGGATTGCTGGTGATCTCAGGACTTTTTCCTGTATCAATACCAATCACGGCAGGAGCATGGTACCTG
 E  E  Q  T  L  T  I  L  I  R  T  G  L  L  V  I  S  G  L  F  P  V  S  I  P  I  T  A  A  A  W  Y  L

                    > NS3
      4510       4520       4530       4540       4550       4560       4570       4580       4590       4600
TGGGAAGTGAAGAAACAACGGGCCGGAGTATTGTGGGATGTTCCTTCACCCCCACCCATGGGAAAGGCTGAACTGGAAGATGGAGCCTATAGAATTAAGC
W  E  V  K  K  Q  R  A  G  V  L  W  D  V  P  S  P  P  P  M  G  K  A  E  L  E  D  G  A  Y  R  I  K  Q

      4610       4620       4630       4640       4650       4660       4670       4680       4690       4700
AAAAAGGGATTCTTGGATATTCCCAGATCGGAGCCGGAGTTTACAAAGAAGGAACATTCCATACAATGTGGCATGTCACACGTGGCGCTGTTCTAATGCA
  K  G  I  L  G  Y  S  Q  I  G  A  G  V  Y  K  E  G  T  F  H  T  M  W  H  V  T  R  G  A  V  L  M  H

      4710       4720       4730       4740       4750       4760       4770       4780       4790       4800
TAAAGGAAAGAGGATTGAACCATCATGGGCGGACGTCAAGAAAGACCTAATATCATATGGAGGAGGCTGGAAGTTAGAAGGAGAATGGAAGGAAGGAGAA
 K  G  K  R  I  E  P  S  W  A  D  V  K  K  D  L  I  S  Y  G  G  G  W  K  L  E  G  E  W  K  E  G  E

      4810       4820       4830       4840       4850       4860       4870       4880       4890       4900
GAAGTCCAGGTATTGGCACTGGAGCCTGGAAAAAATCCAAGAGCCGTCCAAACGAAACCTGGTCTTTTCAAAACCAACGCCGGAACAATAGGTGCTGTAT
E  V  Q  V  L  A  L  E  P  G  K  N  P  R  A  V  Q  T  K  P  G  L  F  K  T  N  A  G  T  I  G  A  V  S

      4910       4920       4930       4940       4950       4960       4970       4980       4990       5000
CTCTGGACTTTTCTCCTGGAACGTCAGGATCTCCAATTATCGACAAAAAAGGAAAAGTTGTGGGTCTTTATGGTAATGGTGTTGTTACAAGGAGTGGAGC
  L  D  F  S  P  G  T  S  G  S  P  I  I  D  K  K  G  K  V  V  G  L  Y  G  N  G  V  V  T  R  S  G  A

      5010       5020       5030       5040       5050       5060       5070       5080       5090       5100
ATATGTGAGTGCTATAGCCCAGACTGAAAAAAGCATTGAAGACAACCCAGAGATCGAAGATGACATTTTCCGAAAGAGAAGACTGACCATCATGGACCTC
  Y  V  S  A  I  A  Q  T  E  K  S  I  E  D  N  P  E  I  E  D  D  I  F  R  K  R  R  L  T  I  M  D  L

      5110       5120       5130       5140       5150       5160       5170       5180       5190       5200
CACCCAGGAGCGGGAAAGACGAAGAGATACCTTCCGGCCATAGTCAGAGAAGCTATAAAACGGGGTTTGAGAACATTAATCTTGGCCCCCACTAGAGTTG
H  P  G  A  G  K  T  K  R  Y  L  P  A  I  V  R  E  A  I  K  R  G  L  R  T  L  I  L  A  P  T  R  V  V

      5210       5220       5230       5240       5250       5260       5270       5280       5290       5300
TGGCAGCTGAAATGGAGGAAGCCCTTAGAGGACTTCCAATAAGATACCAGACCCCAGCCATCAGAGCTGTGCACACCGGGCGGGAGATTGTGGACCTAAT
  A  A  E  M  E  E  A  L  R  G  L  P  I  R  Y  Q  T  P  A  I  R  A  V  H  T  G  R  E  I  V  D  L  M
                                                                      |
                               D2 PDK-53 NS3-250-Val attenuation locus (D2 16681: Glu, nt-5270-A)

      5310       5320       5330       5340       5350       5360       5370       5380       5390       5400
GTGTCATGCCACATTTACCATGAGGCTGCTATCACCAGTTAGAGTGCCAAACTACAACCTGATTATCATGGACGAAGCCCATTTCACAGATCCAGCAAGT
  C  H  A  T  F  T  M  R  L  L  S  P  V  R  V  P  N  Y  N  L  I  I  M  D  E  A  H  F  T  D  P  A  S
                                                                                         |
                              Additional nt-5391 C-to-T silent mutation in mater and pre-master seeds

      5410       5420       5430       5440       5450       5460       5470       5480       5490       5500
ATAGGAGCTAGAGGATACATCTCAACTCGAGTGGAGATGGGTGAGGCAGCTGGGATTTTTATGACAGCCACTCCCCCGGGAAGGAGAGACCCATTTCCTC
I  A  A  R  G  Y  I  S  T  R  V  E  M  G  E  A  A  G  I  F  M  T  A  T  P  P  G  S  R  D  P  F  P  Q

      5510       5520       5530       5540       5550       5560       5570       5580       5590       5600
AGAGCAATGCACCAATCATAGATGAAGAAAGAGAAATCCCTGAACGCCTCGTGGAATTCCGGACATGAATGGGTCACGGATTTTAAAGGGAAGACTGTTTG
  S  N  A  P  I  I  D  E  E  R  E  I  P  E  R  S  W  N  S  G  H  E  W  V  T  D  F  K  G  K  T  V  W
                                                  |
                                     D2 PDK-53 specific silent mutation nt-5547-C (D2 16681: T)

      5610       5620       5630       5640       5650       5660       5670       5680       5690       5700
GTTCGTTCCAAGTATAAAAGGAGGAAATGATATAGGAGCTTGCCTGAGGAAAAATGGAAAGAAAGTGATACAACTCAGTAGGAAGACCTTTGATTCTGAG
  F  V  P  S  I  K  A  G  N  D  I  A  A  C  L  R  K  N  G  K  K  V  I  Q  L  S  R  K  T  F  D  S  E

      5710       5720       5730       5740       5750       5760       5770       5780       5790       5800
TATGTCAAGACTAGAACCAATGATTGGGACTTCGTGGTTACAACTGACATTTCAGAAATGGGTGCCAATTTCAAGGCTGAGAGGGTTATAGACCCCAGAC
Y  V  K  T  R  T  N  D  W  D  F  V  V  T  T  D  I  S  E  M  G  A  N  F  K  A  E  R  V  I  D  P  R  R
```

-continued

```
      5810       5820       5830       5840       5850       5860       5870       5880       5890       5900
GCTGCATGAAACCAGTCATACTAACAGATGGTGAAGAGCGGGTGATTCTGGCAGGACCTATGCCAGTGACCCACTCTAGTGCAGCACAAAGAAGAGGGAG
  C  M  K  P  V  I  L  T  D  G  E  E  R  V  I  L  A  G  P  M  P  V  T  H  S  S  A  A  Q  R  R  G  R

      5910       5920       5930       5940       5950       5960       5970       5980       5990       6000
AATAGGAAGAAATCCAAAAAATGAGAATGACCAGTACATATACATGGGGGAACCTCTGGAAAATGATGAAGACTGTGCACACTGGAAAGAAGCTAAAATG
 I  G  R  N  P  K  N  E  N  D  Q  Y  I  Y  M  G  E  P  L  E  N  D  E  D  C  A  H  W  K  E  A  K  M

      6010       6020       6030       6040       6050       6060       6070       6080       6090       6100
CTCCTAGATAACATCAACACGCCAGAAGGAATCATTCCTAGCATGTTCGAACCAGAGCGTGAAAAGGTGGATGCCATTGATGGCGAATACCGCTTGAGAG
L  L  D  N  I  N  T  P  E  G  I  I  P  S  M  F  E  P  E  R  E  K  V  D  A  I  D  G  E  Y  R  L  R  G

      6110       6120       6130       6140       6150       6160       6170       6180       6190       6200
GAGAAGCAAGGAAAACCTTTGTAGACTTAATGAGAAGAGGAGACCTACCAGTCTGGTTGGCCTACAGAGTGGCAGCTGAAGGCATCAACTACGCAGACAG
  E  A  R  K  T  F  V  D  L  M  R  R  G  D  L  P  V  W  L  A  Y  R  V  A  A  E  G  I  N  Y  A  D  R

      6210       6220       6230       6240       6250       6260       6270       6280       6290       6300
AAGGTGGTGTTTTGATGGAGTCAAGAACAACCAAATCCTAGAAGAAAACGTGGAAGTTGAAATCTGGACAAAAGAAGGGGAAAGGAAGAAATTGAAACCC
 R  W  C  F  D  G  V  K  N  N  Q  I  L  E  E  N  V  E  V  E  I  W  T  K  E  G  E  R  K  K  L  K  P

                                                                              > NS4A
      6310       6320       6330       6340       6350       6360       6370       6380       6390       6400
AGATGGTTGGATGCTAGGATCTATTCTGACCCACTGGCGCTAAAAGAATTTAAGGAATTTGCAGCCGGAAGAAAGTCTCTGACCCTGAACCTAATCACAG
R  W  L  D  A  R  I  Y  S  D  P  L  A  L  K  E  F  K  E  F  A  A  G  R  K  S  L  T  L  N  L  I  T  E

      6410       6420       6430       6440       6450       6460       6470       6480       6490       6500
AAATGGGTAGGCTCCCAACCTTCATGACTCAGAAGGTAAGAGACGCACTGGACAACTTAGCAGTGCTGCACACGGCTGAGGCAGGTGGAAGGGCGTACAA
  M  G  R  L  P  T  F  M  T  Q  K  V  R  D  A  L  D  N  L  A  V  L  H  T  A  E  A  G  G  R  A  Y  N
                                      |
              Additional NS4A-21 Ala-to-Val (nt-6437 C-to-T) mutation in mater and pre-master seeds

      6510       6520       6530       6540       6550       6560       6570       6580       6590       6600
CCATGCTCTCAGTGAACTGCCGGAGACCCTGGAGACATTGCTTTTACTGACACTTCTGGCTACAGTCACGGGAGGGATCTTTTTATTCTTGATGAGCGCA
 H  A  L  S  E  L  P  E  T  L  E  T  L  L  L  L  T  L  L  A  T  V  T  G  G  I  F  L  F  L  M  S  A
                                                                                                  |
                                          D2 PDK-53 specific NS4A-75-Ala (wt D2 16681: Gly, nt-6599-G)

      6610       6620       6630       6640       6650       6660       6670       6680       6690       6700
AGGGGCATAGGGAAGATGACCCTGGGAATGTGCTGCATAATCACGGCTAGCATCCTCCTATGGTACGCACAAATACAGCCACACTGGATAGCAGCTTCAA
R  G  I  G  K  M  T  L  G  M  C  C  I  I  T  A  S  I  L  L  W  Y  A  Q  I  Q  P  H  W  I  A  A  S  I

      6710       6720       6730       6740       6750       6760       6770       6780       6790       6800
TAATACTGGAGTTTTTCTCATAGTTTTGCTTATTCCAGAACCTGAAAAACAGAGAACACCCCAAGACAACCAACTGACCTACGTTGTCATAGCCATCCT
  I  L  E  F  F  L  I  V  L  L  I  P  E  P  E  K  Q  R  T  P  Q  D  N  Q  L  T  Y  V  V  I  A  I  L

                          > NS4B
      6810       6820       6830       6840       6850       6860       6870       6880       6890       6900
CACAGTGGTGGCCGCAACCATGGCAAACGAGATGGGTTTCCTAGAAAAAACGAAGAAAGATCTCGGATTGGGAAGCATTGCAACCCAGCAACCCGAGAGC
 T  V  V  A  A  T  M  A  N  E  M  G  F  L  E  K  T  K  K  D  L  G  L  G  S  I  A  T  Q  Q  P  E  S

      6910       6920       6930       6940       6950       6960       6970       6980       6990       7000
AACATCCTGGACATAGATCTACGTCCTGCATCAGCATGGACGCTGTATGCCGTGGCCACAACATTTGTTACACCAATGTTGAGACATAGCATTGAAAATT
N  I  L  D  I  D  L  R  P  A  S  A  W  T  L  Y  A  V  A  T  T  F  V  T  P  M  L  R  H  S  I  E  N  S

      7010       7020       7030       7040       7050       7060       7070       7080       7090       7100
CCTCAGTGAATGTGTCCCTAACAGCCATAGCCAACCAAGCCACAGTGTTAATGGGTCTCGGGAAAGGATGGCCATTGTCAAAGATGGACATCGGAGTTCC
  S  V  N  V  S  L  T  A  I  A  N  Q  A  T  V  L  M  G  L  G  K  G  W  P  L  S  K  M  D  I  G  V  P
                             |
                      Additional nt-7026 T-to-C/T mix silent mutation in master and pre-master seeds

      7110       7120       7130       7140       7150       7160       7170       7180       7190       7200
CCTTCTCGCCATTGGATGCTACTCACAAGTCAACCCCATAACTCTCACAGGAGCTCTTTTCTTATTGGTAGCACATTATGCCATCATAGGGCCAGGACTC
 L  L  A  I  G  C  Y  S  Q  V  N  P  I  T  L  T  A  A  L  F  L  L  V  A  H  Y  A  I  I  G  P  G  L

      7210       7220       7230       7240       7250       7260       7270       7280       7290       7300
CAAGCAAAAGCAACCAGAGAAGCTCAGAAAAGAGGAGCGGCGGGCATCATGAAAAACCCAACTGTCGATGGAATAACAGTGATTGACCTAGATCCAATAC
Q  A  K  A  T  R  E  A  Q  K  R  A  A  A  G  I  M  K  N  P  T  V  D  G  I  T  V  I  D  L  D  P  I  P

      7310       7320       7330       7340       7350       7360       7370       7380       7390       7400
CTTATGATCCAAAGTTTGAAAAGGAGTTGGGACAAGTAATGCTCCTAGTCCTCTGCGTGACTCAAGTATTGATGATGAGGACTACATGGGCTCTGTGTGA
  Y  D  P  K  F  E  K  Q  L  G  Q  V  M  L  L  V  L  C  V  T  Q  V  L  M  M  R  T  T  W  A  L  C  E

      7410       7420       7430       7440       7450       7460       7470       7480       7490       7500
GGCTTTAACCTTAGCTACCGGGCCCATCTCCACATTGTGGGAAGGAAATCCAGGGAGGTTTTGGAACACTACCATTGCGGTGTCAATGGCTAACATTTTT
 A  L  T  L  A  T  G  P  I  S  T  L  W  E  G  N  P  G  R  F  W  N  T  T  I  A  V  S  M  A  N  I  F

                                                                       > NS5
      7510       7520       7530       7540       7550       7560       7570       7580       7590       7600
AGAGGGAGTTACTTGGCCGGAGCTGGACTTCTCTTTTCTATTATGAAGAACACAACCAACACAAGAAGGGGAACTGGCAACATAGGAGAGACGCTTGGAG
R  G  S  Y  L  A  G  A  G  L  L  F  S  I  M  K  N  T  T  N  T  R  R  G  T  G  N  I  G  E  T  L  G  E
```

-continued

```
      7610       7620       7630       7640       7650       7660       7670       7680       7690       7700
AGAAATGGAAAAGCCGATTGAACGCATTGGGAAAAAGTGAATTCCAGATCTACAAGAAAAGTGGAATCCAGGAAGTGGATAGAACCTTAGCAAAAGAAGG
 K  W  K  S  R  L  N  A  L  G  K  S  E  F  Q  I  Y  K  K  S  G  I  Q  E  V  D  R  T  L  A  K  E  G

      7710       7720       7730       7740       7750       7760       7770       7780       7790       7800
CATTAAAAGAGGAGAAACGGACCATCACGCTGTGTCGCGAGGCTCAGCAAAACTGAGATGGTTCGTTGAGAGAAACATGGTCACACCAGAAGGGAAAGTA
 I  K  R  G  E  T  D  H  H  A  V  S  R  G  S  A  K  L  R  W  F  V  E  R  N  M  V  T  P  E  G  K  V

      7810       7820       7830       7840       7850       7860       7870       7880       7890       7900
GTGGACCTCGGTTGTGGCAGAGGAGGCTGGTCATACTATTGTGGAGGACTAAAGAATGTAAGAGAAGTCAAAGGCCTAACAAAAGGAGGACCAGGACACG
V  D  L  G  C  G  R  G  G  W  S  Y  Y  C  G  G  L  K  N  V  R  E  V  K  G  L  T  K  G  G  P  G  H  E

      7910       7920       7930       7940       7950       7960       7970       7980       7990       8000
AAGAACCCATCCCCATGTCAACATATGGGTGGAATCTAGTGCGTCTTCAAAGTGGAGTTGACGTTTTCTTCATCCCGCCAGAAAAGTGTGACACATTATT
 E  P  I  P  M  S  T  Y  G  W  N  L  V  R  L  Q  S  G  V  D  V  F  F  I  P  P  E  K  C  D  T  L  L

      8010       8020       8030       8040       8050       8060       8070       8080       8090       8100
GTGTGACATAGGGGAGTCATCACCAAATCCCACAGTGGAAGGAGGACGAACACTCAGAGTCCTTAACTTAGTAGAAAATTGGTTGAACAACAACACTCAA
 C  D  I  G  E  S  S  P  N  P  T  V  E  A  G  R  T  L  R  V  L  N  L  V  E  N  W  L  N  N  N  T  Q

      8110       8120       8130       8140       8150       8160       8170       8180       8190       8200
TTTTGCATAAAGGTTCTCAACCCATATATGCCCTCAGTCATAGAAAAAATGGAAGCACTACAAAGGAAATATGGAGGAGCCTTAGTGAGGAATCCACTCT
F  C  I  K  V  L  N  P  Y  M  P  S  V  I  E  K  M  E  A  L  Q  R  K  Y  G  G  A  L  V  R  N  P  L  S

      8210       8220       8230       8240       8250       8260       8270       8280       8290       8300
CACGAAACTCCACACATGAGATGTACTGGGTATCCAATGCTTCCGGGAACATAGTGTCATCAGTGAACATGATTTCAAGGATGTTGATCAACAGATTTAC
 R  N  S  T  H  E  M  Y  W  V  S  N  A  S  G  N  I  V  S  S  V  N  M  I  S  R  M  L  I  N  R  F  T

      8310       8320       8330       8340       8350       8360       8370       8380       8390       8400
AATGAGATACAAGAAAGCCACTTACGAGCCGGATGTTGACCTCGGAAGCGGAACCCGTAACATCGGGATTGAAAGTGAGATACCAAACCTAGATATAATT
 M  R  Y  K  K  A  T  Y  E  P  D  V  D  L  G  S  G  T  R  N  I  G  I  E  S  E  I  P  N  L  D  I  I

      8410       8420       8430       8440       8450       8460       8470       8480       8490       8500
GGGAAAAGAATAGAAAAAATAAAGCAAGAGCATGAAACATCATGGCACTATGACCAAGACCACCCATACAAAACGTGGGCATACCATGGTAGCTATGAAA
G  K  R  I  E  K  I  K  Q  E  H  E  T  S  W  H  Y  D  Q  D  H  P  Y  K  T  W  A  Y  H  G  S  Y  E  T

      8510       8520       8530       8540       8550       8560       8570       8580       8590       8600
CAAAACAGACTGGATCAGCATCATCCATGGTCAACGGAGTGGTCAGGCTGCTGACAAAACCTTGGGACGTCGTCCCCATGGTGACACAGATGGCAATGAC
 K  Q  T  G  S  A  S  S  M  V  N  G  V  V  R  L  L  T  K  P  W  D  V  V  P  M  V  T  Q  M  A  M  T

      8610       8620       8630       8640       8650       8660       8670       8680       8690       8700
AGACACGACTCCATTTGGACAACAGCGCGTTTTTAAAGAGAAAGTGGACACGAGAACCCAAGAACCGAAAGAAGGCACGAAGAAACTAATGAAAATAACA
 D  T  T  P  F  G  Q  Q  R  V  F  K  E  K  V  D  T  R  T  Q  E  P  K  E  G  T  K  K  L  M  K  I  T

      8710       8720       8730       8740       8750       8760       8770       8780       8790       8800
GCAGAGTGGCTTTGGAAAGAATTAGGGAAGAAAAAGACACCCAGGATGTGCACCAGAGAAGAATTCACAAGAAAGGTGAGAAGCAATGCAGCCTTGGGGG
A  E  W  L  W  K  E  L  G  K  K  K  T  P  R  M  C  T  R  E  E  F  T  R  K  V  R  S  N  A  A  L  G  A

      8810       8820       8830       8840       8850       8860       8870       8880       8890       8900
CCATATTCACTGATGAGAACAAGTGGAAGTCGGCACGTGAGGCTGTTGAAGATAGTAGGTTTTGGGAGCTGGTTGACAAGGAAAGGAATCTCCATCTTGA
 I  F  T  D  E  N  K  W  K  S  A  R  E  A  V  E  D  S  R  F  W  E  L  V  D  K  E  R  N  L  H  L  E

      8910       8920       8930       8940       8950       8960       8970       8980       8990       9000
AGGAAAGTGTGAAACATGTGTGTACAACATGATGGGAAAAAGAGAGAAGAAGCTAGGGGAATTCGGCAAGGCAAAAGGCAGGAGAGCCATATGGTACATG
 G  K  C  E  T  C  V  Y  N  M  M  G  K  R  E  K  K  L  G  E  F  G  K  A  K  G  S  R  A  I  W  Y  M

      9010       9020       9030       9040       9050       9060       9070       9080       9090       9100
TGGCTTGGAGCACGCTTCTTAGAGTTTGAAGCCCTAGGATTCTTAAATGAAGATCACTGGTTCTCCAGAGAGAACTCCCTGAGTGGAGTGGAAGGAGAAG
W  L  G  A  R  F  L  E  F  E  A  L  G  F  L  N  E  D  H  W  F  S  R  E  N  S  L  S  G  V  E  G  E  G

      9110       9120       9130       9140       9150       9160       9170       9180       9190       9200
GGCTGCACAAGCTAGGTTACATTCTAAGAGACGTGAGCAAGAAAGAGGGAGGAGCAATGTATGCCGATGACACCGCAGGATGGGATACAAGAATCACACT
 L  H  K  L  G  Y  I  L  R  D  V  S  K  K  E  G  G  A  M  Y  A  D  D  T  A  G  W  D  T  R  I  T  L

      9210       9220       9230       9240       9250       9260       9270       9280       9290       9300
AGAAGACCTAAAAAATGAAGAAATGGTAACAAACCACATGGAAGGAGAACACAAGAAACTAGCCGAGGCCATTTTCAAACTAACGTACCAAAACAAGGTG
 E  D  L  K  N  E  E  M  V  T  N  H  M  E  G  E  H  K  K  L  A  E  A  I  F  K  L  T  Y  Q  N  K  V

      9310       9320       9330       9340       9350       9360       9370       9380       9390       9400
GTGCGTGTGCAAAGACCAACACCAAGAGGCACAGTAATGGACATCATATCGAGAAGAGACCAAAGAGGTAGTGGACAAGTTGGCACCTATGGACTCAATA
V  R  V  Q  R  P  T  P  R  G  T  V  M  D  I  I  S  R  R  D  Q  R  G  S  G  Q  V  G  T  Y  G  L  N  T

      9410       9420       9430       9440       9450       9460       9470       9480       9490       9500
CTTTCACCAATATGGAAGCCCAACTAATCAGACAGATGGAGGGAGAAGGAGTCTTTAAAAGCATTCAGCACCTAACAATCACAGAAGAAATCGCTGTGCA
 F  T  N  M  E  A  Q  L  I  R  Q  M  E  G  E  G  V  F  K  S  I  Q  H  L  T  I  T  E  E  I  A  V  Q

      9510       9520       9530       9540       9550       9560       9570       9580       9590       9600
AAACTGGTTAGCAAGAGTGGGGCGCGAAAGGTTATCAAGAATGGCCATCAGTGGAGATGATTGTGTTGTGAAACCTTTAGATGACAGGTTCGCAAGCGCT
 N  W  L  A  R  V  G  R  E  R  L  S  R  M  A  I  S  G  D  D  C  V  V  K  P  L  D  D  R  F  A  S  A
```

-continued

```
     9610      9620      9630      9640      9650      9660      9670      9680      9690      9700
TTAACAGCTCTAAATGACATGGGAAAGATTAGGAAAGACATACAACAATGGGAACCTTCAAGAGGATGGAATGATTGGACACAAGTGCCCTTCTGTTCAC
L  T  A  L  N  D  M  G  K  I  R  K  D  I  Q  Q  W  E  P  S  R  G  W  N  D  W  T  Q  V  P  F  C  S  H

     9710      9720      9730      9740      9750      9760      9770      9780      9790      9800
ACCATTTCCATGAGTTAATCATGAAAGACGGTCGCGTACTCGTTGTTCCCTGTAGAAACCAAGATGAACTGATTGGCAGAGCCCGAATCTCCCAAGGAGC
  H  F  H  E  L  I  M  K  D  G  R  V  L  V  V  P  C  R  N  Q  D  E  L  I  G  R  A  R  I  S  Q  G  A
                                                   |
                           Additional nt-9750 A-to-C silent mutation in master and pre-master seeds

     9810      9820      9830      9840      9850      9860      9870      9880      9890      9900
AGGGTGGTCTTTGCGGGAGACGGCCTGTTTGGGGAAGTCTTACGCCCAAATGTGGAGCTTGATGTACTTCCACAGACGCGACCTCAGGCTGGCGGCAAAT
 G  W  S  L  R  E  T  A  C  L  G  K  S  Y  A  Q  M  W  S  L  M  Y  F  H  R  R  D  L  R  L  A  A  N

     9910      9920      9930      9940      9950      9960      9970      9980      9990     10000
GCTATTTGCTCGGCAGTACCATCACATTGGGTTCCAACAAGTCGAACAACCTGGTCCATACATGCTAAACATGAATGGATGACAACGGAAGACATGCTGA
A  I  C  S  A  V  P  S  H  W  V  P  T  S  R  T  T  W  S  I  H  A  K  H  E  W  M  T  T  E  D  M  L  T

    10010     10020     10030     10040     10050     10060     10070     10080     10090     10100
CAGTCTGGAACAGGGTGTGGATTCAAGAAAACCCATGGATGGAAGACAAAACTCCAGTGGAATCATGGGAGGAAATCCCATACTTGGGGAAAAGAGAAGA
  V  W  N  R  V  W  I  Q  E  N  P  W  M  E  D  K  T  P  V  E  S  W  E  E  I  P  Y  L  G  K  R  E  D

    10110     10120     10130     10140     10150     10160     10170     10180     10190     10200
CCAATGGTGCGGCTCATTGATTGGGTTAACAAGGAGGGCCACCTGGGCAAAGAACATCCAAGGAGCAATAAATCAAGTTAGATCCCTTATAGGCAATGAA
 Q  W  C  G  S  L  I  G  L  T  S  R  A  T  W  A  K  N  I  Q  A  A  I  N  Q  V  R  S  L  I  G  N  E

                                                                        >3'-Noncoding Region
    10210     10220     10230     10240     10250     10260     10270     10280     10290     10300
GAATACACAGATTACATGCCATCCATGAAAAGATTCAGAAGAGAAGAGGAAGAAGGAGGAGTTCTGTGGTAGAAAGCAAAACTAACATGAAACAAGGCTA
E  Y  T  D  Y  M  P  S  M  K  R  F  R  R  E  E  E  E  A  G  V  L  W  *

    10310     10320     10330     10340     10350     10360     10370     10380     10390     10400
GAAGTCAGGTCGGATTAAGCCATAGTACGGAAAAAACTATGCTACCTGTGAGCCCCGTCCAAGGACGTTAAAAGAAGTCAGGCCATCATAAATGCCATAG

    10410     10120     10430     10440     10450     10460     10470     10480     10490     10500
CTTGAGTAAACTATGCAGCCTGTAGCTCCACCTGAGAAGGTGTAAAAAATCCGGGAGGCCACAAACCATGGAAGCTGTACGCATGGGCGTAGTGGACTAG

    10510     10520     10530     10540     10550     10560     10570     10580     10590     10600
GGTTAGAGGAGACCCCTCCCTTACAAATCGCAGCAACAATGGGGGCCCAAGGCGAGATGAAGCTGTAGTCTCGCTGGAAGGACTAGAGGTTAGAGGAGAC

    10610     10620     10630     10640     10650     10660     10670     10680     10690     10700
CCCCCCGAAACAAAAAACAGCATATTGACGCTGGGAAAGACCAGAGATCCTGCTGTCTCCTCAGCATCATTCCAGGCACAGAACGCCAGAAAATGGAATG

    10710     10720
GTGCTGTTGAATCAACAGGTTCT
```

The invention claimed is:

1. An immunogenic composition comprising a modified live, attenuated dengue-2 virus strain PDK-53, the immunogenic composition being a tetravalent composition, wherein the modified live, attenuated dengue-2 virus strain PDK-53 is encoded by a polynucleotide molecule encoding a modified live, attenuated dengue-2 virus strain PDK-53 polypeptide molecule, comprises an RNA transcribed from a cDNA comprising a polynucleotide molecule encoding the modified live, attenuated dengue-2 virus strain PDK-53 polypeptide molecule, comprises one or more polypeptide molecules encoded by a polynucleotide molecule encoding the modified live, attenuated dengue-2 virus strain PDK-53 polypeptide molecule, or is obtainable by a method for producing a modified live, attenuated dengue-2 virus strain PDK-53, the method comprising the following steps:

a) transcribing an RNA from a cDNA comprising a polynucleotide molecule encoding the modified live, attenuated dengue-2 virus strain PDK-53 polypeptide molecule, and b) introducing the RNA transcribed in step a) into cells for production of the modified live, attenuated dengue-2 virus strain PDK-53, wherein the polynucleotide molecule encoding the modified live, attenuated dengue-2 virus strain PDK-53 polypeptide molecule comprises at least one mutation, wherein one or more mutation is selected from the group consisting of:

an adenine to guanine mutation at position 592 in the numbering of SEQ ID NO: 14 encoding a glutamic acid instead of a lysine in the polypeptide molecule at amino acid position 166 in the numbering of SEQ ID NO: 6 corresponding to prM-52, and an adenine to guanine mutation at position 8803 in the numbering of SEQ ID NO: 14 encoding a valine instead of an isoleucine in the polypeptide molecule at amino acid position 2903 in the numbering of SEQ ID NO: 6 corresponding to NS5-412, and comprising a dengue-1/dengue-2 chimera, wherein the dengue-1/dengue-2 chimera comprises an adenine to guanine mutation at position 7311 in the numbering of SEO ID NO: 13.

2. The immunogenic composition according to claim 1, wherein the polynucleotide molecule encoding the modified live, attenuated dengue-2 virus strain PDK-53 polypeptide molecule further comprises at least one additional mutation of:

a guanine to cytosine mutation at nucleic acid position 6481 in the numbering of SEQ ID NO: 14 encoding a proline instead of an alanine in the polypeptide molecule at amino acid position 2129 in the numbering of SEQ ID NO: 6 corresponding to NS4A-36, and a cytosine to thymine mutation at position 7156 in the numbering of SEQ ID NO: 14 encoding a phenylalanine instead of a leucine in the polypeptide molecule at amino acid position 2354 in the numbering of SEQ ID NO: 6 corresponding to NS4B-111.

3. The immunogenic composition according to claim 1, wherein the polynucleotide molecule encoding the modified live, attenuated dengue-2 virus strain PDK-53 polypeptide molecule is represented by SEQ ID NO: 4 or SEQ ID NO: 14.

4. The immunogenic composition according to claim 1, wherein the modified, live attenuated dengue-2 virus strain PDK-53 polypeptide molecule is represented by SEQ ID NO: 5 or SEQ ID NO: 6.

5. A pharmaceutical composition comprising the immunogenic composition according to claim 1, and a pharmaceutically acceptable excipient.

6. A method for inducing an immune response against dengue virus in a subject, the method comprising administering to the subject a pharmaceutically acceptable amount of the composition of claim 5.

7. The immunogenic composition according to claim 1 further comprising a pharmaceutically acceptable carrier.

8. The immunogenic composition of claim 7, wherein the dengue-1/dengue-2 chimera is encoded by a polynucleotide molecule encoding a dengue-1/dengue-2 polypeptide chimera, comprises an RNA transcribed from a cDNA comprising a polynucleotide molecule encoding the dengue-1/dengue-2 polypeptide chimera, comprises one or more polypeptide molecules encoded by a polynucleotide molecule encoding the dengue-1/dengue-2 polypeptide chimera, or is obtainable by a method for producing a dengue-1/dengue-2 chimera, the method comprising the following steps:

a) transcribing an RNA from a cDNA comprising a polynucleotide molecule encoding the dengue-1/dengue-2 polypeptide chimera, and b) introducing the RNA transcribed in step a) into cells for production of the dengue-1/dengue-2 chimera, wherein the polynucleotide molecule encoding the dengue-1/dengue-2 polypeptide chimera comprises a first nucleotide sequence encoding nonstructural proteins from a modified live, attenuated dengue-2 virus strain PDK-53, a second nucleotide sequence encoding at least one structural protein from dengue-1, and at least one mutation, wherein one or more mutation is selected from the group consisting of:

an adenine to cytosine mutation at position 3823 in the numbering of SEQ ID NO: 13 encoding a leucine instead of an isoleucine in the dengue-1/dengue-2 polypeptide chimera at amino acid position 1243 in the numbering of SEQ ID NO: 3 corresponding to NS2A-116; and an adenine to thymine mutation at position 4407 in the numbering of SEQ ID NO: 13 encoding an aspartic acid instead of a glutamic acid in the dengue-1/dengue-2 polypeptide chimera at amino acid position 1437 in the numbering of SEQ ID NO: 3 corresponding to NS2B-92.

9. The immunogenic composition according to claim 8, wherein the polynucleotide molecule encoding the dengue-1/dengue-2 polypeptide chimera further comprises at least one additional mutation of:

a cytosine to thymine mutation at position 7148 in the numbering of SEQ ID NO: 13 encoding an isoleucine instead of a threonine in the dengue-1/dengue-2 polypeptide chimera at amino acid position 2351 in the numbering of SEQ ID NO: 3 corresponding to NS4B-108; and a guanine to cytosine mutation at position 2384 in the numbering of SEQ ID NO: 13 encoding an alanine instead of glycine in the dengue-1/dengue-2 polypeptide chimera at amino acid position 763 in the numbering of SEQ ID NO: 3 corresponding to E-483.

10. The immunogenic composition according to claim 8, wherein the polynucleotide molecule encoding the dengue-1/dengue-2 polypeptide chimera is represented by SEQ ID NO: 1 or SEQ ID NO: 13.

11. The immunogenic composition according to claim 8, wherein the dengue-1/dengue-2 polypeptide chimera is represented by SEQ ID NO: 2 or SEQ ID NO: 3.

12. The immunogenic composition of claim 8, wherein the nonstructural proteins from the modified live, attenuated dengue-2 virus strain PDK-53 are selected from the group consisting of NS1, NS2A, NS2B, NS3, NS4A, NS4B and NS5.

13. The immunogenic composition of claim 8, wherein the at least one structural protein from dengue-1 is selected from the group consisting of capsid protein (C), premembrane/membrane protein (prM) and envelope protein (E).

14. The immunogenic composition of claim 7, further comprising a dengue-3/dengue-2 chimera, wherein the dengue-3/dengue-2 chimera is encoded by a polynucleotide molecule encoding a dengue-3/dengue-2 polypeptide chimera, comprises an RNA transcribed from a cDNA comprising a polynucleotide molecule encoding the dengue-3/dengue-2 polypeptide chimera, comprises one or more polypeptide molecules encoded by a polynucleotide molecule encoding the dengue-3/dengue-2 polypeptide chimera, or is obtainable by a method for producing a dengue-3/dengue-2 chimera, the method comprising the following steps:

a) transcribing an RNA from a cDNA comprising a polynucleotide molecule encoding the dengue-3/dengue-2 polypeptide chimera, and b) introducing the RNA transcribed in step a) into cells for production of the dengue-3/dengue-2 chimera, wherein the polynucleotide molecule encoding the dengue-3/dengue-2 polypeptide chimera comprises a first nucleotide sequence encoding nonstructural proteins from a modified live, attenuated dengue-2 virus strain PDK-53, a second nucleotide sequence encoding at least one structural protein from dengue-3, and at least one mutation, wherein one or more mutation is selected from the group consisting of:

an adenine to thymine mutation at position 1603 in the numbering of SEQ ID NO: 15 encoding a serine instead of a threonine in the dengue-3/dengue-2 polypeptide chimera at amino acid position 503 in the numbering of SEQ ID NO: 9 corresponding to E-223; and an adenine to guanine mutation at position 7620 in the numbering of SEQ ID NO: 15.

15. The immunogenic composition of claim 14, wherein the polynucleotide molecule encoding the dengue-3/dengue-2 polypeptide chimera further comprises a guanine to adenine mutation at position 6436 in the numbering of SEQ ID NO: 15 encoding an asparagine instead of an aspartic acid in the dengue-3/dengue-2 polypeptide chimera at amino acid position 2114 in the numbering of SEQ ID NO: 19 corresponding to NS4A-23.

16. The immunogenic composition of claim 14, wherein the polynucleotide molecule encoding the dengue-3/dengue-2 polypeptide chimera is represented by SEQ ID NO: 7 or SEQ ID NO: 15.

17. The immunogenic composition of claim 14, wherein the dengue-3/dengue-2 polypeptide chimera is represented by SEQ ID NO: 8 or SEQ ID NO: 9.

18. The immunogenic composition of claim 14, wherein the nonstructural proteins from the modified live, attenuated dengue-2 virus strain PDK-53 are selected from the group consisting of NS1, NS2A, NS2B, NS3, NS4A, NS4B and NS5.

19. The immunogenic composition of claim 14, wherein the at least one structural protein from dengue-3 is selected from the group consisting of capsid protein (C), premembrane/membrane protein (prM) and envelope protein (E).

20. The immunogenic composition of claim 7, further comprising a dengue-4/dengue-2 chimera, wherein the dengue-4/dengue-2 chimera is encoded by a polynucleotide molecule encoding a dengue-4/dengue-2 polypeptide chimera, comprises an RNA transcribed from a cDNA comprising a polynucleotide molecule encoding the dengue-4/dengue-2 polypeptide chimera, comprises one or more polypeptide molecules encoded by a polynucleotide molecule encoding the dengue-4/dengue-2 polypeptide chimera, or is obtainable by a method for producing a dengue-4/dengue-2 chimera, the method comprising the following steps:

a) transcribing an RNA from a cDNA comprising a polynucleotide molecule encoding the dengue-4/dengue-2 polypeptide chimera, and b) introducing the RNA transcribed in step a) into cells for production of the dengue-4/dengue-2 chimera, wherein the polynucleotide molecule encoding the dengue-4/dengue-2 polypeptide chimera comprises a first nucleotide sequence encoding nonstructural proteins from a modified live, attenuated dengue-2 virus strain PDK-53, a second nucleotide sequence encoding at least one structural protein from dengue-4, and at least one mutation, wherein one or more mutation is selected from the group consisting of:

an adenine to thymine mutation at position 225 in the numbering of SEQ ID NO: 16;

an adenine to guanine mutation at position 3674 in the numbering of SEQ ID NO: 16 encoding a glycine instead of an aspartic acid in the dengue-4/dengue-2 polypeptide chimera at amino acid position 1193 in the numbering of SEQ ID NO: 12 corresponding to NS2A-66;

a cytosine to thymine mutation at position 5391 in the numbering of SEQ ID NO: 16;

a cytosine to thymine mutation at position 6437 in the numbering of SEQ ID NO: 16 encoding a valine instead of an alanine in the dengue-4/dengue-2 polypeptide chimera at amino acid position 2114 in the numbering of SEQ ID NO: 12 corresponding to NS4A-21, and an adenine to cytosine mutation at position 9750 in the numbering of SEQ ID NO: 16.

21. The immunogenic composition of claim 20, wherein the polynucleotide molecule encoding the dengue-4/dengue-2 polypeptide chimera further comprises a thymine to cytosine mutation at position 7026 in the numbering of SEQ ID NO: 16.

22. The immunogenic composition of claim 20, wherein the polynucleotide molecule encoding the dengue-4/dengue-2 polypeptide chimera further comprises an adenine to guanine mutation at position 3773 in the numbering of SEQ ID NO: 16 encoding an arginine instead of a lysine in the dengue-4/dengue-2 polypeptide chimera at amino acid position 1226 in the numbering of SEQ ID NO: 12 corresponding to NS2A-99.

23. The immunogenic composition of claim 20, wherein the polynucleotide molecule encoding the dengue-4/dengue-2 polypeptide chimera further comprises a cytosine to thymine mutation at position 7538 in the numbering of SEQ ID NO: 16 encoding a phenylalanine instead of a serine in the dengue-4/dengue-2 polypeptide chimera at amino acid position 2481 in the numbering of SEQ ID NO: 12 corresponding to NS4B-238.

24. The immunogenic composition of claim 20, wherein the polynucleotide molecule encoding the dengue-4/dengue-2 polypeptide chimera is represented by SEQ ID NO: 10 or SEQ ID NO: 16.

25. The immunogenic composition of claim 20, wherein the dengue-4/dengue-2 polypeptide chimera is represented by SEQ ID NO: 11 or SEQ ID NO: 12.

26. The immunogenic composition of claim 20, wherein the nonstructural proteins from the modified live, attenuated dengue-2 virus strain PDK-53 are selected from the group consisting of NS1, NS2A, NS2B, NS3, NS4A, NS4B and NS5.

27. The immunogenic composition of claim 20, wherein the at least one structural protein from dengue-4 is selected from the group consisting of capsid protein (C), premembrane/membrane protein (prM) and envelope protein (E).

28. The immunogenic composition of claim 1, wherein the dengue-1/dengue-2 chimera is encoded by a polynucleotide molecule encoding a dengue-1/dengue-2 polypeptide chimera, comprises an RNA transcribed from a cDNA comprising a polynucleotide molecule encoding the dengue-1/dengue-2 polypeptide chimera, comprises one or more polypeptide molecules encoded by a polynucleotide molecule encoding the dengue-1/dengue-2 polypeptide chimera, or is obtainable by a method for producing a dengue-1/dengue-2 chimera, the method comprising the following steps:

a) transcribing an RNA from a cDNA comprising a polynucleotide molecule encoding the dengue-1/dengue-2 polypeptide chimera, and b) introducing the RNA transcribed in step a) into cells for production of the dengue-1/dengue-2 chimera, wherein the polynucleotide molecule encoding the dengue-1/dengue-2 polypeptide chimera comprises a first nucleotide sequence encoding nonstructural proteins from a modified live, attenuated dengue-2 virus strain PDK-53, a second nucleotide sequence encoding at least one structural protein from dengue-1, and at least one mutation, wherein one or more mutation is selected from the group consisting of:

an adenine to cytosine mutation at position 3823 in the numbering of SEQ ID NO: 13 encoding a leucine instead of an isoleucine in the dengue-1/dengue-2 polypeptide chimera at amino acid position 1243 in the numbering of SEQ ID NO: 3 corresponding to NS2A-116;

an adenine to thymine mutation at position 4407 in the numbering of SEQ ID NO: 13 encoding an aspartic acid instead of a glutamic acid in the dengue-1/dengue-2 polypeptide chimera at amino acid position 1437 in the numbering of SEQ ID NO: 3 corresponding to NS2B-92; and an adenine to guanine mutation at position 7311;

and further comprising one or more of:

ii) a dengue-3/dengue-2 chimera, wherein the dengue-3/dengue-2 chimera is encoded by a polynucleotide molecule encoding a dengue-3/dengue-2 polypeptide chimera, comprises an RNA transcribed from a cDNA comprising a polynucleotide molecule encoding the dengue-3/dengue-2 polypeptide chimera, comprises one or more polypeptide molecules encoded by a polynucleotide molecule encoding the dengue-3/dengue-2 polypeptide chimera, or is obtainable by a method for producing a dengue-3/dengue-2 chimera, the method comprising the following steps:

a) transcribing an RNA from a cDNA comprising a polynucleotide molecule encoding the dengue-3/dengue-2 polypeptide chimera, and b) introducing the RNA transcribed in step a) into cells for production of the dengue-3/dengue-2 chimera, wherein the polynucleotide molecule encoding the dengue-3/dengue-2 polypeptide chimera comprises a first nucleotide sequence encoding nonstructural proteins from a modified live, attenuated dengue-2 virus strain PDK-53, a second nucleotide sequence encoding at least one structural protein from dengue-3, and at least one mutation, wherein one or more mutation is selected from the group consisting of:

an adenine to thymine mutation at position 1603 in the numbering of SEQ ID NO: 15 encoding a serine instead of a threonine in the dengue-3/dengue-2 polypeptide chimera at amino acid position 503 in the numbering of SEQ ID NO: 9 corresponding to E-223; and an adenine to guanine mutation at position 7620 in the numbering of SEQ ID NO: 15; and iii) a dengue-4/dengue-2 chimera, wherein the dengue-4/dengue-2 chimera is encoded by a polynucleotide molecule encoding a dengue-4/dengue-2 polypeptide chimera, comprises an RNA transcribed from a cDNA comprising a polynucleotide molecule encoding the dengue-4/dengue-2 polypeptide chimera, comprises one or more polypeptide molecules encoded by a polynucleotide molecule encoding the dengue-4/dengue-2 polypeptide chimera, or is obtainable by a method for producing a dengue-4/dengue-2 chimera, the method comprising the following steps:

a) transcribing an RNA from a cDNA comprising a polynucleotide molecule encoding the dengue-4/dengue-2 polypeptide chimera, and b) introducing the RNA transcribed in step a) into cells for production of the dengue-4/dengue-2 chimera, wherein the polynucleotide molecule encoding the dengue-4/dengue-2 polypeptide chimera comprises a first nucleotide sequence encoding nonstructural proteins from a modified live, attenuated dengue-2 virus strain PDK-53, a second nucleotide sequence encoding at least one structural protein from dengue-4, and at least one mutation, wherein one or more mutation is selected from the group consisting of:

an adenine to thymine mutation at position 225 in the numbering of SEQ ID NO: 16;

an adenine to guanine mutation at position 3674 in the numbering of SEQ ID NO: 16 encoding a glycine instead of an aspartic acid in the dengue-4/dengue-2 polypeptide chimera at amino acid position 1193 in the numbering of SEQ ID NO: 12 corresponding to NS2A-66;

a cytosine to thymine mutation at position 5391 in the numbering of SEQ ID NO: 16;

a cytosine to thymine mutation at position 6437 in the numbering of SEQ ID NO: 16 encoding a valine instead of an alanine in the dengue-4/dengue-2 polypeptide chimera at amino acid position 2114 in the numbering of SEQ ID NO: 12 corresponding to NS4A-21, and an adenine to cytosine mutation at position 9750 in the numbering of SEQ ID NO: 16.

29. The immunogenic composition of claim 1, in combination with an immunogenic composition for a flavivirus selected from the group consisting of yellow fever virus, tick-borne encephalitis virus, Japanese encephalitis virus, West Nile virus, hepatitis C virus, and a combination of two or more thereof.

30. A kit comprising at least one immunogenic composition according to claim 1; or at least one composition comprising an immunogenic composition according to claim 1 and a pharmaceutically acceptable excipient;

and a container.

* * * * *

SEQUENCE LISTING

```
<160> NUMBER OF SEQ ID NOS: 16

<210> SEQ ID NO 1
<211> LENGTH: 10723
<212> TYPE: DNA
<213> ORGANISM: Artificial Sequence
<220> FEATURE:
<223> OTHER INFORMATION: Dengue virus serotype 1, BVS

<400> SEQUENCE: 1

agttgttagt ctacgtggac cgacaaagac agattctttg agggagctaa gctcaatgta      60

gttctaacag ttttttaatt agagagcaga tctctgatga ataaccaacg gaaaaaggcg     120

aaaaacacgc ctttcaatat gctgaaacgc gagagaaacc gcgtgtcgac tgtgcaacag     180

ctgacaaaga gattctcact tggaatgctg cagggacgag gaccattaaa actgttcatg     240

gccctggtgg cgttccttcg tttcctaaca atcccaccaa cagcagggat attgaagaga     300

tggggaacaa ttaaaaaatc aaaagctatt aatgttttga gagggttcag gaaagagatt     360

ggaaggatgc tgaacatctt gaataggaga cgcagatctg caggcatgat cattatgctg     420

attccaacag tgatggcgtt ccatttaacc acgcgtgggg gagagccgca tatgatagtt     480

agcaagcagg aaagaggaaa gtcacttttg ttcaagacct ctgcaggtgt caacatgtgc     540
```

-continued

```
accctcattg cgatggattt gggagagttg tgtgaggaca cgatgaccta caaatgcccc    600
cggatcactg aggcggaacc agatgacgtt gactgttggt gcaatgccac ggacacatgg    660
gtgacctatg gaacgtgctc tcaaactggc gaacaccgac gagacaaacg ttccgtcgca    720
ttggccccac acgtggggct tggcctagaa acaagagccg aaacgtggat gtcctctgaa    780
ggtgcttgga aacagataca aaaagtagag acttgggctc tgagacatcc aggattcacg    840
gtgatagccc tttttctagc acatgccata ggaacatcca tcacccagaa agggatcatt    900
ttcattttgc tgatgctggt aacaccatct atggccatgc gatgcgtggg aataggcaac    960
agagacttcg tggaaggact gtcaggagca acatgggtgg atgtggtact ggagcatgga   1020
agttgcgtca ccaccatggc aaaaaacaaa ccaacactgg acattgaact cttgaagacg   1080
gaggtcacaa accctgcagt tctgcgtaaa ttgtgcattg aagctaaaat atcaaacacc   1140
accaccgatt cgagatgtcc aacacaagga gaagccacac tggtggaaga acaagacgcg   1200
aactttgtgt gccgacgaac gttcgtggac agaggctggg gcaatggctg tgggctattc   1260
ggaaaaggta gtctaataac gtgtgccaag tttaagtgtg tgacaaaact agaaggaaag   1320
atagttcaat atgaaaacct aaaatattca gtgatagtca ccgtccacac tggagatcag   1380
caccaggtgg gaaatgagac tacagaacat ggaacaactg caaccataac acctcaagct   1440
cctacgtcgg aaatacagct gaccgactac ggaaccctta cattagattg ttcacctagg   1500
acagggctag attttaacga gatggtgttg ctgacaatga aagaaaagatc atggcttgtc   1560
cacaaacaat ggttcctaga cttaccactg ccttggacct ctggggcttc aacatcccaa   1620
gagacttgga acagacaaga tttactggtc acatttaaga cagctcatgc aaagaagcag   1680
gaagtagtcg tactaggatc acaagaagga gcaatgcaca ctgcgctgac tggagcgaca   1740
gaaatccaaa cgtcaggaac gacaacaatt ttcgcaggac acctaaaatg cagactaaaa   1800
atggacaaac taactttaaa agggatgtca tatgtgatgt gcacaggctc attcaagtta   1860
gagaaagaag tggctgagac ccagcatgga actgttctgg tgcaggttaa atatgaagga   1920
acagacgcac catgcaagat tccctttcg acccaagatg agaaaggagc aacccagaat   1980
gggagattaa taacagccaa ccccatagtc actgacaaag aaaaaccagt caatattgag   2040
gcagaaccac cctttggtga gagctacatc gtggtaggag caggtgaaaa agctttgaaa   2100
ctaagctggt tcaagaaagg aagcagcata gggaaaatgt ttgaagcaac tgcccgagga   2160
gcacgaagga tggccattct gggagacacc gcatgggact tcggttctat aggaggagtg   2220
ttcacgtcta tgggaaaact ggtacaccag gtttttggaa ctgcatatgg agttttgttt   2280
agcggagttt cttggaccat gaaaatagga atagggattc tgctgacatg gctaggatta   2340
aattcaagga acacgtccct ttcgatgatg tgcatcgcag ccgccattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
```

aaacaggatg tattctgcga ctcaaaactc atgtcagcgg ccataaaaga caacagagcc 3000
gtccatgccg atatgggtta ttggatagaa agtgcactca atgacacatg gaagatagag 3060
aaagcctctt tcattgaagt taaaaactgc cactggccaa aatcacacac cctctggagc 3120
aatggagtgc tagaaagtga gatgataatt ccaaagaatc tcgctggacc agtgtctcaa 3180
cacaactata gaccaggcta ccatacacaa ataacaggac catggcatct aggtaagctt 3240
gagatggact ttgatttctg tgatggaaca acagtggtag tgactgagga ctgcggaaat 3300
agaggaccct ctttgagaac aaccactgcc tctggaaaac tcataacaga atggtgctgc 3360
cgatcttgca cattaccacc gctaagatac agaggtgagg atgggtgctg gtacgggatg 3420
gaaatcagac cattgaagga gaaagaagag aatttggtca actccttggt cacagctgga 3480
catgggcagg tcgacaactt ttcactagga gtcttgggaa tggcattgtt cctggaggaa 3540
atgcttagga cccgagtagg aacgaaacat gcaatactac tagttgcagt ttcttttgtg 3600
acattgatca cagggaacat gtcctttaga gacctgggaa gagtgatggt tatggtaggc 3660
gccactatga cggatgacat aggtatgggc gtgacttatc ttgccctact agcagccttc 3720
aaagtcagac caacttttgc agctggacta ctcttgagaa agctgacctc caaggaattg 3780
atgatgacta ctataggaat tgtactcctc tcccagagca ccctaccaga gaccattctt 3840
gagttgactg atgcgttagc cttaggcatg atggtcctca aaatggtgag aaatatggaa 3900
aagtatcaat tggcagtgac tatcatggct atcttgtgcg tcccaaacgc agtgatatta 3960
caaaacgcat ggaaagtgag ttgcacaata ttggcagtgg tgtccgtttc cccactgttc 4020
ttaacatcct cacagcaaaa aacagattgg ataccattag cattgacgat caaaggtctc 4080
aatccaacag ctatttttct aacaaccctc tcaagaacca gcaagaaaag gagctggcca 4140
ttaaatgagg ctatcatggc agtcgggatg gtgagcattt tagccagttc tctcctaaaa 4200
aatgatattc ccatgacagg accattagtg gctggagggc tcctcactgt gtgctacgtg 4260
ctcactggac gatcggccga tttggaactg gagagagcag ccgatgtcaa atgggaagac 4320
caggcagaga tatcaggaag cagtccaatc ctgtcaataa caatatcaga agatggtagc 4380
atgtcgataa aaaatgaaga ggaagatcaa acactgacca tactcattag aacaggattg 4440
ctggtgatct caggactttt tcctgtatca ataccaatca cggcagcagc atggtacctg 4500
tgggaagtga agaaacaacg ggccggagta ttgtgggatg ttccttcacc cccacccatg 4560
ggaaaggctg aactggaaga tggagcctat agaattaagc aaaaagggat tcttggatat 4620
tcccagatcg gagccggagt ttacaaagaa ggaacattcc atacaatgtg gcatgtcaca 4680
cgtggcgctg ttctaatgca taaaggaaag aggattgaac catcatgggc ggacgtcaag 4740
aaagacctaa tatcatatgg aggaggctgg aagttagaag gagaatggaa ggaaggagaa 4800
gaagtccagg tattggcact ggagcctgga aaaaatccaa gagccgtcca aacgaaacct 4860
ggtcttttca aaaccaacgc cggaacaata ggtgctgtat ctctggactt ttctcctgga 4920
acgtcaggat ctccaattat cgacaaaaaa ggaaaagttg tgggtcttta tggtaatggt 4980
gttgttacaa ggagtggagc atatgtgagt gctatagccc agactgaaaa aagcattgaa 5040
gacaacccag agatcgaaga tgacattttc cgaaagagaa gactgaccat catggacctc 5100
cacccaggag cgggaaagac gaagagatac cttccggcca tagtcagaga agctataaaa 5160
cggggtttga gaacattaat cttggccccc actagagttg tggcagctga aatggaggaa 5220
gcccttagag gacttccaat aagataccag accccagcca tcagagctgt gcacaccggg 5280

-continued cgggagattg tggacctaat gtgtcatgcc acatttacca tgaggctgct atcaccagtt 5340
agagtgccaa actacaacct gattatcatg gacgaagccc atttcacaga cccagcaagt 5400
atagcagcta gaggatacat ctcaactcga gtggagatgg gtgaggcagc tgggattttt 5460
atgacagcca ctcccccggg aagcagagac ccatttcctc agagcaatgc accaatcata 5520
gatgaagaaa gagaaatccc tgaacgctcg tggaattccg gacatgaatg ggtcacggat 5580
tttaaaggga agactgtttg gttcgttcca agtataaaag caggaaatga tatagcagct 5640
tgcctgagga aaaatggaaa gaaagtgata caactcagta ggaagacctt tgattctgag 5700
tatgtcaaga ctagaaccaa tgattgggac ttcgtggtta caactgacat ttcagaaatg 5760
ggtgccaatt tcaaggctga gagggttata gaccccagac gctgcatgaa accagtcata 5820
ctaacagatg gtgaagagcg ggtgattctg gcaggaccta tgccagtgac ccactctagt 5880
gcagcacaaa gaagagggag aataggaaga aatccaaaaa atgagaatga ccagtacata 5940
tacatggggg aacctctgga aaatgatgaa gactgtgcac actggaaaga agctaaaatg 6000
ctcctagata acatcaacac gccagaagga atcattccta gcatgttcga accagagcgt 6060
gaaaaggtgg atgccattga tggcgaatac cgcttgagag gagaagcaag gaaaaccttt 6120
gtagacttaa tgagaagagg agacctacca gtctggttgg cctacagagt ggcagctgaa 6180
ggcatcaact acgcagacag aaggtggtgt tttgatggag tcaagaacaa ccaaatccta 6240
gaagaaaacg tggaagttga aatctggaca aaagaagggg aaaggaagaa attgaaaccc 6300
agatggttgg atgctaggat ctattctgac ccactggcgc taaaagaatt taaggaattt 6360
gcagccggaa gaaagtctct gaccctgaac ctaatcacag aaatgggtag gctcccaacc 6420
ttcatgactc agaaggcaag agacgcactg gacaacttag cagtgctgca cacggctgag 6480
gcaggtggaa gggcgtacaa ccatgctctc agtgaactgc cggagaccct ggagacattg 6540
cttttactga cacttctggc tacagtcacg ggagggatct tttttattct gatgagcgca 6600
aggggcatag ggaagatgac cctgggaatg tgctgcataa tcacggctag catcctccta 6660
tggtacgcac aaatacagcc acactggata gcagcttcaa taatactgga gtttttttctc 6720 atagttttgc ttattccaga acctgaaaaa cagagaacac cccaagacaa ccaactgacc 6780
tacgttgtca tagccatcct cacagtggtg gccgcaacca tggcaaacga gatgggtttc 6840
ctagaaaaaa cgaagaaaga tctcggattg ggaagcattg caacccagca acccgagagc 6900
aacatcctgg acatagatct acgtcctgca tcagcatgga cgctgtatgc cgtggccaca 6960
acatttgtta caccaatgtt gagacatagc attgaaaatt cctcagtgaa tgtgtcccta 7020
acagctatag ccaaccaagc cacagtgtta atgggtctcg ggaaaggatg gccattgtca 7080
aagatggaca tcggagttcc ccttctcgcc attggatgct actcacaagt caaccccata 7140
actctcatag cagctctttt cttattggta gcacattatg ccatcatagg gccaggactc 7200
caagcaaaag caaccagaga agctcagaaa agagcagcgg cgggcatcat gaaaaaccca 7260
actgtcgatg gaataacagt gattgaccta gatccaatac cttatgatcc gaagtttgaa 7320
aagcagttgg gacaagtaat gctcctagtc ctctgcgtga ctcaagtatt gatgatgagg 7380
actacatggg ctctgtgtga ggctttaacc ttagctaccg ggcccatctc cacattgtgg 7440
gaaggaaatc cagggaggtt ttggaacact accattgcgg tgtcaatggc taacattttt 7500
agagggagtt acttggccgg agctggactt ctcttttcta ttatgaagaa cacaaccaac 7560
acaagaaggg gaactggcaa cataggagag acgcttggag agaaatggaa aagccgattg 7620
aacgcattgg gaaaaagtga attccagatc tacaagaaaa gtggaatcca ggaagtggat 7680

```
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag    8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
```

-continued

```
attcaagaaa acccatggat ggaagacaaa actccagtgg aatcatggga ggaaatccca  10080

tacttgggga aaagagaaga ccaatggtgc ggctcattga ttgggttaac aagcagggcc  10140

acctgggcaa agaacatcca agcagcaata aatcaagtta gatcccttat aggcaatgaa  10200

gaatacacag attacatgcc atccatgaaa agattcagaa gagaagagga agaagcagga  10260

gttctgtggt agaaagcaaa actaacatga aacaaggcta gaagtcaggt cggattaagc  10320

catagtacgg aaaaaactat gctacctgtg agccccgtcc aaggacgtta aaagaagtca  10380

ggccatcata aatgccatag cttgagtaaa ctatgcagcc tgtagctcca cctgagaagg  10440

tgtaaaaaat ccgggaggcc acaaaccatg gaagctgtac gcatggcgta gtggactagc  10500

ggttagagga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tct                   10723
```

```
<210> SEQ ID NO 2
<211> LENGTH: 3391
<212> TYPE: PRT
<213> ORGANISM: Artificial Sequence
<220> FEATURE:
<223> OTHER INFORMATION: Dengue virus serotype 1, BVS

<400> SEQUENCE: 2

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Gly Gly Glu Pro His Met Ile Val
        115                 120                 125

Ser Lys Gln Glu Arg Gly Lys Ser Leu Leu Phe Lys Thr Ser Ala Gly
    130                 135                 140

Val Asn Met Cys Thr Leu Ile Ala Met Asp Leu Gly Glu Leu Cys Glu
145                 150                 155                 160

Asp Thr Met Thr Tyr Lys Cys Pro Arg Ile Thr Glu Ala Glu Pro Asp
                165                 170                 175

Asp Val Asp Cys Trp Cys Asn Ala Thr Asp Thr Trp Val Thr Tyr Gly
            180                 185                 190

Thr Cys Ser Gln Thr Gly Glu His Arg Arg Asp Lys Arg Ser Val Ala
        195                 200                 205

Leu Ala Pro His Val Gly Leu Gly Leu Glu Thr Arg Ala Glu Thr Trp
    210                 215                 220

Met Ser Ser Glu Gly Ala Trp Lys Gln Ile Gln Lys Val Glu Thr Trp
225                 230                 235                 240
```

```
Ala Leu Arg His Pro Gly Phe Thr Val Ile Ala Leu Phe Leu Ala His
                245                 250                 255

Ala Ile Gly Thr Ser Ile Thr Gln Lys Gly Ile Ile Phe Ile Leu Leu
            260                 265                 270

Met Leu Val Thr Pro Ser Met Ala Met Arg Cys Val Gly Ile Gly Asn
        275                 280                 285

Arg Asp Phe Val Glu Gly Leu Ser Gly Ala Thr Trp Val Asp Val Val
    290                 295                 300

Leu Glu His Gly Ser Cys Val Thr Thr Met Ala Lys Asn Lys Pro Thr
305                 310                 315                 320

Leu Asp Ile Glu Leu Leu Lys Thr Glu Val Thr Asn Pro Ala Val Leu
                325                 330                 335

Arg Lys Leu Cys Ile Glu Ala Lys Ile Ser Asn Thr Thr Thr Asp Ser
            340                 345                 350

Arg Cys Pro Thr Gln Gly Glu Ala Thr Leu Val Glu Glu Gln Asp Ala
        355                 360                 365

Asn Phe Val Cys Arg Arg Thr Phe Val Asp Arg Gly Trp Gly Asn Gly
    370                 375                 380

Cys Gly Leu Phe Gly Lys Gly Ser Leu Ile Thr Cys Ala Lys Phe Lys
385                 390                 395                 400

Cys Val Thr Lys Leu Glu Gly Lys Ile Val Gln Tyr Glu Asn Leu Lys
                405                 410                 415

Tyr Ser Val Ile Val Thr Val His Thr Gly Asp Gln His Gln Val Gly
            420                 425                 430

Asn Glu Thr Thr Glu His Gly Thr Thr Ala Thr Ile Thr Pro Gln Ala
        435                 440                 445

Pro Thr Ser Glu Ile Gln Leu Thr Asp Tyr Gly Thr Leu Thr Leu Asp
    450                 455                 460

Cys Ser Pro Arg Thr Gly Leu Asp Phe Asn Glu Met Val Leu Leu Thr
465                 470                 475                 480

Met Lys Glu Arg Ser Trp Leu Val His Lys Gln Trp Phe Leu Asp Leu
                485                 490                 495

Pro Leu Pro Trp Thr Ser Gly Ala Ser Thr Ser Gln Glu Thr Trp Asn
            500                 505                 510

Arg Gln Asp Leu Leu Val Thr Phe Lys Thr Ala His Ala Lys Lys Gln
        515                 520                 525

Glu Val Val Val Leu Gly Ser Gln Glu Gly Ala Met His Thr Ala Leu
    530                 535                 540

Thr Gly Ala Thr Glu Ile Gln Thr Ser Gly Thr Thr Thr Ile Phe Ala
545                 550                 555                 560

Gly His Leu Lys Cys Arg Leu Lys Met Asp Lys Leu Thr Leu Lys Gly
                565                 570                 575

Met Ser Tyr Val Met Cys Thr Gly Ser Phe Lys Leu Glu Lys Glu Val
            580                 585                 590

Ala Glu Thr Gln His Gly Thr Val Leu Val Gln Val Lys Tyr Glu Gly
        595                 600                 605

Thr Asp Ala Pro Cys Lys Ile Pro Phe Ser Thr Gln Asp Glu Lys Gly
    610                 615                 620

Ala Thr Gln Asn Gly Arg Leu Ile Thr Ala Asn Pro Ile Val Thr Asp
625                 630                 635                 640

Lys Glu Lys Pro Val Asn Ile Glu Ala Glu Pro Pro Phe Gly Glu Ser
                645                 650                 655

Tyr Ile Val Val Gly Ala Gly Glu Lys Ala Leu Lys Leu Ser Trp Phe
```

-continued

```
            660                 665                 670

Lys Lys Gly Ser Ser Ile Gly Lys Met Phe Glu Ala Thr Ala Arg Gly
        675                 680                 685

Ala Arg Arg Met Ala Ile Leu Gly Asp Thr Ala Trp Asp Phe Gly Ser
    690                 695                 700

Ile Gly Gly Val Phe Thr Ser Met Gly Lys Leu Val His Gln Val Phe
705                 710                 715                 720

Gly Thr Ala Tyr Gly Val Leu Phe Ser Gly Val Ser Trp Thr Met Lys
            725                 730                 735

Ile Gly Ile Gly Ile Leu Leu Thr Trp Leu Gly Leu Asn Ser Arg Asn
            740                 745                 750

Thr Ser Leu Ser Met Met Cys Ile Ala Ala Ala Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
            805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
            885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
            965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080
```

-continued

```
Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Asp Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Lys Glu Leu Met Met  Thr Thr Ile
    1220                 1225                 1230

Gly Ile  Val Leu Leu Ser Gln  Ser Thr Leu Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290

Val Ser  Cys Thr Ile Leu Ala  Val Val Ser Val Ser  Pro Leu Phe
    1295                 1300                 1305

Leu Thr  Ser Ser Gln Gln Lys  Thr Asp Trp Ile Pro  Leu Ala Leu
    1310                 1315                 1320

Thr Ile  Lys Gly Leu Asn Pro  Thr Ala Ile Phe Leu  Thr Thr Leu
    1325                 1330                 1335

Ser Arg  Thr Ser Lys Lys Arg  Ser Trp Pro Leu Asn  Glu Ala Ile
    1340                 1345                 1350

Met Ala  Val Gly Met Val Ser  Ile Leu Ala Ser Ser  Leu Leu Lys
    1355                 1360                 1365

Asn Asp  Ile Pro Met Thr Gly  Pro Leu Val Ala Gly  Gly Leu Leu
    1370                 1375                 1380

Thr Val  Cys Tyr Val Leu Thr  Gly Arg Ser Ala Asp  Leu Glu Leu
    1385                 1390                 1395

Glu Arg  Ala Ala Asp Val Lys  Trp Glu Asp Gln Ala  Glu Ile Ser
    1400                 1405                 1410

Gly Ser  Ser Pro Ile Leu Ser  Ile Thr Ile Ser Glu  Asp Gly Ser
    1415                 1420                 1425

Met Ser  Ile Lys Asn Glu Glu  Glu Asp Gln Thr Leu  Thr Ile Leu
    1430                 1435                 1440

Ile Arg  Thr Gly Leu Leu Val  Ile Ser Gly Leu Phe  Pro Val Ser
    1445                 1450                 1455

Ile Pro  Ile Thr Ala Ala Ala  Trp Tyr Leu Trp Glu  Val Lys Lys
    1460                 1465                 1470
```

-continued

```
Gln Arg  Ala Gly Val Leu Trp  Asp Val Pro Ser Pro  Pro Pro Met
    1475                 1480                 1485

Gly Lys  Ala Glu Leu Glu Asp  Gly Ala Tyr Arg Ile  Lys Gln Lys
    1490                 1495                 1500

Gly Ile  Leu Gly Tyr Ser Gln  Ile Gly Ala Gly Val  Tyr Lys Glu
    1505                 1510                 1515

Gly Thr  Phe His Thr Met Trp  His Val Thr Arg Gly  Ala Val Leu
    1520                 1525                 1530

Met His  Lys Gly Lys Arg Ile  Glu Pro Ser Trp Ala  Asp Val Lys
    1535                 1540                 1545

Lys Asp  Leu Ile Ser Tyr Gly  Gly Gly Trp Lys Leu  Glu Gly Glu
    1550                 1555                 1560

Trp Lys  Glu Gly Glu Glu Val  Gln Val Leu Ala Leu  Glu Pro Gly
    1565                 1570                 1575

Lys Asn  Pro Arg Ala Val Gln  Thr Lys Pro Gly Leu  Phe Lys Thr
    1580                 1585                 1590

Asn Ala  Gly Thr Ile Gly Ala  Val Ser Leu Asp Phe  Ser Pro Gly
    1595                 1600                 1605

Thr Ser  Gly Ser Pro Ile Ile  Asp Lys Lys Gly Lys  Val Val Gly
    1610                 1615                 1620

Leu Tyr  Gly Asn Gly Val Val  Thr Arg Ser Gly Ala  Tyr Val Ser
    1625                 1630                 1635

Ala Ile  Ala Gln Thr Glu Lys  Ser Ile Glu Asp Asn  Pro Glu Ile
    1640                 1645                 1650

Glu Asp  Asp Ile Phe Arg Lys  Arg Arg Leu Thr Ile  Met Asp Leu
    1655                 1660                 1665

His Pro  Gly Ala Gly Lys Thr  Lys Arg Tyr Leu Pro  Ala Ile Val
    1670                 1675                 1680

Arg Glu  Ala Ile Lys Arg Gly  Leu Arg Thr Leu Ile  Leu Ala Pro
    1685                 1690                 1695

Thr Arg  Val Val Ala Ala Glu  Met Glu Glu Ala Leu  Arg Gly Leu
    1700                 1705                 1710

Pro Ile  Arg Tyr Gln Thr Pro  Ala Ile Arg Ala Val  His Thr Gly
    1715                 1720                 1725

Arg Glu  Ile Val Asp Leu Met  Cys His Ala Thr Phe  Thr Met Arg
    1730                 1735                 1740

Leu Leu  Ser Pro Val Arg Val  Pro Asn Tyr Asn Leu  Ile Ile Met
    1745                 1750                 1755

Asp Glu  Ala His Phe Thr Asp  Pro Ala Ser Ile Ala  Ala Arg Gly
    1760                 1765                 1770

Tyr Ile  Ser Thr Arg Val Glu  Met Gly Glu Ala Ala  Gly Ile Phe
    1775                 1780                 1785

Met Thr  Ala Thr Pro Pro Gly  Ser Arg Asp Pro Phe  Pro Gln Ser
    1790                 1795                 1800

Asn Ala  Pro Ile Ile Asp Glu  Glu Arg Glu Ile Pro  Glu Arg Ser
    1805                 1810                 1815

Trp Asn  Ser Gly His Glu Trp  Val Thr Asp Phe Lys  Gly Lys Thr
    1820                 1825                 1830

Val Trp  Phe Val Pro Ser Ile  Lys Ala Gly Asn Asp  Ile Ala Ala
    1835                 1840                 1845

Cys Leu  Arg Lys Asn Gly Lys  Lys Val Ile Gln Leu  Ser Arg Lys
    1850                 1855                 1860

Thr Phe  Asp Ser Glu Tyr Val  Lys Thr Arg Thr Asn  Asp Trp Asp
```

```
    1865                1870                1875

Phe Val  Val Thr Thr Asp Ile  Ser Glu Met Gly Ala  Asn Phe Lys
    1880                1885                1890

Ala Glu  Arg Val Ile Asp Pro  Arg Arg Cys Met Lys  Pro Val Ile
    1895                1900                1905

Leu Thr  Asp Gly Glu Glu Arg  Val Ile Leu Ala Gly  Pro Met Pro
    1910                1915                1920

Val Thr  His Ser Ser Ala Ala  Gln Arg Arg Gly Arg  Ile Gly Arg
    1925                1930                1935

Asn Pro  Lys Asn Glu Asn Asp  Gln Tyr Ile Tyr Met  Gly Glu Pro
    1940                1945                1950

Leu Glu  Asn Asp Glu Asp Cys  Ala His Trp Lys Glu  Ala Lys Met
    1955                1960                1965

Leu Leu  Asp Asn Ile Asn Thr  Pro Glu Gly Ile Ile  Pro Ser Met
    1970                1975                1980

Phe Glu  Pro Glu Arg Glu Lys  Val Asp Ala Ile Asp  Gly Glu Tyr
    1985                1990                1995

Arg Leu  Arg Gly Glu Ala Arg  Lys Thr Phe Val Asp  Leu Met Arg
    2000                2005                2010

Arg Gly  Asp Leu Pro Val Trp  Leu Ala Tyr Arg Val  Ala Ala Glu
    2015                2020                2025

Gly Ile  Asn Tyr Ala Asp Arg  Arg Trp Cys Phe Asp  Gly Val Lys
    2030                2035                2040

Asn Asn  Gln Ile Leu Glu Glu  Asn Val Glu Val Glu  Ile Trp Thr
    2045                2050                2055

Lys Glu  Gly Glu Arg Lys Lys  Leu Lys Pro Arg Trp  Leu Asp Ala
    2060                2065                2070

Arg Ile  Tyr Ser Asp Pro Leu  Ala Leu Lys Glu Phe  Lys Glu Phe
    2075                2080                2085

Ala Ala  Gly Arg Lys Ser Leu  Thr Leu Asn Leu Ile  Thr Glu Met
    2090                2095                2100

Gly Arg  Leu Pro Thr Phe Met  Thr Gln Lys Ala Arg  Asp Ala Leu
    2105                2110                2115

Asp Asn  Leu Ala Val Leu His  Thr Ala Glu Ala Gly  Gly Arg Ala
    2120                2125                2130

Tyr Asn  His Ala Leu Ser Glu  Leu Pro Glu Thr Leu  Glu Thr Leu
    2135                2140                2145

Leu Leu  Leu Thr Leu Leu Ala  Thr Val Thr Gly Gly  Ile Phe Leu
    2150                2155                2160

Phe Leu  Met Ser Ala Arg Gly  Ile Gly Lys Met Thr  Leu Gly Met
    2165                2170                2175

Cys Cys  Ile Ile Thr Ala Ser  Ile Leu Leu Trp Tyr  Ala Gln Ile
    2180                2185                2190

Gln Pro  His Trp Ile Ala Ala  Ser Ile Ile Leu Glu  Phe Phe Leu
    2195                2200                2205

Ile Val  Leu Leu Ile Pro Glu  Pro Glu Lys Gln Arg  Thr Pro Gln
    2210                2215                2220

Asp Asn  Gln Leu Thr Tyr Val  Val Ile Ala Ile Leu  Thr Val Val
    2225                2230                2235

Ala Ala  Thr Met Ala Asn Glu  Met Gly Phe Leu Glu  Lys Thr Lys
    2240                2245                2250

Lys Asp  Leu Gly Leu Gly Ser  Ile Ala Thr Gln Gln  Pro Glu Ser
    2255                2260                2265
```

-continued

```
Asn Ile Leu Asp Ile Asp Leu Arg Pro Ala Ser Ala Trp Thr Leu
    2270                2275                2280

Tyr Ala Val Ala Thr Thr Phe Val Thr Pro Met Leu Arg His Ser
    2285                2290                2295

Ile Glu Asn Ser Ser Val Asn Val Ser Leu Thr Ala Ile Ala Asn
    2300                2305                2310

Gln Ala Thr Val Leu Met Gly Leu Gly Lys Gly Trp Pro Leu Ser
    2315                2320                2325

Lys Met Asp Ile Gly Val Pro Leu Leu Ala Ile Gly Cys Tyr Ser
    2330                2335                2340

Gln Val Asn Pro Ile Thr Leu Ile Ala Ala Leu Phe Leu Leu Val
    2345                2350                2355

Ala His Tyr Ala Ile Ile Gly Pro Gly Leu Gln Ala Lys Ala Thr
    2360                2365                2370

Arg Glu Ala Gln Lys Arg Ala Ala Ala Gly Ile Met Lys Asn Pro
    2375                2380                2385

Thr Val Asp Gly Ile Thr Val Ile Asp Leu Asp Pro Ile Pro Tyr
    2390                2395                2400

Asp Pro Lys Phe Glu Lys Gln Leu Gly Gln Val Met Leu Leu Val
    2405                2410                2415

Leu Cys Val Thr Gln Val Leu Met Met Arg Thr Thr Trp Ala Leu
    2420                2425                2430

Cys Glu Ala Leu Thr Leu Ala Thr Gly Pro Ile Ser Thr Leu Trp
    2435                2440                2445

Glu Gly Asn Pro Gly Arg Phe Trp Asn Thr Thr Ile Ala Val Ser
    2450                2455                2460

Met Ala Asn Ile Phe Arg Gly Ser Tyr Leu Ala Gly Ala Gly Leu
    2465                2470                2475

Leu Phe Ser Ile Met Lys Asn Thr Thr Asn Thr Arg Arg Gly Thr
    2480                2485                2490

Gly Asn Ile Gly Glu Thr Leu Gly Glu Lys Trp Lys Ser Arg Leu
    2495                2500                2505

Asn Ala Leu Gly Lys Ser Glu Phe Gln Ile Tyr Lys Lys Ser Gly
    2510                2515                2520

Ile Gln Glu Val Asp Arg Thr Leu Ala Lys Glu Gly Ile Lys Arg
    2525                2530                2535

Gly Glu Thr Asp His His Ala Val Ser Arg Gly Ser Ala Lys Leu
    2540                2545                2550

Arg Trp Phe Val Glu Arg Asn Met Val Thr Pro Glu Gly Lys Val
    2555                2560                2565

Val Asp Leu Gly Cys Gly Arg Gly Gly Trp Ser Tyr Tyr Cys Gly
    2570                2575                2580

Gly Leu Lys Asn Val Arg Glu Val Lys Gly Leu Thr Lys Gly Gly
    2585                2590                2595

Pro Gly His Glu Glu Pro Ile Pro Met Ser Thr Tyr Gly Trp Asn
    2600                2605                2610

Leu Val Arg Leu Gln Ser Gly Val Asp Val Phe Phe Ile Pro Pro
    2615                2620                2625

Glu Lys Cys Asp Thr Leu Leu Cys Asp Ile Gly Glu Ser Ser Pro
    2630                2635                2640

Asn Pro Thr Val Glu Ala Gly Arg Thr Leu Arg Val Leu Asn Leu
    2645                2650                2655
```

-continued

```
Val Glu Asn Trp Leu Asn Asn Asn Thr Gln Phe Cys Ile Lys Val
    2660                2665                2670

Leu Asn Pro Tyr Met Pro Ser Val Ile Glu Lys Met Glu Ala Leu
    2675                2680                2685

Gln Arg Lys Tyr Gly Gly Ala Leu Val Arg Asn Pro Leu Ser Arg
    2690                2695                2700

Asn Ser Thr His Glu Met Tyr Trp Val Ser Asn Ala Ser Gly Asn
    2705                2710                2715

Ile Val Ser Ser Val Asn Met Ile Ser Arg Met Leu Ile Asn Arg
    2720                2725                2730

Phe Thr Met Arg Tyr Lys Lys Ala Thr Tyr Glu Pro Asp Val Asp
    2735                2740                2745

Leu Gly Ser Gly Thr Arg Asn Ile Gly Ile Glu Ser Glu Ile Pro
    2750                2755                2760

Asn Leu Asp Ile Ile Gly Lys Arg Ile Glu Lys Ile Lys Gln Glu
    2765                2770                2775

His Glu Thr Ser Trp His Tyr Asp Gln Asp His Pro Tyr Lys Thr
    2780                2785                2790

Trp Ala Tyr His Gly Ser Tyr Glu Thr Lys Gln Thr Gly Ser Ala
    2795                2800                2805

Ser Ser Met Val Asn Gly Val Val Arg Leu Leu Thr Lys Pro Trp
    2810                2815                2820

Asp Val Val Pro Met Val Thr Gln Met Ala Met Thr Asp Thr Thr
    2825                2830                2835

Pro Phe Gly Gln Gln Arg Val Phe Lys Glu Lys Val Asp Thr Arg
    2840                2845                2850

Thr Gln Glu Pro Lys Glu Gly Thr Lys Lys Leu Met Lys Ile Thr
    2855                2860                2865

Ala Glu Trp Leu Trp Lys Glu Leu Gly Lys Lys Lys Thr Pro Arg
    2870                2875                2880

Met Cys Thr Arg Glu Glu Phe Thr Arg Lys Val Arg Ser Asn Ala
    2885                2890                2895

Ala Leu Gly Ala Ile Phe Thr Asp Glu Asn Lys Trp Lys Ser Ala
    2900                2905                2910

Arg Glu Ala Val Glu Asp Ser Arg Phe Trp Glu Leu Val Asp Lys
    2915                2920                2925

Glu Arg Asn Leu His Leu Glu Gly Lys Cys Glu Thr Cys Val Tyr
    2930                2935                2940

Asn Met Met Gly Lys Arg Glu Lys Lys Leu Gly Glu Phe Gly Lys
    2945                2950                2955

Ala Lys Gly Ser Arg Ala Ile Trp Tyr Met Trp Leu Gly Ala Arg
    2960                2965                2970

Phe Leu Glu Phe Glu Ala Leu Gly Phe Leu Asn Glu Asp His Trp
    2975                2980                2985

Phe Ser Arg Glu Asn Ser Leu Ser Gly Val Glu Gly Glu Gly Leu
    2990                2995                3000

His Lys Leu Gly Tyr Ile Leu Arg Asp Val Ser Lys Lys Glu Gly
    3005                3010                3015

Gly Ala Met Tyr Ala Asp Asp Thr Ala Gly Trp Asp Thr Arg Ile
    3020                3025                3030

Thr Leu Glu Asp Leu Lys Asn Glu Glu Met Val Thr Asn His Met
    3035                3040                3045

Glu Gly Glu His Lys Lys Leu Ala Glu Ala Ile Phe Lys Leu Thr
```

3050 3055 3060

Tyr Gln Asn Lys Val Val Arg Val Gln Arg Pro Thr Pro Arg Gly
3065 3070 3075

Thr Val Met Asp Ile Ile Ser Arg Arg Asp Gln Arg Gly Ser Gly
3080 3085 3090

Gln Val Gly Thr Tyr Gly Leu Asn Thr Phe Thr Asn Met Glu Ala
3095 3100 3105

Gln Leu Ile Arg Gln Met Glu Gly Glu Gly Val Phe Lys Ser Ile
3110 3115 3120

Gln His Leu Thr Ile Thr Glu Glu Ile Ala Val Gln Asn Trp Leu
3125 3130 3135

Ala Arg Val Gly Arg Glu Arg Leu Ser Arg Met Ala Ile Ser Gly
3140 3145 3150

Asp Asp Cys Val Val Lys Pro Leu Asp Asp Arg Phe Ala Ser Ala
3155 3160 3165

Leu Thr Ala Leu Asn Asp Met Gly Lys Ile Arg Lys Asp Ile Gln
3170 3175 3180

Gln Trp Glu Pro Ser Arg Gly Trp Asn Asp Trp Thr Gln Val Pro
3185 3190 3195

Phe Cys Ser His His Phe His Glu Leu Ile Met Lys Asp Gly Arg
3200 3205 3210

Val Leu Val Val Pro Cys Arg Asn Gln Asp Glu Leu Ile Gly Arg
3215 3220 3225

Ala Arg Ile Ser Gln Gly Ala Gly Trp Ser Leu Arg Glu Thr Ala
3230 3235 3240

Cys Leu Gly Lys Ser Tyr Ala Gln Met Trp Ser Leu Met Tyr Phe
3245 3250 3255

His Arg Arg Asp Leu Arg Leu Ala Ala Asn Ala Ile Cys Ser Ala
3260 3265 3270

Val Pro Ser His Trp Val Pro Thr Ser Arg Thr Thr Trp Ser Ile
3275 3280 3285

His Ala Lys His Glu Trp Met Thr Thr Glu Asp Met Leu Thr Val
3290 3295 3300

Trp Asn Arg Val Trp Ile Gln Glu Asn Pro Trp Met Glu Asp Lys
3305 3310 3315

Thr Pro Val Glu Ser Trp Glu Glu Ile Pro Tyr Leu Gly Lys Arg
3320 3325 3330

Glu Asp Gln Trp Cys Gly Ser Leu Ile Gly Leu Thr Ser Arg Ala
3335 3340 3345

Thr Trp Ala Lys Asn Ile Gln Ala Ala Ile Asn Gln Val Arg Ser
3350 3355 3360

Leu Ile Gly Asn Glu Glu Tyr Thr Asp Tyr Met Pro Ser Met Lys
3365 3370 3375

Arg Phe Arg Arg Glu Glu Glu Glu Ala Gly Val Leu Trp
3380 3385 3390

<210> SEQ ID NO 3
<211> LENGTH: 3391
<212> TYPE: PRT
<213> ORGANISM: Artificial Sequence
<220> FEATURE:
<223> OTHER INFORMATION: Dengue virus serotype 1, MVS

<400> SEQUENCE: 3

Met Asn Asn Gln Arg Lys Lys Ala Lys Asn Thr Pro Phe Asn Met Leu

-continued

```
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Gly Gly Glu Pro His Met Ile Val
        115                 120                 125

Ser Lys Gln Glu Arg Gly Lys Ser Leu Leu Phe Lys Thr Ser Ala Gly
    130                 135                 140

Val Asn Met Cys Thr Leu Ile Ala Met Asp Leu Gly Glu Leu Cys Glu
145                 150                 155                 160

Asp Thr Met Thr Tyr Lys Cys Pro Arg Ile Thr Glu Ala Glu Pro Asp
                165                 170                 175

Asp Val Asp Cys Trp Cys Asn Ala Thr Asp Thr Trp Val Thr Tyr Gly
            180                 185                 190

Thr Cys Ser Gln Thr Gly Glu His Arg Arg Asp Lys Arg Ser Val Ala
        195                 200                 205

Leu Ala Pro His Val Gly Leu Gly Leu Glu Thr Arg Ala Glu Thr Trp
    210                 215                 220

Met Ser Ser Glu Gly Ala Trp Lys Gln Ile Gln Lys Val Glu Thr Trp
225                 230                 235                 240

Ala Leu Arg His Pro Gly Phe Thr Val Ile Ala Leu Phe Leu Ala His
                245                 250                 255

Ala Ile Gly Thr Ser Ile Thr Gln Lys Gly Ile Ile Phe Ile Leu Leu
            260                 265                 270

Met Leu Val Thr Pro Ser Met Ala Met Arg Cys Val Gly Ile Gly Asn
        275                 280                 285

Arg Asp Phe Val Glu Gly Leu Ser Gly Ala Thr Trp Val Asp Val Val
    290                 295                 300

Leu Glu His Gly Ser Cys Val Thr Thr Met Ala Lys Asn Lys Pro Thr
305                 310                 315                 320

Leu Asp Ile Glu Leu Leu Lys Thr Glu Val Thr Asn Pro Ala Val Leu
                325                 330                 335

Arg Lys Leu Cys Ile Glu Ala Lys Ile Ser Asn Thr Thr Thr Asp Ser
            340                 345                 350

Arg Cys Pro Thr Gln Gly Glu Ala Thr Leu Val Glu Glu Gln Asp Ala
        355                 360                 365

Asn Phe Val Cys Arg Arg Thr Phe Val Asp Arg Gly Trp Gly Asn Gly
    370                 375                 380

Cys Gly Leu Phe Gly Lys Gly Ser Leu Ile Thr Cys Ala Lys Phe Lys
385                 390                 395                 400

Cys Val Thr Lys Leu Glu Gly Lys Ile Val Gln Tyr Glu Asn Leu Lys
                405                 410                 415

Tyr Ser Val Ile Val Thr Val His Thr Gly Asp Gln His Gln Val Gly
            420                 425                 430
```

-continued

```
Asn Glu Thr Thr Glu His Gly Thr Thr Ala Thr Ile Thr Pro Gln Ala
        435                 440                 445

Pro Thr Ser Glu Ile Gln Leu Thr Asp Tyr Gly Thr Leu Thr Leu Asp
    450                 455                 460

Cys Ser Pro Arg Thr Gly Leu Asp Phe Asn Glu Met Val Leu Leu Thr
465                 470                 475                 480

Met Lys Glu Arg Ser Trp Leu Val His Lys Gln Trp Phe Leu Asp Leu
                485                 490                 495

Pro Leu Pro Trp Thr Ser Gly Ala Ser Thr Ser Gln Glu Thr Trp Asn
            500                 505                 510

Arg Gln Asp Leu Leu Val Thr Phe Lys Thr Ala His Ala Lys Lys Gln
        515                 520                 525

Glu Val Val Val Leu Gly Ser Gln Glu Gly Ala Met His Thr Ala Leu
    530                 535                 540

Thr Gly Ala Thr Glu Ile Gln Thr Ser Gly Thr Thr Thr Ile Phe Ala
545                 550                 555                 560

Gly His Leu Lys Cys Arg Leu Lys Met Asp Lys Leu Thr Leu Lys Gly
                565                 570                 575

Met Ser Tyr Val Met Cys Thr Gly Ser Phe Lys Leu Glu Lys Glu Val
            580                 585                 590

Ala Glu Thr Gln His Gly Thr Val Leu Val Gln Val Lys Tyr Glu Gly
        595                 600                 605

Thr Asp Ala Pro Cys Lys Ile Pro Phe Ser Thr Gln Asp Glu Lys Gly
    610                 615                 620

Ala Thr Gln Asn Gly Arg Leu Ile Thr Ala Asn Pro Ile Val Thr Asp
625                 630                 635                 640

Lys Glu Lys Pro Val Asn Ile Glu Ala Glu Pro Pro Phe Gly Glu Ser
                645                 650                 655

Tyr Ile Val Val Gly Ala Gly Glu Lys Ala Leu Lys Leu Ser Trp Phe
            660                 665                 670

Lys Lys Gly Ser Ser Ile Gly Lys Met Phe Glu Ala Thr Ala Arg Gly
        675                 680                 685

Ala Arg Arg Met Ala Ile Leu Gly Asp Thr Ala Trp Asp Phe Gly Ser
    690                 695                 700

Ile Gly Gly Val Phe Thr Ser Met Gly Lys Leu Val His Gln Val Phe
705                 710                 715                 720

Gly Thr Ala Tyr Gly Val Leu Phe Ser Gly Val Ser Trp Thr Met Lys
                725                 730                 735

Ile Gly Ile Gly Ile Leu Leu Thr Trp Leu Gly Leu Asn Ser Arg Asn
            740                 745                 750

Thr Ser Leu Ser Met Met Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845
```

-continued

```
Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Asp Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Lys Glu Leu Met Met  Thr Thr Ile
    1220                 1225                 1230

Gly Ile  Val Leu Leu Ser Gln  Ser Thr Leu Pro Glu  Thr Ile Leu
    1235                 1240                 1245

Glu Leu  Thr Asp Ala Leu Ala  Leu Gly Met Met Val  Leu Lys Met
```

```
    1250                1255                1260

Val Arg Asn Met Glu Lys Tyr Gln Leu Ala Val Thr Ile Met Ala
    1265                1270                1275

Ile Leu Cys Val Pro Asn Ala Val Ile Leu Gln Asn Ala Trp Lys
    1280                1285                1290

Val Ser Cys Thr Ile Leu Ala Val Val Ser Val Ser Pro Leu Phe
    1295                1300                1305

Leu Thr Ser Ser Gln Gln Lys Thr Asp Trp Ile Pro Leu Ala Leu
    1310                1315                1320

Thr Ile Lys Gly Leu Asn Pro Thr Ala Ile Phe Leu Thr Thr Leu
    1325                1330                1335

Ser Arg Thr Ser Lys Lys Arg Ser Trp Pro Leu Asn Glu Ala Ile
    1340                1345                1350

Met Ala Val Gly Met Val Ser Ile Leu Ala Ser Ser Leu Leu Lys
    1355                1360                1365

Asn Asp Ile Pro Met Thr Gly Pro Leu Val Ala Gly Gly Leu Leu
    1370                1375                1380

Thr Val Cys Tyr Val Leu Thr Gly Arg Ser Ala Asp Leu Glu Leu
    1385                1390                1395

Glu Arg Ala Ala Asp Val Lys Trp Glu Asp Gln Ala Glu Ile Ser
    1400                1405                1410

Gly Ser Ser Pro Ile Leu Ser Ile Thr Ile Ser Glu Asp Gly Ser
    1415                1420                1425

Met Ser Ile Lys Asn Glu Glu Glu Asp Gln Thr Leu Thr Ile Leu
    1430                1435                1440

Ile Arg Thr Gly Leu Leu Val Ile Ser Gly Leu Phe Pro Val Ser
    1445                1450                1455

Ile Pro Ile Thr Ala Ala Ala Trp Tyr Leu Trp Glu Val Lys Lys
    1460                1465                1470

Gln Arg Ala Gly Val Leu Trp Asp Val Pro Ser Pro Pro Pro Met
    1475                1480                1485

Gly Lys Ala Glu Leu Glu Asp Gly Ala Tyr Arg Ile Lys Gln Lys
    1490                1495                1500

Gly Ile Leu Gly Tyr Ser Gln Ile Gly Ala Gly Val Tyr Lys Glu
    1505                1510                1515

Gly Thr Phe His Thr Met Trp His Val Thr Arg Gly Ala Val Leu
    1520                1525                1530

Met His Lys Gly Lys Arg Ile Glu Pro Ser Trp Ala Asp Val Lys
    1535                1540                1545

Lys Asp Leu Ile Ser Tyr Gly Gly Gly Trp Lys Leu Glu Gly Glu
    1550                1555                1560

Trp Lys Glu Gly Glu Glu Val Gln Val Leu Ala Leu Glu Pro Gly
    1565                1570                1575

Lys Asn Pro Arg Ala Val Gln Thr Lys Pro Gly Leu Phe Lys Thr
    1580                1585                1590

Asn Ala Gly Thr Ile Gly Ala Val Ser Leu Asp Phe Ser Pro Gly
    1595                1600                1605

Thr Ser Gly Ser Pro Ile Ile Asp Lys Lys Gly Lys Val Val Gly
    1610                1615                1620

Leu Tyr Gly Asn Gly Val Val Thr Arg Ser Gly Ala Tyr Val Ser
    1625                1630                1635

Ala Ile Ala Gln Thr Glu Lys Ser Ile Glu Asp Asn Pro Glu Ile
    1640                1645                1650
```

Glu Asp Asp Ile Phe Arg Lys Arg Arg Leu Thr Ile Met Asp Leu
    1655                1660                1665

His Pro Gly Ala Gly Lys Thr Lys Arg Tyr Leu Pro Ala Ile Val
    1670                1675                1680

Arg Glu Ala Ile Lys Arg Gly Leu Arg Thr Leu Ile Leu Ala Pro
    1685                1690                1695

Thr Arg Val Val Ala Ala Glu Met Glu Glu Ala Leu Arg Gly Leu
    1700                1705                1710

Pro Ile Arg Tyr Gln Thr Pro Ala Ile Arg Ala Val His Thr Gly
    1715                1720                1725

Arg Glu Ile Val Asp Leu Met Cys His Ala Thr Phe Thr Met Arg
    1730                1735                1740

Leu Leu Ser Pro Val Arg Val Pro Asn Tyr Asn Leu Ile Ile Met
    1745                1750                1755

Asp Glu Ala His Phe Thr Asp Pro Ala Ser Ile Ala Ala Arg Gly
    1760                1765                1770

Tyr Ile Ser Thr Arg Val Glu Met Gly Glu Ala Ala Gly Ile Phe
    1775                1780                1785

Met Thr Ala Thr Pro Pro Gly Ser Arg Asp Pro Phe Pro Gln Ser
    1790                1795                1800

Asn Ala Pro Ile Ile Asp Glu Glu Arg Glu Ile Pro Glu Arg Ser
    1805                1810                1815

Trp Asn Ser Gly His Glu Trp Val Thr Asp Phe Lys Gly Lys Thr
    1820                1825                1830

Val Trp Phe Val Pro Ser Ile Lys Ala Gly Asn Asp Ile Ala Ala
    1835                1840                1845

Cys Leu Arg Lys Asn Gly Lys Lys Val Ile Gln Leu Ser Arg Lys
    1850                1855                1860

Thr Phe Asp Ser Glu Tyr Val Lys Thr Arg Thr Asn Asp Trp Asp
    1865                1870                1875

Phe Val Val Thr Thr Asp Ile Ser Glu Met Gly Ala Asn Phe Lys
    1880                1885                1890

Ala Glu Arg Val Ile Asp Pro Arg Arg Cys Met Lys Pro Val Ile
    1895                1900                1905

Leu Thr Asp Gly Glu Glu Arg Val Ile Leu Ala Gly Pro Met Pro
    1910                1915                1920

Val Thr His Ser Ser Ala Ala Gln Arg Arg Gly Arg Ile Gly Arg
    1925                1930                1935

Asn Pro Lys Asn Glu Asn Asp Gln Tyr Ile Tyr Met Gly Glu Pro
    1940                1945                1950

Leu Glu Asn Asp Glu Asp Cys Ala His Trp Lys Glu Ala Lys Met
    1955                1960                1965

Leu Leu Asp Asn Ile Asn Thr Pro Glu Gly Ile Ile Pro Ser Met
    1970                1975                1980

Phe Glu Pro Glu Arg Glu Lys Val Asp Ala Ile Asp Gly Glu Tyr
    1985                1990                1995

Arg Leu Arg Gly Glu Ala Arg Lys Thr Phe Val Asp Leu Met Arg
    2000                2005                2010

Arg Gly Asp Leu Pro Val Trp Leu Ala Tyr Arg Val Ala Ala Glu
    2015                2020                2025

Gly Ile Asn Tyr Ala Asp Arg Arg Trp Cys Phe Asp Gly Val Lys
    2030                2035                2040

-continued

```
Asn Asn  Gln Ile Leu Glu Glu  Asn Val Glu Val Glu  Ile Trp Thr
    2045                 2050                 2055

Lys Glu  Gly Glu Arg Lys Lys  Leu Lys Pro Arg Trp  Leu Asp Ala
    2060                 2065                 2070

Arg Ile  Tyr Ser Asp Pro Leu  Ala Leu Lys Glu Phe  Lys Glu Phe
    2075                 2080                 2085

Ala Ala  Gly Arg Lys Ser Leu  Thr Leu Asn Leu Ile  Thr Glu Met
    2090                 2095                 2100

Gly Arg  Leu Pro Thr Phe Met  Thr Gln Lys Ala Arg  Asp Ala Leu
    2105                 2110                 2115

Asp Asn  Leu Ala Val Leu His  Thr Ala Glu Ala Gly  Gly Arg Ala
    2120                 2125                 2130

Tyr Asn  His Ala Leu Ser Glu  Leu Pro Glu Thr Leu  Glu Thr Leu
    2135                 2140                 2145

Leu Leu  Leu Thr Leu Leu Ala  Thr Val Thr Gly Gly  Ile Phe Leu
    2150                 2155                 2160

Phe Leu  Met Ser Ala Arg Gly  Ile Gly Lys Met Thr  Leu Gly Met
    2165                 2170                 2175

Cys Cys  Ile Ile Thr Ala Ser  Ile Leu Leu Trp Tyr  Ala Gln Ile
    2180                 2185                 2190

Gln Pro  His Trp Ile Ala Ala  Ser Ile Ile Leu Glu  Phe Phe Leu
    2195                 2200                 2205

Ile Val  Leu Leu Ile Pro Glu  Pro Glu Lys Gln Arg  Thr Pro Gln
    2210                 2215                 2220

Asp Asn  Gln Leu Thr Tyr Val  Val Ile Ala Ile Leu  Thr Val Val
    2225                 2230                 2235

Ala Ala  Thr Met Ala Asn Glu  Met Gly Phe Leu Glu  Lys Thr Lys
    2240                 2245                 2250

Lys Asp  Leu Gly Leu Gly Ser  Ile Ala Thr Gln Gln  Pro Glu Ser
    2255                 2260                 2265

Asn Ile  Leu Asp Ile Asp Leu  Arg Pro Ala Ser Ala  Trp Thr Leu
    2270                 2275                 2280

Tyr Ala  Val Ala Thr Thr Phe  Val Thr Pro Met Leu  Arg His Ser
    2285                 2290                 2295

Ile Glu  Asn Ser Ser Val Asn  Val Ser Leu Thr Ala  Ile Ala Asn
    2300                 2305                 2310

Gln Ala  Thr Val Leu Met Gly  Leu Gly Lys Gly Trp  Pro Leu Ser
    2315                 2320                 2325

Lys Met  Asp Ile Gly Val Pro  Leu Leu Ala Ile Gly  Cys Tyr Ser
    2330                 2335                 2340

Gln Val  Asn Pro Ile Thr Leu  Thr Ala Ala Leu Phe  Leu Leu Val
    2345                 2350                 2355

Ala His  Tyr Ala Ile Ile Gly  Pro Gly Leu Gln Ala  Lys Ala Thr
    2360                 2365                 2370

Arg Glu  Ala Gln Lys Arg Ala  Ala Ala Gly Ile Met  Lys Asn Pro
    2375                 2380                 2385

Thr Val  Asp Gly Ile Thr Val  Ile Asp Leu Asp Pro  Ile Pro Tyr
    2390                 2395                 2400

Asp Pro  Lys Phe Glu Lys Gln  Leu Gly Gln Val Met  Leu Leu Val
    2405                 2410                 2415

Leu Cys  Val Thr Gln Val Leu  Met Met Arg Thr Thr  Trp Ala Leu
    2420                 2425                 2430

Cys Glu  Ala Leu Thr Leu Ala  Thr Gly Pro Ile Ser  Thr Leu Trp
```

-continued

```
    2435                2440                2445

Glu Gly  Asn Pro Gly Arg Phe  Trp Asn Thr Thr Ile  Ala Val Ser
    2450                2455                2460

Met Ala  Asn Ile Phe Arg Gly  Ser Tyr Leu Ala Gly  Ala Gly Leu
    2465                2470                2475

Leu Phe  Ser Ile Met Lys Asn  Thr Thr Asn Thr Arg  Arg Gly Thr
    2480                2485                2490

Gly Asn  Ile Gly Glu Thr Leu  Gly Glu Lys Trp Lys  Ser Arg Leu
    2495                2500                2505

Asn Ala  Leu Gly Lys Ser Glu  Phe Gln Ile Tyr Lys  Lys Ser Gly
    2510                2515                2520

Ile Gln  Glu Val Asp Arg Thr  Leu Ala Lys Glu Gly  Ile Lys Arg
    2525                2530                2535

Gly Glu  Thr Asp His His Ala  Val Ser Arg Gly Ser  Ala Lys Leu
    2540                2545                2550

Arg Trp  Phe Val Glu Arg Asn  Met Val Thr Pro Glu  Gly Lys Val
    2555                2560                2565

Val Asp  Leu Gly Cys Gly Arg  Gly Gly Trp Ser Tyr  Tyr Cys Gly
    2570                2575                2580

Gly Leu  Lys Asn Val Arg Glu  Val Lys Gly Leu Thr  Lys Gly Gly
    2585                2590                2595

Pro Gly  His Glu Glu Pro Ile  Pro Met Ser Thr Tyr  Gly Trp Asn
    2600                2605                2610

Leu Val  Arg Leu Gln Ser Gly  Val Asp Val Phe Phe  Ile Pro Pro
    2615                2620                2625

Glu Lys  Cys Asp Thr Leu Leu  Cys Asp Ile Gly Glu  Ser Ser Pro
    2630                2635                2640

Asn Pro  Thr Val Glu Ala Gly  Arg Thr Leu Arg Val  Leu Asn Leu
    2645                2650                2655

Val Glu  Asn Trp Leu Asn Asn  Asn Thr Gln Phe Cys  Ile Lys Val
    2660                2665                2670

Leu Asn  Pro Tyr Met Pro Ser  Val Ile Glu Lys Met  Glu Ala Leu
    2675                2680                2685

Gln Arg  Lys Tyr Gly Gly Ala  Leu Val Arg Asn Pro  Leu Ser Arg
    2690                2695                2700

Asn Ser  Thr His Glu Met Tyr  Trp Val Ser Asn Ala  Ser Gly Asn
    2705                2710                2715

Ile Val  Ser Ser Val Asn Met  Ile Ser Arg Met Leu  Ile Asn Arg
    2720                2725                2730

Phe Thr  Met Arg Tyr Lys Lys  Ala Thr Tyr Glu Pro  Asp Val Asp
    2735                2740                2745

Leu Gly  Ser Gly Thr Arg Asn  Ile Gly Ile Glu Ser  Glu Ile Pro
    2750                2755                2760

Asn Leu  Asp Ile Ile Gly Lys  Arg Ile Glu Lys Ile  Lys Gln Glu
    2765                2770                2775

His Glu  Thr Ser Trp His Tyr  Asp Gln Asp His Pro  Tyr Lys Thr
    2780                2785                2790

Trp Ala  Tyr His Gly Ser Tyr  Glu Thr Lys Gln Thr  Gly Ser Ala
    2795                2800                2805

Ser Ser  Met Val Asn Gly Val  Val Arg Leu Leu Thr  Lys Pro Trp
    2810                2815                2820

Asp Val  Val Pro Met Val Thr  Gln Met Ala Met Thr  Asp Thr Thr
    2825                2830                2835
```

-continued

```
Pro Phe  Gly Gln Gln Arg Val  Phe Lys Glu Lys Val  Asp Thr Arg
    2840                 2845                 2850

Thr Gln  Glu Pro Lys Glu Gly  Thr Lys Lys Leu Met  Lys Ile Thr
    2855                 2860                 2865

Ala Glu  Trp Leu Trp Lys Glu  Leu Gly Lys Lys Lys  Thr Pro Arg
    2870                 2875                 2880

Met Cys  Thr Arg Glu Glu Phe  Thr Arg Lys Val Arg  Ser Asn Ala
    2885                 2890                 2895

Ala Leu  Gly Ala Ile Phe Thr  Asp Glu Asn Lys Trp  Lys Ser Ala
    2900                 2905                 2910

Arg Glu  Ala Val Glu Asp Ser  Arg Phe Trp Glu Leu  Val Asp Lys
    2915                 2920                 2925

Glu Arg  Asn Leu His Leu Glu  Gly Lys Cys Glu Thr  Cys Val Tyr
    2930                 2935                 2940

Asn Met  Met Gly Lys Arg Glu  Lys Lys Leu Gly Glu  Phe Gly Lys
    2945                 2950                 2955

Ala Lys  Gly Ser Arg Ala Ile  Trp Tyr Met Trp Leu  Gly Ala Arg
    2960                 2965                 2970

Phe Leu  Glu Phe Glu Ala Leu  Gly Phe Leu Asn Glu  Asp His Trp
    2975                 2980                 2985

Phe Ser  Arg Glu Asn Ser Leu  Ser Gly Val Glu Gly  Glu Gly Leu
    2990                 2995                 3000

His Lys  Leu Gly Tyr Ile Leu  Arg Asp Val Ser Lys  Lys Glu Gly
    3005                 3010                 3015

Gly Ala  Met Tyr Ala Asp Asp  Thr Ala Gly Trp Asp  Thr Arg Ile
    3020                 3025                 3030

Thr Leu  Glu Asp Leu Lys Asn  Glu Glu Met Val Thr  Asn His Met
    3035                 3040                 3045

Glu Gly  Glu His Lys Lys Leu  Ala Glu Ala Ile Phe  Lys Leu Thr
    3050                 3055                 3060

Tyr Gln  Asn Lys Val Val Arg  Val Gln Arg Pro Thr  Pro Arg Gly
    3065                 3070                 3075

Thr Val  Met Asp Ile Ile Ser  Arg Arg Asp Gln Arg  Gly Ser Gly
    3080                 3085                 3090

Gln Val  Gly Thr Tyr Gly Leu  Asn Thr Phe Thr Asn  Met Glu Ala
    3095                 3100                 3105

Gln Leu  Ile Arg Gln Met Glu  Gly Glu Gly Val Phe  Lys Ser Ile
    3110                 3115                 3120

Gln His  Leu Thr Ile Thr Glu  Glu Ile Ala Val Gln  Asn Trp Leu
    3125                 3130                 3135

Ala Arg  Val Gly Arg Glu Arg  Leu Ser Arg Met Ala  Ile Ser Gly
    3140                 3145                 3150

Asp Asp  Cys Val Val Lys Pro  Leu Asp Asp Arg Phe  Ala Ser Ala
    3155                 3160                 3165

Leu Thr  Ala Leu Asn Asp Met  Gly Lys Ile Arg Lys  Asp Ile Gln
    3170                 3175                 3180

Gln Trp  Glu Pro Ser Arg Gly  Trp Asn Asp Trp Thr  Gln Val Pro
    3185                 3190                 3195

Phe Cys  Ser His His Phe His  Glu Leu Ile Met Lys  Asp Gly Arg
    3200                 3205                 3210

Val Leu  Val Val Pro Cys Arg  Asn Gln Asp Glu Leu  Ile Gly Arg
    3215                 3220                 3225
```

-continued

```
Ala Arg  Ile Ser Gln Gly Ala  Gly Trp Ser Leu Arg  Glu Thr Ala
    3230                 3235                 3240

Cys Leu  Gly Lys Ser Tyr Ala  Gln Met Trp Ser Leu  Met Tyr Phe
    3245                 3250                 3255

His Arg  Arg Asp Leu Arg Leu  Ala Ala Asn Ala Ile  Cys Ser Ala
    3260                 3265                 3270

Val Pro  Ser His Trp Val Pro  Thr Ser Arg Thr Thr  Trp Ser Ile
    3275                 3280                 3285

His Ala  Lys His Glu Trp Met  Thr Thr Glu Asp Met  Leu Thr Val
    3290                 3295                 3300

Trp Asn  Arg Val Trp Ile Gln  Glu Asn Pro Trp Met  Glu Asp Lys
    3305                 3310                 3315

Thr Pro  Val Glu Ser Trp Glu  Glu Ile Pro Tyr Leu  Gly Lys Arg
    3320                 3325                 3330

Glu Asp  Gln Trp Cys Gly Ser  Leu Ile Gly Leu Thr  Ser Arg Ala
    3335                 3340                 3345

Thr Trp  Ala Lys Asn Ile Gln  Ala Ala Ile Asn Gln  Val Arg Ser
    3350                 3355                 3360

Leu Ile  Gly Asn Glu Glu Tyr  Thr Asp Tyr Met Pro  Ser Met Lys
    3365                 3370                 3375

Arg Phe  Arg Arg Glu Glu Glu  Glu Ala Gly Val Leu  Trp
    3380                 3385                 3390


<210> SEQ ID NO 4
<211> LENGTH: 10723
<212> TYPE: DNA
<213> ORGANISM: Artificial Sequence
<220> FEATURE:
<223> OTHER INFORMATION: Dengue virus serotype 2, BVS

<400> SEQUENCE: 4

agttgttagt ctacgtggac cgacaaagac agattctttg agggagctaa gctcaatgta     60

gttctaacag tttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatctg caggcatgat cattatgctg    420

attccaacag tgatggcgtt ccatttaacc acacgtaacg gagaaccaca catgatcgtc    480

agcagacaag agaaagggaa aagtcttctg tttaaaacag aggttggcgt gaacatgtgt    540

accctcatgg ccatggacct tggtgaattg tgtgaagaca caatcacgta cgagtgtccc    600

cttctcaggc agaatgagcc agaagacata gactgttggt gcaactctac gtccacgtgg    660

gtaacttatg ggacgtgtac caccatggga gaacatagaa gagaaaaaag atcagtggca    720

ctcgttccac atgtgggaat gggactggag acacgaactg aaacatggat gtcatcagaa    780

ggggcctgga aacatgtcca gagaattgaa acttggatct tgagacatcc aggcttcacc    840

atgatggcag caatcctggc atacaccata ggaacgacac atttccaaag agccctgatc    900

ttcatcttac tgacagctgt cactccttca atgacaatgc gttgcatagg aatgtcaaat    960

agagactttg tggaaggggt ttcaggagga agctgggttg acatagtctt agaacatgga   1020

agctgtgtga cgacgatggc aaaaaacaaa ccaacattgg attttgaact gataaaaaca   1080
```

-continued

```
gaagccaaac agcctgccac cctaaggaag tactgtatag aggcaaagct aaccaacaca   1140
acaacagaat ctcgctgccc aacacaaggg gaacccagcc taaatgaaga gcaggacaaa   1200
aggttcgtct gcaaacactc catggtagac agaggatggg gaaatggatg tggactattt   1260
ggaaagggag gcattgtgac ctgtgctatg ttcagatgca aaaagaacat ggaaggaaaa   1320
gttgtgcaac cagaaaactt ggaatacacc attgtgataa cacctcactc aggggaagag   1380
catgcagtcg gaaatgacac aggaaaacat ggcaaggaaa tcaaaataac accacagagt   1440
tccatcacag aagcagaatt gacaggttat ggcactgtca caatggagtg ctctccaaga   1500
acgggcctcg acttcaatga gatggtgttg ctgcagatgg aaaataaagc ttggctggtg   1560
cacaggcaat ggttcctaga cctgccgtta ccatggttgc ccggagcgga cacacaaggg   1620
tcaaattgga tacagaaaga gacattggtc actttcaaaa atccccatgc gaagaaacag   1680
gatgttgttg ttttaggatc ccaagaaggg gccatgcaca cagcacttac aggggccaca   1740
gaaatccaaa tgtcatcagg aaacttactc ttcacaggac atctcaagtg caggctgaga   1800
atggacaagc tacagctcaa aggaatgtca tactctatgt gcacaggaaa gtttaaagtt   1860
gtgaaggaaa tagcagaaac acaacatgga acaatagtta tcagagtgca atatgaaggg   1920
gacggctctc catgcaagat cccttttgag ataatggatt tggaaaaaag acatgtctta   1980
ggtcgcctga ttacagtcaa cccaattgtg acagaaaaag atagcccagt caacatagaa   2040
gcagaacctc catttggaga cagctacatc atcataggag tagagccggg acaactgaag   2100
ctcaactggt ttaagaaagg aagttctatc ggccaaatgt ttgagacaac aatgaggggg   2160
gcgaagagaa tggccatttt aggtgacaca gcctgggatt ttggatcctt gggaggagtg   2220
tttacatcta taggaaaggc tctccaccaa gtctttggag caatctatgg agctgccttc   2280
agtggggttt catggactat gaaaatcctc ataggagtca ttatcacatg gataggaatg   2340
aattcacgca gcacctcact gtctgtgaca ctagtattgg tgggaattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
```

-continued

```
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
```

-continued

```
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
ccaggtggaa gggcgtacaa ccatgctctc agtgaactgc cggagaccct ggagacattg   6540
cttttactga cacttctggc tacagtcacg ggagggatct tttattcttt gatgagcgca   6600
aggggcatag ggaagatgac cctgggaatg tgctgcataa tcacggctag catcctccta   6660
tggtacgcac aaatacagcc acactggata gcagcttcaa taatactgga gttttttctc   6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctttttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
```

-continued

```
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccgtattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
```

agctgtagtc tcgctggaag gactagaggt tagaggagac ccccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tct 10723

<210> SEQ ID NO 5
<211> LENGTH: 3391
<212> TYPE: PRT
<213> ORGANISM: Artificial Sequence
<220> FEATURE:
<223> OTHER INFORMATION: Dengue virus serotype 2, BVS

<400> SEQUENCE: 5

Met Asn Asn Gln Arg Lys Lys Ala Lys Asn Thr Pro Phe Asn Met Leu
1 5 10 15

Lys Arg Glu Arg Asn Arg Val Ser Thr Val Gln Gln Leu Thr Lys Arg
20 25 30

Phe Ser Leu Gly Met Leu Gln Gly Arg Gly Pro Leu Lys Leu Phe Met
35 40 45

Ala Leu Val Ala Phe Leu Arg Phe Leu Thr Ile Pro Pro Thr Ala Gly
50 55 60

Ile Leu Lys Arg Trp Gly Thr Ile Lys Lys Ser Lys Ala Ile Asn Val
65 70 75 80

Leu Arg Gly Phe Arg Lys Glu Ile Gly Arg Met Leu Asn Ile Leu Asn
85 90 95

Arg Arg Arg Arg Ser Ala Gly Met Ile Ile Met Leu Ile Pro Thr Val
100 105 110

Met Ala Phe His Leu Thr Thr Arg Asn Gly Glu Pro His Met Ile Val
115 120 125

Ser Arg Gln Glu Lys Gly Lys Ser Leu Leu Phe Lys Thr Glu Val Gly
130 135 140

Val Asn Met Cys Thr Leu Met Ala Met Asp Leu Gly Glu Leu Cys Glu
145 150 155 160

Asp Thr Ile Thr Tyr Glu Cys Pro Leu Leu Arg Gln Asn Glu Pro Glu
165 170 175

Asp Ile Asp Cys Trp Cys Asn Ser Thr Ser Thr Trp Val Thr Tyr Gly
180 185 190

Thr Cys Thr Thr Met Gly Glu His Arg Arg Glu Lys Arg Ser Val Ala
195 200 205

Leu Val Pro His Val Gly Met Gly Leu Glu Thr Arg Thr Glu Thr Trp
210 215 220

Met Ser Ser Glu Gly Ala Trp Lys His Val Gln Arg Ile Glu Thr Trp
225 230 235 240

Ile Leu Arg His Pro Gly Phe Thr Met Met Ala Ala Ile Leu Ala Tyr
245 250 255

Thr Ile Gly Thr Thr His Phe Gln Arg Ala Leu Ile Phe Ile Leu Leu
260 265 270

Thr Ala Val Thr Pro Ser Met Thr Met Arg Cys Ile Gly Met Ser Asn
275 280 285

Arg Asp Phe Val Glu Gly Val Ser Gly Gly Ser Trp Val Asp Ile Val
290 295 300

Leu Glu His Gly Ser Cys Val Thr Thr Met Ala Lys Asn Lys Pro Thr
305 310 315 320

Leu Asp Phe Glu Leu Ile Lys Thr Glu Ala Lys Gln Pro Ala Thr Leu
325 330 335

-continued

```
Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Gly Ile Val Thr Cys Ala Met Phe Arg
385                 390                 395                 400

Cys Lys Lys Asn Met Glu Gly Lys Val Val Gln Pro Glu Asn Leu Glu
                405                 410                 415

Tyr Thr Ile Val Ile Thr Pro His Ser Gly Glu Glu His Ala Val Gly
            420                 425                 430

Asn Asp Thr Gly Lys His Gly Lys Glu Ile Lys Ile Thr Pro Gln Ser
        435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
        515                 520                 525

Asp Val Val Val Leu Gly Ser Gln Glu Gly Ala Met His Thr Ala Leu
    530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
        595                 600                 605

Asp Gly Ser Pro Cys Lys Ile Pro Phe Glu Ile Met Asp Leu Glu Lys
    610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asn Trp Phe
            660                 665                 670

Lys Lys Gly Ser Ser Ile Gly Gln Met Phe Glu Thr Thr Met Arg Gly
        675                 680                 685

Ala Lys Arg Met Ala Ile Leu Gly Asp Thr Ala Trp Asp Phe Gly Ser
    690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
            740                 745                 750

Thr Ser Leu Ser Val Thr Leu Val Leu Val Gly Ile Val Thr Leu Tyr
```

-continued

```
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170
```

-continued

```
Asn Met  Ser Phe Arg Asp Leu  Gly Arg Val Met Val  Met Val Gly
    1175                 1180                 1185

Ala Thr  Met Thr Asp Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Lys Glu Leu Met Met  Thr Thr Ile
    1220                 1225                 1230

Gly Ile  Val Leu Leu Ser Gln  Ser Thr Ile Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290

Val Ser  Cys Thr Ile Leu Ala  Val Val Ser Val Ser  Pro Leu Phe
    1295                 1300                 1305

Leu Thr  Ser Ser Gln Gln Lys  Thr Asp Trp Ile Pro  Leu Ala Leu
    1310                 1315                 1320

Thr Ile  Lys Gly Leu Asn Pro  Thr Ala Ile Phe Leu  Thr Thr Leu
    1325                 1330                 1335

Ser Arg  Thr Ser Lys Lys Arg  Ser Trp Pro Leu Asn  Glu Ala Ile
    1340                 1345                 1350

Met Ala  Val Gly Met Val Ser  Ile Leu Ala Ser Ser  Leu Leu Lys
    1355                 1360                 1365

Asn Asp  Ile Pro Met Thr Gly  Pro Leu Val Ala Gly  Gly Leu Leu
    1370                 1375                 1380

Thr Val  Cys Tyr Val Leu Thr  Gly Arg Ser Ala Asp  Leu Glu Leu
    1385                 1390                 1395

Glu Arg  Ala Ala Asp Val Lys  Trp Glu Asp Gln Ala  Glu Ile Ser
    1400                 1405                 1410

Gly Ser  Ser Pro Ile Leu Ser  Ile Thr Ile Ser Glu  Asp Gly Ser
    1415                 1420                 1425

Met Ser  Ile Lys Asn Glu Glu  Glu Glu Gln Thr Leu  Thr Ile Leu
    1430                 1435                 1440

Ile Arg  Thr Gly Leu Leu Val  Ile Ser Gly Leu Phe  Pro Val Ser
    1445                 1450                 1455

Ile Pro  Ile Thr Ala Ala Ala  Trp Tyr Leu Trp Glu  Val Lys Lys
    1460                 1465                 1470

Gln Arg  Ala Gly Val Leu Trp  Asp Val Pro Ser Pro  Pro Pro Met
    1475                 1480                 1485

Gly Lys  Ala Glu Leu Glu Asp  Gly Ala Tyr Arg Ile  Lys Gln Lys
    1490                 1495                 1500

Gly Ile  Leu Gly Tyr Ser Gln  Ile Gly Ala Gly Val  Tyr Lys Glu
    1505                 1510                 1515

Gly Thr  Phe His Thr Met Trp  His Val Thr Arg Gly  Ala Val Leu
    1520                 1525                 1530

Met His  Lys Gly Lys Arg Ile  Glu Pro Ser Trp Ala  Asp Val Lys
    1535                 1540                 1545

Lys Asp  Leu Ile Ser Tyr Gly  Gly Gly Trp Lys Leu  Glu Gly Glu
    1550                 1555                 1560
```

-continued

```
Trp Lys  Glu Gly Glu Glu Val  Gln Val Leu Ala Leu  Glu Pro Gly
    1565                 1570                 1575

Lys Asn  Pro Arg Ala Val Gln  Thr Lys Pro Gly Leu  Phe Lys Thr
    1580                 1585                 1590

Asn Ala  Gly Thr Ile Gly Ala  Val Ser Leu Asp Phe  Ser Pro Gly
    1595                 1600                 1605

Thr Ser  Gly Ser Pro Ile Ile  Asp Lys Lys Gly Lys  Val Val Gly
    1610                 1615                 1620

Leu Tyr  Gly Asn Gly Val Val  Thr Arg Ser Gly Ala  Tyr Val Ser
    1625                 1630                 1635

Ala Ile  Ala Gln Thr Glu Lys  Ser Ile Glu Asp Asn  Pro Glu Ile
    1640                 1645                 1650

Glu Asp  Asp Ile Phe Arg Lys  Arg Arg Leu Thr Ile  Met Asp Leu
    1655                 1660                 1665

His Pro  Gly Ala Gly Lys Thr  Lys Arg Tyr Leu Pro  Ala Ile Val
    1670                 1675                 1680

Arg Glu  Ala Ile Lys Arg Gly  Leu Arg Thr Leu Ile  Leu Ala Pro
    1685                 1690                 1695

Thr Arg  Val Val Ala Ala Glu  Met Glu Glu Ala Leu  Arg Gly Leu
    1700                 1705                 1710

Pro Ile  Arg Tyr Gln Thr Pro  Ala Ile Arg Ala Val  His Thr Gly
    1715                 1720                 1725

Arg Glu  Ile Val Asp Leu Met  Cys His Ala Thr Phe  Thr Met Arg
    1730                 1735                 1740

Leu Leu  Ser Pro Val Arg Val  Pro Asn Tyr Asn Leu  Ile Ile Met
    1745                 1750                 1755

Asp Glu  Ala His Phe Thr Asp  Pro Ala Ser Ile Ala  Ala Arg Gly
    1760                 1765                 1770

Tyr Ile  Ser Thr Arg Val Glu  Met Gly Glu Ala Ala  Gly Ile Phe
    1775                 1780                 1785

Met Thr  Ala Thr Pro Pro Gly  Ser Arg Asp Pro Phe  Pro Gln Ser
    1790                 1795                 1800

Asn Ala  Pro Ile Ile Asp Glu  Glu Arg Glu Ile Pro  Glu Arg Ser
    1805                 1810                 1815

Trp Asn  Ser Gly His Glu Trp  Val Thr Asp Phe Lys  Gly Lys Thr
    1820                 1825                 1830

Val Trp  Phe Val Pro Ser Ile  Lys Ala Gly Asn Asp  Ile Ala Ala
    1835                 1840                 1845

Cys Leu  Arg Lys Asn Gly Lys  Lys Val Ile Gln Leu  Ser Arg Lys
    1850                 1855                 1860

Thr Phe  Asp Ser Glu Tyr Val  Lys Thr Arg Thr Asn  Asp Trp Asp
    1865                 1870                 1875

Phe Val  Val Thr Thr Asp Ile  Ser Glu Met Gly Ala  Asn Phe Lys
    1880                 1885                 1890

Ala Glu  Arg Val Ile Asp Pro  Arg Arg Cys Met Lys  Pro Val Ile
    1895                 1900                 1905

Leu Thr  Asp Gly Glu Glu Arg  Val Ile Leu Ala Gly  Pro Met Pro
    1910                 1915                 1920

Val Thr  His Ser Ser Ala Ala  Gln Arg Arg Gly Arg  Ile Gly Arg
    1925                 1930                 1935

Asn Pro  Lys Asn Glu Asn Asp  Gln Tyr Ile Tyr Met  Gly Glu Pro
    1940                 1945                 1950

Leu Glu  Asn Asp Glu Asp Cys  Ala His Trp Lys Glu  Ala Lys Met
```

-continued

```
    1955                1960                1965

Leu Leu  Asp Asn Ile Asn Thr  Pro Glu Gly Ile Ile  Pro Ser Met
    1970                1975                1980

Phe Glu  Pro Glu Arg Glu Lys  Val Asp Ala Ile Asp  Gly Glu Tyr
    1985                1990                1995

Arg Leu  Arg Gly Glu Ala Arg  Lys Thr Phe Val Asp  Leu Met Arg
    2000                2005                2010

Arg Gly  Asp Leu Pro Val Trp  Leu Ala Tyr Arg Val  Ala Ala Glu
    2015                2020                2025

Gly Ile  Asn Tyr Ala Asp Arg  Arg Trp Cys Phe Asp  Gly Val Lys
    2030                2035                2040

Asn Asn  Gln Ile Leu Glu Glu  Asn Val Glu Val Glu  Ile Trp Thr
    2045                2050                2055

Lys Glu  Gly Glu Arg Lys Lys  Leu Lys Pro Arg Trp  Leu Asp Ala
    2060                2065                2070

Arg Ile  Tyr Ser Asp Pro Leu  Ala Leu Lys Glu Phe  Lys Glu Phe
    2075                2080                2085

Ala Ala  Gly Arg Lys Ser Leu  Thr Leu Asn Leu Ile  Thr Glu Met
    2090                2095                2100

Gly Arg  Leu Pro Thr Phe Met  Thr Gln Lys Ala Arg  Asp Ala Leu
    2105                2110                2115

Asp Asn  Leu Ala Val Leu His  Thr Ala Glu Pro Gly  Gly Arg Ala
    2120                2125                2130

Tyr Asn  His Ala Leu Ser Glu  Leu Pro Glu Thr Leu  Glu Thr Leu
    2135                2140                2145

Leu Leu  Leu Thr Leu Leu Ala  Thr Val Thr Gly Gly  Ile Phe Leu
    2150                2155                2160

Phe Leu  Met Ser Ala Arg Gly  Ile Gly Lys Met Thr  Leu Gly Met
    2165                2170                2175

Cys Cys  Ile Ile Thr Ala Ser  Ile Leu Leu Trp Tyr  Ala Gln Ile
    2180                2185                2190

Gln Pro  His Trp Ile Ala Ala  Ser Ile Ile Leu Glu  Phe Phe Leu
    2195                2200                2205

Ile Val  Leu Leu Ile Pro Glu  Pro Glu Lys Gln Arg  Thr Pro Gln
    2210                2215                2220

Asp Asn  Gln Leu Thr Tyr Val  Val Ile Ala Ile Leu  Thr Val Val
    2225                2230                2235

Ala Ala  Thr Met Ala Asn Glu  Met Gly Phe Leu Glu  Lys Thr Lys
    2240                2245                2250

Lys Asp  Leu Gly Leu Gly Ser  Ile Ala Thr Gln Gln  Pro Glu Ser
    2255                2260                2265

Asn Ile  Leu Asp Ile Asp Leu  Arg Pro Ala Ser Ala  Trp Thr Leu
    2270                2275                2280

Tyr Ala  Val Ala Thr Thr Phe  Val Thr Pro Met Leu  Arg His Ser
    2285                2290                2295

Ile Glu  Asn Ser Ser Val Asn  Val Ser Leu Thr Ala  Ile Ala Asn
    2300                2305                2310

Gln Ala  Thr Val Leu Met Gly  Leu Gly Lys Gly Trp  Pro Leu Ser
    2315                2320                2325

Lys Met  Asp Ile Gly Val Pro  Leu Leu Ala Ile Gly  Cys Tyr Ser
    2330                2335                2340

Gln Val  Asn Pro Ile Thr Leu  Thr Ala Ala Phe Phe  Leu Leu Val
    2345                2350                2355
```

-continued

Ala His Tyr Ala Ile Ile Gly Pro Gly Leu Gln Ala Lys Ala Thr
2360 2365 2370

Arg Glu Ala Gln Lys Arg Ala Ala Ala Gly Ile Met Lys Asn Pro
2375 2380 2385

Thr Val Asp Gly Ile Thr Val Ile Asp Leu Asp Pro Ile Pro Tyr
2390 2395 2400

Asp Pro Lys Phe Glu Lys Gln Leu Gly Gln Val Met Leu Leu Val
2405 2410 2415

Leu Cys Val Thr Gln Val Leu Met Met Arg Thr Thr Trp Ala Leu
2420 2425 2430

Cys Glu Ala Leu Thr Leu Ala Thr Gly Pro Ile Ser Thr Leu Trp
2435 2440 2445

Glu Gly Asn Pro Gly Arg Phe Trp Asn Thr Thr Ile Ala Val Ser
2450 2455 2460

Met Ala Asn Ile Phe Arg Gly Ser Tyr Leu Ala Gly Ala Gly Leu
2465 2470 2475

Leu Phe Ser Ile Met Lys Asn Thr Thr Asn Thr Arg Arg Gly Thr
2480 2485 2490

Gly Asn Ile Gly Glu Thr Leu Gly Glu Lys Trp Lys Ser Arg Leu
2495 2500 2505

Asn Ala Leu Gly Lys Ser Glu Phe Gln Ile Tyr Lys Lys Ser Gly
2510 2515 2520

Ile Gln Glu Val Asp Arg Thr Leu Ala Lys Glu Gly Ile Lys Arg
2525 2530 2535

Gly Glu Thr Asp His His Ala Val Ser Arg Gly Ser Ala Lys Leu
2540 2545 2550

Arg Trp Phe Val Glu Arg Asn Met Val Thr Pro Glu Gly Lys Val
2555 2560 2565

Val Asp Leu Gly Cys Gly Arg Gly Gly Trp Ser Tyr Tyr Cys Gly
2570 2575 2580

Gly Leu Lys Asn Val Arg Glu Val Lys Gly Leu Thr Lys Gly Gly
2585 2590 2595

Pro Gly His Glu Glu Pro Ile Pro Met Ser Thr Tyr Gly Trp Asn
2600 2605 2610

Leu Val Arg Leu Gln Ser Gly Val Asp Val Phe Phe Ile Pro Pro
2615 2620 2625

Glu Lys Cys Asp Thr Leu Leu Cys Asp Ile Gly Glu Ser Ser Pro
2630 2635 2640

Asn Pro Thr Val Glu Ala Gly Arg Thr Leu Arg Val Leu Asn Leu
2645 2650 2655

Val Glu Asn Trp Leu Asn Asn Asn Thr Gln Phe Cys Ile Lys Val
2660 2665 2670

Leu Asn Pro Tyr Met Pro Ser Val Ile Glu Lys Met Glu Ala Leu
2675 2680 2685

Gln Arg Lys Tyr Gly Gly Ala Leu Val Arg Asn Pro Leu Ser Arg
2690 2695 2700

Asn Ser Thr His Glu Met Tyr Trp Val Ser Asn Ala Ser Gly Asn
2705 2710 2715

Ile Val Ser Ser Val Asn Met Ile Ser Arg Met Leu Ile Asn Arg
2720 2725 2730

Phe Thr Met Arg Tyr Lys Lys Ala Thr Tyr Glu Pro Asp Val Asp
2735 2740 2745

-continued

```
Leu Gly  Ser Gly Thr Arg Asn  Ile Gly Ile Glu Ser  Glu Ile Pro
    2750                 2755                 2760

Asn Leu  Asp Ile Ile Gly Lys  Arg Ile Glu Lys Ile  Lys Gln Glu
    2765                 2770                 2775

His Glu  Thr Ser Trp His Tyr  Asp Gln Asp His Pro  Tyr Lys Thr
    2780                 2785                 2790

Trp Ala  Tyr His Gly Ser Tyr  Glu Thr Lys Gln Thr  Gly Ser Ala
    2795                 2800                 2805

Ser Ser  Met Val Asn Gly Val  Val Arg Leu Leu Thr  Lys Pro Trp
    2810                 2815                 2820

Asp Val  Val Pro Met Val Thr  Gln Met Ala Met Thr  Asp Thr Thr
    2825                 2830                 2835

Pro Phe  Gly Gln Gln Arg Val  Phe Lys Glu Lys Val  Asp Thr Arg
    2840                 2845                 2850

Thr Gln  Glu Pro Lys Glu Gly  Thr Lys Lys Leu Met  Lys Ile Thr
    2855                 2860                 2865

Ala Glu  Trp Leu Trp Lys Glu  Leu Gly Lys Lys Lys  Thr Pro Arg
    2870                 2875                 2880

Met Cys  Thr Arg Glu Glu Phe  Thr Arg Lys Val Arg  Ser Asn Ala
    2885                 2890                 2895

Ala Leu  Gly Ala Val Phe Thr  Asp Glu Asn Lys Trp  Lys Ser Ala
    2900                 2905                 2910

Arg Glu  Ala Val Glu Asp Ser  Arg Phe Trp Glu Leu  Val Asp Lys
    2915                 2920                 2925

Glu Arg  Asn Leu His Leu Glu  Gly Lys Cys Glu Thr  Cys Val Tyr
    2930                 2935                 2940

Asn Met  Met Gly Lys Arg Glu  Lys Lys Leu Gly Glu  Phe Gly Lys
    2945                 2950                 2955

Ala Lys  Gly Ser Arg Ala Ile  Trp Tyr Met Trp Leu  Gly Ala Arg
    2960                 2965                 2970

Phe Leu  Glu Phe Glu Ala Leu  Gly Phe Leu Asn Glu  Asp His Trp
    2975                 2980                 2985

Phe Ser  Arg Glu Asn Ser Leu  Ser Gly Val Glu Gly  Glu Gly Leu
    2990                 2995                 3000

His Lys  Leu Gly Tyr Ile Leu  Arg Asp Val Ser Lys  Lys Glu Gly
    3005                 3010                 3015

Gly Ala  Met Tyr Ala Asp Asp  Thr Ala Gly Trp Asp  Thr Arg Ile
    3020                 3025                 3030

Thr Leu  Glu Asp Leu Lys Asn  Glu Glu Met Val Thr  Asn His Met
    3035                 3040                 3045

Glu Gly  Glu His Lys Lys Leu  Ala Glu Ala Ile Phe  Lys Leu Thr
    3050                 3055                 3060

Tyr Gln  Asn Lys Val Val Arg  Val Gln Arg Pro Thr  Pro Arg Gly
    3065                 3070                 3075

Thr Val  Met Asp Ile Ile Ser  Arg Arg Asp Gln Arg  Gly Ser Gly
    3080                 3085                 3090

Gln Val  Gly Thr Tyr Gly Leu  Asn Thr Phe Thr Asn  Met Glu Ala
    3095                 3100                 3105

Gln Leu  Ile Arg Gln Met Glu  Gly Glu Gly Val Phe  Lys Ser Ile
    3110                 3115                 3120

Gln His  Leu Thr Ile Thr Glu  Glu Ile Ala Val Gln  Asn Trp Leu
    3125                 3130                 3135

Ala Arg  Val Gly Arg Glu Arg  Leu Ser Arg Met Ala  Ile Ser Gly
```

```
    3140                3145                3150

Asp Asp  Cys Val Val Lys Pro  Leu Asp Asp Arg Phe  Ala Ser Ala
    3155                3160                3165

Leu Thr  Ala Leu Asn Asp Met  Gly Lys Ile Arg Lys  Asp Ile Gln
    3170                3175                3180

Gln Trp  Glu Pro Ser Arg Gly  Trp Asn Asp Trp Thr  Gln Val Pro
    3185                3190                3195

Phe Cys  Ser His His Phe His  Glu Leu Ile Met Lys  Asp Gly Arg
    3200                3205                3210

Val Leu  Val Val Pro Cys Arg  Asn Gln Asp Glu Leu  Ile Gly Arg
    3215                3220                3225

Ala Arg  Ile Ser Gln Gly Ala  Gly Trp Ser Leu Arg  Glu Thr Ala
    3230                3235                3240

Cys Leu  Gly Lys Ser Tyr Ala  Gln Met Trp Ser Leu  Met Tyr Phe
    3245                3250                3255

His Arg  Arg Asp Leu Arg Leu  Ala Ala Asn Ala Ile  Cys Ser Ala
    3260                3265                3270

Val Pro  Ser His Trp Val Pro  Thr Ser Arg Thr Thr  Trp Ser Ile
    3275                3280                3285

His Ala  Lys His Glu Trp Met  Thr Thr Glu Asp Met  Leu Thr Val
    3290                3295                3300

Trp Asn  Arg Val Trp Ile Gln  Glu Asn Pro Trp Met  Glu Asp Lys
    3305                3310                3315

Thr Pro  Val Glu Ser Trp Glu  Glu Ile Pro Tyr Leu  Gly Lys Arg
    3320                3325                3330

Glu Asp  Gln Trp Cys Gly Ser  Leu Ile Gly Leu Thr  Ser Arg Ala
    3335                3340                3345

Thr Trp  Ala Lys Asn Ile Gln  Ala Ala Ile Asn Gln  Val Arg Ser
    3350                3355                3360

Leu Ile  Gly Asn Glu Glu Tyr  Thr Asp Tyr Met Pro  Ser Met Lys
    3365                3370                3375

Arg Phe  Arg Arg Glu Glu Glu  Glu Ala Gly Val Leu  Trp
    3380                3385                3390


<210> SEQ ID NO 6
<211> LENGTH: 3391
<212> TYPE: PRT
<213> ORGANISM: Artificial Sequence
<220> FEATURE:
<223> OTHER INFORMATION: Dengue virus serotype 2, MVS

<400> SEQUENCE: 6

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
```

```
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Val Gly
    130                 135                 140

Val Asn Met Cys Thr Leu Met Ala Met Asp Leu Gly Glu Leu Cys Glu
145                 150                 155                 160

Asp Thr Ile Thr Tyr Glu Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Met Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Val Gln Arg Ile Glu Thr Trp
225                 230                 235                 240

Ile Leu Arg His Pro Gly Phe Thr Met Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Thr Pro Ser Met Thr Met Arg Cys Ile Gly Met Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Gly Ile Val Thr Cys Ala Met Phe Arg
385                 390                 395                 400

Cys Lys Lys Asn Met Glu Gly Lys Val Val Gln Pro Glu Asn Leu Glu
                405                 410                 415

Tyr Thr Ile Val Ile Thr Pro His Ser Gly Glu Glu His Ala Val Gly
            420                 425                 430

Asn Asp Thr Gly Lys His Gly Lys Glu Ile Lys Ile Thr Pro Gln Ser
        435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
        515                 520                 525
```

-continued

```
Asp Val Val Val Leu Gly Ser Gln Glu Gly Ala Met His Thr Ala Leu
    530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
        595                 600                 605

Asp Gly Ser Pro Cys Lys Ile Pro Phe Glu Ile Met Asp Leu Glu Lys
    610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asn Trp Phe
            660                 665                 670

Lys Lys Gly Ser Ser Ile Gly Gln Met Phe Glu Thr Thr Met Arg Gly
        675                 680                 685

Ala Lys Arg Met Ala Ile Leu Gly Asp Thr Ala Trp Asp Phe Gly Ser
    690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
            740                 745                 750

Thr Ser Leu Ser Val Thr Leu Val Leu Val Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940
```

-continued

```
Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                 1005

Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Asp Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Lys Glu Leu Met Met  Thr Thr Ile
    1220                 1225                 1230

Gly Ile  Val Leu Leu Ser Gln  Ser Thr Ile Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290

Val Ser  Cys Thr Ile Leu Ala  Val Val Ser Val Ser  Pro Leu Phe
    1295                 1300                 1305

Leu Thr  Ser Ser Gln Gln Lys  Thr Asp Trp Ile Pro  Leu Ala Leu
    1310                 1315                 1320

Thr Ile  Lys Gly Leu Asn Pro  Thr Ala Ile Phe Leu  Thr Thr Leu
    1325                 1330                 1335

Ser Arg  Thr Ser Lys Lys Arg  Ser Trp Pro Leu Asn  Glu Ala Ile
```

-continued

```
    1340                1345                1350

Met Ala  Val Gly Met Val Ser  Ile Leu Ala Ser Ser  Leu Leu Lys
    1355                1360                1365

Asn Asp  Ile Pro Met Thr Gly  Pro Leu Val Ala Gly  Gly Leu Leu
    1370                1375                1380

Thr Val  Cys Tyr Val Leu Thr  Gly Arg Ser Ala Asp  Leu Glu Leu
    1385                1390                1395

Glu Arg  Ala Ala Asp Val Lys  Trp Glu Asp Gln Ala  Glu Ile Ser
    1400                1405                1410

Gly Ser  Ser Pro Ile Leu Ser  Ile Thr Ile Ser Glu  Asp Gly Ser
    1415                1420                1425

Met Ser  Ile Lys Asn Glu Glu  Glu Glu Gln Thr Leu  Thr Ile Leu
    1430                1435                1440

Ile Arg  Thr Gly Leu Leu Val  Ile Ser Gly Leu Phe  Pro Val Ser
    1445                1450                1455

Ile Pro  Ile Thr Ala Ala Ala  Trp Tyr Leu Trp Glu  Val Lys Lys
    1460                1465                1470

Gln Arg  Ala Gly Val Leu Trp  Asp Val Pro Ser Pro  Pro Pro Met
    1475                1480                1485

Gly Lys  Ala Glu Leu Glu Asp  Gly Ala Tyr Arg Ile  Lys Gln Lys
    1490                1495                1500

Gly Ile  Leu Gly Tyr Ser Gln  Ile Gly Ala Gly Val  Tyr Lys Glu
    1505                1510                1515

Gly Thr  Phe His Thr Met Trp  His Val Thr Arg Gly  Ala Val Leu
    1520                1525                1530

Met His  Lys Gly Lys Arg Ile  Glu Pro Ser Trp Ala  Asp Val Lys
    1535                1540                1545

Lys Asp  Leu Ile Ser Tyr Gly  Gly Gly Trp Lys Leu  Glu Gly Glu
    1550                1555                1560

Trp Lys  Glu Gly Glu Glu Val  Gln Val Leu Ala Leu  Glu Pro Gly
    1565                1570                1575

Lys Asn  Pro Arg Ala Val Gln  Thr Lys Pro Gly Leu  Phe Lys Thr
    1580                1585                1590

Asn Ala  Gly Thr Ile Gly Ala  Val Ser Leu Asp Phe  Ser Pro Gly
    1595                1600                1605

Thr Ser  Gly Ser Pro Ile Ile  Asp Lys Lys Gly Lys  Val Val Gly
    1610                1615                1620

Leu Tyr  Gly Asn Gly Val Val  Thr Arg Ser Gly Ala  Tyr Val Ser
    1625                1630                1635

Ala Ile  Ala Gln Thr Glu Lys  Ser Ile Glu Asp Asn  Pro Glu Ile
    1640                1645                1650

Glu Asp  Asp Ile Phe Arg Lys  Arg Arg Leu Thr Ile  Met Asp Leu
    1655                1660                1665

His Pro  Gly Ala Gly Lys Thr  Lys Arg Tyr Leu Pro  Ala Ile Val
    1670                1675                1680

Arg Glu  Ala Ile Lys Arg Gly  Leu Arg Thr Leu Ile  Leu Ala Pro
    1685                1690                1695

Thr Arg  Val Val Ala Ala Glu  Met Glu Glu Ala Leu  Arg Gly Leu
    1700                1705                1710

Pro Ile  Arg Tyr Gln Thr Pro  Ala Ile Arg Ala Val  His Thr Gly
    1715                1720                1725

Arg Glu  Ile Val Asp Leu Met  Cys His Ala Thr Phe  Thr Met Arg
    1730                1735                1740
```

```
Leu Leu Ser Pro Val Arg Val Pro Asn Tyr Asn Leu Ile Ile Met
    1745                1750                1755

Asp Glu Ala His Phe Thr Asp Pro Ala Ser Ile Ala Ala Arg Gly
    1760                1765                1770

Tyr Ile Ser Thr Arg Val Glu Met Gly Glu Ala Ala Gly Ile Phe
    1775                1780                1785

Met Thr Ala Thr Pro Pro Gly Ser Arg Asp Pro Phe Pro Gln Ser
    1790                1795                1800

Asn Ala Pro Ile Ile Asp Glu Glu Arg Glu Ile Pro Glu Arg Ser
    1805                1810                1815

Trp Asn Ser Gly His Glu Trp Val Thr Asp Phe Lys Gly Lys Thr
    1820                1825                1830

Val Trp Phe Val Pro Ser Ile Lys Ala Gly Asn Asp Ile Ala Ala
    1835                1840                1845

Cys Leu Arg Lys Asn Gly Lys Lys Val Ile Gln Leu Ser Arg Lys
    1850                1855                1860

Thr Phe Asp Ser Glu Tyr Val Lys Thr Arg Thr Asn Asp Trp Asp
    1865                1870                1875

Phe Val Val Thr Thr Asp Ile Ser Glu Met Gly Ala Asn Phe Lys
    1880                1885                1890

Ala Glu Arg Val Ile Asp Pro Arg Arg Cys Met Lys Pro Val Ile
    1895                1900                1905

Leu Thr Asp Gly Glu Glu Arg Val Ile Leu Ala Gly Pro Met Pro
    1910                1915                1920

Val Thr His Ser Ser Ala Ala Gln Arg Arg Gly Arg Ile Gly Arg
    1925                1930                1935

Asn Pro Lys Asn Glu Asn Asp Gln Tyr Ile Tyr Met Gly Glu Pro
    1940                1945                1950

Leu Glu Asn Asp Glu Asp Cys Ala His Trp Lys Glu Ala Lys Met
    1955                1960                1965

Leu Leu Asp Asn Ile Asn Thr Pro Glu Gly Ile Ile Pro Ser Met
    1970                1975                1980

Phe Glu Pro Glu Arg Glu Lys Val Asp Ala Ile Asp Gly Glu Tyr
    1985                1990                1995

Arg Leu Arg Gly Glu Ala Arg Lys Thr Phe Val Asp Leu Met Arg
    2000                2005                2010

Arg Gly Asp Leu Pro Val Trp Leu Ala Tyr Arg Val Ala Ala Glu
    2015                2020                2025

Gly Ile Asn Tyr Ala Asp Arg Arg Trp Cys Phe Asp Gly Val Lys
    2030                2035                2040

Asn Asn Gln Ile Leu Glu Glu Asn Val Glu Val Glu Ile Trp Thr
    2045                2050                2055

Lys Glu Gly Glu Arg Lys Lys Leu Lys Pro Arg Trp Leu Asp Ala
    2060                2065                2070

Arg Ile Tyr Ser Asp Pro Leu Ala Leu Lys Glu Phe Lys Glu Phe
    2075                2080                2085

Ala Ala Gly Arg Lys Ser Leu Thr Leu Asn Leu Ile Thr Glu Met
    2090                2095                2100

Gly Arg Leu Pro Thr Phe Met Thr Gln Lys Ala Arg Asp Ala Leu
    2105                2110                2115

Asp Asn Leu Ala Val Leu His Thr Ala Glu Ala Gly Gly Arg Ala
    2120                2125                2130
```

```
Tyr Asn  His Ala Leu Ser Glu  Leu Pro Glu Thr Leu  Glu Thr Leu
    2135                 2140                 2145

Leu Leu  Leu Thr Leu Leu Ala  Thr Val Thr Gly Gly  Ile Phe Leu
    2150                 2155                 2160

Phe Leu  Met Ser Ala Arg Gly  Ile Gly Lys Met Thr  Leu Gly Met
    2165                 2170                 2175

Cys Cys  Ile Ile Thr Ala Ser  Ile Leu Leu Trp Tyr  Ala Gln Ile
    2180                 2185                 2190

Gln Pro  His Trp Ile Ala Ala  Ser Ile Ile Leu Glu  Phe Phe Leu
    2195                 2200                 2205

Ile Val  Leu Leu Ile Pro Glu  Pro Glu Lys Gln Arg  Thr Pro Gln
    2210                 2215                 2220

Asp Asn  Gln Leu Thr Tyr Val  Val Ile Ala Ile Leu  Thr Val Val
    2225                 2230                 2235

Ala Ala  Thr Met Ala Asn Glu  Met Gly Phe Leu Glu  Lys Thr Lys
    2240                 2245                 2250

Lys Asp  Leu Gly Leu Gly Ser  Ile Ala Thr Gln Gln  Pro Glu Ser
    2255                 2260                 2265

Asn Ile  Leu Asp Ile Asp Leu  Arg Pro Ala Ser Ala  Trp Thr Leu
    2270                 2275                 2280

Tyr Ala  Val Ala Thr Thr Phe  Val Thr Pro Met Leu  Arg His Ser
    2285                 2290                 2295

Ile Glu  Asn Ser Ser Val Asn  Val Ser Leu Thr Ala  Ile Ala Asn
    2300                 2305                 2310

Gln Ala  Thr Val Leu Met Gly  Leu Gly Lys Gly Trp  Pro Leu Ser
    2315                 2320                 2325

Lys Met  Asp Ile Gly Val Pro  Leu Leu Ala Ile Gly  Cys Tyr Ser
    2330                 2335                 2340

Gln Val  Asn Pro Ile Thr Leu  Thr Ala Ala Leu Phe  Leu Leu Val
    2345                 2350                 2355

Ala His  Tyr Ala Ile Ile Gly  Pro Gly Leu Gln Ala  Lys Ala Thr
    2360                 2365                 2370

Arg Glu  Ala Gln Lys Arg Ala  Ala Ala Gly Ile Met  Lys Asn Pro
    2375                 2380                 2385

Thr Val  Asp Gly Ile Thr Val  Ile Asp Leu Asp Pro  Ile Pro Tyr
    2390                 2395                 2400

Asp Pro  Lys Phe Glu Lys Gln  Leu Gly Gln Val Met  Leu Leu Val
    2405                 2410                 2415

Leu Cys  Val Thr Gln Val Leu  Met Met Arg Thr Thr  Trp Ala Leu
    2420                 2425                 2430

Cys Glu  Ala Leu Thr Leu Ala  Thr Gly Pro Ile Ser  Thr Leu Trp
    2435                 2440                 2445

Glu Gly  Asn Pro Gly Arg Phe  Trp Asn Thr Thr Ile  Ala Val Ser
    2450                 2455                 2460

Met Ala  Asn Ile Phe Arg Gly  Ser Tyr Leu Ala Gly  Ala Gly Leu
    2465                 2470                 2475

Leu Phe  Ser Ile Met Lys Asn  Thr Thr Asn Thr Arg  Arg Gly Thr
    2480                 2485                 2490

Gly Asn  Ile Gly Glu Thr Leu  Gly Glu Lys Trp Lys  Ser Arg Leu
    2495                 2500                 2505

Asn Ala  Leu Gly Lys Ser Glu  Phe Gln Ile Tyr Lys  Lys Ser Gly
    2510                 2515                 2520

Ile Gln  Glu Val Asp Arg Thr  Leu Ala Lys Glu Gly  Ile Lys Arg
```

```
    2525                2530                2535

Gly Glu  Thr Asp His His Ala  Val Ser Arg Gly Ser  Ala Lys Leu
    2540                2545                2550

Arg Trp  Phe Val Glu Arg Asn  Met Val Thr Pro Glu  Gly Lys Val
    2555                2560                2565

Val Asp  Leu Gly Cys Gly Arg  Gly Gly Trp Ser Tyr  Tyr Cys Gly
    2570                2575                2580

Gly Leu  Lys Asn Val Arg Glu  Val Lys Gly Leu Thr  Lys Gly Gly
    2585                2590                2595

Pro Gly  His Glu Glu Pro Ile  Pro Met Ser Thr Tyr  Gly Trp Asn
    2600                2605                2610

Leu Val  Arg Leu Gln Ser Gly  Val Asp Val Phe Phe  Ile Pro Pro
    2615                2620                2625

Glu Lys  Cys Asp Thr Leu Leu  Cys Asp Ile Gly Glu  Ser Ser Pro
    2630                2635                2640

Asn Pro  Thr Val Glu Ala Gly  Arg Thr Leu Arg Val  Leu Asn Leu
    2645                2650                2655

Val Glu  Asn Trp Leu Asn Asn  Asn Thr Gln Phe Cys  Ile Lys Val
    2660                2665                2670

Leu Asn  Pro Tyr Met Pro Ser  Val Ile Glu Lys Met  Glu Ala Leu
    2675                2680                2685

Gln Arg  Lys Tyr Gly Gly Ala  Leu Val Arg Asn Pro  Leu Ser Arg
    2690                2695                2700

Asn Ser  Thr His Glu Met Tyr  Trp Val Ser Asn Ala  Ser Gly Asn
    2705                2710                2715

Ile Val  Ser Ser Val Asn Met  Ile Ser Arg Met Leu  Ile Asn Arg
    2720                2725                2730

Phe Thr  Met Arg Tyr Lys Lys  Ala Thr Tyr Glu Pro  Asp Val Asp
    2735                2740                2745

Leu Gly  Ser Gly Thr Arg Asn  Ile Gly Ile Glu Ser  Glu Ile Pro
    2750                2755                2760

Asn Leu  Asp Ile Ile Gly Lys  Arg Ile Glu Lys Ile  Lys Gln Glu
    2765                2770                2775

His Glu  Thr Ser Trp His Tyr  Asp Gln Asp His Pro  Tyr Lys Thr
    2780                2785                2790

Trp Ala  Tyr His Gly Ser Tyr  Glu Thr Lys Gln Thr  Gly Ser Ala
    2795                2800                2805

Ser Ser  Met Val Asn Gly Val  Val Arg Leu Leu Thr  Lys Pro Trp
    2810                2815                2820

Asp Val  Val Pro Met Val Thr  Gln Met Ala Met Thr  Asp Thr Thr
    2825                2830                2835

Pro Phe  Gly Gln Gln Arg Val  Phe Lys Glu Lys Val  Asp Thr Arg
    2840                2845                2850

Thr Gln  Glu Pro Lys Glu Gly  Thr Lys Lys Leu Met  Lys Ile Thr
    2855                2860                2865

Ala Glu  Trp Leu Trp Lys Glu  Leu Gly Lys Lys Lys  Thr Pro Arg
    2870                2875                2880

Met Cys  Thr Arg Glu Glu Phe  Thr Arg Lys Val Arg  Ser Asn Ala
    2885                2890                2895

Ala Leu  Gly Ala Val Phe Thr  Asp Glu Asn Lys Trp  Lys Ser Ala
    2900                2905                2910

Arg Glu  Ala Val Glu Asp Ser  Arg Phe Trp Glu Leu  Val Asp Lys
    2915                2920                2925
```

-continued

```
Glu Arg  Asn Leu His Leu Glu  Gly Lys Cys Glu Thr  Cys Val Tyr
    2930                 2935                 2940

Asn Met  Met Gly Lys Arg Glu  Lys Lys Leu Gly Glu  Phe Gly Lys
    2945                 2950                 2955

Ala Lys  Gly Ser Arg Ala Ile  Trp Tyr Met Trp Leu  Gly Ala Arg
    2960                 2965                 2970

Phe Leu  Glu Phe Glu Ala Leu  Gly Phe Leu Asn Glu  Asp His Trp
    2975                 2980                 2985

Phe Ser  Arg Glu Asn Ser Leu  Ser Gly Val Glu Gly  Glu Gly Leu
    2990                 2995                 3000

His Lys  Leu Gly Tyr Ile Leu  Arg Asp Val Ser Lys  Lys Glu Gly
    3005                 3010                 3015

Gly Ala  Met Tyr Ala Asp Asp  Thr Ala Gly Trp Asp  Thr Arg Ile
    3020                 3025                 3030

Thr Leu  Glu Asp Leu Lys Asn  Glu Glu Met Val Thr  Asn His Met
    3035                 3040                 3045

Glu Gly  Glu His Lys Lys Leu  Ala Glu Ala Ile Phe  Lys Leu Thr
    3050                 3055                 3060

Tyr Gln  Asn Lys Val Val Arg  Val Gln Arg Pro Thr  Pro Arg Gly
    3065                 3070                 3075

Thr Val  Met Asp Ile Ile Ser  Arg Arg Asp Gln Arg  Gly Ser Gly
    3080                 3085                 3090

Gln Val  Gly Thr Tyr Gly Leu  Asn Thr Phe Thr Asn  Met Glu Ala
    3095                 3100                 3105

Gln Leu  Ile Arg Gln Met Glu  Gly Glu Gly Val Phe  Lys Ser Ile
    3110                 3115                 3120

Gln His  Leu Thr Ile Thr Glu  Glu Ile Ala Val Gln  Asn Trp Leu
    3125                 3130                 3135

Ala Arg  Val Gly Arg Glu Arg  Leu Ser Arg Met Ala  Ile Ser Gly
    3140                 3145                 3150

Asp Asp  Cys Val Val Lys Pro  Leu Asp Asp Arg Phe  Ala Ser Ala
    3155                 3160                 3165

Leu Thr  Ala Leu Asn Asp Met  Gly Lys Ile Arg Lys  Asp Ile Gln
    3170                 3175                 3180

Gln Trp  Glu Pro Ser Arg Gly  Trp Asn Asp Trp Thr  Gln Val Pro
    3185                 3190                 3195

Phe Cys  Ser His His Phe His  Glu Leu Ile Met Lys  Asp Gly Arg
    3200                 3205                 3210

Val Leu  Val Val Pro Cys Arg  Asn Gln Asp Glu Leu  Ile Gly Arg
    3215                 3220                 3225

Ala Arg  Ile Ser Gln Gly Ala  Gly Trp Ser Leu Arg  Glu Thr Ala
    3230                 3235                 3240

Cys Leu  Gly Lys Ser Tyr Ala  Gln Met Trp Ser Leu  Met Tyr Phe
    3245                 3250                 3255

His Arg  Arg Asp Leu Arg Leu  Ala Ala Asn Ala Ile  Cys Ser Ala
    3260                 3265                 3270

Val Pro  Ser His Trp Val Pro  Thr Ser Arg Thr Thr  Trp Ser Ile
    3275                 3280                 3285

His Ala  Lys His Glu Trp Met  Thr Thr Glu Asp Met  Leu Thr Val
    3290                 3295                 3300

Trp Asn  Arg Val Trp Ile Gln  Glu Asn Pro Trp Met  Glu Asp Lys
    3305                 3310                 3315
```

```
Thr Pro  Val Glu Ser Trp Glu  Glu Ile Pro Tyr Leu  Gly Lys Arg
    3320                 3325                 3330

Glu Asp  Gln Trp Cys Gly Ser  Leu Ile Gly Leu Thr  Ser Arg Ala
    3335                 3340                 3345

Thr Trp  Ala Lys Asn Ile Gln  Ala Ala Ile Asn Gln  Val Arg Ser
    3350                 3355                 3360

Leu Ile  Gly Asn Glu Glu Tyr  Thr Asp Tyr Met Pro  Ser Met Lys
    3365                 3370                 3375

Arg Phe  Arg Arg Glu Glu Glu  Glu Ala Gly Val Leu  Trp
    3380                 3385                 3390


<210> SEQ ID NO 7
<211> LENGTH: 10717
<212> TYPE: DNA
<213> ORGANISM: Artificial Sequence
<220> FEATURE:
<223> OTHER INFORMATION: Dengue virus serotype 3, BVS

<400> SEQUENCE: 7

agttgttagt ctacgtggac cgacaaagac agattctttg agggagctaa gctcaatgta     60

gttctaacag ttttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatctg caggcatgat cattatgctg    420

attccaacag tgatggcgtt ccatttaacc acgcgtgatg gagagccgcg catgattgtg    480

gggaagaatg aaagaggaaa atccctactt ttcaagacag cctctggaat caacatgtgc    540

acactcatag ctatggatct gggagagatg tgtgatgaca cggtcactta caaatgcccc    600

cacattaccg aagtggagcc tgaagacatt gactgctggt gcaaccttac atcgacatgg    660

gtgacttatg gaacatgcaa tcaagctgga gagcatagac gcgataagag atcagtggcg    720

ttagctcccc atgttggcat gggactggac acacgcactc aaacctggat gtcggctgaa    780

ggagcttgga gacaagtcga gaaggtagag acatgggccc ttaggcaccc agggtttacc    840

atactagccc tatttcttgc ccattacata ggcacttcct tgacccagaa agtggttatt    900

tttatactat taatgctggt taccccatcc atgacaatga gatgtgtagg agtaggaaac    960

agagattttg tggaaggcct atcgggagct acgtgggttg acgtggtgct cgagcacggt   1020

gggtgtgtga ctaccatggc taagaacaag cccacgctgg acatagagct tcagaagacc   1080

gaggccaccc aactggcgac cctaaggaag ctatgcattg agggaaaaat taccaacata   1140

acaaccgact caagatgtcc cacccaaggg gaagcgattt tacctgagga gcaggaccag   1200

aactacgtgt gtaagcatac atacgtggac agaggctggg gaaacggttg tggtttgttt   1260

ggcaagggaa gcttggtgac atgcgcgaaa tttcaatgtt tagaatcaat agagggaaaa   1320

gtggtgcaac atgagaacct caaatacacc gtcatcatca cagtgcacac aggagaccaa   1380

caccaggtgg gaaatgaaac gcagggagtc acggctgaga taacacccca ggcatcaacc   1440

gctgaagcca ttttacctga atatggaacc ctcgggctag aatgctcacc acggacaggt   1500

ttggatttca atgaaatgat ctcattgaca atgaagaaca aagcatggat ggtacataga   1560

caatggttct ttgacttacc cctaccatgg acatcaggag cttcagcaga aacaccaact   1620
```

-continued

```
tggaacagga aagagcttct tgtgacattt aaaaatgcac atgcaaaaaa gcaagaagta   1680
gttgttcttg gatcacaaga gggagcaatg catacagcac tgacaggagc tacagagatc   1740
caaacctcag gaggcacaag tatctttgcg gggcacttaa aatgtagact caagatggac   1800
aaattggaac tcaaggggat gagctatgca atgtgcttga gtagctttgt gttgaagaaa   1860
gaagtctccg aaacgcagca tgggacaata ctcattaagg ttgagtacaa aggggaagat   1920
gcaccctgca agattccttt ctccacggag gatggacaag gaaaagctct caatggcaga   1980
ctgatcacag ccaatccagt ggtgaccaag aaggaggagc ctgtcaacat tgaggctgaa   2040
cctccttttg gagaaagtaa catagtaatt ggaattggag acaaagccct gaaaatcaac   2100
tggtacaaga agggaagctc gattgggaag atgttcgagg ccactgccag aggtgcaagg   2160
cgcatggcca tcttgggaga cacagcctgg gactttggat cagtgggtgg tgttttgaat   2220
tcattaggga aaatggtcca ccaaatattt gggagtgctt acacagccct atttggtgga   2280
gtctcctgga tgatgaaaat tggaataggt gtcctcttaa cctggatagg gttgaactca   2340
aaaaatactt ctatgtcatt ttcatgcatc gcggccggca ttgtgacact gtatttggga   2400
gtcatggtgc aggccgatag tggttgcgtt gtgagctgga aaaacaaaga actgaaatgt   2460
ggcagtggga ttttcatcac agacaacgtg cacacatgga cagaacaata caagttccaa   2520
ccagaatccc cttcaaaact agcttcagct atccagaaag cccatgaaga ggacatttgt   2580
ggaatccgct cagtaacaag actggagaat ctgatgtgga aacaaataac accagaattg   2640
aatcacattc tatcagaaaa tgaggtgaag ttaactatta tgacaggaga catcaaagga   2700
atcatgcagg caggaaaacg atctctgcgg cctcagccca ctgagctgaa gtattcatgg   2760
aaaacatggg gcaaagcaaa aatgctctct acagagtctc ataaccagac ctttctcatt   2820
gatggccccg aaacagcaga atgccccaac acaaatagag cttggaattc gttggaagtt   2880
gaagactatg gctttggagt attcaccacc aatatatggc taaaattgaa agaaaaacag   2940
gatgtattct gcgactcaaa actcatgtca gcggccataa aagacaacag agccgtccat   3000
gccgatatgg gttattggat agaaagtgca ctcaatgaca catggaagat agagaaagcc   3060
tctttcattg aagttaaaaa ctgccactgg ccaaaatcac acaccctctg gagcaatgga   3120
gtgctagaaa gtgagatgat aattccaaag aatctcgctg gaccagtgtc tcaacacaac   3180
tatagaccag gctaccatac acaaataaca ggaccatggc atctaggtaa gcttgagatg   3240
gactttgatt tctgtgatgg aacaacagtg gtagtgactg aggactgcgg aaatagagga   3300
ccctctttga gaacaaccac tgcctctgga aaactcataa cagaatggtg ctgccgatct   3360
tgcacattac caccgctaag atacagaggt gaggatgggt gctggtacgg gatggaaatc   3420
agaccattga aggagaaaga agagaatttg gtcaactcct tggtcacagc tggacatggg   3480
caggtcgaca acttttcact aggagtcttg ggaatggcat tgttcctgga ggaaatgctt   3540
aggacccgag taggaacgaa acatgcaata ctactagttg cagtttcttt tgtgacattg   3600
atcacaggga acatgtcctt tagagacctg ggaagagtga tggttatggt aggcgccact   3660
atgacggatg acataggtat gggcgtgact tatcttgccc tactagcagc cttcaaagtc   3720
agaccaactt ttgcagctgg actactcttg agaaagctga cctccaagga attgatgatg   3780
actactatag gaattgtact cctctcccag agcaccatac cagagaccat tcttgagttg   3840
actgatgcgt tagccttagg catgatggtc ctcaaaatgg tgagaaatat ggaaaagtat   3900
caattggcag tgactatcat ggctatcttg tgcgtcccaa acgcagtgat attacaaaac   3960
gcatggaaag tgagttgcac aatattggca gtggtgtccg tttccccact gttcttaaca   4020
```

-continued

```
tcctcacagc aaaaaacaga ttggatacca ttagcattga cgatcaaagg tctcaatcca   4080
acagctattt ttctaacaac cctctcaaga accagcaaga aaaggagctg gccattaaat   4140
gaggctatca tggcagtcgg gatggtgagc attttagcca gttctctcct aaaaaatgat   4200
attcccatga caggaccatt agtggctgga gggctcctca ctgtgtgcta cgtgctcact   4260
ggacgatcgg ccgatttgga actggagaga gcagccgatg tcaaatggga agaccaggca   4320
gagatatcag gaagcagtcc aatcctgtca ataacaatat cagaagatgg tagcatgtcg   4380
ataaaaaatg aagaggaaga acaaacactg accatactca ttagaacagg attgctggtg   4440
atctcaggac tttttcctgt atcaatacca atcacggcag cagcatggta cctgtgggaa   4500
gtgaagaaac aacgggccgg agtattgtgg gatgttcctt cacccccacc catgggaaag   4560
gctgaactgg aagatggagc ctatagaatt aagcaaaaag ggattcttgg atattcccag   4620
atcggagccg gagtttacaa agaaggaaca ttccatacaa tgtggcatgt cacacgtggc   4680
gctgttctaa tgcataaagg aaagaggatt gaaccatcat gggcggacgt caagaaagac   4740
ctaatatcat atggaggagg ctggaagtta gaaggagaat ggaaggaagg agaagaagtc   4800
caggtattgg cactggagcc tggaaaaaat ccaagagccg tccaaacgaa acctggtctt   4860
ttcaaaacca acgccggaac aataggtgct gtatctctgg acttttctcc tggaacgtca   4920
ggatctccaa ttatcgacaa aaaaggaaaa gttgtgggtc tttatggtaa tggtgttgtt   4980
acaaggagtg gagcatatgt gagtgctata gcccagactg aaaaaagcat tgaagacaac   5040
ccagagatcg aagatgacat tttccgaaag agaagactga ccatcatgga cctccaccca   5100
ggagcgggaa agacgaagag ataccttccg gccatagtca gagaagctat aaaacggggt   5160
ttgagaacat taatcttggc ccccactaga gttgtggcag ctgaaatgga ggaagccctt   5220
agaggacttc caataagata ccagacccca gccatcagag ctgtgcacac cgggcgggag   5280
attgtggacc taatgtgtca tgccacattt accatgaggc tgctatcacc agttagagtg   5340
ccaaactaca acctgattat catggacgaa gcccatttca cagacccagc aagtatagca   5400
gctagaggat acatctcaac tcgagtggag atgggtgagg cagctgggat ttttatgaca   5460
gccactcccc cgggaagcag agacccattt cctcagagca atgcaccaat catagatgaa   5520
gaaagagaaa tccctgaacg ctcgtggaat tccggacatg aatgggtcac ggattttaaa   5580
gggaagactg tttggttcgt tccaagtata aaagcaggaa atgatatagc agcttgcctg   5640
aggaaaaatg gaaagaaagt gatacaactc agtaggaaga cctttgattc tgagtatgtc   5700
aagactagaa ccaatgattg ggacttcgtg gttacaactg acatttcaga aatgggtgcc   5760
aatttcaagg ctgagagggt tatagacccc agacgctgca tgaaaccagt catactaaca   5820
gatggtgaag agcgggtgat tctggcagga cctatgccag tgacccactc tagtgcagca   5880
caaagaagag ggagaatagg aagaaatcca aaaaatgaga atgaccagta catatacatg   5940
ggggaacctc tggaaaatga tgaagactgt gcacactgga aagaagctaa aatgctccta   6000
gataacatca acacgccaga aggaatcatt cctagcatgt tcgaaccaga gcgtgaaaag   6060
gtggatgcca ttgatggcga ataccgcttg agaggagaag caaggaaaac ctttgtagac   6120
ttaatgagaa gaggagacct accagtctgg ttggcctaca gagtggcagc tgaaggcatc   6180
aactacgcag acagaaggtg gtgttttgat ggagtcaaga acaaccaaat cctagaagaa   6240
aacgtggaag ttgaaatctg gacaaaagaa ggggaaagga agaaattgaa acccagatgg   6300
ttggatgcta ggatctattc tgacccactg gcgctaaaag aatttaagga atttgcagcc   6360
```

-continued

```
ggaagaaagt ctctgaccct gaacctaatc acagaaatgg gtaggctccc aaccttcatg   6420
actcagaagg caagaaacgc actggacaac ttagcagtgc tgcacacggc tgaggcaggt   6480
ggaagggcgt acaaccatgc tctcagtgaa ctgccggaga ccctggagac attgctttta   6540
ctgacacttc tggctacagt cacgggaggg atctttttat tcttgatgag cgcaaggggc   6600
atagggaaga tgaccctggg aatgtgctgc ataatcacgg ctagcatcct cctatggtac   6660
gcacaaatac agccacactg gatagcagct tcaataatac tggagttttt tctcatagtt   6720
ttgcttattc cagaacctga aaaacagaga acaccccaag acaaccaact gacctacgtt   6780
gtcatagcca tcctcacagt ggtggccgca accatggcaa acgagatggg tttcctagaa   6840
aaaacgaaga aagatctcgg attgggaagc attgcaaccc agcaacccga gagcaacatc   6900
ctggacatag atctacgtcc tgcatcagca tggacgctgt atgccgtggc cacaacattt   6960
gttacaccaa tgttgagaca tagcattgaa aattcctcag tgaatgtgtc cctaacagct   7020
atagccaacc aagccacagt gttaatgggt ctcgggaaag gatggccatt gtcaaagatg   7080
gacatcggag ttccccttct cgccattgga tgctactcac aagtcaaccc cataactctc   7140
acagcagctc ttttcttatt ggtagcacat tatgccatca tagggccagg actccaagca   7200
aaagcaacca gagaagctca gaaaagagca gcggcgggca tcatgaaaaa cccaactgtc   7260
gatggaataa cagtgattga cctagatcca ataccttatg atccaaagtt tgaaaagcag   7320
ttgggacaag taatgctcct agtcctctgc gtgactcaag tattgatgat gaggactaca   7380
tgggctctgt gtgaggcttt aaccttagct accgggccca tctccacatt gtgggaagga   7440
aatccaggga ggttttggaa cactaccatt gcggtgtcaa tggctaacat ttttagaggg   7500
agttacttgg ccggagctgg acttctcttt tctattatga agaacacaac caacacaaga   7560
aggggaactg gcaacatagg agagacgctt ggagagaaat ggaaaagccg attgaacgcg   7620
ttgggaaaaa gtgaattcca gatctacaag aaaagtggaa tccaggaagt ggatagaacc   7680
ttagcaaaag aaggcattaa aagaggagaa acggaccatc acgctgtgtc gcgaggctca   7740
gcaaaactga gatggttcgt tgagagaaac atggtcacac cagaagggaa agtagtggac   7800
ctcggttgtg gcagaggagg ctggtcatac tattgtggag gactaaagaa tgtaagagaa   7860
gtcaaaggcc taacaaaagg aggaccagga cacgaagaac ccatccccat gtcaacatat   7920
gggtggaatc tagtgcgtct tcaaagtgga gttgacgttt tcttcatccc gccagaaaag   7980
tgtgacacat tattgtgtga catagggggag tcatcaccaa atcccacagt ggaagcagga   8040
cgaacactca gagtccttaa cttagtagaa aattggttga acaacaacac tcaattttgc   8100
ataaaggttc tcaacccata tatgccctca gtcatagaaa aaatggaagc actacaaagg   8160
aaatatggag gagccttagt gaggaatcca ctctcacgaa actccacaca tgagatgtac   8220
tgggtatcca atgcttccgg gaacatagtg tcatcagtga acatgatttc aaggatgttg   8280
atcaacagat ttacaatgag atacaagaaa gccacttacg agccggatgt tgacctcgga   8340
agcggaaccc gtaacatcgg gattgaaagt gagataccaa acctagatat aattgggaaa   8400
agaatagaaa aaataaagca agagcatgaa acatcatggc actatgacca agaccaccca   8460
tacaaaacgt gggcatacca tggtagctat gaaacaaaac agactggatc agcatcatcc   8520
atggtcaacg gagtggtcag gctgctgaca aaaccttggg acgtcgtccc catggtgaca   8580
cagatggcaa tgacagacac gactccattt ggacaacagc gcgtttttaa agagaaagtg   8640
gacacgagaa cccaagaacc gaaagaaggc acgaagaaac taatgaaaat aacagcagag   8700
tggctttgga aagaattagg gaagaaaaag acacccagga tgtgcaccag agaagaattc   8760
```

```
acaagaaagg tgagaagcaa tgcagccttg ggggccatat tcactgatga gaacaagtgg   8820

aagtcggcac gtgaggctgt tgaagatagt aggttttggg agctggttga caaggaaagg   8880

aatctccatc ttgaaggaaa gtgtgaaaca tgtgtgtaca acatgatggg aaaaagagag   8940

aagaagctag gggaattcgg caaggcaaaa ggcagcagag ccatatggta catgtggctt   9000

ggagcacgct tcttagagtt tgaagcccta ggattcttaa atgaagatca ctggttctcc   9060

agagagaact ccctgagtgg agtggaagga gaagggctgc acaagctagg ttacattcta   9120

agagacgtga gcaagaaaga gggaggagca atgtatgccg atgacaccgc aggatgggat   9180

acaagaatca cactagaaga cctaaaaaat gaagaaatgg taacaaacca catggaagga   9240

gaacacaaga aactagccga ggccattttc aaactaacgt accaaaacaa ggtggtgcgt   9300

gtgcaaagac caacaccaag aggcacagta atggacatca tatcgagaag agaccaaaga   9360

ggtagtggac aagttggcac ctatggactc aatactttca ccaatatgga agcccaacta   9420

atcagacaga tggagggaga aggagtcttt aaaagcattc agcacctaac aatcacagaa   9480

gaaatcgctg tgcaaaactg gttagcaaga gtggggcgcg aaaggttatc aagaatggcc   9540

atcagtggag atgattgtgt tgtgaaacct ttagatgaca ggttcgcaag cgctttaaca   9600

gctctaaatg acatgggaaa gattaggaaa gacatacaac aatgggaacc ttcaagagga   9660

tggaatgatt ggacacaagt gcccttctgt tcacaccatt tccatgagtt aatcatgaaa   9720

gacggtcgcg tactcgttgt tccatgtaga aaccaagatg aactgattgg cagagcccga   9780

atctcccaag gagcagggtg gtctttgcgg gagacggcct gtttggggaa gtcttacgcc   9840

caaatgtgga gcttgatgta cttccacaga cgcgacctca ggctggcggc aaatgctatt   9900

tgctcggcag taccatcaca ttgggttcca acaagtcgaa caacctggtc catacatgct   9960

aaacatgaat ggatgacaac ggaagacatg ctgacagtct ggaacagggt gtggattcaa  10020

gaaaacccat ggatggaaga caaaactcca gtggaatcat gggaggaaat cccatacttg  10080

gggaaaagag aagaccaatg gtgcggctca ttgattgggt taacaagcag ggccacctgg  10140

gcaaagaaca tccaagcagc aataaatcaa gttagatccc ttataggcaa tgaagaatac  10200

acagattaca tgccatccat gaaaagattc agaagagaag aggaagaagc aggagttctg  10260

tggtagaaag caaaactaac atgaaacaag gctagaagtc aggtcggatt aagccatagt  10320

acggaaaaaa ctatgctacc tgtgagcccc gtccaaggac gttaaaagaa gtcaggccat  10380

cataaatgcc atagcttgag taaactatgc agcctgtagc tccacctgag aaggtgtaaa  10440

aaatccggga ggccacaaac catggaagct gtacgcatgg cgtagtggac tagcggttag  10500

aggagacccc tcccttacaa atcgcagcaa caatgggggc ccaaggcgag atgaagctgt  10560

agtctcgctg gaaggactag aggttagagg agaccccccc gaaacaaaaa acagcatatt  10620

gacgctggga aagaccagag atcctgctgt ctcctcagca tcattccagg cacagaacgc  10680

cagaaaatgg aatggtgctg ttgaatcaac aggttct                           10717
```

<210> SEQ ID NO 8
<211> LENGTH: 3389
<212> TYPE: PRT
<213> ORGANISM: Artificial Sequence
<220> FEATURE:
<223> OTHER INFORMATION: Dengue virus serotype 3, BVS

<400> SEQUENCE: 8

```
Met Asn Asn Gln Arg Lys Lys Ala Lys Asn Thr Pro Phe Asn Met Leu
1               5                   10                  15
```

-continued

```
Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asp Gly Glu Pro Arg Met Ile Val
        115                 120                 125

Gly Lys Asn Glu Arg Gly Lys Ser Leu Leu Phe Lys Thr Ala Ser Gly
    130                 135                 140

Ile Asn Met Cys Thr Leu Ile Ala Met Asp Leu Gly Glu Met Cys Asp
145                 150                 155                 160

Asp Thr Val Thr Tyr Lys Cys Pro His Ile Thr Glu Val Glu Pro Glu
                165                 170                 175

Asp Ile Asp Cys Trp Cys Asn Leu Thr Ser Thr Trp Val Thr Tyr Gly
            180                 185                 190

Thr Cys Asn Gln Ala Gly Glu His Arg Arg Asp Lys Arg Ser Val Ala
        195                 200                 205

Leu Ala Pro His Val Gly Met Gly Leu Asp Thr Arg Thr Gln Thr Trp
    210                 215                 220

Met Ser Ala Glu Gly Ala Trp Arg Gln Val Glu Lys Val Glu Thr Trp
225                 230                 235                 240

Ala Leu Arg His Pro Gly Phe Thr Ile Leu Ala Leu Phe Leu Ala His
                245                 250                 255

Tyr Ile Gly Thr Ser Leu Thr Gln Lys Val Val Ile Phe Ile Leu Leu
            260                 265                 270

Met Leu Val Thr Pro Ser Met Thr Met Arg Cys Val Gly Val Gly Asn
        275                 280                 285

Arg Asp Phe Val Glu Gly Leu Ser Gly Ala Thr Trp Val Asp Val Val
    290                 295                 300

Leu Glu His Gly Gly Cys Val Thr Thr Met Ala Lys Asn Lys Pro Thr
305                 310                 315                 320

Leu Asp Ile Glu Leu Gln Lys Thr Glu Ala Thr Gln Leu Ala Thr Leu
                325                 330                 335

Arg Lys Leu Cys Ile Glu Gly Lys Ile Thr Asn Ile Thr Thr Asp Ser
            340                 345                 350

Arg Cys Pro Thr Gln Gly Glu Ala Ile Leu Pro Glu Glu Gln Asp Gln
        355                 360                 365

Asn Tyr Val Cys Lys His Thr Tyr Val Asp Arg Gly Trp Gly Asn Gly
    370                 375                 380

Cys Gly Leu Phe Gly Lys Gly Ser Leu Val Thr Cys Ala Lys Phe Gln
385                 390                 395                 400

Cys Leu Glu Ser Ile Glu Gly Lys Val Val Gln His Glu Asn Leu Lys
                405                 410                 415

Tyr Thr Val Ile Ile Thr Val His Thr Gly Asp Gln His Gln Val Gly
            420                 425                 430
```

```
Asn Glu Thr Gln Gly Val Thr Ala Glu Ile Thr Pro Gln Ala Ser Thr
        435                 440                 445

Ala Glu Ala Ile Leu Pro Glu Tyr Gly Thr Leu Gly Leu Glu Cys Ser
    450                 455                 460

Pro Arg Thr Gly Leu Asp Phe Asn Glu Met Ile Ser Leu Thr Met Lys
465                 470                 475                 480

Asn Lys Ala Trp Met Val His Arg Gln Trp Phe Phe Asp Leu Pro Leu
                485                 490                 495

Pro Trp Thr Ser Gly Ala Ser Ala Glu Thr Pro Thr Trp Asn Arg Lys
            500                 505                 510

Glu Leu Leu Val Thr Phe Lys Asn Ala His Ala Lys Lys Gln Glu Val
        515                 520                 525

Val Val Leu Gly Ser Gln Glu Gly Ala Met His Thr Ala Leu Thr Gly
    530                 535                 540

Ala Thr Glu Ile Gln Thr Ser Gly Gly Thr Ser Ile Phe Ala Gly His
545                 550                 555                 560

Leu Lys Cys Arg Leu Lys Met Asp Lys Leu Glu Leu Lys Gly Met Ser
                565                 570                 575

Tyr Ala Met Cys Leu Ser Ser Phe Val Leu Lys Lys Glu Val Ser Glu
            580                 585                 590

Thr Gln His Gly Thr Ile Leu Ile Lys Val Glu Tyr Lys Gly Glu Asp
        595                 600                 605

Ala Pro Cys Lys Ile Pro Phe Ser Thr Glu Asp Gly Gln Gly Lys Ala
    610                 615                 620

Leu Asn Gly Arg Leu Ile Thr Ala Asn Pro Val Val Thr Lys Lys Glu
625                 630                 635                 640

Glu Pro Val Asn Ile Glu Ala Glu Pro Pro Phe Gly Glu Ser Asn Ile
                645                 650                 655

Val Ile Gly Ile Gly Asp Lys Ala Leu Lys Ile Asn Trp Tyr Lys Lys
            660                 665                 670

Gly Ser Ser Ile Gly Lys Met Phe Glu Ala Thr Ala Arg Gly Ala Arg
        675                 680                 685

Arg Met Ala Ile Leu Gly Asp Thr Ala Trp Asp Phe Gly Ser Val Gly
    690                 695                 700

Gly Val Leu Asn Ser Leu Gly Lys Met Val His Gln Ile Phe Gly Ser
705                 710                 715                 720

Ala Tyr Thr Ala Leu Phe Gly Gly Val Ser Trp Met Met Lys Ile Gly
                725                 730                 735

Ile Gly Val Leu Leu Thr Trp Ile Gly Leu Asn Ser Lys Asn Thr Ser
            740                 745                 750

Met Ser Phe Ser Cys Ile Ala Ala Gly Ile Val Thr Leu Tyr Leu Gly
        755                 760                 765

Val Met Val Gln Ala Asp Ser Gly Cys Val Val Ser Trp Lys Asn Lys
    770                 775                 780

Glu Leu Lys Cys Gly Ser Gly Ile Phe Ile Thr Asp Asn Val His Thr
785                 790                 795                 800

Trp Thr Glu Gln Tyr Lys Phe Gln Pro Glu Ser Pro Ser Lys Leu Ala
                805                 810                 815

Ser Ala Ile Gln Lys Ala His Glu Glu Asp Ile Cys Gly Ile Arg Ser
            820                 825                 830

Val Thr Arg Leu Glu Asn Leu Met Trp Lys Gln Ile Thr Pro Glu Leu
        835                 840                 845

Asn His Ile Leu Ser Glu Asn Glu Val Lys Leu Thr Ile Met Thr Gly
```

-continued

```
    850                 855                 860

Asp Ile Lys Gly Ile Met Gln Ala Gly Lys Arg Ser Leu Arg Pro Gln
865                 870                 875                 880

Pro Thr Glu Leu Lys Tyr Ser Trp Lys Thr Trp Gly Lys Ala Lys Met
                885                 890                 895

Leu Ser Thr Glu Ser His Asn Gln Thr Phe Leu Ile Asp Gly Pro Glu
            900                 905                 910

Thr Ala Glu Cys Pro Asn Thr Asn Arg Ala Trp Asn Ser Leu Glu Val
        915                 920                 925

Glu Asp Tyr Gly Phe Gly Val Phe Thr Thr Asn Ile Trp Leu Lys Leu
    930                 935                 940

Lys Glu Lys Gln Asp Val Phe Cys Asp Ser Lys Leu Met Ser Ala Ala
945                 950                 955                 960

Ile Lys Asp Asn Arg Ala Val His Ala Asp Met Gly Tyr Trp Ile Glu
                965                 970                 975

Ser Ala Leu Asn Asp Thr Trp Lys Ile Glu Lys Ala Ser Phe Ile Glu
            980                 985                 990

Val Lys Asn Cys His Trp Pro Lys  Ser His Thr Leu Trp  Ser Asn Gly
        995                 1000                1005

Val Leu  Glu Ser Glu Met Ile  Ile Pro Lys Asn Leu  Ala Gly Pro
    1010                1015                1020

Val Ser  Gln His Asn Tyr Arg  Pro Gly Tyr His Thr  Gln Ile Thr
    1025                1030                1035

Gly Pro  Trp His Leu Gly Lys  Leu Glu Met Asp Phe  Asp Phe Cys
    1040                1045                1050

Asp Gly  Thr Thr Val Val Val  Thr Glu Asp Cys Gly  Asn Arg Gly
    1055                1060                1065

Pro Ser  Leu Arg Thr Thr Thr  Ala Ser Gly Lys Leu  Ile Thr Glu
    1070                1075                1080

Trp Cys  Cys Arg Ser Cys Thr  Leu Pro Pro Leu Arg  Tyr Arg Gly
    1085                1090                1095

Glu Asp  Gly Cys Trp Tyr Gly  Met Glu Ile Arg Pro  Leu Lys Glu
    1100                1105                1110

Lys Glu  Glu Asn Leu Val Asn  Ser Leu Val Thr Ala  Gly His Gly
    1115                1120                1125

Gln Val  Asp Asn Phe Ser Leu  Gly Val Leu Gly Met  Ala Leu Phe
    1130                1135                1140

Leu Glu  Glu Met Leu Arg Thr  Arg Val Gly Thr Lys  His Ala Ile
    1145                1150                1155

Leu Leu  Val Ala Val Ser Phe  Val Thr Leu Ile Thr  Gly Asn Met
    1160                1165                1170

Ser Phe  Arg Asp Leu Gly Arg  Val Met Val Met Val  Gly Ala Thr
    1175                1180                1185

Met Thr  Asp Asp Ile Gly Met  Gly Val Thr Tyr Leu  Ala Leu Leu
    1190                1195                1200

Ala Ala  Phe Lys Val Arg Pro  Thr Phe Ala Ala Gly  Leu Leu Leu
    1205                1210                1215

Arg Lys  Leu Thr Ser Lys Glu  Leu Met Met Thr Thr  Ile Gly Ile
    1220                1225                1230

Val Leu  Leu Ser Gln Ser Thr  Ile Pro Glu Thr Ile  Leu Glu Leu
    1235                1240                1245

Thr Asp  Ala Leu Ala Leu Gly  Met Met Val Leu Lys  Met Val Arg
    1250                1255                1260
```

-continued

```
Asn Met  Glu Lys Tyr Gln Leu  Ala Val Thr Ile Met  Ala Ile Leu
    1265                 1270                 1275

Cys Val  Pro Asn Ala Val Ile  Leu Gln Asn Ala Trp  Lys Val Ser
    1280                 1285                 1290

Cys Thr  Ile Leu Ala Val Val  Ser Val Ser Pro Leu  Phe Leu Thr
    1295                 1300                 1305

Ser Ser  Gln Gln Lys Thr Asp  Trp Ile Pro Leu Ala  Leu Thr Ile
    1310                 1315                 1320

Lys Gly  Leu Asn Pro Thr Ala  Ile Phe Leu Thr Thr  Leu Ser Arg
    1325                 1330                 1335

Thr Ser  Lys Lys Arg Ser Trp  Pro Leu Asn Glu Ala  Ile Met Ala
    1340                 1345                 1350

Val Gly  Met Val Ser Ile Leu  Ala Ser Ser Leu Leu  Lys Asn Asp
    1355                 1360                 1365

Ile Pro  Met Thr Gly Pro Leu  Val Ala Gly Gly Leu  Leu Thr Val
    1370                 1375                 1380

Cys Tyr  Val Leu Thr Gly Arg  Ser Ala Asp Leu Glu  Leu Glu Arg
    1385                 1390                 1395

Ala Ala  Asp Val Lys Trp Glu  Asp Gln Ala Glu Ile  Ser Gly Ser
    1400                 1405                 1410

Ser Pro  Ile Leu Ser Ile Thr  Ile Ser Glu Asp Gly  Ser Met Ser
    1415                 1420                 1425

Ile Lys  Asn Glu Glu Glu Glu  Gln Thr Leu Thr Ile  Leu Ile Arg
    1430                 1435                 1440

Thr Gly  Leu Leu Val Ile Ser  Gly Leu Phe Pro Val  Ser Ile Pro
    1445                 1450                 1455

Ile Thr  Ala Ala Ala Trp Tyr  Leu Trp Glu Val Lys  Lys Gln Arg
    1460                 1465                 1470

Ala Gly  Val Leu Trp Asp Val  Pro Ser Pro Pro Pro  Met Gly Lys
    1475                 1480                 1485

Ala Glu  Leu Glu Asp Gly Ala  Tyr Arg Ile Lys Gln  Lys Gly Ile
    1490                 1495                 1500

Leu Gly  Tyr Ser Gln Ile Gly  Ala Gly Val Tyr Lys  Glu Gly Thr
    1505                 1510                 1515

Phe His  Thr Met Trp His Val  Thr Arg Gly Ala Val  Leu Met His
    1520                 1525                 1530

Lys Gly  Lys Arg Ile Glu Pro  Ser Trp Ala Asp Val  Lys Lys Asp
    1535                 1540                 1545

Leu Ile  Ser Tyr Gly Gly Gly  Trp Lys Leu Glu Gly  Glu Trp Lys
    1550                 1555                 1560

Glu Gly  Glu Glu Val Gln Val  Leu Ala Leu Glu Pro  Gly Lys Asn
    1565                 1570                 1575

Pro Arg  Ala Val Gln Thr Lys  Pro Gly Leu Phe Lys  Thr Asn Ala
    1580                 1585                 1590

Gly Thr  Ile Gly Ala Val Ser  Leu Asp Phe Ser Pro  Gly Thr Ser
    1595                 1600                 1605

Gly Ser  Pro Ile Ile Asp Lys  Lys Gly Lys Val Val  Gly Leu Tyr
    1610                 1615                 1620

Gly Asn  Gly Val Val Thr Arg  Ser Gly Ala Tyr Val  Ser Ala Ile
    1625                 1630                 1635

Ala Gln  Thr Glu Lys Ser Ile  Glu Asp Asn Pro Glu  Ile Glu Asp
    1640                 1645                 1650
```

-continued

```
Asp Ile  Phe Arg Lys Arg Arg  Leu Thr Ile Met Asp  Leu His Pro
    1655                 1660                 1665

Gly Ala  Gly Lys Thr Lys Arg  Tyr Leu Pro Ala Ile  Val Arg Glu
    1670                 1675                 1680

Ala Ile  Lys Arg Gly Leu Arg  Thr Leu Ile Leu Ala  Pro Thr Arg
    1685                 1690                 1695

Val Val  Ala Ala Glu Met Glu  Glu Ala Leu Arg Gly  Leu Pro Ile
    1700                 1705                 1710

Arg Tyr  Gln Thr Pro Ala Ile  Arg Ala Val His Thr  Gly Arg Glu
    1715                 1720                 1725

Ile Val  Asp Leu Met Cys His  Ala Thr Phe Thr Met  Arg Leu Leu
    1730                 1735                 1740

Ser Pro  Val Arg Val Pro Asn  Tyr Asn Leu Ile Ile  Met Asp Glu
    1745                 1750                 1755

Ala His  Phe Thr Asp Pro Ala  Ser Ile Ala Ala Arg  Gly Tyr Ile
    1760                 1765                 1770

Ser Thr  Arg Val Glu Met Gly  Glu Ala Ala Gly Ile  Phe Met Thr
    1775                 1780                 1785

Ala Thr  Pro Pro Gly Ser Arg  Asp Pro Phe Pro Gln  Ser Asn Ala
    1790                 1795                 1800

Pro Ile  Ile Asp Glu Glu Arg  Glu Ile Pro Glu Arg  Ser Trp Asn
    1805                 1810                 1815

Ser Gly  His Glu Trp Val Thr  Asp Phe Lys Gly Lys  Thr Val Trp
    1820                 1825                 1830

Phe Val  Pro Ser Ile Lys Ala  Gly Asn Asp Ile Ala  Ala Cys Leu
    1835                 1840                 1845

Arg Lys  Asn Gly Lys Lys Val  Ile Gln Leu Ser Arg  Lys Thr Phe
    1850                 1855                 1860

Asp Ser  Glu Tyr Val Lys Thr  Arg Thr Asn Asp Trp  Asp Phe Val
    1865                 1870                 1875

Val Thr  Thr Asp Ile Ser Glu  Met Gly Ala Asn Phe  Lys Ala Glu
    1880                 1885                 1890

Arg Val  Ile Asp Pro Arg Arg  Cys Met Lys Pro Val  Ile Leu Thr
    1895                 1900                 1905

Asp Gly  Glu Glu Arg Val Ile  Leu Ala Gly Pro Met  Pro Val Thr
    1910                 1915                 1920

His Ser  Ser Ala Ala Gln Arg  Arg Gly Arg Ile Gly  Arg Asn Pro
    1925                 1930                 1935

Lys Asn  Glu Asn Asp Gln Tyr  Ile Tyr Met Gly Glu  Pro Leu Glu
    1940                 1945                 1950

Asn Asp  Glu Asp Cys Ala His  Trp Lys Glu Ala Lys  Met Leu Leu
    1955                 1960                 1965

Asp Asn  Ile Asn Thr Pro Glu  Gly Ile Ile Pro Ser  Met Phe Glu
    1970                 1975                 1980

Pro Glu  Arg Glu Lys Val Asp  Ala Ile Asp Gly Glu  Tyr Arg Leu
    1985                 1990                 1995

Arg Gly  Glu Ala Arg Lys Thr  Phe Val Asp Leu Met  Arg Arg Gly
    2000                 2005                 2010

Asp Leu  Pro Val Trp Leu Ala  Tyr Arg Val Ala Ala  Glu Gly Ile
    2015                 2020                 2025

Asn Tyr  Ala Asp Arg Arg Trp  Cys Phe Asp Gly Val  Lys Asn Asn
    2030                 2035                 2040

Gln Ile  Leu Glu Glu Asn Val  Glu Val Glu Ile Trp  Thr Lys Glu
```

```
    2045                2050                2055

Gly Glu  Arg Lys Lys Leu Lys  Pro Arg Trp Leu Asp  Ala Arg Ile
    2060                2065                2070

Tyr Ser  Asp Pro Leu Ala Leu  Lys Glu Phe Lys Glu  Phe Ala Ala
    2075                2080                2085

Gly Arg  Lys Ser Leu Thr Leu  Asn Leu Ile Thr Glu  Met Gly Arg
    2090                2095                2100

Leu Pro  Thr Phe Met Thr Gln  Lys Ala Arg Asn Ala  Leu Asp Asn
    2105                2110                2115

Leu Ala  Val Leu His Thr Ala  Glu Ala Gly Gly Arg  Ala Tyr Asn
    2120                2125                2130

His Ala  Leu Ser Glu Leu Pro  Glu Thr Leu Glu Thr  Leu Leu Leu
    2135                2140                2145

Leu Thr  Leu Leu Ala Thr Val  Thr Gly Gly Ile Phe  Leu Phe Leu
    2150                2155                2160

Met Ser  Ala Arg Gly Ile Gly  Lys Met Thr Leu Gly  Met Cys Cys
    2165                2170                2175

Ile Ile  Thr Ala Ser Ile Leu  Leu Trp Tyr Ala Gln  Ile Gln Pro
    2180                2185                2190

His Trp  Ile Ala Ala Ser Ile  Ile Leu Glu Phe Phe  Leu Ile Val
    2195                2200                2205

Leu Leu  Ile Pro Glu Pro Glu  Lys Gln Arg Thr Pro  Gln Asp Asn
    2210                2215                2220

Gln Leu  Thr Tyr Val Val Ile  Ala Ile Leu Thr Val  Val Ala Ala
    2225                2230                2235

Thr Met  Ala Asn Glu Met Gly  Phe Leu Glu Lys Thr  Lys Lys Asp
    2240                2245                2250

Leu Gly  Leu Gly Ser Ile Ala  Thr Gln Gln Pro Glu  Ser Asn Ile
    2255                2260                2265

Leu Asp  Ile Asp Leu Arg Pro  Ala Ser Ala Trp Thr  Leu Tyr Ala
    2270                2275                2280

Val Ala  Thr Thr Phe Val Thr  Pro Met Leu Arg His  Ser Ile Glu
    2285                2290                2295

Asn Ser  Ser Val Asn Val Ser  Leu Thr Ala Ile Ala  Asn Gln Ala
    2300                2305                2310

Thr Val  Leu Met Gly Leu Gly  Lys Gly Trp Pro Leu  Ser Lys Met
    2315                2320                2325

Asp Ile  Gly Val Pro Leu Leu  Ala Ile Gly Cys Tyr  Ser Gln Val
    2330                2335                2340

Asn Pro  Ile Thr Leu Thr Ala  Ala Leu Phe Leu Leu  Val Ala His
    2345                2350                2355

Tyr Ala  Ile Ile Gly Pro Gly  Leu Gln Ala Lys Ala  Thr Arg Glu
    2360                2365                2370

Ala Gln  Lys Arg Ala Ala Ala  Gly Ile Met Lys Asn  Pro Thr Val
    2375                2380                2385

Asp Gly  Ile Thr Val Ile Asp  Leu Asp Pro Ile Pro  Tyr Asp Pro
    2390                2395                2400

Lys Phe  Glu Lys Gln Leu Gly  Gln Val Met Leu Leu  Val Leu Cys
    2405                2410                2415

Val Thr  Gln Val Leu Met Met  Arg Thr Thr Trp Ala  Leu Cys Glu
    2420                2425                2430

Ala Leu  Thr Leu Ala Thr Gly  Pro Ile Ser Thr Leu  Trp Glu Gly
    2435                2440                2445
```

-continued

Asn Pro Gly Arg Phe Trp Asn Thr Thr Ile Ala Val Ser Met Ala
2450 2455 2460

Asn Ile Phe Arg Gly Ser Tyr Leu Ala Gly Ala Gly Leu Leu Phe
2465 2470 2475

Ser Ile Met Lys Asn Thr Thr Asn Thr Arg Arg Gly Thr Gly Asn
2480 2485 2490

Ile Gly Glu Thr Leu Gly Glu Lys Trp Lys Ser Arg Leu Asn Ala
2495 2500 2505

Leu Gly Lys Ser Glu Phe Gln Ile Tyr Lys Lys Ser Gly Ile Gln
2510 2515 2520

Glu Val Asp Arg Thr Leu Ala Lys Glu Gly Ile Lys Arg Gly Glu
2525 2530 2535

Thr Asp His His Ala Val Ser Arg Gly Ser Ala Lys Leu Arg Trp
2540 2545 2550

Phe Val Glu Arg Asn Met Val Thr Pro Glu Gly Lys Val Val Asp
2555 2560 2565

Leu Gly Cys Gly Arg Gly Gly Trp Ser Tyr Tyr Cys Gly Gly Leu
2570 2575 2580

Lys Asn Val Arg Glu Val Lys Gly Leu Thr Lys Gly Gly Pro Gly
2585 2590 2595

His Glu Glu Pro Ile Pro Met Ser Thr Tyr Gly Trp Asn Leu Val
2600 2605 2610

Arg Leu Gln Ser Gly Val Asp Val Phe Phe Ile Pro Pro Glu Lys
2615 2620 2625

Cys Asp Thr Leu Leu Cys Asp Ile Gly Glu Ser Ser Pro Asn Pro
2630 2635 2640

Thr Val Glu Ala Gly Arg Thr Leu Arg Val Leu Asn Leu Val Glu
2645 2650 2655

Asn Trp Leu Asn Asn Asn Thr Gln Phe Cys Ile Lys Val Leu Asn
2660 2665 2670

Pro Tyr Met Pro Ser Val Ile Glu Lys Met Glu Ala Leu Gln Arg
2675 2680 2685

Lys Tyr Gly Gly Ala Leu Val Arg Asn Pro Leu Ser Arg Asn Ser
2690 2695 2700

Thr His Glu Met Tyr Trp Val Ser Asn Ala Ser Gly Asn Ile Val
2705 2710 2715

Ser Ser Val Asn Met Ile Ser Arg Met Leu Ile Asn Arg Phe Thr
2720 2725 2730

Met Arg Tyr Lys Lys Ala Thr Tyr Glu Pro Asp Val Asp Leu Gly
2735 2740 2745

Ser Gly Thr Arg Asn Ile Gly Ile Glu Ser Glu Ile Pro Asn Leu
2750 2755 2760

Asp Ile Ile Gly Lys Arg Ile Glu Lys Ile Lys Gln Glu His Glu
2765 2770 2775

Thr Ser Trp His Tyr Asp Gln Asp His Pro Tyr Lys Thr Trp Ala
2780 2785 2790

Tyr His Gly Ser Tyr Glu Thr Lys Gln Thr Gly Ser Ala Ser Ser
2795 2800 2805

Met Val Asn Gly Val Val Arg Leu Leu Thr Lys Pro Trp Asp Val
2810 2815 2820

Val Pro Met Val Thr Gln Met Ala Met Thr Asp Thr Thr Pro Phe
2825 2830 2835

-continued

Gly Gln Gln Arg Val Phe Lys Glu Lys Val Asp Thr Arg Thr Gln
2840 2845 2850

Glu Pro Lys Glu Gly Thr Lys Lys Leu Met Lys Ile Thr Ala Glu
2855 2860 2865

Trp Leu Trp Lys Glu Leu Gly Lys Lys Lys Thr Pro Arg Met Cys
2870 2875 2880

Thr Arg Glu Glu Phe Thr Arg Lys Val Arg Ser Asn Ala Ala Leu
2885 2890 2895

Gly Ala Ile Phe Thr Asp Glu Asn Lys Trp Lys Ser Ala Arg Glu
2900 2905 2910

Ala Val Glu Asp Ser Arg Phe Trp Glu Leu Val Asp Lys Glu Arg
2915 2920 2925

Asn Leu His Leu Glu Gly Lys Cys Glu Thr Cys Val Tyr Asn Met
2930 2935 2940

Met Gly Lys Arg Glu Lys Lys Leu Gly Glu Phe Gly Lys Ala Lys
2945 2950 2955

Gly Ser Arg Ala Ile Trp Tyr Met Trp Leu Gly Ala Arg Phe Leu
2960 2965 2970

Glu Phe Glu Ala Leu Gly Phe Leu Asn Glu Asp His Trp Phe Ser
2975 2980 2985

Arg Glu Asn Ser Leu Ser Gly Val Glu Gly Glu Gly Leu His Lys
2990 2995 3000

Leu Gly Tyr Ile Leu Arg Asp Val Ser Lys Lys Glu Gly Gly Ala
3005 3010 3015

Met Tyr Ala Asp Asp Thr Ala Gly Trp Asp Thr Arg Ile Thr Leu
3020 3025 3030

Glu Asp Leu Lys Asn Glu Glu Met Val Thr Asn His Met Glu Gly
3035 3040 3045

Glu His Lys Lys Leu Ala Glu Ala Ile Phe Lys Leu Thr Tyr Gln
3050 3055 3060

Asn Lys Val Val Arg Val Gln Arg Pro Thr Pro Arg Gly Thr Val
3065 3070 3075

Met Asp Ile Ile Ser Arg Arg Asp Gln Arg Gly Ser Gly Gln Val
3080 3085 3090

Gly Thr Tyr Gly Leu Asn Thr Phe Thr Asn Met Glu Ala Gln Leu
3095 3100 3105

Ile Arg Gln Met Glu Gly Glu Gly Val Phe Lys Ser Ile Gln His
3110 3115 3120

Leu Thr Ile Thr Glu Glu Ile Ala Val Gln Asn Trp Leu Ala Arg
3125 3130 3135

Val Gly Arg Glu Arg Leu Ser Arg Met Ala Ile Ser Gly Asp Asp
3140 3145 3150

Cys Val Val Lys Pro Leu Asp Asp Arg Phe Ala Ser Ala Leu Thr
3155 3160 3165

Ala Leu Asn Asp Met Gly Lys Ile Arg Lys Asp Ile Gln Gln Trp
3170 3175 3180

Glu Pro Ser Arg Gly Trp Asn Asp Trp Thr Gln Val Pro Phe Cys
3185 3190 3195

Ser His His Phe His Glu Leu Ile Met Lys Asp Gly Arg Val Leu
3200 3205 3210

Val Val Pro Cys Arg Asn Gln Asp Glu Leu Ile Gly Arg Ala Arg
3215 3220 3225

Ile Ser Gln Gly Ala Gly Trp Ser Leu Arg Glu Thr Ala Cys Leu 3230                3235                3240

Gly Lys  Ser Tyr Ala Gln Met  Trp Ser Leu Met Tyr  Phe His Arg
    3245                3250                3255

Arg Asp  Leu Arg Leu Ala Ala  Asn Ala Ile Cys Ser  Ala Val Pro
    3260                3265                3270

Ser His  Trp Val Pro Thr Ser  Arg Thr Thr Trp Ser  Ile His Ala
    3275                3280                3285

Lys His  Glu Trp Met Thr Thr  Glu Asp Met Leu Thr  Val Trp Asn
    3290                3295                3300

Arg Val  Trp Ile Gln Glu Asn  Pro Trp Met Glu Asp  Lys Thr Pro
    3305                3310                3315

Val Glu  Ser Trp Glu Glu Ile  Pro Tyr Leu Gly Lys  Arg Glu Asp
    3320                3325                3330

Gln Trp  Cys Gly Ser Leu Ile  Gly Leu Thr Ser Arg  Ala Thr Trp
    3335                3340                3345

Ala Lys  Asn Ile Gln Ala Ala  Ile Asn Gln Val Arg  Ser Leu Ile
    3350                3355                3360

Gly Asn  Glu Glu Tyr Thr Asp  Tyr Met Pro Ser Met  Lys Arg Phe
    3365                3370                3375

Arg Arg  Glu Glu Glu Glu Ala  Gly Val Leu Trp
    3380                3385

<210> SEQ ID NO 9
<211> LENGTH: 3389
<212> TYPE: PRT
<213> ORGANISM: Artificial Sequence
<220> FEATURE:
<223> OTHER INFORMATION: Dengue virus serotype 3, MVS

<400> SEQUENCE: 9

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asp Gly Glu Pro Arg Met Ile Val
        115                 120                 125

Gly Lys Asn Glu Arg Gly Lys Ser Leu Leu Phe Lys Thr Ala Ser Gly
    130                 135                 140

Ile Asn Met Cys Thr Leu Ile Ala Met Asp Leu Gly Glu Met Cys Asp
145                 150                 155                 160

Asp Thr Val Thr Tyr Lys Cys Pro His Ile Thr Glu Val Glu Pro Glu
                165                 170                 175

Asp Ile Asp Cys Trp Cys Asn Leu Thr Ser Thr Trp Val Thr Tyr Gly
            180                 185                 190

Thr Cys Asn Gln Ala Gly Glu His Arg Arg Asp Lys Arg Ser Val Ala

-continued

```
        195                 200                 205

Leu Ala Pro His Val Gly Met Gly Leu Asp Thr Arg Thr Gln Thr Trp
    210                 215                 220

Met Ser Ala Glu Gly Ala Trp Arg Gln Val Glu Lys Val Glu Thr Trp
225                 230                 235                 240

Ala Leu Arg His Pro Gly Phe Thr Ile Leu Ala Leu Phe Leu Ala His
                245                 250                 255

Tyr Ile Gly Thr Ser Leu Thr Gln Lys Val Val Ile Phe Ile Leu Leu
            260                 265                 270

Met Leu Val Thr Pro Ser Met Thr Met Arg Cys Val Gly Val Gly Asn
        275                 280                 285

Arg Asp Phe Val Glu Gly Leu Ser Gly Ala Thr Trp Val Asp Val Val
    290                 295                 300

Leu Glu His Gly Gly Cys Val Thr Thr Met Ala Lys Asn Lys Pro Thr
305                 310                 315                 320

Leu Asp Ile Glu Leu Gln Lys Thr Glu Ala Thr Gln Leu Ala Thr Leu
                325                 330                 335

Arg Lys Leu Cys Ile Glu Gly Lys Ile Thr Asn Ile Thr Thr Asp Ser
            340                 345                 350

Arg Cys Pro Thr Gln Gly Glu Ala Ile Leu Pro Glu Glu Gln Asp Gln
        355                 360                 365

Asn Tyr Val Cys Lys His Thr Tyr Val Asp Arg Gly Trp Gly Asn Gly
    370                 375                 380

Cys Gly Leu Phe Gly Lys Gly Ser Leu Val Thr Cys Ala Lys Phe Gln
385                 390                 395                 400

Cys Leu Glu Ser Ile Glu Gly Lys Val Val Gln His Glu Asn Leu Lys
                405                 410                 415

Tyr Thr Val Ile Ile Thr Val His Thr Gly Asp Gln His Gln Val Gly
            420                 425                 430

Asn Glu Thr Gln Gly Val Thr Ala Glu Ile Thr Pro Gln Ala Ser Thr
        435                 440                 445

Ala Glu Ala Ile Leu Pro Glu Tyr Gly Thr Leu Gly Leu Glu Cys Ser
    450                 455                 460

Pro Arg Thr Gly Leu Asp Phe Asn Glu Met Ile Ser Leu Thr Met Lys
465                 470                 475                 480

Asn Lys Ala Trp Met Val His Arg Gln Trp Phe Phe Asp Leu Pro Leu
                485                 490                 495

Pro Trp Thr Ser Gly Ala Ser Ala Glu Thr Pro Thr Trp Asn Arg Lys
            500                 505                 510

Glu Leu Leu Val Thr Phe Lys Asn Ala His Ala Lys Lys Gln Glu Val
        515                 520                 525

Val Val Leu Gly Ser Gln Glu Gly Ala Met His Thr Ala Leu Thr Gly
    530                 535                 540

Ala Thr Glu Ile Gln Thr Ser Gly Gly Thr Ser Ile Phe Ala Gly His
545                 550                 555                 560

Leu Lys Cys Arg Leu Lys Met Asp Lys Leu Glu Leu Lys Gly Met Ser
                565                 570                 575

Tyr Ala Met Cys Leu Ser Ser Phe Val Leu Lys Lys Glu Val Ser Glu
            580                 585                 590

Thr Gln His Gly Thr Ile Leu Ile Lys Val Glu Tyr Lys Gly Glu Asp
        595                 600                 605

Ala Pro Cys Lys Ile Pro Phe Ser Thr Glu Asp Gly Gln Gly Lys Ala
    610                 615                 620
```

-continued

```
Leu Asn Gly Arg Leu Ile Thr Ala Asn Pro Val Val Thr Lys Lys Glu
625                 630                 635                 640

Glu Pro Val Asn Ile Glu Ala Glu Pro Pro Phe Gly Glu Ser Asn Ile
                645                 650                 655

Val Ile Gly Ile Gly Asp Lys Ala Leu Lys Ile Asn Trp Tyr Lys Lys
            660                 665                 670

Gly Ser Ser Ile Gly Lys Met Phe Glu Ala Thr Ala Arg Gly Ala Arg
        675                 680                 685

Arg Met Ala Ile Leu Gly Asp Thr Ala Trp Asp Phe Gly Ser Val Gly
    690                 695                 700

Gly Val Leu Asn Ser Leu Gly Lys Met Val His Gln Ile Phe Gly Ser
705                 710                 715                 720

Ala Tyr Thr Ala Leu Phe Gly Gly Val Ser Trp Met Met Lys Ile Gly
                725                 730                 735

Ile Gly Val Leu Leu Thr Trp Ile Gly Leu Asn Ser Lys Asn Thr Ser
            740                 745                 750

Met Ser Phe Ser Cys Ile Ala Ala Gly Ile Val Thr Leu Tyr Leu Gly
        755                 760                 765

Val Met Val Gln Ala Asp Ser Gly Cys Val Val Ser Trp Lys Asn Lys
    770                 775                 780

Glu Leu Lys Cys Gly Ser Gly Ile Phe Ile Thr Asp Asn Val His Thr
785                 790                 795                 800

Trp Thr Glu Gln Tyr Lys Phe Gln Pro Glu Ser Pro Ser Lys Leu Ala
                805                 810                 815

Ser Ala Ile Gln Lys Ala His Glu Glu Asp Ile Cys Gly Ile Arg Ser
            820                 825                 830

Val Thr Arg Leu Glu Asn Leu Met Trp Lys Gln Ile Thr Pro Glu Leu
        835                 840                 845

Asn His Ile Leu Ser Glu Asn Glu Val Lys Leu Thr Ile Met Thr Gly
    850                 855                 860

Asp Ile Lys Gly Ile Met Gln Ala Gly Lys Arg Ser Leu Arg Pro Gln
865                 870                 875                 880

Pro Thr Glu Leu Lys Tyr Ser Trp Lys Thr Trp Gly Lys Ala Lys Met
                885                 890                 895

Leu Ser Thr Glu Ser His Asn Gln Thr Phe Leu Ile Asp Gly Pro Glu
            900                 905                 910

Thr Ala Glu Cys Pro Asn Thr Asn Arg Ala Trp Asn Ser Leu Glu Val
        915                 920                 925

Glu Asp Tyr Gly Phe Gly Val Phe Thr Thr Asn Ile Trp Leu Lys Leu
    930                 935                 940

Lys Glu Lys Gln Asp Val Phe Cys Asp Ser Lys Leu Met Ser Ala Ala
945                 950                 955                 960

Ile Lys Asp Asn Arg Ala Val His Ala Asp Met Gly Tyr Trp Ile Glu
                965                 970                 975

Ser Ala Leu Asn Asp Thr Trp Lys Ile Glu Lys Ala Ser Phe Ile Glu
            980                 985                 990

Val Lys Asn Cys His Trp Pro Lys  Ser His Thr Leu Trp  Ser Asn Gly
        995                 1000                1005

Val Leu  Glu Ser Glu Met Ile  Ile Pro Lys Asn Leu  Ala Gly Pro
    1010                1015                1020

Val Ser  Gln His Asn Tyr Arg  Pro Gly Tyr His Thr  Gln Ile Thr
    1025                1030                1035
```

-continued

```
Gly Pro  Trp His Leu Gly Lys  Leu Glu Met Asp Phe  Asp Phe Cys
    1040                 1045                 1050

Asp Gly  Thr Thr Val Val Val  Thr Glu Asp Cys Gly  Asn Arg Gly
    1055                 1060                 1065

Pro Ser  Leu Arg Thr Thr Thr  Ala Ser Gly Lys Leu  Ile Thr Glu
    1070                 1075                 1080

Trp Cys  Cys Arg Ser Cys Thr  Leu Pro Pro Leu Arg  Tyr Arg Gly
    1085                 1090                 1095

Glu Asp  Gly Cys Trp Tyr Gly  Met Glu Ile Arg Pro  Leu Lys Glu
    1100                 1105                 1110

Lys Glu  Glu Asn Leu Val Asn  Ser Leu Val Thr Ala  Gly His Gly
    1115                 1120                 1125

Gln Val  Asp Asn Phe Ser Leu  Gly Val Leu Gly Met  Ala Leu Phe
    1130                 1135                 1140

Leu Glu  Glu Met Leu Arg Thr  Arg Val Gly Thr Lys  His Ala Ile
    1145                 1150                 1155

Leu Leu  Val Ala Val Ser Phe  Val Thr Leu Ile Thr  Gly Asn Met
    1160                 1165                 1170

Ser Phe  Arg Asp Leu Gly Arg  Val Met Val Met Val  Gly Ala Thr
    1175                 1180                 1185

Met Thr  Asp Asp Ile Gly Met  Gly Val Thr Tyr Leu  Ala Leu Leu
    1190                 1195                 1200

Ala Ala  Phe Lys Val Arg Pro  Thr Phe Ala Ala Gly  Leu Leu Leu
    1205                 1210                 1215

Arg Lys  Leu Thr Ser Lys Glu  Leu Met Met Thr Thr  Ile Gly Ile
    1220                 1225                 1230

Val Leu  Leu Ser Gln Ser Thr  Ile Pro Glu Thr Ile  Leu Glu Leu
    1235                 1240                 1245

Thr Asp  Ala Leu Ala Leu Gly  Met Met Val Leu Lys  Met Val Arg
    1250                 1255                 1260

Asn Met  Glu Lys Tyr Gln Leu  Ala Val Thr Ile Met  Ala Ile Leu
    1265                 1270                 1275

Cys Val  Pro Asn Ala Val Ile  Leu Gln Asn Ala Trp  Lys Val Ser
    1280                 1285                 1290

Cys Thr  Ile Leu Ala Val Val  Ser Val Ser Pro Leu  Phe Leu Thr
    1295                 1300                 1305

Ser Ser  Gln Gln Lys Thr Asp  Trp Ile Pro Leu Ala  Leu Thr Ile
    1310                 1315                 1320

Lys Gly  Leu Asn Pro Thr Ala  Ile Phe Leu Thr Thr  Leu Ser Arg
    1325                 1330                 1335

Thr Ser  Lys Lys Arg Ser Trp  Pro Leu Asn Glu Ala  Ile Met Ala
    1340                 1345                 1350

Val Gly  Met Val Ser Ile Leu  Ala Ser Ser Leu Leu  Lys Asn Asp
    1355                 1360                 1365

Ile Pro  Met Thr Gly Pro Leu  Val Ala Gly Gly Leu  Leu Thr Val
    1370                 1375                 1380

Cys Tyr  Val Leu Thr Gly Arg  Ser Ala Asp Leu Glu  Leu Glu Arg
    1385                 1390                 1395

Ala Ala  Asp Val Lys Trp Glu  Asp Gln Ala Glu Ile  Ser Gly Ser
    1400                 1405                 1410

Ser Pro  Ile Leu Ser Ile Thr  Ile Ser Glu Asp Gly  Ser Met Ser
    1415                 1420                 1425

Ile Lys  Asn Glu Glu Glu Glu  Gln Thr Leu Thr Ile  Leu Ile Arg
```

1430 1435 1440

Thr Gly Leu Leu Val Ile Ser Gly Leu Phe Pro Val Ser Ile Pro
1445 1450 1455

Ile Thr Ala Ala Ala Trp Tyr Leu Trp Glu Val Lys Lys Gln Arg
1460 1465 1470

Ala Gly Val Leu Trp Asp Val Pro Ser Pro Pro Pro Met Gly Lys
1475 1480 1485

Ala Glu Leu Glu Asp Gly Ala Tyr Arg Ile Lys Gln Lys Gly Ile
1490 1495 1500

Leu Gly Tyr Ser Gln Ile Gly Ala Gly Val Tyr Lys Glu Gly Thr
1505 1510 1515

Phe His Thr Met Trp His Val Thr Arg Gly Ala Val Leu Met His
1520 1525 1530

Lys Gly Lys Arg Ile Glu Pro Ser Trp Ala Asp Val Lys Lys Asp
1535 1540 1545

Leu Ile Ser Tyr Gly Gly Gly Trp Lys Leu Glu Gly Glu Trp Lys
1550 1555 1560

Glu Gly Glu Glu Val Gln Val Leu Ala Leu Glu Pro Gly Lys Asn
1565 1570 1575

Pro Arg Ala Val Gln Thr Lys Pro Gly Leu Phe Lys Thr Asn Ala
1580 1585 1590

Gly Thr Ile Gly Ala Val Ser Leu Asp Phe Ser Pro Gly Thr Ser
1595 1600 1605

Gly Ser Pro Ile Ile Asp Lys Lys Gly Lys Val Val Gly Leu Tyr
1610 1615 1620

Gly Asn Gly Val Val Thr Arg Ser Gly Ala Tyr Val Ser Ala Ile
1625 1630 1635

Ala Gln Thr Glu Lys Ser Ile Glu Asp Asn Pro Glu Ile Glu Asp
1640 1645 1650

Asp Ile Phe Arg Lys Arg Arg Leu Thr Ile Met Asp Leu His Pro
1655 1660 1665

Gly Ala Gly Lys Thr Lys Arg Tyr Leu Pro Ala Ile Val Arg Glu
1670 1675 1680

Ala Ile Lys Arg Gly Leu Arg Thr Leu Ile Leu Ala Pro Thr Arg
1685 1690 1695

Val Val Ala Ala Glu Met Glu Glu Ala Leu Arg Gly Leu Pro Ile
1700 1705 1710

Arg Tyr Gln Thr Pro Ala Ile Arg Ala Val His Thr Gly Arg Glu
1715 1720 1725

Ile Val Asp Leu Met Cys His Ala Thr Phe Thr Met Arg Leu Leu
1730 1735 1740

Ser Pro Val Arg Val Pro Asn Tyr Asn Leu Ile Ile Met Asp Glu
1745 1750 1755

Ala His Phe Thr Asp Pro Ala Ser Ile Ala Ala Arg Gly Tyr Ile
1760 1765 1770

Ser Thr Arg Val Glu Met Gly Glu Ala Ala Gly Ile Phe Met Thr
1775 1780 1785

Ala Thr Pro Pro Gly Ser Arg Asp Pro Phe Pro Gln Ser Asn Ala
1790 1795 1800

Pro Ile Ile Asp Glu Glu Arg Glu Ile Pro Glu Arg Ser Trp Asn
1805 1810 1815

Ser Gly His Glu Trp Val Thr Asp Phe Lys Gly Lys Thr Val Trp
1820 1825 1830

Phe Val Pro Ser Ile Lys Ala Gly Asn Asp Ile Ala Ala Cys Leu
1835 1840 1845

Arg Lys Asn Gly Lys Lys Val Ile Gln Leu Ser Arg Lys Thr Phe
1850 1855 1860

Asp Ser Glu Tyr Val Lys Thr Arg Thr Asn Asp Trp Asp Phe Val
1865 1870 1875

Val Thr Thr Asp Ile Ser Glu Met Gly Ala Asn Phe Lys Ala Glu
1880 1885 1890

Arg Val Ile Asp Pro Arg Arg Cys Met Lys Pro Val Ile Leu Thr
1895 1900 1905

Asp Gly Glu Glu Arg Val Ile Leu Ala Gly Pro Met Pro Val Thr
1910 1915 1920

His Ser Ser Ala Ala Gln Arg Arg Gly Arg Ile Gly Arg Asn Pro
1925 1930 1935

Lys Asn Glu Asn Asp Gln Tyr Ile Tyr Met Gly Glu Pro Leu Glu
1940 1945 1950

Asn Asp Glu Asp Cys Ala His Trp Lys Glu Ala Lys Met Leu Leu
1955 1960 1965

Asp Asn Ile Asn Thr Pro Glu Gly Ile Ile Pro Ser Met Phe Glu
1970 1975 1980

Pro Glu Arg Glu Lys Val Asp Ala Ile Asp Gly Glu Tyr Arg Leu
1985 1990 1995

Arg Gly Glu Ala Arg Lys Thr Phe Val Asp Leu Met Arg Arg Gly
2000 2005 2010

Asp Leu Pro Val Trp Leu Ala Tyr Arg Val Ala Ala Glu Gly Ile
2015 2020 2025

Asn Tyr Ala Asp Arg Arg Trp Cys Phe Asp Gly Val Lys Asn Asn
2030 2035 2040

Gln Ile Leu Glu Glu Asn Val Glu Val Glu Ile Trp Thr Lys Glu
2045 2050 2055

Gly Glu Arg Lys Lys Leu Lys Pro Arg Trp Leu Asp Ala Arg Ile
2060 2065 2070

Tyr Ser Asp Pro Leu Ala Leu Lys Glu Phe Lys Glu Phe Ala Ala
2075 2080 2085

Gly Arg Lys Ser Leu Thr Leu Asn Leu Ile Thr Glu Met Gly Arg
2090 2095 2100

Leu Pro Thr Phe Met Thr Gln Lys Ala Arg Asp Ala Leu Asp Asn
2105 2110 2115

Leu Ala Val Leu His Thr Ala Glu Ala Gly Gly Arg Ala Tyr Asn
2120 2125 2130

His Ala Leu Ser Glu Leu Pro Glu Thr Leu Glu Thr Leu Leu Leu
2135 2140 2145

Leu Thr Leu Leu Ala Thr Val Thr Gly Gly Ile Phe Leu Phe Leu
2150 2155 2160

Met Ser Ala Arg Gly Ile Gly Lys Met Thr Leu Gly Met Cys Cys
2165 2170 2175

Ile Ile Thr Ala Ser Ile Leu Leu Trp Tyr Ala Gln Ile Gln Pro
2180 2185 2190

His Trp Ile Ala Ala Ser Ile Ile Leu Glu Phe Phe Leu Ile Val
2195 2200 2205

Leu Leu Ile Pro Glu Pro Glu Lys Gln Arg Thr Pro Gln Asp Asn
2210 2215 2220

-continued

```
Gln Leu  Thr Tyr Val Val Ile  Ala Ile Leu Thr Val  Val Ala Ala
    2225                 2230                 2235

Thr Met  Ala Asn Glu Met Gly  Phe Leu Glu Lys Thr  Lys Lys Asp
    2240                 2245                 2250

Leu Gly  Leu Gly Ser Ile Ala  Thr Gln Gln Pro Glu  Ser Asn Ile
    2255                 2260                 2265

Leu Asp  Ile Asp Leu Arg Pro  Ala Ser Ala Trp Thr  Leu Tyr Ala
    2270                 2275                 2280

Val Ala  Thr Thr Phe Val Thr  Pro Met Leu Arg His  Ser Ile Glu
    2285                 2290                 2295

Asn Ser  Ser Val Asn Val Ser  Leu Thr Ala Ile Ala  Asn Gln Ala
    2300                 2305                 2310

Thr Val  Leu Met Gly Leu Gly  Lys Gly Trp Pro Leu  Ser Lys Met
    2315                 2320                 2325

Asp Ile  Gly Val Pro Leu Leu  Ala Ile Gly Cys Tyr  Ser Gln Val
    2330                 2335                 2340

Asn Pro  Ile Thr Leu Thr Ala  Ala Leu Phe Leu Leu  Val Ala His
    2345                 2350                 2355

Tyr Ala  Ile Ile Gly Pro Gly  Leu Gln Ala Lys Ala  Thr Arg Glu
    2360                 2365                 2370

Ala Gln  Lys Arg Ala Ala Ala  Gly Ile Met Lys Asn  Pro Thr Val
    2375                 2380                 2385

Asp Gly  Ile Thr Val Ile Asp  Leu Asp Pro Ile Pro  Tyr Asp Pro
    2390                 2395                 2400

Lys Phe  Glu Lys Gln Leu Gly  Gln Val Met Leu Leu  Val Leu Cys
    2405                 2410                 2415

Val Thr  Gln Val Leu Met Met  Arg Thr Thr Trp Ala  Leu Cys Glu
    2420                 2425                 2430

Ala Leu  Thr Leu Ala Thr Gly  Pro Ile Ser Thr Leu  Trp Glu Gly
    2435                 2440                 2445

Asn Pro  Gly Arg Phe Trp Asn  Thr Thr Ile Ala Val  Ser Met Ala
    2450                 2455                 2460

Asn Ile  Phe Arg Gly Ser Tyr  Leu Ala Gly Ala Gly  Leu Leu Phe
    2465                 2470                 2475

Ser Ile  Met Lys Asn Thr Thr  Asn Thr Arg Arg Gly  Thr Gly Asn
    2480                 2485                 2490

Ile Gly  Glu Thr Leu Gly Glu  Lys Trp Lys Ser Arg  Leu Asn Ala
    2495                 2500                 2505

Leu Gly  Lys Ser Glu Phe Gln  Ile Tyr Lys Lys Ser  Gly Ile Gln
    2510                 2515                 2520

Glu Val  Asp Arg Thr Leu Ala  Lys Glu Gly Ile Lys  Arg Gly Glu
    2525                 2530                 2535

Thr Asp  His His Ala Val Ser  Arg Gly Ser Ala Lys  Leu Arg Trp
    2540                 2545                 2550

Phe Val  Glu Arg Asn Met Val  Thr Pro Glu Gly Lys  Val Val Asp
    2555                 2560                 2565

Leu Gly  Cys Gly Arg Gly Gly  Trp Ser Tyr Tyr Cys  Gly Gly Leu
    2570                 2575                 2580

Lys Asn  Val Arg Glu Val Lys  Gly Leu Thr Lys Gly  Gly Pro Gly
    2585                 2590                 2595

His Glu  Glu Pro Ile Pro Met  Ser Thr Tyr Gly Trp  Asn Leu Val
    2600                 2605                 2610

Arg Leu  Gln Ser Gly Val Asp  Val Phe Phe Ile Pro  Pro Glu Lys
```

-continued 2615 2620 2625

Cys Asp Thr Leu Leu Cys Asp Ile Gly Glu Ser Ser Pro Asn Pro
2630 2635 2640

Thr Val Glu Ala Gly Arg Thr Leu Arg Val Leu Asn Leu Val Glu
2645 2650 2655

Asn Trp Leu Asn Asn Asn Thr Gln Phe Cys Ile Lys Val Leu Asn
2660 2665 2670

Pro Tyr Met Pro Ser Val Ile Glu Lys Met Glu Ala Leu Gln Arg
2675 2680 2685

Lys Tyr Gly Gly Ala Leu Val Arg Asn Pro Leu Ser Arg Asn Ser
2690 2695 2700

Thr His Glu Met Tyr Trp Val Ser Asn Ala Ser Gly Asn Ile Val
2705 2710 2715

Ser Ser Val Asn Met Ile Ser Arg Met Leu Ile Asn Arg Phe Thr
2720 2725 2730

Met Arg Tyr Lys Lys Ala Thr Tyr Glu Pro Asp Val Asp Leu Gly
2735 2740 2745

Ser Gly Thr Arg Asn Ile Gly Ile Glu Ser Glu Ile Pro Asn Leu
2750 2755 2760

Asp Ile Ile Gly Lys Arg Ile Glu Lys Ile Lys Gln Glu His Glu
2765 2770 2775

Thr Ser Trp His Tyr Asp Gln Asp His Pro Tyr Lys Thr Trp Ala
2780 2785 2790

Tyr His Gly Ser Tyr Glu Thr Lys Gln Thr Gly Ser Ala Ser Ser
2795 2800 2805

Met Val Asn Gly Val Val Arg Leu Leu Thr Lys Pro Trp Asp Val
2810 2815 2820

Val Pro Met Val Thr Gln Met Ala Met Thr Asp Thr Thr Pro Phe
2825 2830 2835

Gly Gln Gln Arg Val Phe Lys Glu Lys Val Asp Thr Arg Thr Gln
2840 2845 2850

Glu Pro Lys Glu Gly Thr Lys Lys Leu Met Lys Ile Thr Ala Glu
2855 2860 2865

Trp Leu Trp Lys Glu Leu Gly Lys Lys Lys Thr Pro Arg Met Cys
2870 2875 2880

Thr Arg Glu Glu Phe Thr Arg Lys Val Arg Ser Asn Ala Ala Leu
2885 2890 2895

Gly Ala Ile Phe Thr Asp Glu Asn Lys Trp Lys Ser Ala Arg Glu
2900 2905 2910

Ala Val Glu Asp Ser Arg Phe Trp Glu Leu Val Asp Lys Glu Arg
2915 2920 2925

Asn Leu His Leu Glu Gly Lys Cys Glu Thr Cys Val Tyr Asn Met
2930 2935 2940

Met Gly Lys Arg Glu Lys Lys Leu Gly Glu Phe Gly Lys Ala Lys
2945 2950 2955

Gly Ser Arg Ala Ile Trp Tyr Met Trp Leu Gly Ala Arg Phe Leu
2960 2965 2970

Glu Phe Glu Ala Leu Gly Phe Leu Asn Glu Asp His Trp Phe Ser
2975 2980 2985

Arg Glu Asn Ser Leu Ser Gly Val Glu Gly Glu Gly Leu His Lys
2990 2995 3000

Leu Gly Tyr Ile Leu Arg Asp Val Ser Lys Lys Glu Gly Gly Ala
3005 3010 3015

```
Met Tyr Ala Asp Asp Thr Ala Gly Trp Asp Thr Arg Ile Thr Leu
    3020                3025                3030

Glu Asp Leu Lys Asn Glu Glu Met Val Thr Asn His Met Glu Gly
    3035                3040                3045

Glu His Lys Lys Leu Ala Glu Ala Ile Phe Lys Leu Thr Tyr Gln
    3050                3055                3060

Asn Lys Val Val Arg Val Gln Arg Pro Thr Pro Arg Gly Thr Val
    3065                3070                3075

Met Asp Ile Ile Ser Arg Arg Asp Gln Arg Gly Ser Gly Gln Val
    3080                3085                3090

Gly Thr Tyr Gly Leu Asn Thr Phe Thr Asn Met Glu Ala Gln Leu
    3095                3100                3105

Ile Arg Gln Met Glu Gly Glu Gly Val Phe Lys Ser Ile Gln His
    3110                3115                3120

Leu Thr Ile Thr Glu Glu Ile Ala Val Gln Asn Trp Leu Ala Arg
    3125                3130                3135

Val Gly Arg Glu Arg Leu Ser Arg Met Ala Ile Ser Gly Asp Asp
    3140                3145                3150

Cys Val Val Lys Pro Leu Asp Asp Arg Phe Ala Ser Ala Leu Thr
    3155                3160                3165

Ala Leu Asn Asp Met Gly Lys Ile Arg Lys Asp Ile Gln Gln Trp
    3170                3175                3180

Glu Pro Ser Arg Gly Trp Asn Asp Trp Thr Gln Val Pro Phe Cys
    3185                3190                3195

Ser His His Phe His Glu Leu Ile Met Lys Asp Gly Arg Val Leu
    3200                3205                3210

Val Val Pro Cys Arg Asn Gln Asp Glu Leu Ile Gly Arg Ala Arg
    3215                3220                3225

Ile Ser Gln Gly Ala Gly Trp Ser Leu Arg Glu Thr Ala Cys Leu
    3230                3235                3240

Gly Lys Ser Tyr Ala Gln Met Trp Ser Leu Met Tyr Phe His Arg
    3245                3250                3255

Arg Asp Leu Arg Leu Ala Ala Asn Ala Ile Cys Ser Ala Val Pro
    3260                3265                3270

Ser His Trp Val Pro Thr Ser Arg Thr Thr Trp Ser Ile His Ala
    3275                3280                3285

Lys His Glu Trp Met Thr Thr Glu Asp Met Leu Thr Val Trp Asn
    3290                3295                3300

Arg Val Trp Ile Gln Glu Asn Pro Trp Met Glu Asp Lys Thr Pro
    3305                3310                3315

Val Glu Ser Trp Glu Glu Ile Pro Tyr Leu Gly Lys Arg Glu Asp
    3320                3325                3330

Gln Trp Cys Gly Ser Leu Ile Gly Leu Thr Ser Arg Ala Thr Trp
    3335                3340                3345

Ala Lys Asn Ile Gln Ala Ala Ile Asn Gln Val Arg Ser Leu Ile
    3350                3355                3360

Gly Asn Glu Glu Tyr Thr Asp Tyr Met Pro Ser Met Lys Arg Phe
    3365                3370                3375

Arg Arg Glu Glu Glu Glu Ala Gly Val Leu Trp
    3380                3385
```

<210> SEQ ID NO 10
<211> LENGTH: 10723

<212> TYPE: DNA
<213> ORGANISM: Artificial Sequence
<220> FEATURE:
<223> OTHER INFORMATION: Dengue virus serotype 4, BVS
<220> FEATURE:
<221> NAME/KEY: n
<222> LOCATION: (3773)..(3773)
<223> OTHER INFORMATION: a or g
<220> FEATURE:
<221> NAME/KEY: n
<222> LOCATION: (7026)..(7026)
<223> OTHER INFORMATION: t or c
<220> FEATURE:
<221> NAME/KEY: n
<222> LOCATION: (7538)..(7538)
<223> OTHER INFORMATION: t or c

<400> SEQUENCE: 10

```
agttgttagt ctacgtggac cgacaaagac agattctttg agggagctaa gctcaatgta     60
gttctaacag tttttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg cagggacgag gacctttaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagctctg caggcatgat cattatgctg    420
attccaacag tgatggcgtt ccatttaacc acgcgtgatg gcgaacccct catgatagtg    480
gcaaaacatg aaagggggag acctctcttg tttaagacaa cagaggggat caacaaatgc    540
actctcattg ccatggactt gggtgaaatg tgtgaggaca ctgtcacgta taaatgcccc    600
ttactggtca ataccgaacc tgaagacatt gattgctggt gcaatctcac gtctacctgg    660
gtcatgtatg ggacatgcac ccagagcgga gaacggagac gagagaagcg ctcagtagct    720
ttaacaccac attcaggaat gggattggaa acaagagctg agacatggat gtcatcggaa    780
ggggcttgga agcatgctca gagagtagag agctggatac tcagaaaccc aggattcgcg    840
ctcttggcag gatttatggc ttatatgatt gggcaaacag gaatccagcg aactgtcttc    900
tttgtcctaa tgatgctggt cgccccatcc tacggaatgc gatgcgtagg agtaggaaac    960
agagactttg tggaaggagt ctcaggtgga gcatgggtcg atctggtgct agaacatgga   1020
ggatgcgtca caaccatggc ccagggaaaa ccaaccttgg attttgaact gactaagaca   1080
acagccaagg aagtggctct gttaagaacc tattgcattg aagcctcaat atcaaacata   1140
accacggcaa caagatgtcc aacgcaagga gagccttatc taaaagagga acaagaccaa   1200
cagtacattt gccggagaga tgtggtagac agagggtggg gcaatggctg tggcttgttt   1260
ggaaaaggag gagttgtgac atgtgcgaag ttttcatgtt cggggaagat aacaggcaat   1320
ttggtccaaa ttgagaacct tgaatacaca gtggttgtaa cagtccacaa tggagacacc   1380
catgcagtag gaaatgacac gtccaatcat ggagttacag ccacgataac tcccaggtca   1440
ccatcggtgg aagtcaaatt gccggactat ggagaactaa cactcgattg tgaacccagg   1500
tctggaattg actttaatga gatgattctg atgaaaatga aaaagaaaac atggcttgtg   1560
cataagcaat ggtttttgga tctacctcta ccatggacag caggagcaga cacatcagag   1620
gttcactgga attacaaaga gagaatggtg acatttaagg ttcctcatgc caagagacag   1680
gatgtgacag tgctgggatc tcaggaagga gccatgcatt ctgccctcgc tggagccaca   1740
gaagtggact ccggtgatgg aaatcacatg tttgcaggac atctcaagtg caaagtccgt   1800
```

-continued

```
atggagaaat tgagaatcaa gggaatgtca tacacgatgt gttcaggaaa gttctcaatt   1860

gacaaagaga tggcagaaac acagcatggg acaacagtgg tgaaagtcaa gtatgaaggt   1920

gctggagctc cgtgtaaagt ccccatagag ataagagatg tgaacaagga aaaagtggtt   1980

gggcgtatca tctcatccac ccctttggct gagaatacca acagtgtaac caacatagag   2040

ttagaacccc cctttgggga cagctacata gtgataggtg ttggaaacag tgcattaaca   2100

ctccattggt tcaggaaagg gagttccatt ggcaagatgt ttgagtccac atacagaggt   2160

gcaaaacgaa tggccattct aggtgaaaca gcttgggatt ttggttccgt tggtggactg   2220

ttcacatcat tgggaaaggc tgtgcaccag gtttttggaa gtgtgtatac aaccctgttt   2280

ggaggagtct catggatgat tagaatccta attgggttcc tagtgttgtg gattggcacg   2340

aactcaagga acacttcaat ggctatgacg tgcatagctg ccggcattgt gacactgtat   2400

ttgggagtca tggtgcaggc cgatagtggt tgcgttgtga gctggaaaaa caaagaactg   2460

aaatgtggca gtgggatttt catcacagac aacgtgcaca catggacaga acaatacaag   2520

ttccaaccag aatccccttc aaaactagct tcagctatcc agaaagccca tgaagaggac   2580

atttgtggaa tccgctcagt aacaagactg gagaatctga tgtggaaaca aataacacca   2640

gaattgaatc acattctatc agaaaatgag gtgaagttaa ctattatgac aggagacatc   2700

aaaggaatca tgcaggcagg aaaacgatct ctgcggcctc agcccactga gctgaagtat   2760

tcatggaaaa catggggcaa agcaaaaatg ctctctacag agtctcataa ccagaccttt   2820

ctcattgatg gccccgaaac agcagaatgc cccaacacaa atagagcttg gaattcgttg   2880

gaagttgaag actatggctt tggagtattc accaccaata tatggctaaa attgaaagaa   2940

aaacaggatg tattctgcga ctcaaaactc atgtcagcgg ccataaaaga caacagagcc   3000

gtccatgccg atatgggtta ttggatagaa agtgcactca atgacacatg gaagatagag   3060

aaagcctctt tcattgaagt taaaaactgc cactggccaa aatcacacac cctctggagc   3120

aatggagtgc tagaaagtga gatgataatt ccaaagaatc tcgctggacc agtgtctcaa   3180

cacaactata gaccaggcta ccatacacaa ataacaggac catggcatct aggtaagctt   3240

gagatggact ttgatttctg tgatggaaca acagtggtag tgactgagga ctgcggaaat   3300

agaggaccct ctttgagaac aaccactgcc tctggaaaac tcataacaga atggtgctgc   3360

cgatcttgca cattaccacc gctaagatac agaggtgagg atgggtgctg gtacgggatg   3420

gaaatcagac cattgaagga gaaagaagag aatttggtca actccttggt cacagctgga   3480

catgggcagg tcgacaactt ttcactagga gtcttgggaa tggcattgtt cctggaggaa   3540

atgcttagga cccgagtagg aacgaaacat gcaatactac tagttgcagt ttcttttgtg   3600

acattgatca cagggaacat gtcctttaga gacctgggaa gagtgatggt tatggtaggc   3660

gccactatga cgggtgacat aggtatgggc gtgacttatc ttgccctact agcagccttc   3720

aaagtcagac caacttttgc agctggacta ctcttgagaa agctgacctc canggaattg   3780

atgatgacta ctataggaat tgtactcctc tcccagagca ccataccaga gaccattctt   3840

gagttgactg atgcgttagc cttaggcatg atggtcctca aaatggtgag aaatatggaa   3900

aagtatcaat tggcagtgac tatcatggct atcttgtgcg tcccaaacgc agtgatatta   3960

caaaacgcat ggaaagtgag ttgcacaata ttggcagtgg tgtccgtttc cccactgttc   4020

ttaacatcct cacagcaaaa aacagattgg ataccattag cattgacgat caaaggtctc   4080

aatccaacag ctatttttct aacaaccctc tcaagaacca gcaagaaaag gagctggcca   4140

ttaaatgagg ctatcatggc agtcgggatg gtgagcattt tagccagttc tctcctaaaa   4200
```

-continued

```
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga tccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggtaag agacgcactg gacaacttag cagtgctgca cacggctgag   6480
gcaggtggaa gggcgtacaa ccatgctctc agtgaactgc cggagaccct ggagacattg   6540
```

```
cttttactga cacttctggc tacagtcacg ggagggatct ttttattctt gatgagcgca   6600
aggggcatag ggaagatgac cctgggaatg tgctgcataa tcacggctag catcctccta   6660
tggtacgcac aaatacagcc acactggata gcagcttcaa taatactgga gtttttctc   6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagcnatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttnta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
```

-continued agagagaaga agctagggga attcggcaag gcaaaaggca gcagagccat atggtacatg 9000
tggcttggag cacgcttctt agagtttgaa gccctaggat tcttaaatga agatcactgg 9060
ttctccagag agaactccct gagtggagtg gaaggagaag ggctgcacaa gctaggttac 9120
attctaagag acgtgagcaa gaaagaggga ggagcaatgt atgccgatga caccgcagga 9180
tgggatacaa gaatcacact agaagaccta aaaaatgaag aaatggtaac aaaccacatg 9240
gaaggagaac acaagaaact agccgaggcc attttcaaac taacgtacca aaacaaggtg 9300
gtgcgtgtgc aaagaccaac accaagaggc acagtaatgg acatcatatc gagaagagac 9360
caaagaggta gtggacaagt tggcacctat ggactcaata ctttcaccaa tatggaagcc 9420
caactaatca gacagatgga gggagaagga gtctttaaaa gcattcagca cctaacaatc 9480
acagaagaaa tcgctgtgca aaactggtta gcaagagtgg ggcgcgaaag gttatcaaga 9540
atggccatca gtggagatga ttgtgttgtg aaacctttag atgacaggtt cgcaagcgct 9600
ttaacagctc taaatgacat gggaaagatt aggaaagaca tacaacaatg ggaaccttca 9660
agaggatgga atgattggac acaagtgccc ttctgttcac accatttcca tgagttaatc 9720
atgaaagacg gtcgcgtact cgttgttccc tgtagaaacc aagatgaact gattggcaga 9780
gcccgaatct cccaaggagc agggtggtct ttgcgggaga cggcctgttt ggggaagtct 9840
tacgcccaaa tgtggagctt gatgtacttc cacagacgcg acctcaggct ggcggcaaat 9900
gctatttgct cggcagtacc atcacattgg gttccaacaa gtcgaacaac ctggtccata 9960
catgctaaac atgaatggat gacaacggaa gacatgctga cagtctggaa cagggtgtgg 10020
attcaagaaa acccatggat ggaagacaaa actccagtgg aatcatggga ggaaatccca 10080
tacttgggga aaagagaaga ccaatggtgc ggctcattga ttgggttaac aagcagggcc 10140
acctgggcaa agaacatcca agcagcaata aatcaagtta gatcccttat aggcaatgaa 10200
gaatacacag attacatgcc atccatgaaa agattcagaa gagaagagga agaagcagga 10260
gttctgtggt agaaagcaaa actaacatga aacaaggcta gaagtcaggt cggattaagc 10320
catagtacgg aaaaaactat gctacctgtg agccccgtcc aaggacgtta aaagaagtca 10380
ggccatcata aatgccatag cttgagtaaa ctatgcagcc tgtagctcca cctgagaagg 10440
tgtaaaaaat ccgggaggcc acaaaccatg gaagctgtac gcatggcgta gtggactagc 10500
ggttagagga gacccctccc ttacaaatcg cagcaacaat gggggcccaa ggcgagatga 10560
agctgtagtc tcgctggaag gactagaggt tagaggagac ccccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tct 10723

<210> SEQ ID NO 11
<211> LENGTH: 3391
<212> TYPE: PRT
<213> ORGANISM: Artificial Sequence
<220> FEATURE:
<223> OTHER INFORMATION: Dengue virus serotype 4, BVS
<220> FEATURE:
<221> NAME/KEY: Xaa
<222> LOCATION: (1226)..(1226)
<223> OTHER INFORMATION: Lys or Arg
<220> FEATURE:
<221> NAME/KEY: Xaa
<222> LOCATION: (2481)..(2481)
<223> OTHER INFORMATION: Ser or Phe

<400> SEQUENCE: 11

-continued

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Ser Ser Ala Gly Met Ile Ile Met Leu Ile Pro Thr Val
            100                 105                 110

Met Ala Phe His Leu Thr Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Arg Glu Lys Arg Ser Val Ala
        195                 200                 205

Leu Thr Pro His Ser Gly Met Gly Leu Glu Thr Arg Ala Glu Thr Trp
    210                 215                 220

Met Ser Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
                245                 250                 255

Met Ile Gly Gln Thr Gly Ile Gln Arg Thr Val Phe Phe Val Leu Met
            260                 265                 270

Met Leu Val Ala Pro Ser Tyr Gly Met Arg Cys Val Gly Val Gly Asn
        275                 280                 285

Arg Asp Phe Val Glu Gly Val Ser Gly Gly Ala Trp Val Asp Leu Val
    290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
```

-continued

```
            420                 425                 430

Asn Asp Thr Ser Asn His Gly Val Thr Ala Thr Ile Thr Pro Arg Ser
        435                 440                 445

Pro Ser Val Glu Val Lys Leu Pro Asp Tyr Gly Glu Leu Thr Leu Asp
    450                 455                 460

Cys Glu Pro Arg Ser Gly Ile Asp Phe Asn Glu Met Ile Leu Met Lys
465                 470                 475                 480

Met Lys Lys Lys Thr Trp Leu Val His Lys Gln Trp Phe Leu Asp Leu
                485                 490                 495

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
        515                 520                 525

Asp Val Thr Val Leu Gly Ser Gln Glu Gly Ala Met His Ser Ala Leu
    530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
                565                 570                 575

Met Ser Tyr Thr Met Cys Ser Gly Lys Phe Ser Ile Asp Lys Glu Met
            580                 585                 590

Ala Glu Thr Gln His Gly Thr Thr Val Val Lys Val Lys Tyr Glu Gly
        595                 600                 605

Ala Gly Ala Pro Cys Lys Val Pro Ile Glu Ile Arg Asp Val Asn Lys
    610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
                645                 650                 655

Tyr Ile Val Ile Gly Val Gly Asn Ser Ala Leu Thr Leu His Trp Phe
            660                 665                 670

Arg Lys Gly Ser Ser Ile Gly Lys Met Phe Glu Ser Thr Tyr Arg Gly
        675                 680                 685

Ala Lys Arg Met Ala Ile Leu Gly Glu Thr Ala Trp Asp Phe Gly Ser
    690                 695                 700

Val Gly Gly Leu Phe Thr Ser Leu Gly Lys Ala Val His Gln Val Phe
705                 710                 715                 720

Gly Ser Val Tyr Thr Thr Leu Phe Gly Gly Val Ser Trp Met Ile Arg
                725                 730                 735

Ile Leu Ile Gly Phe Leu Val Leu Trp Ile Gly Thr Asn Ser Arg Asn
            740                 745                 750

Thr Ser Met Ala Met Thr Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845
```

-continued

```
Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Gly Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Xaa Glu Leu Met Met  Thr Thr Ile
    1220                 1225                 1230

Gly Ile  Val Leu Leu Ser Gln  Ser Thr Ile Pro Glu  Thr Ile Leu
    1235                 1240                 1245
```

-continued

```
Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290

Val Ser  Cys Thr Ile Leu Ala  Val Val Ser Val Ser  Pro Leu Phe
    1295                 1300                 1305

Leu Thr  Ser Ser Gln Gln Lys  Thr Asp Trp Ile Pro  Leu Ala Leu
    1310                 1315                 1320

Thr Ile  Lys Gly Leu Asn Pro  Thr Ala Ile Phe Leu  Thr Thr Leu
    1325                 1330                 1335

Ser Arg  Thr Ser Lys Lys Arg  Ser Trp Pro Leu Asn  Glu Ala Ile
    1340                 1345                 1350

Met Ala  Val Gly Met Val Ser  Ile Leu Ala Ser Ser  Leu Leu Lys
    1355                 1360                 1365

Asn Asp  Ile Pro Met Thr Gly  Pro Leu Val Ala Gly  Gly Leu Leu
    1370                 1375                 1380

Thr Val  Cys Tyr Val Leu Thr  Gly Arg Ser Ala Asp  Leu Glu Leu
    1385                 1390                 1395

Glu Arg  Ala Ala Asp Val Lys  Trp Glu Asp Gln Ala  Glu Ile Ser
    1400                 1405                 1410

Gly Ser  Ser Pro Ile Leu Ser  Ile Thr Ile Ser Glu  Asp Gly Ser
    1415                 1420                 1425

Met Ser  Ile Lys Asn Glu Glu  Glu Glu Gln Thr Leu  Thr Ile Leu
    1430                 1435                 1440

Ile Arg  Thr Gly Leu Leu Val  Ile Ser Gly Leu Phe  Pro Val Ser
    1445                 1450                 1455

Ile Pro  Ile Thr Ala Ala Ala  Trp Tyr Leu Trp Glu  Val Lys Lys
    1460                 1465                 1470

Gln Arg  Ala Gly Val Leu Trp  Asp Val Pro Ser Pro  Pro Pro Met
    1475                 1480                 1485

Gly Lys  Ala Glu Leu Glu Asp  Gly Ala Tyr Arg Ile  Lys Gln Lys
    1490                 1495                 1500

Gly Ile  Leu Gly Tyr Ser Gln  Ile Gly Ala Gly Val  Tyr Lys Glu
    1505                 1510                 1515

Gly Thr  Phe His Thr Met Trp  His Val Thr Arg Gly  Ala Val Leu
    1520                 1525                 1530

Met His  Lys Gly Lys Arg Ile  Glu Pro Ser Trp Ala  Asp Val Lys
    1535                 1540                 1545

Lys Asp  Leu Ile Ser Tyr Gly  Gly Gly Trp Lys Leu  Glu Gly Glu
    1550                 1555                 1560

Trp Lys  Glu Gly Glu Glu Val  Gln Val Leu Ala Leu  Glu Pro Gly
    1565                 1570                 1575

Lys Asn  Pro Arg Ala Val Gln  Thr Lys Pro Gly Leu  Phe Lys Thr
    1580                 1585                 1590

Asn Ala  Gly Thr Ile Gly Ala  Val Ser Leu Asp Phe  Ser Pro Gly
    1595                 1600                 1605

Thr Ser  Gly Ser Pro Ile Ile  Asp Lys Lys Gly Lys  Val Val Gly
    1610                 1615                 1620

Leu Tyr  Gly Asn Gly Val Val  Thr Arg Ser Gly Ala  Tyr Val Ser
    1625                 1630                 1635

Ala Ile  Ala Gln Thr Glu Lys  Ser Ile Glu Asp Asn  Pro Glu Ile
```

-continued

```
    1640                1645                1650

Glu Asp  Asp Ile Phe Arg Lys  Arg Arg Leu Thr Ile  Met Asp Leu
    1655                1660                1665

His Pro  Gly Ala Gly Lys Thr  Lys Arg Tyr Leu Pro  Ala Ile Val
    1670                1675                1680

Arg Glu  Ala Ile Lys Arg Gly  Leu Arg Thr Leu Ile  Leu Ala Pro
    1685                1690                1695

Thr Arg  Val Val Ala Ala Glu  Met Glu Glu Ala Leu  Arg Gly Leu
    1700                1705                1710

Pro Ile  Arg Tyr Gln Thr Pro  Ala Ile Arg Ala Val  His Thr Gly
    1715                1720                1725

Arg Glu  Ile Val Asp Leu Met  Cys His Ala Thr Phe  Thr Met Arg
    1730                1735                1740

Leu Leu  Ser Pro Val Arg Val  Pro Asn Tyr Asn Leu  Ile Ile Met
    1745                1750                1755

Asp Glu  Ala His Phe Thr Asp  Pro Ala Ser Ile Ala  Ala Arg Gly
    1760                1765                1770

Tyr Ile  Ser Thr Arg Val Glu  Met Gly Glu Ala Ala  Gly Ile Phe
    1775                1780                1785

Met Thr  Ala Thr Pro Pro Gly  Ser Arg Asp Pro Phe  Pro Gln Ser
    1790                1795                1800

Asn Ala  Pro Ile Ile Asp Glu  Glu Arg Glu Ile Pro  Glu Arg Ser
    1805                1810                1815

Trp Asn  Ser Gly His Glu Trp  Val Thr Asp Phe Lys  Gly Lys Thr
    1820                1825                1830

Val Trp  Phe Val Pro Ser Ile  Lys Ala Gly Asn Asp  Ile Ala Ala
    1835                1840                1845

Cys Leu  Arg Lys Asn Gly Lys  Lys Val Ile Gln Leu  Ser Arg Lys
    1850                1855                1860

Thr Phe  Asp Ser Glu Tyr Val  Lys Thr Arg Thr Asn  Asp Trp Asp
    1865                1870                1875

Phe Val  Val Thr Thr Asp Ile  Ser Glu Met Gly Ala  Asn Phe Lys
    1880                1885                1890

Ala Glu  Arg Val Ile Asp Pro  Arg Arg Cys Met Lys  Pro Val Ile
    1895                1900                1905

Leu Thr  Asp Gly Glu Glu Arg  Val Ile Leu Ala Gly  Pro Met Pro
    1910                1915                1920

Val Thr  His Ser Ser Ala Ala  Gln Arg Arg Gly Arg  Ile Gly Arg
    1925                1930                1935

Asn Pro  Lys Asn Glu Asn Asp  Gln Tyr Ile Tyr Met  Gly Glu Pro
    1940                1945                1950

Leu Glu  Asn Asp Glu Asp Cys  Ala His Trp Lys Glu  Ala Lys Met
    1955                1960                1965

Leu Leu  Asp Asn Ile Asn Thr  Pro Glu Gly Ile Ile  Pro Ser Met
    1970                1975                1980

Phe Glu  Pro Glu Arg Glu Lys  Val Asp Ala Ile Asp  Gly Glu Tyr
    1985                1990                1995

Arg Leu  Arg Gly Glu Ala Arg  Lys Thr Phe Val Asp  Leu Met Arg
    2000                2005                2010

Arg Gly  Asp Leu Pro Val Trp  Leu Ala Tyr Arg Val  Ala Ala Glu
    2015                2020                2025

Gly Ile  Asn Tyr Ala Asp Arg  Arg Trp Cys Phe Asp  Gly Val Lys
    2030                2035                2040
```

-continued

Asn Asn Gln Ile Leu Glu Glu Asn Val Glu Val Glu Ile Trp Thr
2045 2050 2055

Lys Glu Gly Glu Arg Lys Lys Leu Lys Pro Arg Trp Leu Asp Ala
2060 2065 2070

Arg Ile Tyr Ser Asp Pro Leu Ala Leu Lys Glu Phe Lys Glu Phe
2075 2080 2085

Ala Ala Gly Arg Lys Ser Leu Thr Leu Asn Leu Ile Thr Glu Met
2090 2095 2100

Gly Arg Leu Pro Thr Phe Met Thr Gln Lys Val Arg Asp Ala Leu
2105 2110 2115

Asp Asn Leu Ala Val Leu His Thr Ala Glu Ala Gly Gly Arg Ala
2120 2125 2130

Tyr Asn His Ala Leu Ser Glu Leu Pro Glu Thr Leu Glu Thr Leu
2135 2140 2145

Leu Leu Leu Thr Leu Leu Ala Thr Val Thr Gly Gly Ile Phe Leu
2150 2155 2160

Phe Leu Met Ser Ala Arg Gly Ile Gly Lys Met Thr Leu Gly Met
2165 2170 2175

Cys Cys Ile Ile Thr Ala Ser Ile Leu Leu Trp Tyr Ala Gln Ile
2180 2185 2190

Gln Pro His Trp Ile Ala Ala Ser Ile Ile Leu Glu Phe Phe Leu
2195 2200 2205

Ile Val Leu Leu Ile Pro Glu Pro Glu Lys Gln Arg Thr Pro Gln
2210 2215 2220

Asp Asn Gln Leu Thr Tyr Val Val Ile Ala Ile Leu Thr Val Val
2225 2230 2235

Ala Ala Thr Met Ala Asn Glu Met Gly Phe Leu Glu Lys Thr Lys
2240 2245 2250

Lys Asp Leu Gly Leu Gly Ser Ile Ala Thr Gln Gln Pro Glu Ser
2255 2260 2265

Asn Ile Leu Asp Ile Asp Leu Arg Pro Ala Ser Ala Trp Thr Leu
2270 2275 2280

Tyr Ala Val Ala Thr Thr Phe Val Thr Pro Met Leu Arg His Ser
2285 2290 2295

Ile Glu Asn Ser Ser Val Asn Val Ser Leu Thr Ala Ile Ala Asn
2300 2305 2310

Gln Ala Thr Val Leu Met Gly Leu Gly Lys Gly Trp Pro Leu Ser
2315 2320 2325

Lys Met Asp Ile Gly Val Pro Leu Leu Ala Ile Gly Cys Tyr Ser
2330 2335 2340

Gln Val Asn Pro Ile Thr Leu Thr Ala Ala Leu Phe Leu Leu Val
2345 2350 2355

Ala His Tyr Ala Ile Ile Gly Pro Gly Leu Gln Ala Lys Ala Thr
2360 2365 2370

Arg Glu Ala Gln Lys Arg Ala Ala Ala Gly Ile Met Lys Asn Pro
2375 2380 2385

Thr Val Asp Gly Ile Thr Val Ile Asp Leu Asp Pro Ile Pro Tyr
2390 2395 2400

Asp Pro Lys Phe Glu Lys Gln Leu Gly Gln Val Met Leu Leu Val
2405 2410 2415

Leu Cys Val Thr Gln Val Leu Met Met Arg Thr Thr Trp Ala Leu
2420 2425 2430

Cys Glu Ala Leu Thr Leu Ala Thr Gly Pro Ile Ser Thr Leu Trp
2435 2440 2445

Glu Gly Asn Pro Gly Arg Phe Trp Asn Thr Thr Ile Ala Val Ser
2450 2455 2460

Met Ala Asn Ile Phe Arg Gly Ser Tyr Leu Ala Gly Ala Gly Leu
2465 2470 2475

Leu Phe Xaa Ile Met Lys Asn Thr Thr Asn Thr Arg Arg Gly Thr
2480 2485 2490

Gly Asn Ile Gly Glu Thr Leu Gly Glu Lys Trp Lys Ser Arg Leu
2495 2500 2505

Asn Ala Leu Gly Lys Ser Glu Phe Gln Ile Tyr Lys Lys Ser Gly
2510 2515 2520

Ile Gln Glu Val Asp Arg Thr Leu Ala Lys Glu Gly Ile Lys Arg
2525 2530 2535

Gly Glu Thr Asp His His Ala Val Ser Arg Gly Ser Ala Lys Leu
2540 2545 2550

Arg Trp Phe Val Glu Arg Asn Met Val Thr Pro Glu Gly Lys Val
2555 2560 2565

Val Asp Leu Gly Cys Gly Arg Gly Gly Trp Ser Tyr Tyr Cys Gly
2570 2575 2580

Gly Leu Lys Asn Val Arg Glu Val Lys Gly Leu Thr Lys Gly Gly
2585 2590 2595

Pro Gly His Glu Glu Pro Ile Pro Met Ser Thr Tyr Gly Trp Asn
2600 2605 2610

Leu Val Arg Leu Gln Ser Gly Val Asp Val Phe Phe Ile Pro Pro
2615 2620 2625

Glu Lys Cys Asp Thr Leu Leu Cys Asp Ile Gly Glu Ser Ser Pro
2630 2635 2640

Asn Pro Thr Val Glu Ala Gly Arg Thr Leu Arg Val Leu Asn Leu
2645 2650 2655

Val Glu Asn Trp Leu Asn Asn Asn Thr Gln Phe Cys Ile Lys Val
2660 2665 2670

Leu Asn Pro Tyr Met Pro Ser Val Ile Glu Lys Met Glu Ala Leu
2675 2680 2685

Gln Arg Lys Tyr Gly Gly Ala Leu Val Arg Asn Pro Leu Ser Arg
2690 2695 2700

Asn Ser Thr His Glu Met Tyr Trp Val Ser Asn Ala Ser Gly Asn
2705 2710 2715

Ile Val Ser Ser Val Asn Met Ile Ser Arg Met Leu Ile Asn Arg
2720 2725 2730

Phe Thr Met Arg Tyr Lys Lys Ala Thr Tyr Glu Pro Asp Val Asp
2735 2740 2745

Leu Gly Ser Gly Thr Arg Asn Ile Gly Ile Glu Ser Glu Ile Pro
2750 2755 2760

Asn Leu Asp Ile Ile Gly Lys Arg Ile Glu Lys Ile Lys Gln Glu
2765 2770 2775

His Glu Thr Ser Trp His Tyr Asp Gln Asp His Pro Tyr Lys Thr
2780 2785 2790

Trp Ala Tyr His Gly Ser Tyr Glu Thr Lys Gln Thr Gly Ser Ala
2795 2800 2805

Ser Ser Met Val Asn Gly Val Val Arg Leu Leu Thr Lys Pro Trp
2810 2815 2820

Asp Val Val Pro Met Val Thr Gln Met Ala Met Thr Asp Thr Thr

-continued

```
    2825                2830                2835

Pro Phe  Gly Gln Gln Arg Val  Phe Lys Glu Lys Val  Asp Thr Arg
    2840                2845                2850

Thr Gln  Glu Pro Lys Glu Gly  Thr Lys Lys Leu Met  Lys Ile Thr
    2855                2860                2865

Ala Glu  Trp Leu Trp Lys Glu  Leu Gly Lys Lys Lys  Thr Pro Arg
    2870                2875                2880

Met Cys  Thr Arg Glu Glu Phe  Thr Arg Lys Val Arg  Ser Asn Ala
    2885                2890                2895

Ala Leu  Gly Ala Ile Phe Thr  Asp Glu Asn Lys Trp  Lys Ser Ala
    2900                2905                2910

Arg Glu  Ala Val Glu Asp Ser  Arg Phe Trp Glu Leu  Val Asp Lys
    2915                2920                2925

Glu Arg  Asn Leu His Leu Glu  Gly Lys Cys Glu Thr  Cys Val Tyr
    2930                2935                2940

Asn Met  Met Gly Lys Arg Glu  Lys Lys Leu Gly Glu  Phe Gly Lys
    2945                2950                2955

Ala Lys  Gly Ser Arg Ala Ile  Trp Tyr Met Trp Leu  Gly Ala Arg
    2960                2965                2970

Phe Leu  Glu Phe Glu Ala Leu  Gly Phe Leu Asn Glu  Asp His Trp
    2975                2980                2985

Phe Ser  Arg Glu Asn Ser Leu  Ser Gly Val Glu Gly  Glu Gly Leu
    2990                2995                3000

His Lys  Leu Gly Tyr Ile Leu  Arg Asp Val Ser Lys  Lys Glu Gly
    3005                3010                3015

Gly Ala  Met Tyr Ala Asp Asp  Thr Ala Gly Trp Asp  Thr Arg Ile
    3020                3025                3030

Thr Leu  Glu Asp Leu Lys Asn  Glu Glu Met Val Thr  Asn His Met
    3035                3040                3045

Glu Gly  Glu His Lys Lys Leu  Ala Glu Ala Ile Phe  Lys Leu Thr
    3050                3055                3060

Tyr Gln  Asn Lys Val Val Arg  Val Gln Arg Pro Thr  Pro Arg Gly
    3065                3070                3075

Thr Val  Met Asp Ile Ile Ser  Arg Arg Asp Gln Arg  Gly Ser Gly
    3080                3085                3090

Gln Val  Gly Thr Tyr Gly Leu  Asn Thr Phe Thr Asn  Met Glu Ala
    3095                3100                3105

Gln Leu  Ile Arg Gln Met Glu  Gly Glu Gly Val Phe  Lys Ser Ile
    3110                3115                3120

Gln His  Leu Thr Ile Thr Glu  Glu Ile Ala Val Gln  Asn Trp Leu
    3125                3130                3135

Ala Arg  Val Gly Arg Glu Arg  Leu Ser Arg Met Ala  Ile Ser Gly
    3140                3145                3150

Asp Asp  Cys Val Val Lys Pro  Leu Asp Asp Arg Phe  Ala Ser Ala
    3155                3160                3165

Leu Thr  Ala Leu Asn Asp Met  Gly Lys Ile Arg Lys  Asp Ile Gln
    3170                3175                3180

Gln Trp  Glu Pro Ser Arg Gly  Trp Asn Asp Trp Thr  Gln Val Pro
    3185                3190                3195

Phe Cys  Ser His His Phe His  Glu Leu Ile Met Lys  Asp Gly Arg
    3200                3205                3210

Val Leu  Val Val Pro Cys Arg  Asn Gln Asp Glu Leu  Ile Gly Arg
    3215                3220                3225
```

```
Ala Arg Ile Ser Gln Gly Ala Gly Trp Ser Leu Arg Glu Thr Ala
    3230                3235                3240

Cys Leu Gly Lys Ser Tyr Ala Gln Met Trp Ser Leu Met Tyr Phe
    3245                3250                3255

His Arg Arg Asp Leu Arg Leu Ala Ala Asn Ala Ile Cys Ser Ala
    3260                3265                3270

Val Pro Ser His Trp Val Pro Thr Ser Arg Thr Thr Trp Ser Ile
    3275                3280                3285

His Ala Lys His Glu Trp Met Thr Thr Glu Asp Met Leu Thr Val
    3290                3295                3300

Trp Asn Arg Val Trp Ile Gln Glu Asn Pro Trp Met Glu Asp Lys
    3305                3310                3315

Thr Pro Val Glu Ser Trp Glu Glu Ile Pro Tyr Leu Gly Lys Arg
    3320                3325                3330

Glu Asp Gln Trp Cys Gly Ser Leu Ile Gly Leu Thr Ser Arg Ala
    3335                3340                3345

Thr Trp Ala Lys Asn Ile Gln Ala Ala Ile Asn Gln Val Arg Ser
    3350                3355                3360

Leu Ile Gly Asn Glu Glu Tyr Thr Asp Tyr Met Pro Ser Met Lys
    3365                3370                3375

Arg Phe Arg Arg Glu Glu Glu Glu Ala Gly Val Leu Trp
    3380                3385                3390
```

<210> SEQ ID NO 12
<211> LENGTH: 3391
<212> TYPE: PRT
<213> ORGANISM: Artificial Sequence
<220> FEATURE:
<223> OTHER INFORMATION: Dengue virus serotype 4, MVS
<220> FEATURE:
<221> NAME/KEY: Xaa
<222> LOCATION: (1226)..(1226)
<223> OTHER INFORMATION: Lys or Arg

<400> SEQUENCE: 12

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Ser Ser Ala Gly Met Ile Ile Met Leu Ile Pro Thr Val
            100                 105                 110

Met Ala Phe His Leu Thr Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
```

-continued

```
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Arg Glu Lys Arg Ser Val Ala
        195                 200                 205

Leu Thr Pro His Ser Gly Met Gly Leu Glu Thr Arg Ala Glu Thr Trp
    210                 215                 220

Met Ser Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
                245                 250                 255

Met Ile Gly Gln Thr Gly Ile Gln Arg Thr Val Phe Phe Val Leu Met
            260                 265                 270

Met Leu Val Ala Pro Ser Tyr Gly Met Arg Cys Val Gly Val Gly Asn
        275                 280                 285

Arg Asp Phe Val Glu Gly Val Ser Gly Gly Ala Trp Val Asp Leu Val
    290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
            420                 425                 430

Asn Asp Thr Ser Asn His Gly Val Thr Ala Thr Ile Thr Pro Arg Ser
        435                 440                 445

Pro Ser Val Glu Val Lys Leu Pro Asp Tyr Gly Glu Leu Thr Leu Asp
    450                 455                 460

Cys Glu Pro Arg Ser Gly Ile Asp Phe Asn Glu Met Ile Leu Met Lys
465                 470                 475                 480

Met Lys Lys Lys Thr Trp Leu Val His Lys Gln Trp Phe Leu Asp Leu
                485                 490                 495

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
        515                 520                 525

Asp Val Thr Val Leu Gly Ser Gln Glu Gly Ala Met His Ser Ala Leu
    530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
                565                 570                 575

Met Ser Tyr Thr Met Cys Ser Gly Lys Phe Ser Ile Asp Lys Glu Met
            580                 585                 590
```

Ala Glu Thr Gln His Gly Thr Thr Val Val Lys Val Lys Tyr Glu Gly
595 600 605

Ala Gly Ala Pro Cys Lys Val Pro Ile Glu Ile Arg Asp Val Asn Lys
610 615 620

Glu Lys Val Val Gly Arg Ile Ile Ser Ser Thr Pro Leu Ala Glu Asn
625 630 635 640

Thr Asn Ser Val Thr Asn Ile Glu Leu Glu Pro Pro Phe Gly Asp Ser
645 650 655

Tyr Ile Val Ile Gly Val Gly Asn Ser Ala Leu Thr Leu His Trp Phe
660 665 670

Arg Lys Gly Ser Ser Ile Gly Lys Met Phe Glu Ser Thr Tyr Arg Gly
675 680 685

Ala Lys Arg Met Ala Ile Leu Gly Glu Thr Ala Trp Asp Phe Gly Ser
690 695 700

Val Gly Gly Leu Phe Thr Ser Leu Gly Lys Ala Val His Gln Val Phe
705 710 715 720

Gly Ser Val Tyr Thr Thr Leu Phe Gly Gly Val Ser Trp Met Ile Arg
725 730 735

Ile Leu Ile Gly Phe Leu Val Leu Trp Ile Gly Thr Asn Ser Arg Asn
740 745 750

Thr Ser Met Ala Met Thr Cys Ile Ala Ala Gly Ile Val Thr Leu Tyr
755 760 765

Leu Gly Val Met Val Gln Ala Asp Ser Gly Cys Val Val Ser Trp Lys
770 775 780

Asn Lys Glu Leu Lys Cys Gly Ser Gly Ile Phe Ile Thr Asp Asn Val
785 790 795 800

His Thr Trp Thr Glu Gln Tyr Lys Phe Gln Pro Glu Ser Pro Ser Lys
805 810 815

Leu Ala Ser Ala Ile Gln Lys Ala His Glu Glu Asp Ile Cys Gly Ile
820 825 830

Arg Ser Val Thr Arg Leu Glu Asn Leu Met Trp Lys Gln Ile Thr Pro
835 840 845

Glu Leu Asn His Ile Leu Ser Glu Asn Glu Val Lys Leu Thr Ile Met
850 855 860

Thr Gly Asp Ile Lys Gly Ile Met Gln Ala Gly Lys Arg Ser Leu Arg
865 870 875 880

Pro Gln Pro Thr Glu Leu Lys Tyr Ser Trp Lys Thr Trp Gly Lys Ala
885 890 895

Lys Met Leu Ser Thr Glu Ser His Asn Gln Thr Phe Leu Ile Asp Gly
900 905 910

Pro Glu Thr Ala Glu Cys Pro Asn Thr Asn Arg Ala Trp Asn Ser Leu
915 920 925

Glu Val Glu Asp Tyr Gly Phe Gly Val Phe Thr Thr Asn Ile Trp Leu
930 935 940

Lys Leu Lys Glu Lys Gln Asp Val Phe Cys Asp Ser Lys Leu Met Ser
945 950 955 960

Ala Ala Ile Lys Asp Asn Arg Ala Val His Ala Asp Met Gly Tyr Trp
965 970 975

Ile Glu Ser Ala Leu Asn Asp Thr Trp Lys Ile Glu Lys Ala Ser Phe
980 985 990

Ile Glu Val Lys Asn Cys His Trp Pro Lys Ser His Thr Leu Trp Ser
995 1000 1005

-continued

```
Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Gly Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Xaa Glu Leu Met Met  Thr Thr Ile
    1220                 1225                 1230

Gly Ile  Val Leu Leu Ser Gln  Ser Thr Ile Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290

Val Ser  Cys Thr Ile Leu Ala  Val Val Ser Val Ser  Pro Leu Phe
    1295                 1300                 1305

Leu Thr  Ser Ser Gln Gln Lys  Thr Asp Trp Ile Pro  Leu Ala Leu
    1310                 1315                 1320

Thr Ile  Lys Gly Leu Asn Pro  Thr Ala Ile Phe Leu  Thr Thr Leu
    1325                 1330                 1335

Ser Arg  Thr Ser Lys Lys Arg  Ser Trp Pro Leu Asn  Glu Ala Ile
    1340                 1345                 1350

Met Ala  Val Gly Met Val Ser  Ile Leu Ala Ser Ser  Leu Leu Lys
    1355                 1360                 1365

Asn Asp  Ile Pro Met Thr Gly  Pro Leu Val Ala Gly  Gly Leu Leu
    1370                 1375                 1380

Thr Val  Cys Tyr Val Leu Thr  Gly Arg Ser Ala Asp  Leu Glu Leu
    1385                 1390                 1395

Glu Arg  Ala Ala Asp Val Lys  Trp Glu Asp Gln Ala  Glu Ile Ser
```

-continued

```
    1400                1405                1410

Gly Ser  Ser Pro Ile Leu Ser  Ile Thr Ile Ser Glu  Asp Gly Ser
    1415                1420                1425

Met Ser  Ile Lys Asn Glu Glu  Glu Glu Gln Thr Leu  Thr Ile Leu
    1430                1435                1440

Ile Arg  Thr Gly Leu Leu Val  Ile Ser Gly Leu Phe  Pro Val Ser
    1445                1450                1455

Ile Pro  Ile Thr Ala Ala Ala  Trp Tyr Leu Trp Glu  Val Lys Lys
    1460                1465                1470

Gln Arg  Ala Gly Val Leu Trp  Asp Val Pro Ser Pro  Pro Pro Met
    1475                1480                1485

Gly Lys  Ala Glu Leu Glu Asp  Gly Ala Tyr Arg Ile  Lys Gln Lys
    1490                1495                1500

Gly Ile  Leu Gly Tyr Ser Gln  Ile Gly Ala Gly Val  Tyr Lys Glu
    1505                1510                1515

Gly Thr  Phe His Thr Met Trp  His Val Thr Arg Gly  Ala Val Leu
    1520                1525                1530

Met His  Lys Gly Lys Arg Ile  Glu Pro Ser Trp Ala  Asp Val Lys
    1535                1540                1545

Lys Asp  Leu Ile Ser Tyr Gly  Gly Gly Trp Lys Leu  Glu Gly Glu
    1550                1555                1560

Trp Lys  Glu Gly Glu Glu Val  Gln Val Leu Ala Leu  Glu Pro Gly
    1565                1570                1575

Lys Asn  Pro Arg Ala Val Gln  Thr Lys Pro Gly Leu  Phe Lys Thr
    1580                1585                1590

Asn Ala  Gly Thr Ile Gly Ala  Val Ser Leu Asp Phe  Ser Pro Gly
    1595                1600                1605

Thr Ser  Gly Ser Pro Ile Ile  Asp Lys Lys Gly Lys  Val Val Gly
    1610                1615                1620

Leu Tyr  Gly Asn Gly Val Val  Thr Arg Ser Gly Ala  Tyr Val Ser
    1625                1630                1635

Ala Ile  Ala Gln Thr Glu Lys  Ser Ile Glu Asp Asn  Pro Glu Ile
    1640                1645                1650

Glu Asp  Asp Ile Phe Arg Lys  Arg Arg Leu Thr Ile  Met Asp Leu
    1655                1660                1665

His Pro  Gly Ala Gly Lys Thr  Lys Arg Tyr Leu Pro  Ala Ile Val
    1670                1675                1680

Arg Glu  Ala Ile Lys Arg Gly  Leu Arg Thr Leu Ile  Leu Ala Pro
    1685                1690                1695

Thr Arg  Val Val Ala Ala Glu  Met Glu Glu Ala Leu  Arg Gly Leu
    1700                1705                1710

Pro Ile  Arg Tyr Gln Thr Pro  Ala Ile Arg Ala Val  His Thr Gly
    1715                1720                1725

Arg Glu  Ile Val Asp Leu Met  Cys His Ala Thr Phe  Thr Met Arg
    1730                1735                1740

Leu Leu  Ser Pro Val Arg Val  Pro Asn Tyr Asn Leu  Ile Ile Met
    1745                1750                1755

Asp Glu  Ala His Phe Thr Asp  Pro Ala Ser Ile Ala  Ala Arg Gly
    1760                1765                1770

Tyr Ile  Ser Thr Arg Val Glu  Met Gly Glu Ala Ala  Gly Ile Phe
    1775                1780                1785

Met Thr  Ala Thr Pro Pro Gly  Ser Arg Asp Pro Phe  Pro Gln Ser
    1790                1795                1800
```

-continued

```
Asn Ala  Pro Ile Ile Asp Glu  Glu Arg Glu Ile Pro  Glu Arg Ser
    1805                 1810                 1815

Trp Asn  Ser Gly His Glu Trp  Val Thr Asp Phe Lys  Gly Lys Thr
    1820                 1825                 1830

Val Trp  Phe Val Pro Ser Ile  Lys Ala Gly Asn Asp  Ile Ala Ala
    1835                 1840                 1845

Cys Leu  Arg Lys Asn Gly Lys  Lys Val Ile Gln Leu  Ser Arg Lys
    1850                 1855                 1860

Thr Phe  Asp Ser Glu Tyr Val  Lys Thr Arg Thr Asn  Asp Trp Asp
    1865                 1870                 1875

Phe Val  Val Thr Thr Asp Ile  Ser Glu Met Gly Ala  Asn Phe Lys
    1880                 1885                 1890

Ala Glu  Arg Val Ile Asp Pro  Arg Arg Cys Met Lys  Pro Val Ile
    1895                 1900                 1905

Leu Thr  Asp Gly Glu Glu Arg  Val Ile Leu Ala Gly  Pro Met Pro
    1910                 1915                 1920

Val Thr  His Ser Ser Ala Ala  Gln Arg Arg Gly Arg  Ile Gly Arg
    1925                 1930                 1935

Asn Pro  Lys Asn Glu Asn Asp  Gln Tyr Ile Tyr Met  Gly Glu Pro
    1940                 1945                 1950

Leu Glu  Asn Asp Glu Asp Cys  Ala His Trp Lys Glu  Ala Lys Met
    1955                 1960                 1965

Leu Leu  Asp Asn Ile Asn Thr  Pro Glu Gly Ile Ile  Pro Ser Met
    1970                 1975                 1980

Phe Glu  Pro Glu Arg Glu Lys  Val Asp Ala Ile Asp  Gly Glu Tyr
    1985                 1990                 1995

Arg Leu  Arg Gly Glu Ala Arg  Lys Thr Phe Val Asp  Leu Met Arg
    2000                 2005                 2010

Arg Gly  Asp Leu Pro Val Trp  Leu Ala Tyr Arg Val  Ala Ala Glu
    2015                 2020                 2025

Gly Ile  Asn Tyr Ala Asp Arg  Arg Trp Cys Phe Asp  Gly Val Lys
    2030                 2035                 2040

Asn Asn  Gln Ile Leu Glu Glu  Asn Val Glu Val Glu  Ile Trp Thr
    2045                 2050                 2055

Lys Glu  Gly Glu Arg Lys Lys  Leu Lys Pro Arg Trp  Leu Asp Ala
    2060                 2065                 2070

Arg Ile  Tyr Ser Asp Pro Leu  Ala Leu Lys Glu Phe  Lys Glu Phe
    2075                 2080                 2085

Ala Ala  Gly Arg Lys Ser Leu  Thr Leu Asn Leu Ile  Thr Glu Met
    2090                 2095                 2100

Gly Arg  Leu Pro Thr Phe Met  Thr Gln Lys Val Arg  Asp Ala Leu
    2105                 2110                 2115

Asp Asn  Leu Ala Val Leu His  Thr Ala Glu Ala Gly  Gly Arg Ala
    2120                 2125                 2130

Tyr Asn  His Ala Leu Ser Glu  Leu Pro Glu Thr Leu  Glu Thr Leu
    2135                 2140                 2145

Leu Leu  Leu Thr Leu Leu Ala  Thr Val Thr Gly Gly  Ile Phe Leu
    2150                 2155                 2160

Phe Leu  Met Ser Ala Arg Gly  Ile Gly Lys Met Thr  Leu Gly Met
    2165                 2170                 2175

Cys Cys  Ile Ile Thr Ala Ser  Ile Leu Leu Trp Tyr  Ala Gln Ile
    2180                 2185                 2190
```

-continued

```
Gln Pro  His Trp Ile Ala Ala  Ser Ile Ile Leu Glu  Phe Phe Leu
    2195                 2200                 2205

Ile Val  Leu Leu Ile Pro Glu  Pro Glu Lys Gln Arg  Thr Pro Gln
    2210                 2215                 2220

Asp Asn  Gln Leu Thr Tyr Val  Val Ile Ala Ile Leu  Thr Val Val
    2225                 2230                 2235

Ala Ala  Thr Met Ala Asn Glu  Met Gly Phe Leu Glu  Lys Thr Lys
    2240                 2245                 2250

Lys Asp  Leu Gly Leu Gly Ser  Ile Ala Thr Gln Gln  Pro Glu Ser
    2255                 2260                 2265

Asn Ile  Leu Asp Ile Asp Leu  Arg Pro Ala Ser Ala  Trp Thr Leu
    2270                 2275                 2280

Tyr Ala  Val Ala Thr Thr Phe  Val Thr Pro Met Leu  Arg His Ser
    2285                 2290                 2295

Ile Glu  Asn Ser Ser Val Asn  Val Ser Leu Thr Ala  Ile Ala Asn
    2300                 2305                 2310

Gln Ala  Thr Val Leu Met Gly  Leu Gly Lys Gly Trp  Pro Leu Ser
    2315                 2320                 2325

Lys Met  Asp Ile Gly Val Pro  Leu Leu Ala Ile Gly  Cys Tyr Ser
    2330                 2335                 2340

Gln Val  Asn Pro Ile Thr Leu  Thr Ala Ala Leu Phe  Leu Leu Val
    2345                 2350                 2355

Ala His  Tyr Ala Ile Ile Gly  Pro Gly Leu Gln Ala  Lys Ala Thr
    2360                 2365                 2370

Arg Glu  Ala Gln Lys Arg Ala  Ala Ala Gly Ile Met  Lys Asn Pro
    2375                 2380                 2385

Thr Val  Asp Gly Ile Thr Val  Ile Asp Leu Asp Pro  Ile Pro Tyr
    2390                 2395                 2400

Asp Pro  Lys Phe Glu Lys Gln  Leu Gly Gln Val Met  Leu Leu Val
    2405                 2410                 2415

Leu Cys  Val Thr Gln Val Leu  Met Met Arg Thr Thr  Trp Ala Leu
    2420                 2425                 2430

Cys Glu  Ala Leu Thr Leu Ala  Thr Gly Pro Ile Ser  Thr Leu Trp
    2435                 2440                 2445

Glu Gly  Asn Pro Gly Arg Phe  Trp Asn Thr Thr Ile  Ala Val Ser
    2450                 2455                 2460

Met Ala  Asn Ile Phe Arg Gly  Ser Tyr Leu Ala Gly  Ala Gly Leu
    2465                 2470                 2475

Leu Phe  Ser Ile Met Lys Asn  Thr Thr Asn Thr Arg  Arg Gly Thr
    2480                 2485                 2490

Gly Asn  Ile Gly Glu Thr Leu  Gly Glu Lys Trp Lys  Ser Arg Leu
    2495                 2500                 2505

Asn Ala  Leu Gly Lys Ser Glu  Phe Gln Ile Tyr Lys  Lys Ser Gly
    2510                 2515                 2520

Ile Gln  Glu Val Asp Arg Thr  Leu Ala Lys Glu Gly  Ile Lys Arg
    2525                 2530                 2535

Gly Glu  Thr Asp His His Ala  Val Ser Arg Gly Ser  Ala Lys Leu
    2540                 2545                 2550

Arg Trp  Phe Val Glu Arg Asn  Met Val Thr Pro Glu  Gly Lys Val
    2555                 2560                 2565

Val Asp  Leu Gly Cys Gly Arg  Gly Gly Trp Ser Tyr  Tyr Cys Gly
    2570                 2575                 2580

Gly Leu  Lys Asn Val Arg Glu  Val Lys Gly Leu Thr  Lys Gly Gly
```

-continued 2585 2590 2595

Pro Gly His Glu Glu Pro Ile Pro Met Ser Thr Tyr Gly Trp Asn
2600 2605 2610

Leu Val Arg Leu Gln Ser Gly Val Asp Val Phe Phe Ile Pro Pro
2615 2620 2625

Glu Lys Cys Asp Thr Leu Leu Cys Asp Ile Gly Glu Ser Ser Pro
2630 2635 2640

Asn Pro Thr Val Glu Ala Gly Arg Thr Leu Arg Val Leu Asn Leu
2645 2650 2655

Val Glu Asn Trp Leu Asn Asn Asn Thr Gln Phe Cys Ile Lys Val
2660 2665 2670

Leu Asn Pro Tyr Met Pro Ser Val Ile Glu Lys Met Glu Ala Leu
2675 2680 2685

Gln Arg Lys Tyr Gly Gly Ala Leu Val Arg Asn Pro Leu Ser Arg
2690 2695 2700

Asn Ser Thr His Glu Met Tyr Trp Val Ser Asn Ala Ser Gly Asn
2705 2710 2715

Ile Val Ser Ser Val Asn Met Ile Ser Arg Met Leu Ile Asn Arg
2720 2725 2730

Phe Thr Met Arg Tyr Lys Lys Ala Thr Tyr Glu Pro Asp Val Asp
2735 2740 2745

Leu Gly Ser Gly Thr Arg Asn Ile Gly Ile Glu Ser Glu Ile Pro
2750 2755 2760

Asn Leu Asp Ile Ile Gly Lys Arg Ile Glu Lys Ile Lys Gln Glu
2765 2770 2775

His Glu Thr Ser Trp His Tyr Asp Gln Asp His Pro Tyr Lys Thr
2780 2785 2790

Trp Ala Tyr His Gly Ser Tyr Glu Thr Lys Gln Thr Gly Ser Ala
2795 2800 2805

Ser Ser Met Val Asn Gly Val Val Arg Leu Leu Thr Lys Pro Trp
2810 2815 2820

Asp Val Val Pro Met Val Thr Gln Met Ala Met Thr Asp Thr Thr
2825 2830 2835

Pro Phe Gly Gln Gln Arg Val Phe Lys Glu Lys Val Asp Thr Arg
2840 2845 2850

Thr Gln Glu Pro Lys Glu Gly Thr Lys Lys Leu Met Lys Ile Thr
2855 2860 2865

Ala Glu Trp Leu Trp Lys Glu Leu Gly Lys Lys Lys Thr Pro Arg
2870 2875 2880

Met Cys Thr Arg Glu Glu Phe Thr Arg Lys Val Arg Ser Asn Ala
2885 2890 2895

Ala Leu Gly Ala Ile Phe Thr Asp Glu Asn Lys Trp Lys Ser Ala
2900 2905 2910

Arg Glu Ala Val Glu Asp Ser Arg Phe Trp Glu Leu Val Asp Lys
2915 2920 2925

Glu Arg Asn Leu His Leu Glu Gly Lys Cys Glu Thr Cys Val Tyr
2930 2935 2940

Asn Met Met Gly Lys Arg Glu Lys Lys Leu Gly Glu Phe Gly Lys
2945 2950 2955

Ala Lys Gly Ser Arg Ala Ile Trp Tyr Met Trp Leu Gly Ala Arg
2960 2965 2970

Phe Leu Glu Phe Glu Ala Leu Gly Phe Leu Asn Glu Asp His Trp
2975 2980 2985

-continued

```
Phe Ser Arg Glu Asn Ser Leu Ser Gly Val Glu Gly Glu Gly Leu
    2990                2995                3000

His Lys Leu Gly Tyr Ile Leu Arg Asp Val Ser Lys Lys Glu Gly
    3005                3010                3015

Gly Ala Met Tyr Ala Asp Asp Thr Ala Gly Trp Asp Thr Arg Ile
    3020                3025                3030

Thr Leu Glu Asp Leu Lys Asn Glu Glu Met Val Thr Asn His Met
    3035                3040                3045

Glu Gly Glu His Lys Lys Leu Ala Glu Ala Ile Phe Lys Leu Thr
    3050                3055                3060

Tyr Gln Asn Lys Val Val Arg Val Gln Arg Pro Thr Pro Arg Gly
    3065                3070                3075

Thr Val Met Asp Ile Ile Ser Arg Arg Asp Gln Arg Gly Ser Gly
    3080                3085                3090

Gln Val Gly Thr Tyr Gly Leu Asn Thr Phe Thr Asn Met Glu Ala
    3095                3100                3105

Gln Leu Ile Arg Gln Met Glu Gly Glu Gly Val Phe Lys Ser Ile
    3110                3115                3120

Gln His Leu Thr Ile Thr Glu Glu Ile Ala Val Gln Asn Trp Leu
    3125                3130                3135

Ala Arg Val Gly Arg Glu Arg Leu Ser Arg Met Ala Ile Ser Gly
    3140                3145                3150

Asp Asp Cys Val Val Lys Pro Leu Asp Asp Arg Phe Ala Ser Ala
    3155                3160                3165

Leu Thr Ala Leu Asn Asp Met Gly Lys Ile Arg Lys Asp Ile Gln
    3170                3175                3180

Gln Trp Glu Pro Ser Arg Gly Trp Asn Asp Trp Thr Gln Val Pro
    3185                3190                3195

Phe Cys Ser His His Phe His Glu Leu Ile Met Lys Asp Gly Arg
    3200                3205                3210

Val Leu Val Val Pro Cys Arg Asn Gln Asp Glu Leu Ile Gly Arg
    3215                3220                3225

Ala Arg Ile Ser Gln Gly Ala Gly Trp Ser Leu Arg Glu Thr Ala
    3230                3235                3240

Cys Leu Gly Lys Ser Tyr Ala Gln Met Trp Ser Leu Met Tyr Phe
    3245                3250                3255

His Arg Arg Asp Leu Arg Leu Ala Ala Asn Ala Ile Cys Ser Ala
    3260                3265                3270

Val Pro Ser His Trp Val Pro Thr Ser Arg Thr Thr Trp Ser Ile
    3275                3280                3285

His Ala Lys His Glu Trp Met Thr Thr Glu Asp Met Leu Thr Val
    3290                3295                3300

Trp Asn Arg Val Trp Ile Gln Glu Asn Pro Trp Met Glu Asp Lys
    3305                3310                3315

Thr Pro Val Glu Ser Trp Glu Glu Ile Pro Tyr Leu Gly Lys Arg
    3320                3325                3330

Glu Asp Gln Trp Cys Gly Ser Leu Ile Gly Leu Thr Ser Arg Ala
    3335                3340                3345

Thr Trp Ala Lys Asn Ile Gln Ala Ala Ile Asn Gln Val Arg Ser
    3350                3355                3360

Leu Ile Gly Asn Glu Glu Tyr Thr Asp Tyr Met Pro Ser Met Lys
    3365                3370                3375
```

```
Arg Phe  Arg Arg Glu Glu Glu  Glu Ala Gly Val Leu  Trp
    3380                3385                3390

<210> SEQ ID NO 13
<211> LENGTH: 10723
<212> TYPE: DNA
<213> ORGANISM: Artificial Sequence
<220> FEATURE:
<223> OTHER INFORMATION: Dengue virus seroytpe 1, MVS

<400> SEQUENCE: 13

agttgttagt ctacgtggac cgacaaagac agattctttg agggagctaa gctcaatgta     60
gttctaacag tttttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagatctg caggcatgat cattatgctg    420
attccaacag tgatggcgtt ccatttaacc acgcgtgggg gagagccgca tatgatagtt    480
agcaagcagg aaagaggaaa gtcacttttg ttcaagacct ctgcaggtgt caacatgtgc    540
accctcattg cgatggattt gggagagttg tgtgaggaca cgatgaccta caaatgcccc    600
cggatcactg aggcggaacc agatgacgtt gactgttggt gcaatgccac ggacacatgg    660
gtgacctatg gaacgtgctc tcaaactggc gaacaccgac gagacaaacg ttccgtcgca    720
ttggccccac acgtggggct tggcctagaa acaagagccg aaacgtggat gtcctctgaa    780
ggtgcttgga aacagataca aaaagtagag acttgggctc tgagacatcc aggattcacg    840
gtgatagccc tttttctagc acatgccata ggaacatcca tcacccagaa agggatcatt    900
ttcattttgc tgatgctggt aacaccatct atggccatgc gatgcgtggg aataggcaac    960
agagacttcg tggaaggact gtcaggagca acatgggtgg atgtggtact ggagcatgga   1020
agttgcgtca ccaccatggc aaaaaacaaa ccaacactgg acattgaact cttgaagacg   1080
gaggtcacaa accctgcagt tctgcgtaaa ttgtgcattg aagctaaaat atcaaacacc   1140
accaccgatt cgagatgtcc aacacaagga gaagccacac tggtggaaga acaagacgcg   1200
aactttgtgt gccgacgaac gttcgtggac agaggctggg gcaatggctg tgggctattc   1260
ggaaaaggta gtctaataac gtgtgccaag tttaagtgtg tgacaaaact agaaggaaag   1320
atagttcaat atgaaaacct aaaatattca gtgatagtca ccgtccacac tggagatcag   1380
caccaggtgg gaaatgagac tacagaacat ggaacaactg caaccataac acctcaagct   1440
cctacgtcgg aaatacagct gaccgactac ggaaccctta cattagattg ttcacctagg   1500
acagggctag attttaacga gatggtgttg ctgacaatga aagaaagatc atggcttgtc   1560
cacaaacaat ggttcctaga cttaccactg ccttggacct ctggggcttc aacatcccaa   1620
gagacttgga acagacaaga tttactggtc acatttaaga cagctcatgc aaagaagcag   1680
gaagtagtcg tactaggatc acaagaagga gcaatgcaca ctgcgctgac tggagcgaca   1740
gaaatccaaa cgtcaggaac gacaacaatt ttcgcaggac acctaaaatg cagactaaaa   1800
atggacaaac taactttaaa agggatgtca tatgtgatgt gcacaggctc attcaagtta   1860
gagaaagaag tggctgagac ccagcatgga actgttctgg tgcaggttaa atatgaagga   1920
acagacgcac catgcaagat tccctttttcg acccaagatg agaaaggagc aacccagaat   1980
```

-continued gggagattaa taacagccaa ccccatagtc actgacaaag aaaaaccagt caatattgag 2040
gcagaaccac cctttggtga gagctacatc gtggtaggag caggtgaaaa agctttgaaa 2100
ctaagctggt tcaagaaagg aagcagcata gggaaaatgt ttgaagcaac tgcccgagga 2160
gcacgaagga tggccattct gggagacacc gcatgggact tcggttctat aggaggagtg 2220
ttcacgtcta tgggaaaact ggtacaccag gtttttggaa ctgcatatgg agttttgttt 2280
agcggagttt cttggaccat gaaaatagga atagggattc tgctgacatg gctaggatta 2340
aattcaagga acacgtccct ttcgatgatg tgcatcgcag ccggcattgt gacactgtat 2400
ttgggagtca tggtgcaggc cgatagtggt tgcgttgtga gctggaaaaa caaagaactg 2460
aaatgtggca gtgggatttt catcacagac aacgtgcaca catggacaga acaatacaag 2520
ttccaaccag aatccccttc aaaactagct tcagctatcc agaaagccca tgaagaggac 2580
atttgtggaa tccgctcagt aacaagactg gagaatctga tgtggaaaca aataacacca 2640
gaattgaatc acattctatc agaaaatgag gtgaagttaa ctattatgac aggagacatc 2700
aaaggaatca tgcaggcagg aaaacgatct ctgcggcctc agcccactga gctgaagtat 2760
tcatggaaaa catggggcaa agcaaaaatg ctctctacag agtctcataa ccagaccttt 2820
ctcattgatg gccccgaaac agcagaatgc cccaacacaa atagagcttg gaattcgttg 2880
gaagttgaag actatggctt tggagtattc accaccaata tatggctaaa attgaaagaa 2940
aaacaggatg tattctgcga ctcaaaactc atgtcagcgg ccataaaaga caacagagcc 3000
gtccatgccg atatgggtta ttggatagaa agtgcactca atgacacatg gaagatagag 3060
aaagcctctt tcattgaagt taaaaactgc cactggccaa aatcacacac cctctggagc 3120
aatggagtgc tagaaagtga gatgataatt ccaaagaatc tcgctggacc agtgtctcaa 3180
cacaactata gaccaggcta ccatacacaa ataacaggac catggcatct aggtaagctt 3240
gagatggact ttgatttctg tgatggaaca acagtggtag tgactgagga ctgcggaaat 3300
agaggaccct ctttgagaac aaccactgcc tctggaaaac tcataacaga atggtgctgc 3360
cgatcttgca cattaccacc gctaagatac agaggtgagg atgggtgctg gtacgggatg 3420
gaaatcagac cattgaagga gaaagaagag aatttggtca actccttggt cacagctgga 3480
catgggcagg tcgacaactt ttcactagga gtcttgggaa tggcattgtt cctggaggaa 3540
atgcttagga cccgagtagg aacgaaacat gcaatactac tagttgcagt ttcttttgtg 3600
acattgatca cagggaacat gtcctttaga gacctgggaa gagtgatggt tatggtaggc 3660
gccactatga cggatgacat aggtatgggc gtgacttatc ttgccctact agcagccttc 3720
aaagtcagac caacttttgc agctggacta ctcttgagaa agctgacctc caaggaattg 3780
atgatgacta ctataggaat tgtactcctc tcccagagca ccctaccaga gaccattctt 3840
gagttgactg atgcgttagc cttaggcatg atggtcctca aaatggtgag aaatatggaa 3900
aagtatcaat tggcagtgac tatcatggct atcttgtgcg tcccaaacgc agtgatatta 3960
caaaacgcat ggaaagtgag ttgcacaata ttggcagtgg tgtccgtttc cccactgttc 4020
ttaacatcct cacagcaaaa aacagattgg ataccattag cattgacgat caaaggtctc 4080
aatccaacag ctatttttct aacaaccctc tcaagaacca gcaagaaaag gagctggcca 4140
ttaaatgagg ctatcatggc agtcgggatg gtgagcattt tagccagttc tctcctaaaa 4200
aatgatattc ccatgacagg accattagtg gctggagggc tcctcactgt gtgctacgtg 4260
ctcactggac gatcggccga tttggaactg gagagagcag ccgatgtcaa atgggaagac 4320
caggcagaga tatcaggaag cagtccaatc ctgtcaataa caatatcaga agatggtagc 4380

-continued

```
atgtcgataa aaaatgaaga ggaagatcaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattcttt gatgagcgca   6600
aggggcatag ggaagatgac cctgggaatg tgctgcataa tcacggctag catcctccta   6660
tggtacgcac aaatacagcc acactggata gcagcttcaa taatactgga gtttttctc    6720
```

-continued

```
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc gaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag    8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
```

```
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
agctgtagtc tcgctggaag gactagaggt tagaggagac ccccccgaaa caaaaaacag  10620
catattgacg ctgggaaaga ccagagatcc tgctgtctcc tcagcatcat tccaggcaca  10680
gaacgccaga aaatggaatg gtgctgttga atcaacaggt tct                     10723
```

<210> SEQ ID NO 14
<211> LENGTH: 10723
<212> TYPE: DNA
<213> ORGANISM: Artificial Sequence
<220> FEATURE:
<223> OTHER INFORMATION: Dengue virus serotype 2, MVS

<400> SEQUENCE: 14

```
agttgttagt ctacgtggac cgacaaagac agattctttg agggagctaa gctcaatgta     60
gttctaacag ttttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagatctg caggcatgat cattatgctg    420
```

-continued

```
attccaacag tgatggcgtt ccatttaacc acacgtaacg gagaaccaca catgatcgtc    480
agcagacaag agaaagggaa aagtcttctg tttaaaacag aggttggcgt gaacatgtgt    540
accctcatgg ccatggacct tggtgaattg tgtgaagaca caatcacgta cgagtgtccc    600
cttctcaggc agaatgagcc agaagacata gactgttggt gcaactctac gtccacgtgg    660
gtaacttatg ggacgtgtac caccatggga gaacatagaa gagaaaaaag atcagtggca    720
ctcgttccac atgtgggaat gggactggag acacgaactg aaacatggat gtcatcagaa    780
ggggcctgga aacatgtcca gagaattgaa acttggatct tgagacatcc aggcttcacc    840
atgatggcag caatcctggc atacaccata ggaacgacac atttccaaag agccctgatc    900
ttcatcttac tgacagctgt cactccttca atgacaatgc gttgcatagg aatgtcaaat    960
agagactttg tggaaggggt ttcaggagga agctgggttg acatagtctt agaacatgga   1020
agctgtgtga cgacgatggc aaaaaacaaa ccaacattgg attttgaact gataaaaaca   1080
gaagccaaac agcctgccac cctaaggaag tactgtatag aggcaaagct aaccaacaca   1140
acaacagaat ctcgctgccc aacacaaggg gaacccagcc taaatgaaga gcaggacaaa   1200
aggttcgtct gcaaacactc catggtagac agaggatggg gaaatggatg tggactattt   1260
ggaaagggag gcattgtgac ctgtgctatg ttcagatgca aaaagaacat ggaaggaaaa   1320
gttgtgcaac cagaaaactt ggaatacacc attgtgataa cacctcactc aggggaagag   1380
catgcagtcg gaaatgacac aggaaaacat ggcaaggaaa tcaaaataac accacagagt   1440
tccatcacag aagcagaatt gacaggttat ggcactgtca caatggagtg ctctccaaga   1500
acgggcctcg acttcaatga gatggtgttg ctgcagatgg aaaataaagc ttggctggtg   1560
cacaggcaat ggttcctaga cctgccgtta ccatggttgc ccggagcgga cacacaaggg   1620
tcaaattgga tacagaaaga gacattggtc actttcaaaa atccccatgc gaagaaacag   1680
gatgttgttg ttttaggatc ccaagaaggg gccatgcaca cagcacttac aggggccaca   1740
gaaatccaaa tgtcatcagg aaacttactc ttcacaggac atctcaagtg caggctgaga   1800
atggacaagc tacagctcaa aggaatgtca tactctatgt gcacaggaaa gtttaaagtt   1860
gtgaaggaaa tagcagaaac acaacatgga acaatagtta tcagagtgca atatgaaggg   1920
gacggctctc catgcaagat cccttttgag ataatggatt tggaaaaaag acatgtctta   1980
ggtcgcctga ttacagtcaa cccaattgtg acagaaaaag atagcccagt caacatagaa   2040
gcagaacctc catttggaga cagctacatc atcataggag tagagccggg acaactgaag   2100
ctcaactggt ttaagaaagg aagttctatc ggccaaatgt ttgagacaac aatgaggggg   2160
gcgaagagaa tggccatttt aggtgacaca gcctgggatt ttggatcctt gggaggagtg   2220
tttacatcta taggaaaggc tctccaccaa gtctttggag caatctatgg agctgccttc   2280
agtggggttt catggactat gaaaatcctc ataggagtca ttatcacatg gataggaatg   2340
aattcacgca gcacctcact gtctgtgaca ctagtattgg tgggaattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
```

-continued ctcattgatg gccccgaaac agcagaatgc cccaacacaa atagagcttg gaattcgttg 2880
gaagttgaag actatggctt tggagtattc accaccaata tatggctaaa attgaaagaa 2940
aaacaggatg tattctgcga ctcaaaactc atgtcagcgg ccataaaaga caacagagcc 3000
gtccatgccg atatgggtta ttggatagaa agtgcactca atgacacatg gaagatagag 3060
aaagcctctt tcattgaagt taaaaactgc cactggccaa aatcacacac cctctggagc 3120
aatggagtgc tagaaagtga gatgataatt ccaaagaatc tcgctggacc agtgtctcaa 3180
cacaactata gaccaggcta ccatacacaa ataacaggac catggcatct aggtaagctt 3240
gagatggact ttgatttctg tgatggaaca acagtggtag tgactgagga ctgcggaaat 3300
agaggaccct ctttgagaac aaccactgcc tctggaaaac tcataacaga atggtgctgc 3360
cgatcttgca cattaccacc gctaagatac agaggtgagg atgggtgctg gtacgggatg 3420
gaaatcagac cattgaagga gaaagaagag aatttggtca actccttggt cacagctgga 3480
catgggcagg tcgacaactt ttcactagga gtcttgggaa tggcattgtt cctggaggaa 3540
atgcttagga cccgagtagg aacgaaacat gcaatactac tagttgcagt ttcttttgtg 3600
acattgatca cagggaacat gtcctttaga gacctgggaa gagtgatggt tatggtaggc 3660
gccactatga cggatgacat aggtatgggc gtgacttatc ttgccctact agcagccttc 3720
aaagtcagac caacttttgc agctggacta ctcttgagaa agctgacctc caaggaattg 3780
atgatgacta ctataggaat tgtactcctc tcccagagca ccataccaga gaccattctt 3840
gagttgactg atgcgttagc cttaggcatg atggtcctca aaatggtgag aaatatggaa 3900
aagtatcaat tggcagtgac tatcatggct atcttgtgcg tcccaaacgc agtgatatta 3960
caaaacgcat ggaaagtgag ttgcacaata ttggcagtgg tgtccgtttc cccactgttc 4020
ttaacatcct cacagcaaaa aacagattgg ataccattag cattgacgat caaaggtctc 4080
aatccaacag ctatttttct aacaaccctc tcaagaacca gcaagaaaag gagctggcca 4140
ttaaatgagg ctatcatggc agtcgggatg gtgagcattt tagccagttc tctcctaaaa 4200
aatgatattc ccatgacagg accattagtg gctggagggc tcctcactgt gtgctacgtg 4260
ctcactggac gatcggccga tttggaactg gagagagcag ccgatgtcaa atgggaagac 4320
caggcagaga tatcaggaag cagtccaatc ctgtcaataa caatatcaga agatggtagc 4380
atgtcgataa aaaatgaaga ggaagaacaa acactgacca tactcattag aacaggattg 4440
ctggtgatct caggactttt tcctgtatca ataccaatca cggcagcagc atggtacctg 4500
tgggaagtga agaaacaacg ggccggagta ttgtgggatg ttccttcacc cccacccatg 4560
ggaaaggctg aactggaaga tggagcctat agaattaagc aaaaagggat tcttggatat 4620
tcccagatcg gagccggagt ttacaaagaa ggaacattcc atacaatgtg gcatgtcaca 4680
cgtggcgctg ttctaatgca taaaggaaag aggattgaac catcatgggc ggacgtcaag 4740
aaagacctaa tatcatatgg aggaggctgg aagttagaag gagaatggaa ggaaggagaa 4800
gaagtccagg tattggcact ggagcctgga aaaaatccaa gagccgtcca aacgaaacct 4860
ggtcttttca aaaccaacgc cggaacaata ggtgctgtat ctctggactt ttctcctgga 4920
acgtcaggat ctccaattat cgacaaaaaa ggaaaagttg tgggtcttta tggtaatggt 4980
gttgttacaa ggagtggagc atatgtgagt gctatagccc agactgaaaa aagcattgaa 5040
gacaacccag agatcgaaga tgacattttc cgaaagagaa gactgaccat catggacctc 5100
cacccaggag cgggaaagac gaagagatac cttccggcca tagtcagaga agctataaaa 5160

-continued

```
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattcttt gatgagcgca   6600
aggggcatag ggaagatgac cctgggaatg tgctgcataa tcacggctag catcctccta   6660
tggtacgcac aaatacagcc acactggata gcagcttcaa taatactgga gtttttttctc   6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
```

-continued

```
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag    8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccgtattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
```

```
gctatttgct cggcagtacc atcacattgg gttccaacaa gtcgaacaac ctggtcccata   9960

catgctaaac atgaatggat gacaacggaa gacatgctga cagtctggaa cagggtgtgg  10020

attcaagaaa acccatggat ggaagacaaa actccagtgg aatcatggga ggaaatccca  10080

tacttgggga aaagagaaga ccaatggtgc ggctcattga ttgggttaac aagcagggcc  10140

acctgggcaa agaacatcca agcagcaata aatcaagtta gatcccttat aggcaatgaa  10200

gaatacacag attacatgcc atccatgaaa agattcagaa gagaagagga agaagcagga  10260

gttctgtggt agaaagcaaa actaacatga aacaaggcta gaagtcaggt cggattaagc  10320

catagtacgg aaaaaactat gctacctgtg agccccgtcc aaggacgtta aaagaagtca  10380

ggccatcata aatgccatag cttgagtaaa ctatgcagcc tgtagctcca cctgagaagg  10440

tgtaaaaaat ccgggaggcc acaaaccatg gaagctgtac gcatggcgta gtggactagc  10500

ggttagagga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tct                    10723
```

<210> SEQ ID NO 15
<211> LENGTH: 10717
<212> TYPE: DNA
<213> ORGANISM: Artificial Sequence
<220> FEATURE:
<223> OTHER INFORMATION: Dengue virus serotype 3, MVS

<400> SEQUENCE: 15

```
agttgttagt ctacgtggac cgacaaagac agattctttg agggagctaa gctcaatgta     60

gttctaacag tttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatctg caggcatgat cattatgctg    420

attccaacag tgatggcgtt ccatttaacc acgcgtgatg gagagccgcg catgattgtg    480

gggaagaatg aaagaggaaa atccctactt ttcaagacag cctctggaat caacatgtgc    540

acactcatag ctatggatct gggagagatg tgtgatgaca cggtcactta caaatgcccc    600

cacattaccg aagtggagcc tgaagacatt gactgctggt gcaaccttac atcgacatgg    660

gtgacttatg gaacatgcaa tcaagctgga gagcatagac gcgataagag atcagtggcg    720

ttagctcccc atgttggcat gggactggac acacgcactc aaacctggat gtcggctgaa    780

ggagcttgga gacaagtcga gaaggtagag acatgggccc ttaggcaccc agggtttacc    840

atactagccc tatttcttgc ccattacata ggcacttcct tgacccagaa agtggttatt    900

tttatactat taatgctggt taccccatcc atgacaatga gatgtgtagg agtaggaaac    960

agagattttg tggaaggcct atcgggagct acgtgggttg acgtggtgct cgagcacggt   1020

gggtgtgtga ctaccatggc taagaacaag cccacgctgg acatagagct tcagaagacc   1080

gaggccaccc aactggcgac cctaaggaag ctatgcattg agggaaaaat taccaacata   1140

acaaccgact caagatgtcc cacccaaggg gaagcgattt tacctgagga gcaggaccag   1200

aactacgtgt gtaagcatac atacgtggac agaggctggg gaaacggttg tggtttgttt   1260
```

-continued

```
ggcaagggaa gcttggtgac atgcgcgaaa tttcaatgtt tagaatcaat agagggaaaa   1320
gtggtgcaac atgagaacct caaatacacc gtcatcatca cagtgcacac aggagaccaa   1380
caccaggtgg gaaatgaaac gcagggagtc acggctgaga taacacccca ggcatcaacc   1440
gctgaagcca ttttacctga atatggaacc ctcgggctag aatgctcacc acggacaggt   1500
ttggatttca atgaaatgat ctcattgaca atgaagaaca aagcatggat ggtacataga   1560
caatggttct ttgacttacc cctaccatgg acatcaggag cttcagcaga aacaccaact   1620
tggaacagga aagagcttct tgtgacattt aaaaatgcac atgcaaaaaa gcaagaagta   1680
gttgttcttg gatcacaaga gggagcaatg catacagcac tgacaggagc tacagagatc   1740
caaacctcag gaggcacaag tatctttgcg gggcacttaa aatgtagact caagatggac   1800
aaattggaac tcaaggggat gagctatgca atgtgcttga gtagctttgt gttgaagaaa   1860
gaagtctccg aaacgcagca tgggacaata ctcattaagg ttgagtacaa aggggaagat   1920
gcaccctgca agattccttt ctccacggag gatggacaag gaaaagctct caatggcaga   1980
ctgatcacag ccaatccagt ggtgaccaag aaggaggagc ctgtcaacat tgaggctgaa   2040
cctccttttg gagaaagtaa catagtaatt ggaattggag acaaagccct gaaaatcaac   2100
tggtacaaga agggaagctc gattgggaag atgttcgagg ccactgccag aggtgcaagg   2160
cgcatggcca tcttgggaga cacagcctgg gactttggat cagtgggtgg tgttttgaat   2220
tcattaggga aaatggtcca ccaaatattt gggagtgctt acacagccct atttggtgga   2280
gtctcctgga tgatgaaaat tggaataggt gtcctcttaa cctggatagg gttgaactca   2340
aaaaatactt ctatgtcatt ttcatgcatc gcggccggca ttgtgacact gtatttggga   2400
gtcatggtgc aggccgatag tggttgcgtt gtgagctgga aaaacaaaga actgaaatgt   2460
ggcagtggga ttttcatcac agacaacgtg cacacatgga cagaacaata caagttccaa   2520
ccagaatccc cttcaaaact agcttcagct atccagaaag cccatgaaga ggacatttgt   2580
ggaatccgct cagtaacaag actggagaat ctgatgtgga aacaaataac accagaattg   2640
aatcacattc tatcagaaaa tgaggtgaag ttaactatta tgacaggaga catcaaagga   2700
atcatgcagg caggaaaacg atctctgcgg cctcagccca ctgagctgaa gtattcatgg   2760
aaaacatggg gcaaagcaaa aatgctctct acagagtctc ataaccagac ctttctcatt   2820
gatggccccg aaacagcaga atgccccaac acaaatagag cttggaattc gttggaagtt   2880
gaagactatg gctttggagt attcaccacc aatatatggc taaaattgaa agaaaaacag   2940
gatgtattct gcgactcaaa actcatgtca gcggccataa aagacaacag agccgtccat   3000
gccgatatgg gttattggat agaaagtgca ctcaatgaca catggaagat agagaaagcc   3060
tctttcattg aagttaaaaa ctgccactgg ccaaaatcac acaccctctg gagcaatgga   3120
gtgctagaaa gtgagatgat aattccaaag aatctcgctg gaccagtgtc tcaacacaac   3180
tatagaccag gctaccatac acaaataaca ggaccatggc atctaggtaa gcttgagatg   3240
gactttgatt tctgtgatgg aacaacagtg gtagtgactg aggactgcgg aaatagagga   3300
ccctctttga gaacaaccac tgcctctgga aaactcataa cagaatggtg ctgccgatct   3360
tgcacattac caccgctaag atacagaggt gaggatgggt gctggtacgg gatggaaatc   3420
agaccattga aggagaaaga agagaatttg gtcaactcct tggtcacagc tggacatggg   3480
caggtcgaca acttttcact aggagtcttg ggaatggcat tgttcctgga ggaaatgctt   3540
aggacccgag taggaacgaa acatgcaata ctactagttg cagtttcttt tgtgacattg   3600
```

-continued

```
atcacaggga acatgtcctt tagagacctg ggaagagtga tggttatggt aggcgccact   3660
atgacggatg acataggtat gggcgtgact tatcttgccc tactagcagc cttcaaagtc   3720
agaccaactt ttgcagctgg actactcttg agaaagctga cctccaagga attgatgatg   3780
actactatag gaattgtact cctctcccag agcaccatac cagagaccat tcttgagttg   3840
actgatgcgt tagccttagg catgatggtc ctcaaaatgg tgagaaatat ggaaaagtat   3900
caattggcag tgactatcat ggctatcttg tgcgtcccaa acgcagtgat attacaaaac   3960
gcatggaaag tgagttgcac aatattggca gtggtgtccg tttccccact gttcttaaca   4020
tcctcacagc aaaaaacaga ttggatacca ttagcattga cgatcaaagg tctcaatcca   4080
acagctattt ttctaacaac cctctcaaga accagcaaga aaaggagctg gccattaaat   4140
gaggctatca tggcagtcgg gatggtgagc attttagcca gttctctcct aaaaaatgat   4200
attcccatga caggaccatt agtggctgga gggctcctca ctgtgtgcta cgtgctcact   4260
ggacgatcgg ccgatttgga actggagaga gcagccgatg tcaaatggga agaccaggca   4320
gagatatcag gaagcagtcc aatcctgtca ataacaatat cagaagatgg tagcatgtcg   4380
ataaaaaatg aagaggaaga acaaacactg accatactca ttagaacagg attgctggtg   4440
atctcaggac tttttcctgt atcaatacca atcacggcag cagcatggta cctgtgggaa   4500
gtgaagaaac aacgggccgg agtattgtgg gatgttcctt cacccccacc catgggaaag   4560
gctgaactgg aagatggagc ctatagaatt aagcaaaaag ggattcttgg atattcccag   4620
atcggagccg gagtttacaa agaaggaaca ttccatacaa tgtggcatgt cacacgtggc   4680
gctgttctaa tgcataaagg aaagaggatt gaaccatcat gggcggacgt caagaaagac   4740
ctaatatcat atggaggagg ctggaagtta gaaggagaat ggaaggaagg agaagaagtc   4800
caggtattgg cactggagcc tggaaaaaat ccaagagccg tccaaacgaa acctggtctt   4860
ttcaaaacca acgccggaac aataggtgct gtatctctgg acttttctcc tggaacgtca   4920
ggatctccaa ttatcgacaa aaaaggaaaa gttgtgggtc tttatggtaa tggtgttgtt   4980
acaaggagtg gagcatatgt gagtgctata gcccagactg aaaaaagcat tgaagacaac   5040
ccagagatcg aagatgacat tttccgaaag agaagactga ccatcatgga cctccaccca   5100
ggagcgggaa agacgaagag ataccttccg gccatagtca gagaagctat aaaacggggt   5160
ttgagaacat taatcttggc ccccactaga gttgtggcag ctgaaatgga ggaagccctt   5220
agaggacttc caataagata ccagacccca gccatcagag ctgtgcacac cgggcgggag   5280
attgtggacc taatgtgtca tgccacattt accatgaggc tgctatcacc agttagagtg   5340
ccaaactaca acctgattat catggacgaa gcccatttca cagacccagc aagtatagca   5400
gctagaggat acatctcaac tcgagtggag atgggtgagg cagctgggat ttttatgaca   5460
gccactcccc cgggaagcag agacccattt cctcagagca atgcaccaat catagatgaa   5520
gaaagagaaa tccctgaacg ctcgtggaat tccggacatg aatgggtcac ggattttaaa   5580
gggaagactg tttggttcgt tccaagtata aaagcaggaa atgatatagc agcttgcctg   5640
aggaaaaatg gaaagaaagt gatacaactc agtaggaaga cctttgattc tgagtatgtc   5700
aagactagaa ccaatgattg ggacttcgtg gttacaactg acatttcaga aatgggtgcc   5760
aatttcaagg ctgagagggt tatagacccc agacgctgca tgaaaccagt catactaaca   5820
gatggtgaag agcgggtgat tctggcagga cctatgccag tgacccactc tagtgcagca   5880
caaagaagag ggagaatagg aagaaatcca aaaaatgaga atgaccagta catatacatg   5940
ggggaacctc tggaaaatga tgaagactgt gcacactgga aagaagctaa aatgctccta   6000
```

gataacatca acacgccaga aggaatcatt cctagcatgt tcgaaccaga gcgtgaaaag 6060
gtggatgcca ttgatggcga ataccgcttg agaggagaag caaggaaaac ctttgtagac 6120
ttaatgagaa gaggagacct accagtctgg ttggcctaca gagtggcagc tgaaggcatc 6180
aactacgcag acagaaggtg gtgttttgat ggagtcaaga acaaccaaat cctagaagaa 6240
aacgtggaag ttgaaatctg gacaaaagaa ggggaaagga agaaattgaa acccagatgg 6300
ttggatgcta ggatctattc tgacccactg gcgctaaaag aatttaagga atttgcagcc 6360
ggaagaaagt ctctgaccct gaacctaatc acagaaatgg gtaggctccc aaccttcatg 6420
actcagaagg caagagacgc actggacaac ttagcagtgc tgcacacggc tgaggcaggt 6480
ggaagggcgt acaaccatgc tctcagtgaa ctgccggaga ccctggagac attgctttta 6540
ctgacacttc tggctacagt cacgggaggg atctttttat tcttgatgag cgcaaggggc 6600
atagggaaga tgaccctggg aatgtgctgc ataatcacgg ctagcatcct cctatggtac 6660
gcacaaatac agccacactg gatagcagct tcaataatac tggagttttt tctcatagtt 6720
ttgcttattc cagaacctga aaaacagaga acaccccaag acaaccaact gacctacgtt 6780
gtcatagcca tcctcacagt ggtggccgca accatggcaa acgagatggg tttcctagaa 6840
aaaacgaaga aagatctcgg attgggaagc attgcaaccc agcaacccga gagcaacatc 6900
ctggacatag atctacgtcc tgcatcagca tggacgctgt atgccgtggc cacaacattt 6960
gttacaccaa tgttgagaca tagcattgaa aattcctcag tgaatgtgtc cctaacagct 7020
atagccaacc aagccacagt gttaatgggt ctcgggaaag gatggccatt gtcaaagatg 7080
gacatcggag ttccccttct cgccattgga tgctactcac aagtcaaccc cataactctc 7140
acagcagctc ttttcttatt ggtagcacat tatgccatca tagggccagg actccaagca 7200
aaagcaacca gagaagctca gaaaagagca gcggcgggca tcatgaaaaa cccaactgtc 7260
gatggaataa cagtgattga cctagatcca ataccttatg atccaaagtt tgaaaagcag 7320
ttgggacaag taatgctcct agtcctctgc gtgactcaag tattgatgat gaggactaca 7380
tgggctctgt gtgaggcttt aaccttagct accgggccca tctccacatt gtgggaagga 7440
aatccaggga ggttttggaa cactaccatt gcggtgtcaa tggctaacat ttttagaggg 7500
agttacttgg ccggagctgg acttctcttt tctattatga agaacacaac caacacaaga 7560
aggggaactg gcaacatagg agagacgctt ggagagaaat ggaaaagccg attgaacgcg 7620
ttgggaaaaa gtgaattcca gatctacaag aaaagtggaa tccaggaagt ggatagaacc 7680
ttagcaaaag aaggcattaa aagaggagaa acggaccatc acgctgtgtc gcgaggctca 7740
gcaaaactga gatggttcgt tgagagaaac atggtcacac cagaagggaa agtagtggac 7800
ctcggttgtg gcagaggagg ctggtcatac tattgtggag gactaaagaa tgtaagagaa 7860
gtcaaaggcc taacaaaagg aggaccagga cacgaagaac ccatccccat gtcaacatat 7920
gggtggaatc tagtgcgtct tcaaagtgga gttgacgttt tcttcatccc gccagaaaag 7980
tgtgacacat tattgtgtga catagggggag tcatcaccaa atcccacagt ggaagcagga 8040
cgaacactca gagtccttaa cttagtagaa aattggttga acaacaacac tcaattttgc 8100
ataaaggttc tcaacccata tatgccctca gtcatagaaa aaatggaagc actacaaagg 8160
aaatatggag gagccttagt gaggaatcca ctctcacgaa actccacaca tgagatgtac 8220
tgggtatcca atgcttccgg gaacatagtg tcatcagtga acatgatttc aaggatgttg 8280
atcaacagat ttacaatgag atacaagaaa gccacttacg agccggatgt tgacctcgga 8340

-continued

```
agcggaaccc gtaacatcgg gattgaaagt gagataccaa acctagatat aattgggaaa   8400
agaatagaaa aaataaagca agagcatgaa acatcatggc actatgacca agaccaccca   8460
tacaaaacgt gggcatacca tggtagctat gaaacaaaac agactggatc agcatcatcc   8520
atggtcaacg gagtggtcag gctgctgaca aaaccttggg acgtcgtccc catggtgaca   8580
cagatggcaa tgacagacac gactccattt ggacaacagc gcgtttttaa agagaaagtg   8640
gacacgagaa cccaagaacc gaaagaaggc acgaagaaac taatgaaaat aacagcagag   8700
tggctttgga aagaattagg gaagaaaaag acacccagga tgtgcaccag agaagaattc   8760
acaagaaagg tgagaagcaa tgcagccttg gggggccatat tcactgatga gaacaagtgg   8820
aagtcggcac gtgaggctgt tgaagatagt aggttttggg agctggttga caaggaaagg   8880
aatctccatc ttgaaggaaa gtgtgaaaca tgtgtgtaca acatgatggg aaaaagagag   8940
aagaagctag gggaattcgg caaggcaaaa ggcagcagag ccatatggta catgtggctt   9000
ggagcacgct tcttagagtt tgaagcccta ggattcttaa atgaagatca ctggttctcc   9060
agagagaact ccctgagtgg agtggaagga gaagggctgc acaagctagg ttacattcta   9120
agagacgtga gcaagaaaga gggaggagca atgtatgccg atgacaccgc aggatgggat   9180
acaagaatca cactagaaga cctaaaaaat gaagaaatgg taacaaacca catggaagga   9240
gaacacaaga aactagccga ggccattttc aaactaacgt accaaaacaa ggtggtgcgt   9300
gtgcaaagac caacaccaag aggcacagta atggacatca tatcgagaag agaccaaaga   9360
ggtagtggac aagttggcac ctatggactc aatactttca ccaatatgga agcccaacta   9420
atcagacaga tggagggaga aggagtcttt aaaagcattc agcacctaac aatcacagaa   9480
gaaatcgctg tgcaaaactg gttagcaaga gtggggcgcg aaaggttatc aagaatggcc   9540
atcagtggag atgattgtgt tgtgaaacct ttagatgaca ggttcgcaag cgctttaaca   9600
gctctaaatg acatgggaaa gattaggaaa gacatacaac aatgggaacc ttcaagagga   9660
tggaatgatt ggacacaagt gcccttctgt tcacaccatt tccatgagtt aatcatgaaa   9720
gacggtcgcg tactcgttgt tccatgtaga aaccaagatg aactgattgg cagagcccga   9780
atctcccaag gagcagggtg gtctttgcgg gagacggcct gtttggggaa gtcttacgcc   9840
caaatgtgga gcttgatgta cttccacaga cgcgacctca ggctggcggc aaatgctatt   9900
tgctcggcag taccatcaca ttgggttcca acaagtcgaa caacctggtc catacatgct   9960
aaacatgaat ggatgacaac ggaagacatg ctgacagtct ggaacagggt gtggattcaa  10020
gaaaacccat ggatggaaga caaaactcca gtggaatcat gggaggaaat cccatacttg  10080
gggaaaagag aagaccaatg gtgcggctca ttgattgggt taacaagcag ggccacctgg  10140
gcaaagaaca tccaagcagc aataaatcaa gttagatccc ttataggcaa tgaagaatac  10200
acagattaca tgccatccat gaaaagattc agaagagaag aggaagaagc aggagttctg  10260
tggtagaaag caaaactaac atgaaacaag gctagaagtc aggtcggatt aagccatagt  10320
acggaaaaaa ctatgctacc tgtgagcccc gtccaaggac gttaaaagaa gtcaggccat  10380
cataaatgcc atagcttgag taaactatgc agcctgtagc tccacctgag aaggtgtaaa  10440
aaatccggga ggccacaaac catggaagct gtacgcatgg cgtagtggac tagcggttag  10500
aggagacccc tcccttacaa atcgcagcaa caatgggggc ccaaggcgag atgaagctgt  10560
agtctcgctg gaaggactag aggttagagg agaccccccc gaaacaaaaa acagcatatt  10620
gacgctggga aagaccagag atcctgctgt ctcctcagca tcattccagg cacagaacgc  10680
cagaaaatgg aatggtgctg ttgaatcaac aggttct                             10717
```

<210> SEQ ID NO 16
<211> LENGTH: 10723
<212> TYPE: DNA
<213> ORGANISM: Artificial Sequence
<220> FEATURE:
<223> OTHER INFORMATION: Dengue virus serotype 4, MVS
<220> FEATURE:
<221> NAME/KEY: n
<222> LOCATION: (3773)..(3773)
<223> OTHER INFORMATION: a or g
<220> FEATURE:
<221> NAME/KEY: n
<222> LOCATION: (7026)..(7026)
<223> OTHER INFORMATION: t or c

<400> SEQUENCE: 16
agttgttagt ctacgtggac cgacaaagac agattctttg agggagctaa gctcaatgta 60
gttctaacag tttttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gacctttaaa actgttcatg 240
gccctggtgg cgttccttcg tttcctaaca atcccaccaa cagcagggat attgaagaga 300
tggggaacaa ttaaaaaatc aaaagctatt aatgttttga gagggttcag gaaagagatt 360
ggaaggatgc tgaacatctt gaataggaga cgcagctctg caggcatgat cattatgctg 420
attccaacag tgatggcgtt ccatttaacc acgcgtgatg gcgaacccct catgatagtg 480
gcaaaacatg aaagggggag acctctcttg tttaagacaa cagaggggat caacaaatgc 540
actctcattg ccatggactt gggtgaaatg tgtgaggaca ctgtcacgta taaatgcccc 600
ttactggtca ataccgaacc tgaagacatt gattgctggt gcaatctcac gtctacctgg 660
gtcatgtatg ggacatgcac ccagagcgga gaacggagac gagagaagcg ctcagtagct 720
ttaacaccac attcaggaat gggattggaa acaagagctg agacatggat gtcatcggaa 780
ggggcttgga agcatgctca gagagtagag agctggatac tcagaaaccc aggattcgcg 840
ctcttggcag gatttatggc ttatatgatt gggcaaacag gaatccagcg aactgtcttc 900
tttgtcctaa tgatgctggt cgccccatcc tacggaatgc gatgcgtagg agtaggaaac 960
agagactttg tggaaggagt ctcaggtgga gcatgggtcg atctggtgct agaacatgga 1020
ggatgcgtca caaccatggc ccagggaaaa ccaaccttgg attttgaact gactaagaca 1080
acagccaagg aagtggctct gttaagaacc tattgcattg aagcctcaat atcaaacata 1140
accacggcaa caagatgtcc aacgcaagga gagccttatc taaaagagga acaagaccaa 1200
cagtacattt gccggagaga tgtggtagac agagggtggg gcaatggctg tggcttgttt 1260
ggaaaaggag gagttgtgac atgtgcgaag ttttcatgtt cggggaagat aacaggcaat 1320
ttggtccaaa ttgagaacct tgaatacaca gtggttgtaa cagtccacaa tggagacacc 1380
catgcagtag gaaatgacac gtccaatcat ggagttacag ccacgataac tcccaggtca 1440
ccatcggtgg aagtcaaatt gccggactat ggagaactaa cactcgattg tgaacccagg 1500
tctggaattg actttaatga gatgattctg atgaaaatga aaaagaaaac atggcttgtg 1560
cataagcaat ggtttttgga tctacctcta ccatggacag caggagcaga cacatcagag 1620
gttcactgga attacaaaga gagaatggtg acatttaagg ttcctcatgc caagagacag 1680
gatgtgacag tgctgggatc tcaggaagga gccatgcatt ctgccctcgc tggagccaca 1740
gaagtggact ccggtgatgg aaatcacatg tttgcaggac atctcaagtg caaagtccgt 1800

-continued

```
atggagaaat tgagaatcaa gggaatgtca tacacgatgt gttcaggaaa gttctcaatt   1860
gacaaagaga tggcagaaac acagcatggg acaacagtgg tgaaagtcaa gtatgaaggt   1920
gctggagctc cgtgtaaagt ccccatagag ataagagatg tgaacaagga aaaagtggtt   1980
gggcgtatca tctcatccac ccctttggct gagaatacca acagtgtaac caacatagag   2040
ttagaacccc cctttgggga cagctacata gtgataggtg ttggaaacag tgcattaaca   2100
ctccattggt tcaggaaagg gagttccatt ggcaagatgt ttgagtccac atacagaggt   2160
gcaaaacgaa tggccattct aggtgaaaca gcttgggatt ttggttccgt tggtggactg   2220
ttcacatcat tgggaaaggc tgtgcaccag gtttttggaa gtgtgtatac aaccctgttt   2280
ggaggagtct catggatgat tagaatccta attgggttcc tagtgttgtg gattggcacg   2340
aactcaagga acacttcaat ggctatgacg tgcatagctg ccggcattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cgggtgacat aggtatgggc gtgacttatc ttgccctact agcagccttc   3720
aaagtcagac caacttttgc agctggacta ctcttgagaa agctgacctc canggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
```

```
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga tccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggtaag agacgcactg gacaacttag cagtgctgca cacggctgag   6480
gcaggtggaa gggcgtacaa ccatgctctc agtgaactgc cggagaccct ggagacattg   6540
```

-continued

```
cttttactga cacttctggc tacagtcacg ggagggatct ttttattctt gatgagcgca   6600
aggggcatag ggaagatgac cctgggaatg tgctgcataa tcacggctag catcctccta   6660
tggtacgcac aaatacagcc acactggata gcagcttcaa taatactgga gttttttctc   6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagcnatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
```

-continued

```
agagagaaga agctagggga attcggcaag gcaaaaggca gcagagccat atggtacatg    9000
tggcttggag cacgcttctt agagtttgaa gccctaggat tcttaaatga agatcactgg    9060
ttctccagag agaactccct gagtggagtg gaaggagaag ggctgcacaa gctaggttac    9120
attctaagag acgtgagcaa gaaagaggga ggagcaatgt atgccgatga caccgcagga    9180
tgggatacaa gaatcacact agaagaccta aaaaatgaag aaatggtaac aaaccacatg    9240
gaaggagaac acaagaaact agccgaggcc attttcaaac taacgtacca aaacaaggtg    9300
gtgcgtgtgc aaagaccaac accaagaggc acagtaatgg acatcatatc gagaagagac    9360
caaagaggta gtggacaagt tggcacctat ggactcaata ctttcaccaa tatggaagcc    9420
caactaatca gacagatgga gggagaagga gtctttaaaa gcattcagca cctaacaatc    9480
acagaagaaa tcgctgtgca aaactggtta gcaagagtgg ggcgcgaaag gttatcaaga    9540
atggccatca gtggagatga ttgtgttgtg aaacctttag atgacaggtt cgcaagcgct    9600
ttaacagctc taaatgacat gggaaagatt aggaaagaca tacaacaatg ggaaccttca    9660
agaggatgga atgattggac acaagtgccc ttctgttcac accatttcca tgagttaatc    9720
atgaaagacg gtcgcgtact cgttgttccc tgtagaaacc aagatgaact gattggcaga    9780
gcccgaatct cccaaggagc agggtggtct ttgcgggaga cggcctgttt ggggaagtct    9840
tacgcccaaa tgtggagctt gatgtacttc cacagacgcg acctcaggct ggcggcaaat    9900
gctatttgct cggcagtacc atcacattgg gttccaacaa gtcgaacaac ctggtccata    9960
catgctaaac atgaatggat gacaacggaa gacatgctga cagtctggaa cagggtgtgg   10020
attcaagaaa acccatggat ggaagacaaa actccagtgg aatcatggga ggaaatccca   10080
tacttgggga aaagagaaga ccaatggtgc ggctcattga ttgggttaac aagcagggcc   10140
acctgggcaa agaacatcca agcagcaata aatcaagtta gatcccttat aggcaatgaa   10200
gaatacacag attacatgcc atccatgaaa agattcagaa gagaagagga agaagcagga   10260
gttctgtggt agaaagcaaa actaacatga aacaaggcta gaagtcaggt cggattaagc   10320
catagtacgg aaaaaactat gctacctgtg agccccgtcc aaggacgtta aaagaagtca   10380
ggccatcata aatgccatag cttgagtaaa ctatgcagcc tgtagctcca cctgagaagg   10440
tgtaaaaaat ccgggaggcc acaaaccatg gaagctgtac gcatggcgta gtggactagc   10500
ggttagagga gacccctccc ttacaaatcg cagcaacaat gggggcccaa ggcgagatga   10560
agctgtagtc tcgctggaag gactagaggt tagaggagac ccccccgaaa caaaaaacag   10620
catattgacg ctgggaaaga ccagagatcc tgctgtctcc tcagcatcat tccaggcaca   10680
gaacgccaga aaatggaatg gtgctgttga atcaacaggt tct                     10723
```